(12) United States Patent
Dahl et al.

(10) Patent No.: US 9,023,789 B2
(45) Date of Patent: May 5, 2015

(54) AMYLIN ANALOGS AND PHARMACEUTICAL COMPOSITIONS THEREOF

(71) Applicant: Novo Nordisk A/S, Bagsvaerd (DK)

(72) Inventors: Kirsten Dahl, Smoerum (DK); Lauge Schaeffer, Lyngby (DK); Thomas Kruse, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 93 days.

(21) Appl. No.: 14/035,501

(22) Filed: Sep. 24, 2013

(65) Prior Publication Data

US 2014/0087995 A1   Mar. 27, 2014

Related U.S. Application Data

(63) Continuation of application No. 13/930,075, filed on Jun. 28, 2013, now Pat. No. 8,575,091, which is a continuation of application No. PCT/EP2013/058165, filed on Apr. 19, 2013.

(60) Provisional application No. 61/637,806, filed on Apr. 24, 2012.

(30) Foreign Application Priority Data

Apr. 19, 2012  (EP) .................... 12164692

(51) Int. Cl.
*C07K 14/47* (2006.01)
*C07K 14/575* (2006.01)

(52) U.S. Cl.
CPC ............... *C07K 14/47* (2013.01); *C07K 14/575* (2013.01)

(58) Field of Classification Search
None
See application file for complete search history.

(56) References Cited

U.S. PATENT DOCUMENTS

| 5,739,106 | A | 4/1998 | Rink et al. |
| 2013/0059770 | A1* | 3/2013 | Schaeffer et al. .............. 514/1.9 |

FOREIGN PATENT DOCUMENTS

| EP | 2233497 | A2 | 9/2010 |
| WO | 9426292 | A1 | 11/1994 |
| WO | 98/55144 | A1 | 12/1998 |
| WO | 2007/104789 | A2 | 9/2007 |
| WO | 2009/034119 | A1 | 3/2009 |
| WO | 2010/046357 | A1 | 4/2010 |
| WO | 2010/107874 | A2 | 9/2010 |

OTHER PUBLICATIONS

Moriarty et al. Biochemistry, vol. 38, No. 6,, 1999.*
Daniel F. Moriarty et al. Biochemistry. "Effects of Sequential Proline Substitutions on Amyloid Formation by Human Amylin." 1999. vol. 38(6). pp. 1811-1818.
Ryan G et al., Drug Design, Development and Therapy, Review of Pramlintide as Adjunctive Therapy in Treatment of Type 1 and Type 2 Diabetes, 2008, vol. 2, pp. 203-214.

* cited by examiner

*Primary Examiner* — Amber D Steele
*Assistant Examiner* — Schuyler Milton
(74) *Attorney, Agent, or Firm* — Jianjie Hu

(57) ABSTRACT

The invention relates to polypeptides comprising an amino acid sequence which is an analog of human amylin, pharmaceutical compositions comprising these polypeptides, and these polypeptides for use as medicaments.

14 Claims, 22 Drawing Sheets

Fig. 1

| Example no. | Sequence modifications | Albumin binding moiety | Linker | Acylation sites | hAmylin-R bind I

| Example no. | Sequence modifications | Albumin binding moiety | Linker | Acylation sites | hAmylin-R bind IC50 (pM) | hCTR bind IC50 (pM) | Ratio hCT/hAmylin binding |
|---|---|---|---|---|---|---|---|
| 19 | 14E, 17R, 21P, 27P | C20 diacid | gGlu-2xOEG | N-terminal | 556 | 20390 | 36.7 |
| 20 | 14E, 17R, 21P, 27P, 37P | C20 diacid | gGlu-2xOEG | N-terminal | 217 | 787 | 3.6 |
| 21 | 17R, 21P, 27P | C20 diacid | gGlu | N-terminal | 585 | 14240 | 24.4 |
| 22 | 14E, 17R, 21P, 27P, 35E | C20 diacid | gGlu | N-terminal | 794 | 9729 | 12.3 |
| 23 | 17R, 21P, 27P, 35E | C20 diacid | gGlu | N-terminal | 871 | 21810 | 25.0 |
| 24 | 17R, 21P, 27P | C20 diacid | gGlu-2xOEG | N-terminal | 1138 | 102400 | 90.0 |
| 25 | 17R, 21P, 27P, 35E | C20 diacid | gGlu-2xOEG | 1K | 768 | 43390 | 56.5 |
| 26 | 17R, 21P, 27P, 35E | C20 diacid | gGlu-OEG | 1K | 532 | 25265 | 47.5 |
| 27 | 17R, 21P, 27P, 35E | C20 diacid | gGlu | 1K | 837 | 34545 | 41.3 |
| 28 | 17R, 21P, 27P, 31P, 35E | C20 diacid | gGlu | N-terminal | 610 | 12522 | 20.5 |
| 29 | 17R, 21P, 27P, 34P, 35E | C20 diacid | gGlu | N-terminal | 577 | 8006 | 13.9 |
| 30 | 14H, 17R, 21P, 27P, 35E | C20 diacid | gGlu | N-terminal | 919 | 21650 | 23.6 |
| 31 | 14E, 17R, 21P, 27P, 31P | C20 diacid | gGlu | N-terminal | 204 | 3259 | 16.0 |
| 32 | 14E, 17R, 21P, 27P, 34P | C20 diacid | gGlu | N-terminal | 100 | 1088 | 10.9 |
| 33 | 14E, 17R, 21P, 28P, 35E | C20 diacid | gGlu | N-terminal | 915 | 3606 | 3.9 |
| 34 | 17R, 21P, 27P, 35K | C20 diacid | gGlu | N-terminal | 1139 | 73390 | 64.4 |
| 35 | 17R, 21P, 27P, 35K | C20 diacid | gGlu | 1K | 970 | 48750 | 50.3 |
| 36 | 14E, 17R, 21P, 27P, 34K | C20 diacid | gGlu | N-terminal | 403 | 6305 | 15.7 |
| 37 | 14E, 17R, 21P, 27P, 29P | C20 diacid | gGlu | N-terminal | 970 | 2184 | 2.3 |

Fig. 1 continued

| Example no. | Sequence modifications | Albumin binding moiety | Linker | Acylation sites | hAmylin-R bind IC50 (pM) | hCTR bind IC50 (pM) | Ratio hCTR/hAmylin binding |
|---|---|---|---|---|---|---|---|
| 38 | 17R, 21P, 27P, 35R | C20 diacid | gGlu-OEG | 1K | 249 | 21170 | 84.9 |
| 39 | 17R, 21P, 27P, 34R | C20 diacid | gGlu | N-terminal | 665 | 19280 | 29.0 |
| 40 | 17R, 21P, 27P, 34H | C20 diacid | gGlu | N-terminal | 549 | 17057 | 31.1 |
| 41 | 17R, 21P, 27P | C20 diacid | gGlu-OEG | 1K | 427 | 21310 | 49.9 |
| 42 | 17R, 21P, 27P | C20 diacid | none | 1K | 264 | 8105 | 30.7 |
| 43 | 17R, 21P, 27P | C20 diacid | OEG | 1K | 76 | 2636 | 34.7 |
| 44 | -1K, 1R, 17R, 21P, 27P, 35H | C20 diacid | gGlu | -1K | 275 | 4872 | 17.7 |
| 45 | -1K, 1R, 17R, 21P, 27P, 35H | C20 diacid | gGlu-OEG | -1K | 552 | 14790 | 26.8 |
| 46 | -1G, 1R, 17R, 21P, 27P | C20 diacid | gGlu | N-terminal | 195 | 9530 | 48.9 |
| 47 | -1G, 1R, 17R, 21P, 27P, 35H | C20 diacid | gGlu | N-terminal | 344 | 15460 | 44.9 |
| 48 | 17R, 21P, 27P | C20 diacid | gGlu | 1K | 443 | 30870 | 69.7 |
| 49 | 17R, 21P, 27P, 31P | C20 diacid | gGlu-OEG | 1K | 1191 | 12861 | 10.8 |
| 50 | 17R, 21P, 27P, 34P | C20 diacid | gGlu-OEG | 1K | 38 | 1380 | 36.0 |
| 51 | 14E, 17R, 21P, 27P, 35R | C20 diacid | gGlu | 1K | 828 | 31065 | 37.5 |
| 52 | 14D, 17R, 21P, 27P, 35R | C20 diacid | 2xgGlu | 1K | 697 | 56874 | 81.6 |
| 53 | 17R, 21P, 27P, 28P, 31P | C20 diacid | gGlu-OEG | 1K | 52 | 5383 | 103.5 |
| 54 | 17R, 21P, 27P, 29P, 31P | C20 diacid | gGlu-OEG | 1K | 30 | 4382 | 146.1 |
| 55 | 17R, 21P, 27P, 28P, 34P | C20 diacid | gGlu-OEG | 1K | 42 | 2175 | 51.8 |
| 56 | 17R, 21P, 27P, 29P, 34P | C20 diacid | gGlu-OEG | 1K | 49 | 2088 | 42.6 |
| 57 | 17R, 21P, 27P, 31P, 35H | C20 diacid | gGlu-OEG | 1K | 115 | 15300 | 133.0 |
| 58 | 17R, 21P, 27P, 34P, 35H | C20 diacid | gGlu-OEG | 1K | 88 | 9626 | 109.4 |

Fig. 1 continued

| Example no. | Sequence modifications | Albumin binding moiety | Linker | Acylation sites | hAmylin-R bind IC50 (pM) | hCTR bind IC50 (pM) | Ratio hCT/hAmylin binding |
|---|---|---|---|---|---|---|---|
| 59 | 14D, 17R, 21K, 27P, 35D | C20 diacid | 2xgGlu | 21K | 1193 | 5143 | 4.3 |
| 60 | 17R, 21P, 27P, 35H | C20 diacid | gGlu | 1K | 695 | 31410 | 45.2 |
| 61 | 14H, 17R, 21P, 27P, 31P | C20 diacid | gGlu-OEG | 1K | 122 | 8111 | 66.7 |
| 62 | 14H, 17R, 21P, 27P, 31P | C20 diacid | gGlu | 1K | 98 | 6174 | 63.0 |
| 63 | 14R, 17R, 21P, 27P, 31P | C20 diacid | gGlu | 1K | 825 | 129600 | 157.1 |
| 64 | 14R, 17R, 21P, 27P, 31P | C20 diacid | gGlu-OEG | 1K | 444 | 55970 | 126.1 |
| 65 | 14R, 17R, 21P, 27P, 34P | C20 diacid | gGlu | 1K | 649 | 53461 | 82.4 |
| 66 | 14H, 17R, 21P, 27P, 35H | C20 diacid | gGlu | 1K | 396 | 18020 | 45.5 |
| 67 | 14H, 17R, 21P, 27P, 34P | C20 diacid | gGlu | 1K | 90 | 4633 | 51.6 |
| 68 | 14H, 17R, 21P, 27P, 34P | C20 diacid | gGlu-OEG | 1K | 88 | 5664 | 64.4 |
| 69 | 14H, 17R, 21P, 27P | C20 diacid | gGlu-OEG | 1K | 133 | 8680 | 65.3 |
| 70 | 14H, 17R, 21P, 27P | C20 diacid | gGlu | 1K | 169 | 10280 | 60.8 |
| 71 | 14G, 17R, 21P, 27P, 31P | C20 diacid | gGlu-OEG | 1K | 48 | 1535 | 32.0 |
| 72 | 14A, 17R, 21P, 27P, 31P | C20 diacid | gGlu-OEG | 1K | 172 | 42410 | 246.6 |
| 73 | 14S, 17R, 21P, 27P, 31P | C20 diacid | gGlu-OEG | 1K | 104 | 5377 | 51.7 |
| 74 | 14K, 17R, 21P, 27P, 31P | C20 diacid | gGlu-OEG | 1K | 791 | 79875 | 101.0 |
| 75 | 14T, 17R, 21P, 27P, 31P | C20 diacid | gGlu-OEG | 1K | 666 | 60870 | 91.4 |
| 76 | 17R, 21P, 27P, 34H | C20 diacid | gGlu-OEG | 1K | 215 | 17207 | 80.0 |
| 77 | 17R, 21P, 27P, 34H | C20 diacid | gGlu | 1K | 428 | 50664 | 118.4 |
| 78 | 17R, 21P, 27P, 34R | C20 diacid | gGlu-OEG | 1K | 602 | 36550 | 60.7 |
| 79 | 17R, 21P, 27P, 34R | C20 diacid | gGlu | 1K | 790 | 36390 | 46.1 |

Fig. 1 continued

| Example no. | Sequence modifications | Albumin binding moiety | Linker | Acylation sites | hAmylin-R bind IC50 (pM) | hCTR bind IC50 (pM) | Ratio hCT/hAmylin binding |
|---|---|---|---|---|---|---|---|
| 80 | 14H, 17R, 21P, 27P, 34H | C20 diacid | gGlu-OEG | 1K | 290 | 19760 | 68.1 |
| 81 | 14H, 17R, 21P, 27P, 34H | C20 diacid | gGlu | 1K | 271 | 23640 | 87.2 |
| 82 | 14R, 17R, 21P, 27P | C20 diacid | gGlu-OEG | 1K | 636 | 88760 | 139.6 |
| 83 | 14R, 17R, 21P, 27P | C20 diacid | gGlu | 1K | 939 | 136700 | 145.6 |
| 84 | 14H, 17R, 21P, 27P, 34R | C20 diacid | gGlu-OEG | 1K | 743 | 88860 | 119.6 |
| 85 | 14H, 17R, 21P, 27P, 34R | C20 diacid | gGlu | 1K | 876 | 80420 | 91.8 |
| 86 | 17R, 21P, 27P, 34H | C20 diacid | 2xgGlu | 1K | 833 | 132723 | 159.3 |
| 87 | 14E, 17R, 21P, 27P, 34H | C20 diacid | 2xgGlu | 1K | 633 | 22523 | 35.6 |
| 88 | 14E, 17R, 21P, 27P, 34R | C20 diacid | 2xgGlu | 1K | 750 | 34870 | 46.5 |
| 89 | 14E, 17R, 21P, 27P, 35R | C20 diacid | 2xgGlu | 1K | 1160 | 32510 | 28.0 |
| 90 | 14H, 17R, 21P, 27P | C20 diacid | OEG | 1K | 61 | 2574 | 42.2 |
| 91 | 17R, 21P, 27P, 34H | C20 diacid | OEG | 1K | 119 | 12000 | 100.8 |
| 92 | 14H, 17R, 21P, 27P | C20 diacid | 2xgGlu | 1K | 179 | 25960 | 145.0 |
| 93 | 14A, 17R, 21P, 27P, 34H | C20 diacid | gGlu | 1K | 176 | 17780 | 101.0 |
| 94 | 14A, 17R, 21P, 27P, 34P | C20 diacid | gGlu | 1K | 148 | 6857 | 46.3 |
| 95 | 17R, 21P, 27P, 34R | C20 diacid | gGlu-2xOEG | 1K | 967 | 61280 | 63.4 |
| 96 | 17R, 21P, 27P, 31P | C20 diacid | gGlu-2xOEG | 1K | 166 | 13210 | 79.6 |
| 97 | 17R, 21P, 27P, 34H | C20 diacid | gGlu-2xOEG | 1K | 568 | 58920 | 103.7 |
| 98 | 17R, 21P, 27P, 34P | C20 diacid | gGlu-2xOEG | 1K | 91 | 6739 | 74.1 |

Fig. 1 continued

| Example no. | Sequence modifications | Albumin binding moiety | Linker | Acylation sites | hAmylin-R bind IC50 (pM) | hCTR bind IC50 (pM) | Ratio hCT/hAmylin binding |
|---|---|---|---|---|---|---|---|
| 99 | -1G, 1R, 14H, 17R, 21P, 27P | C20 diacid | gGlu | N-terminal | 348 | 34950 | 100.4 |
| 100 | -1G, 1R, 14H, 17R, 21P, 27P, 34H | C20 diacid | gGlu | N-terminal | 1015 | 66275 | 65.3 |
| 101 | -1G, 1R, 14A, 17R, 21P, 27P, 34H | C20 diacid | gGlu | N-terminal | 426 | 29175 | 68.6 |
| 102 | -1G, 1R, 14H, 17R, 21P, 27P, 34P | C20 diacid | gGlu | N-terminal | 217 | 7865 | 36.2 |
| 103 | -1G, 1R, 14A, 17R, 21P, 27P, 34P | C20 diacid | gGlu | N-terminal | 114 | 3004 | 26.5 |
| 104 | 14E, 17R, 21P, 27P, 34H, 35E | C20 diacid | 2xgGlu | 1K | 525 | 15245 | 29.1 |
| 105 | 14E, 17R, 21P, 27P, 34R, 35E | C20 diacid | 2xgGlu | 1K | 957 | 14099 | 14.7 |
| 106 | 14E, 17R, 21P, 27P, 34P, 35E | C20 diacid | 2xgGlu | 1K | 121 | 2135 | 17.6 |
| 107 | 14E, 17R, 21P, 27P, 34H, 35E | C20 diacid | gGlu | 1K | 387 | 4283 | 11.1 |
| 108 | 14E, 17R, 21P, 27P, 34R, 35E | C20 diacid | gGlu | 1K | 232 | 6623 | 28.5 |
| 109 | 14E, 17R, 21P, 27P, 34P, 35E | C20 diacid | gGlu | 1K | 140 | 1861 | 13.3 |
| 110 | 14E, 17R, 21P, 27P, 34P, 35R | C20 diacid | 2xgGlu | 1K | 326 | 17455 | 53.6 |
| 111 | 17R, 21P, 27P, 34H | C16 diacid | gGlu | 1K | 580 | 10750 | 18.5 |
| 112 | 17R, 21P, 27P, 34H | C14 diacid | gGlu | 1K | 1037 | 24320 | 23.5 |
| 113 | 17R, 21P, 27P, 34H | C18 diacid | gGlu | 1K | 382 | 22690 | 59.4 |
| 114 | 14E, 17R, 21P, 27P, 34P, 37P | C20 diacid | gGlu | 1K | 214 | 117 | 0.5 |
| 115 | 14H, 17R, 21P, 27P, 34P, 37P | C20 diacid | gGlu | 1K | 131 | 157 | 1.2 |
| 116 | 14H, 17R, 21P, 27P, 31P, 34P | C20 diacid | gGlu | 1K | 82 | 2036 | 24.8 |
| 117 | 14E, 17R, 21P, 27P, 34P, 35R | C20 diacid | gGlu | 1K | 163 | 6298 | 38.6 |

Fig. 1 continued

| Example no. | Sequence modifications | Albumin binding moiety | Linker | Acylation sites | hAmylin-R bind IC50 (pM) | hCTR bind IC50 (pM) | Ratio hCT/hAmylin binding |
|---|---|---|---|---|---|---|---|
| 118 | 14E, 17R, 21P, 27P, 34P, 35H | C20 diacid | gGlu | 1K | 179 | 3801 | 21.2 |
| 119 | 17R, 21P, 27P, 31P, 34P, 35R | C20 diacid | 2xgGlu | 1K | 880 | 42770 | 48.6 |
| 120 | 14S, 17R, 21P, 27P, 34P, 35E | C20 diacid | 2xgGlu | 1K | 76 | 3439 | 45.3 |
| 121 | 14E, 17R, 21P, 31P, 34P, 35E | C20 diacid | 2xgGlu | 1K | 69 | 1561 | 22.6 |
| 122 | 14D, 17R, 21P, 27P, 34P, 35E | C20 diacid | 2xgGlu | 1K | 172 | 8565 | 49.8 |
| 123 | 14D, 17R, 21P, 27P, 34P, 35E | C20 diacid | gGlu | 1K | 196 | 3273 | 16.7 |
| 124 | 14E, 17R, 21P, 27P, 34P, 35H | C20 diacid | 2xgGlu | 1K | 377 | 10314 | 27.3 |
| 125 | 14E, 17R, 21P, 27P, 34P, 35E, 37P | C20 diacid | 2xgGlu | 1K | 533 | 226 | 0.4 |
| 126 | 14E, 17R, 23P, 34P, 35E | C20 diacid | 2xgGlu | 1K | 1187 | 9294 | 7.8 |
| 127 | 14E, 17R, 21P, 27P, 34P, 37F | C20 diacid | 2xgGlu | 1K | 152 | 2733 | 18.0 |
| 128 | 14E, 17R, 21P, 27P, 35H | C20 diacid | gGlu | 1K | 992 | 26140 | 26.4 |
| 129 | 14D, 17R, 21P, 27P, 34P, 35R | C20 diacid | gGlu | 1K | 281 | 42470 | 151.1 |
| 130 | 14D, 17R, 21P, 27P, 34P, 35R | C20 diacid | 2xgGlu | 1K | 453 | 126850 | 280.0 |
| 131 | 14d, 17R, 21P, 27P, 35R | C20 diacid | 2xgGlu | 1K | 365 | 111900 | 306.6 |
| 132 | 14D, 17R, 21P, 27P, 35R | none | none |  | 266 | 7504 | 28.2 |

Fig. 1 continued

α-nitrogen and γ-carboxy group form the amide bonds
to the two neighboring residues

SEQUENCE LISTING

```
<160> NUMBER OF SEQ ID NOS: 5

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

```
<210> SEQ ID NO 2
<211> LENGTH: 37
<212> TYPE: PRT
<213> ORGANISM: Artificial Sequence
<220> FEATURE:
<223> OTHER INFORMATION: Synthetic

<400> SEQUENCE: 2

Ala Cys Asn Thr Ala Thr Cys Ala Thr Gln Arg Leu Ala Asp Phe Leu
1               5                   10                  15

Arg His Ser Ser Pro Asn Phe Gly Pro Pro Pro Pro Thr Pro Val
            20                  25                  30

Gly Pro Asp Thr Pro
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic

<400> SEQUENCE: 3

Lys Cys Asn Thr Ala Thr Cys Ala Thr Gln Arg Leu Ala Asp Phe Leu
1               5                   10                  15

Arg His Ser Ser Pro Asn Phe Gly Ala Ile Pro Ser Ser Thr Asn Val
            20                  25                  30

Gly Ser Asn Thr Tyr
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic

<400> SEQUENCE: 4

Lys Cys Asn Thr Ala Thr Cys Ala Thr Gln Arg Leu Ala Asp Phe Leu
1               5                   10                  15

Arg His Ser Ser Pro Asn Phe Gly Ala Ile Pro Ser Ser Thr Asn Val
            20                  25                  30

Gly Ser Arg Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Cys, Glu, Gly, His, Arg, Ser or Lys
<220> FEATURE:
<221> NAME/KEY: MISC_FEATURE
<222> LOCATION: (14)..(14)
<223> OTHER INFORMATION: Xaa = Asp, Glu, His, Asn, Arg, Gly, Ala, Ser,
      Lys, Thr or Cys
<220> FEATURE:
<221> NAME/KEY: MISC_FEATURE
<222> LOCATION: (17)..(17)
<223> OTHER INFORMATION: Xaa = Arg or Val
<220> FEATURE:
```

```
<221> NAME/KEY: MISC_FEATURE
<222> LOCATION: (21)..(21)
<223> OTHER INFORMATION: Xaa = Pro
<220> FEATURE:
<221> NAME/KEY: MISC_FEATURE
<222> LOCATION: (25)..(25)
<223> OTHER INFORMATION: Xaa = Pro or Ala
<220> FEATURE:
<221> NAME/KEY: MISC_FEATURE
<222> LOCATION: (26)..(26)
<223> OTHER INFORMATION: Xaa = Pro or Ile
<220> FEATURE:
<221> NAME/KEY: MISC_FEATURE
<222> LOCATION: (27)..(27)
<223> OTHER INFORMATION: Xaa = Pro or Leu
<220> FEATURE:
<221> NAME/KEY: MISC_FEATURE
<222> LOCATION: (28)..(28)
<223> OTHER INFORMATION: Xaa = Pro or Ser
<220> FEATURE:
<221> NAME/KEY: MISC_FEATURE
<222> LOCATION: (29)..(29)
<223> OTHER INFORMATION: Xaa = Pro or Ser
<220> FEATURE:
<221> NAME/KEY: MISC_FEATURE
<222> LOCATION: (31)..(31)
<223> OTHER INFORMATION: Xaa = Pro or Asn
<220> FEATURE:
<221> NAME/KEY: MISC_FEATURE
<222> LOCATION: (34)..(34)
<223> OTHER INFORMATION: Xaa = Pro, His, Lys, Arg or Ser
<220> FEATURE:
<221> NAME/KEY: MISC_FEATURE
<222> LOCATION: (35)..(35)
<223> OTHER INFORMATION: Xaa = Asp, Arg, Glu, Lys, His or Asn
<220> FEATURE:
<221> NAME/KEY: MISC_FEATURE
<222> LOCATION: (37)..(37)
<223> OTHER INFORMATION: Xaa = Pro or Tyr

<400> SEQUENCE: 5

Xaa Cys Asn Thr Ala Thr Cys Ala Thr Gln Arg Leu Ala Xaa Phe Leu
1               5                   10                  15

Xaa His Ser Ser Xaa Asn Phe Gly Xaa Xaa Xaa Xaa Xaa Thr Xaa Val
            20                  25                  30

Gly Xaa Xaa Thr Xaa
        35
```

AMYLIN ANALOGS AND PHARMACEUTICAL COMPOSITIONS THEREOF

CROSS-REFERENCE TO RELATED APPLICATIONS

This application is a continuation of U.S. application Ser. No. 13/930,075, filed Jun. 28, 2013, which is a continuation of International Application No. PCT/EP2013/058165, filed Apr. 19, 2013, which claimed priority of European Patent Application 12164692.1, filed Apr. 19, 2012; this application also claims priority under 35 U.S.C. §119(e) of U.S. Provisional application 61/637,806, filed Apr. 24, 2012; the contents of all above-named applications are incorporated herein by reference.

FIELD OF THE INVENTION

The invention relates to polypeptides comprising an amino acid sequence which is an analogue of SEQ ID No: 1 (human amylin), pharmaceutical compositions comprising these polypeptides, and these polypeptides for use as medicaments.

BACKGROUND OF THE INVENTION

A large and growing number of people suffer from diabetes mellitus and obesity. Diabetes mellitus is a metabolic disorder in which the ability to utilize glucose is partly or completely lost.

A number of treatment regimes target excessive blood glucose whereas others are focused primarily on weight reduction. The most efficient anti-diabetic agent used to lower blood glucose is insulin and analogue(s) thereof. It has been known for a long time that when traditional insulin is used to treat diabetes, it is associated with an increase in body weight. Insulin has to be injected subcutaneously up to several times per day.

Type 2 diabetes is generally treated in the early phases with diet and exercise. As the condition progresses, various oral anti-diabetic agents are added. Injected agents such as GLP-1 analogues may also be used at this stage. In general, these agents are most efficient in patients with functioning beta-cells capable of releasing insulin and amylin.

Human amylin is a 37 amino acid long polypeptide which has physico-chemical properties that make its use as a drug troublesome. In particular, it has a tendency for fibrillogenesis, i.e. the formation of fibrils, in vitro and/or ex vivo and becomes ineffective due to precipitation. Additionally amylin is difficult to formulate as it is chemically unstable and it precipitates at physiologic pH. Therefore it is formulated in acidic solution.

Human amylin binds to two distinct receptor complexes. These two complexes contain the calcitonin receptor plus a receptor activity-modifying proteins, RAMP1 or RAMP3. From the close relationship between the calcitonin receptor and the amylin receptor some cross-reactivity to the calcitonin receptor may be expected of amylin receptor agonist. As an example pramlintide has some affinity to the calcitonin receptor but is 14 times more potent on the amylin receptor.

Pramlintide is a drug product marketed by Amylin Pharmaceuticals as Symlin® for the treatment of diabetes as an add-on to insulin. Pramlintide is an amylin receptor agonist. It is approximately 14 times less active on the calcitonin receptor.

The chemical structure of pramlintide is presented below and also in FIG. 5.

Pramlintide is chemically unstable at neutral pH and it is therefore provided in an acidic solution. Compared to human amylin, the amino acids in position 25, 28 and 29 in pramlintide are substituted with proline. This modification reduces the tendency of the protein for fibrillogenesis. Parmlintide has a very short plasma half-life and therefore has to be injected two to three times daily WO 2010/046357 discloses polypeptides comprising human amylin analogues (having an albumin binding moiety. WO 2009/034119 also discloses polypeptides comprising human amylin analogues having an albumin binding moiety. Even though these polypeptides with albumin binding moieties show improved pharmacokinetic (PK) or pharmacodynamic (PD) properties compared to pramlintide, they may still show poor physical stability under certain conditions. In addition, the polypeptides generally do not show selectivity for the amylin receptor over the calcitonin receptor.

The calcitonin receptor is found in many tissues throughout the body and it is believed to be involved in regulation of bone metabolism. However, apart from bone regulation, very little is known about the physiology of calcitonin receptors in humans. It is therefore believed that amylin based polypeptides that have an increased selectivity for the amylin receptor compared to calcitonin activity could offer an advantageous pharmacokinetic and pharmacological profile.

SUMMARY OF THE INVENTION

It has been surprisingly found that polypeptides comprising an amino acid which is an analogue of SEQ ID No: 1 (human amylin) wherein the amino acid residue at position 21 is proline can demonstrate increased selectivity for the amylin receptor over the calcitonin receptor.

At least in some embodiments the polypeptides of the present invention have an increased selectivity for the amylin receptor compared to calcitonin activity.

At least in some embodiments the polypeptides of the present invention display an advantageous pharmacokinetic profile and/or advantageous pharmacological profile. An example of an advantageous pharmacokinetic profile is a long acting profile.

In one broad embodiment, the present invention relates to a polypeptide comprising an amino acid sequence which is an analogue of SEQ ID No: 1 wherein said analogue comprises a proline residue at position 21, wherein the amino acid sequence numbering of the analogue corresponds to the amino acid numbering sequence of SEQ ID No: 1. Optionally, the polypeptide has an $IC_{50}$ in a human amylin receptor binding assay (such as that disclosed herein) of about 1200 pM or less. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad embodiment, the present invention relates to a polypeptide comprising an amino acid sequence which is an analogue of SEQ ID No: 1 wherein said analogue comprises a proline residue at position 21 and a proline residue at position 27, wherein the amino acid sequence numbering of the analogue corresponds to the amino acid numbering sequence of SEQ ID No: 1. Optionally, the polypeptide has an $IC_{50}$ in a human amylin receptor binding assay (such as that disclosed herein) of about 1200 pM or less. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad embodiment, the present invention relates to a polypeptide comprising an amino acid sequence which is an analogue of SEQ ID No: 1 wherein said analogue comprises a proline residue at position 21, a proline residue at position 27 and an arginine residue at position 17, wherein the amino acid sequence numbering of the analogue corresponds to the amino acid numbering sequence of SEQ ID No: 1. Optionally, the polypeptide has an $IC_{50}$ in a human amylin receptor binding assay (such as that disclosed herein) of about 1200 pM or less. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad embodiment, the present invention relates to a polypeptide comprising an amino acid sequence which is an analogue of SEQ ID No: 1 wherein said analogue comprises a proline residue at position 21, a proline residue at position 27, an arginine residue at position 17 and an aspartic acid residue at position 14, wherein the amino acid sequence numbering of the analogue corresponds to the amino acid numbering sequence of SEQ ID No: 1. Optionally, the polypeptide has an $IC_{50}$ in a human amylin receptor binding assay (such as that disclosed herein) of about 1200 pM or less. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad embodiment, the present invention relates to a polypeptide comprising an amino acid sequence which is an analogue of SEQ ID No: 1 wherein said analogue comprises a proline residue at position 21, a proline residue at position 27, an arginine residue at position 17, an aspartic acid residue at position 14 and an arginine residue at position 35, wherein the amino acid sequence numbering of the analogue corresponds to the amino acid numbering sequence of SEQ ID No: 1. Optionally, the polypeptide has an $IC_{50}$ in a human amylin receptor binding assay (such as that disclosed herein) of about 1200 pM or less. Optionally the polypeptide has at least one substituent attached to at least one of its amino acid residues. The present invention also relates to pharmaceutical formulations comprising same. The present invention also relates to pharmaceutical uses of same. The present invention also relates to the delivery (such as administration) of same to patients in need of treatment of same.

In another broad embodiment, the present invention relates to a polypeptide comprising an amino acid sequence which is an analogue of SEQ ID No: 1 of formula (I):

(I)
(SEQ ID NO: 5)
$Xaa_1$-Cys-Asn-Thr-Ala-Thr-Cys-Ala-Thr-Gln-Arg-Leu-Ala-$Xaa_{14}$-Phe-Leu-$Xaa_{17}$-His-Ser-Ser-$Xaa_{21}$-Asn-Phe-Gly-$Xaa_{25}$-$Xaa_{26}$-$Xaa_{27}$-$Xaa_{28}$-$Xaa_{29}$-Thr-$Xaa_{31}$-Val-Gly-$Xaa_{34}$-$Xaa_{35}$-Thr-$Xaa_{37}$;

wherein
   $Xaa_1$ is independently selected from Ala, Cys, Glu, Gly, His, Arg, Ser and Lys;
   $Xaa_{14}$ is independently selected from Asp, Glu, His, Asn, Arg, Gly, Ala, Ser, Lys, Thr and Cys;
   $Xaa_{17}$ is independently selected from Arg and Val;
   $Xaa_{21}$ is Pro;
   $Xaa_{25}$ is independently selected from Pro and Ala;
   $Xaa_{26}$ is independently selected from Pro and Ile;
   $Xaa_{27}$ is independently selected from Pro and Leu;
   $Xaa_{28}$ is independently selected from Pro and Ser;
   $Xaa_{29}$ is independently selected from Pro and Ser;
   $Xaa_{31}$ is independently selected from Pro and Asn;
   $Xaa_{34}$ is independently selected from Pro, His, Lys, Arg and Ser
   $Xaa_{35}$ is independently selected from Asp, Arg, Glu, Lys, His and Asn;
   $Xaa_{37}$ is independently selected from Pro and Tyr;
   and where the C-terminal may optionally be derivatized.

For the purpose of illustration, one example of formula (I) is Ala-Cys-Asn-Thr-Ala-Thr-Cys-Ala-Thr-Gln-Arg-Leu-Ala-Asp-Phe-Leu-Arg-His-Ser-Ser-Pro-Asn-Phe-Gly-Pro-Pro-Pro-Pro-Pro-Thr-Pro-Val-Gly-Pro-Asp-Thr-Pro (SEQ ID NO: 2)

The present invention also relates to pharmaceutical formulations comprising same. The present invention also relates to pharmaceutical uses of same. The present invention also relates to the delivery (such as administration) of same to patients in need of treatment of same.

In one embodiment, the present invention concerns a polypeptide comprising an amino acid sequence which is an analogue of SEQ ID No: 1 wherein:
   (a) said analogue comprises a proline residue at position 21;
wherein the amino acid sequence numbering of the analogue corresponds to the amino acid numbering sequence of SEQ ID No: 1;
   optionally wherein (b) the polypeptide has an $IC_{50}$ in a human amylin receptor binding assay of about 1200 pM or less;

optionally wherein the polypeptide has at least one substituent attached to at least one of its amino acid residues.

In one embodiment, the present invention concerns a polypeptide comprising an amino acid sequence which is an analogue of SEQ ID No: 1 wherein:
  (a) said analogue comprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In one embodiment, the present invention concerns a polypeptide comprising an amino acid sequence which is an analogue of SEQ ID No: 1 wherein:
  (a) said analogue comprises a proline residue at position 21,
wherein the amino acid sequence numbering of the analogue corresponds to the amino acid numbering sequence of SEQ ID No: 1; and
  wherein the polypeptide has at least one substituent attached to at least one of its amino acid residues.

In one embodiment, the present invention concerns a polypeptide comprising an amino acid sequence which is an analogue of SEQ ID No: 1 wherein:
  (a) said analogue comprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1; and
  wherein the polypeptide has at least one substituent attached to at least one of its amino acid residues.

In another embodiment, the invention further comprises a pharmaceutical composition comprising the above polypeptide.

In another embodiment, the invention further comprises a process for preparing a pharmaceutical composition comprising the above polypeptide.

In another embodiment, the invention further comprises the above polypeptide for use as a medicament.

The polypeptides of the present invention are advantageous as they possess an increased selectivity for the amylin receptor.

A suitable human amylin receptor binding assay to determine the $IC_{50}$ is described herein. For example, see Assay (V).

Figure 1:
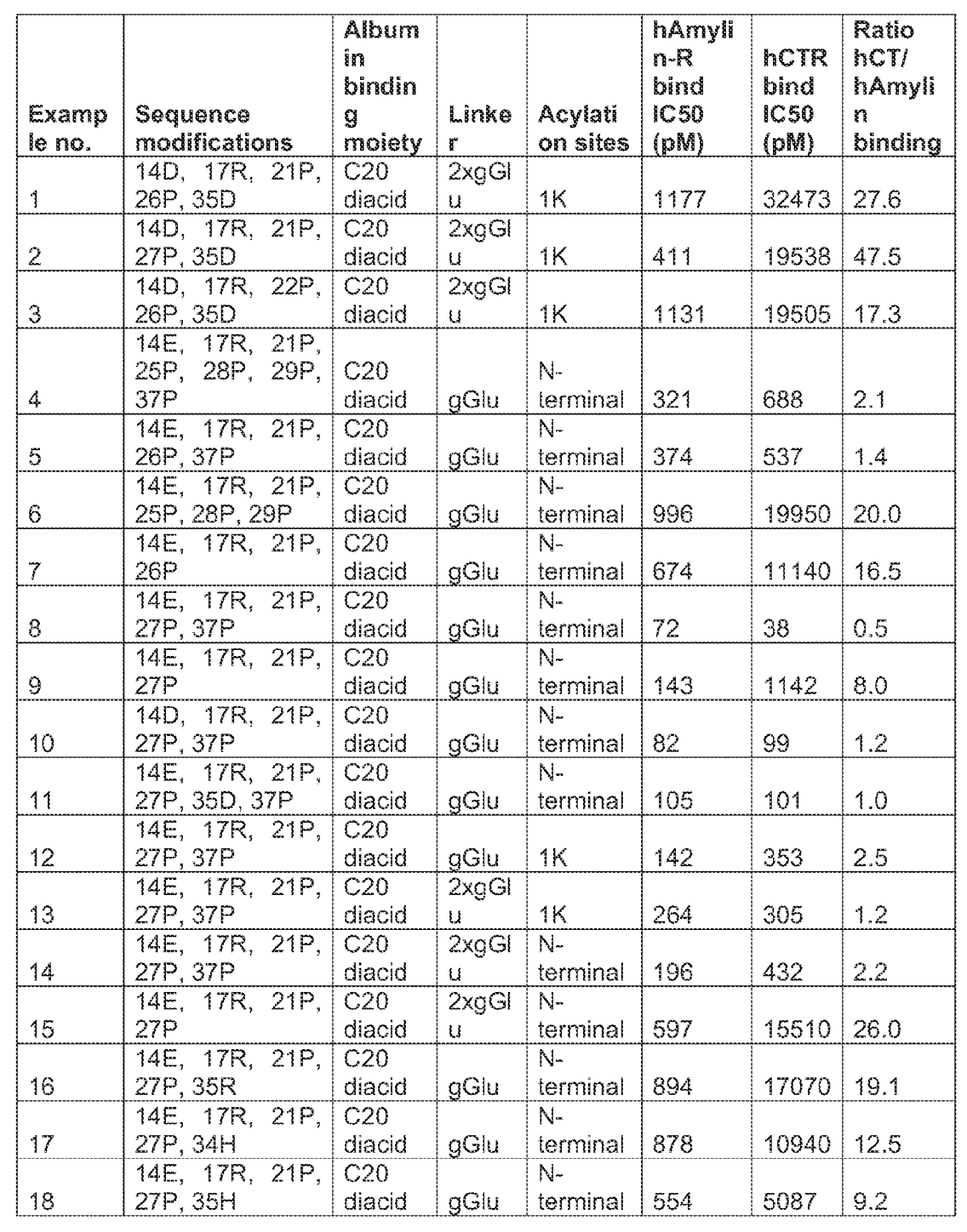

FIG. 1 presents a Table of a series of polypeptides according to the present invention.

FIG. 2 presents a structure of human amylin.

FIG. 3 presents a structure of gammaGlu.

FIG. 4 presents a structure of epsilon amino group and alpha amino group.

FIG. 5 presents a structure of pralintide.

In addition, FIG. 1 presents data for the recited polypeptides. In the Table of compounds shown in FIG. 1 the term "sequence modifications" means modifications with respect to human amylin.

In summary FIGS. 6 to 16 present that salmon calcitonin has comparable binding affinities to amylin receptors and calcitonin receptors. Thus, salmon calcitonin mediates both decrease in plasma calcium (below 1.7 mM) and reduction of food intake when administered to rats (dose 30 nmol/kg). This is in contrast to the polypeptides of the present invention, which are improved amylin selective compounds and able to reduce food intake with only minimal decrease of plasma calcium (see FIGS. 6 to 16).

In the Tables and FIG. 1: the term "acylation site" means the attachment site of the albumin binding moiety or linker to the polypeptide; the term "N-terminal" means that it is attached to the alpha amino group of the N-terminal amino acid of the polypeptide sequence; the term "1K" means that it is attached to the epsilon amino group of the lysine in position 1 of the sequence; the term "21K" means that it is attached to the epsilon amino group of the lysine in position 21 of the polypeptide sequence; the term "–1K" means that it is attached to the epsilon amino group of the lysine in position –1, i.e. adjacent position 1; the term "sequence modifications" means modifications with respect to human amylin.

BRIEF DESCRIPTION OF DRAWINGS

FIG. 1 presents a Table of a series of polypeptides according to the present invention.

DEFINITIONS

The term "human amylin" as used herein relates to the polypeptide human amylin having the sequence as depicted in SEQ ID No 1. The term includes, but is not limited to, a human polypeptide hormone of 37 amino acids referred to as amylin, which in nature is co-secreted with insulin from n-cells of the pancreas. Human amylin has the following primary amino acid sequence:
Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 1)

Figure 2:
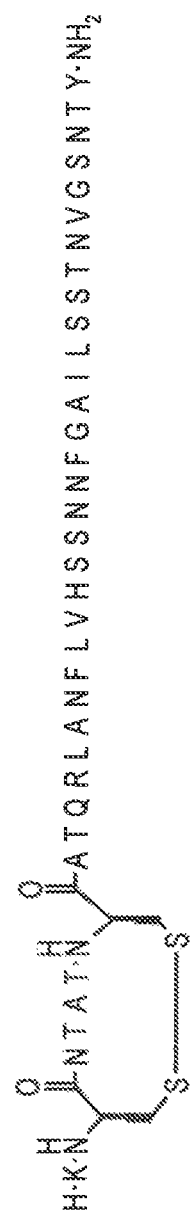
FIG. 2 presents a structure of human amylin.

Human amylin has a disulfide bridge between the two Cys residues and a C-terminal amide group. This structure is shown below and also in FIG. 2.

Herein, SEQ ID No: 1 and human amylin may be used interchangeably.

The term "amylin peptide", "amylin polypeptide" or "amylin protein" as used herein refers to a human amylin, an amylin analogue or and/or an amylin derivative. The terms "peptide", "polypeptide" or "protein" used herein are referring to amylin, unless different is indicated. The term "analogue of amylin" or "amylin analogue" as used herein refers to a variant of SEQ ID No: 1.

For instance, said variants include, but are not limited to, one or more substitution and/or one or more deletion and/or one or more addition of any one of the amino acid residues for any natural or unnatural amino acid, synthetic amino acids or peptidomimetics and/or the attachment of a substituent to any one of the natural or unnatural amino acids, synthetic amino acids or peptidomimetics at any available position. In case of an attachment of a substituent to any one of the natural or unnatural amino acids, synthetic amino acids or peptidomimetics at any available position in the amylin analogue or peptide as defined above, the resulting amylin polypeptide-may then also be referred to herein as "a amylin derivative", "a derivative according to the present invention", "derivative of amylin" or "derivative of a peptide".

The variant may have the same number of amino acid residues as human amylin (i.e. 37). Alternatively, the variant may comprise less amino acid residues than human amylin. Alternatively, the variant may comprise more amino acid residues than human amylin. In some embodiments, the variant has the same number of amino acid residues as human amylin (i.e. 37). In some embodiments, the variant includes substitutions of any one of the amino acid residues for any natural or unnatural amino acid, synthetic amino acids or peptidomimetics and/or the attachment of a substituent to any one of the natural or unnatural amino acids, synthetic amino acids or peptidomimetics at any available position.

If the analogue contains either more than 37 amino acid residues or less than 37 amino acid residues then the skilled person can still align that sequence with the sequence of human amylin (SEQ ID No. 1) to determine the placement number of the corresponding, respective amino acid residue. A suitable alignment program is "needle", which is a Needleman-Wunsch alignment. The alogorithm for this alignment program is described in Needleman, S. B. and Wunsch, C. D., (1970), Journal of Molecular Biology, 48: 443-453.

The polypeptide may comprise one or more amino acid substitutions. Hence, for some embodiments, the number of amino acid substitutions in the amylin analogue may be at least one. Preferably, the number of amino substitutions is between one and fifteen, more preferably between one and twelve, more preferably still between one and nine, more preferably still between one and five.

The polypeptide may comprise one or more substituents on one or more of the amino acid residues. The term "amylin derivative" as used herein refers to an amylin polypeptide (including human amylin and amylin analogues as defined above), comprising one or more substituents on one or more of the amino acid residues.

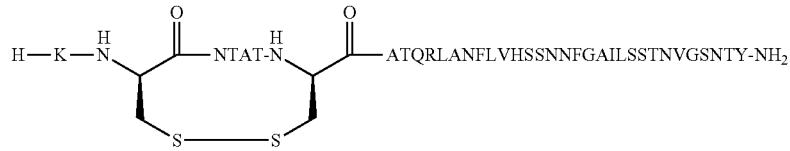

The term "substituent" as used herein means any suitable moiety bonded, in particular covalently bonded, to an amino acid residue, in particular to any available position on an amino acid residue. Typically, the suitable moiety is a chemical moiety.

For some embodiments, the substituent comprises a linker.

For some embodiments, the polypeptide has a substituent on one amino acid residue, which amino acid residue is either the amino acid residue in the N-terminal residue or the amino acid residue is a Lysine.

For some embodiments, the polypeptide has a substituent on the N-terminal amino acid residue bound via the α-amino group of the N-terminal amino acid residue.

For some embodiments, the N-terminal amino acid residue is Lysine and the polypeptide has a substituent on the N-terminal amino acid residue bound via the ε-amino group of the lysine amino residue.

For some embodiments, the polypeptide is extended by addition of a Lysine residue at the N-terminal and the polypeptide has a substituent on the N-terminal amino acid residue bound via the ε-amino group of the lysine amino residue.

For some embodiments, the polypeptide is extended by addition of an amino acid residue at the N-terminal and the polypeptide has a substituent on the N-terminal amino acid residue bound via the α-amino group of the N-terminal amino acid residue.

For some embodiments, substitution by acylation in the epsilon amino group of Lys1 versus the alpha amino group surprisingly leads to an improvement in selectivity, such as to levels of about 1.5 to 5 fold.

In the numbering sequence of SEQ ID No: 1, and according to established practice in the art, the amino acid residue at the N-terminal (Lys) is assigned no. 1 and subsequent amino acid residues are numbered consecutively, ending at the C-terminal with tyrosine assigned no. 37. Therefore, generally, any reference herein to position number of an amino acid residue provides its location in a 37 amino acid sequence; said 37 amino acid sequence being an analogue of human amylin. For example, a reference to an analogue modified at position 21 refers to an analogue wherein the 21$^{st}$ amino residue out of the 37 amino acids in the analogue has been modified.

In other words, the amino acid sequence numbering of the analogue provides the position of each analogue with respect to a 37 amino acid sequence, wherein the numbering is consecutive and ascending in the direction from the N-terminal to the C-terminal.

Analogues may be described by reference to the number of the amino acid residue in human amylin which is modified, i.e. by its position, and the nature of the modification. The following are non-limiting examples of appropriate analogue nomenclature.

For example:
Pro21 human amylin designates an analogue of human amylin wherein the modification from human amylin is the Asn at position 21 which has been substituted with Pro.
Pro21 human amylin designates an analogue of human amylin wherein the modification from human amylin is the Asn at position 21 of the human amylin sequence (SEQ ID NO 1) which has been substituted with Pro.
Pro21 Pro27 human amylin designates an analogue of human amylin wherein the modifications from human amylin are that the Asn at position 21 and the Leu at position 27 have both been substituted with Pro.
Pro21 Pro27 human amylin designates an analogue of human amylin wherein the modifications from human amylin are that the Asn at position 21 of the human amylin sequence (SEQ ID NO 1) and the Leu at position 27 have both been substituted with Pro.

As is apparent from the above examples, amino acid residues may be identified by their full name, their one-letter code, and/or their three-letter code. These three ways are fully equivalent.

The expressions "conforms to", "corresponds to", "a position equivalent to" or "corresponding position" may be used to characterise the site of modification in an analogue of human amylin by reference to SEQ ID No: 1. Equivalent or corresponding positions are easily deduced, e.g. by simple handwriting and eyeballing; and/or a standard protein or polypeptide alignment program may be used, such as "needle" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −10 and the penalties for additional residues in a gap at −0.5.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the polypeptides of the present invention are, preferably, amino acids which can be coded for by a nucleic acid.

As used herein, the term "hydrocarbyl" refers to a group comprising at least carbon and hydrogen that may optionally comprise one or more other suitable substituents. Examples of such substituents may include hydroxy, alkyl, halo, alkoxy, haloalkyl, haloalkoxy, amino, aminoalkyl or a cyclic group. In addition to the possibility of the substituents being a cyclic group, a combination of substituents may form a cyclic group. If the hydrocarbyl group comprises more than one carbon atom then those carbon atoms need not necessarily be linked to each other. For example, at least two of the carbon atoms may be linked via a suitable atom or group. Thus, the hydrocarbyl group may contain heteroatoms. Suitable heteroatoms will be apparent to those skilled in the art and include, for instance, sulphur, nitrogen, oxygen, phosphorus and silicon. In one embodiment the hydrocarbyl group is selected from the group consisting of an alkyl group, an alkenyl group, an alkynyl group, an aryl group, a heteroaryl group or a cycloalkyl group, each of which may be optionally substituted. Examples of such substituents may include hydroxy, alkyl, halo, alkoxy, haloalkyl, haloalkoxy, amino, aminoalkyl, or a cycloalkyl group.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-10}$ alkyl group, more preferably still a $C_{1-8}$ alkyl group, more preferably still a $C_{1-8}$ alkyl group. Particularly preferred alkyl groups include, for example, methyl, ethyl, n-propyl, iso-propyl, n-butyl, sec-butyl, iso-butyl, tert-butyl, n-pentyl, n-hexyl, n-heptyl and n-octyl. Suitable substituents include, for example, hydroxy, alkyl, halo, alkoxy, haloalkyl, haloalkoxy, amino, aminoalkyl, or a cycloalkyl group.

As used herein, the term "cycloalkyl" refers to a cyclic alkyl group which may be substituted (mono- or poly-) or unsubstituted. Suitable substituents include, for example, hydroxy, alkyl, halo, alkoxy, haloalkyl, haloalkoxy, amino, aminoalkyl, or a cycloalkyl group.

As used herein, the term "alkenyl" refers to a carbon chain containing one or more carbon-carbon double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably still a $C_{2-10}$ alkenyl group, more preferably still a $C_{2-8}$ alkenyl group, or more preferably still a $C_{2-6}$ alkenyl group. Suitable substituents include, for example, hydroxy, alkyl, halo, alkoxy, haloalkyl, haloalkoxy, amino, aminoalkyl, or a cycloalkyl group.

As used herein, the term "alkynyl" refers to a carbon chain containing one or more carbon-carbon triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, more preferably still a $C_{2-8}$ alkynyl group, or more preferably still a $C_{2-6}$ alkynyl group. Suitable substituents include, for example, hydroxy, alkyl, halo, alkoxy, haloalkyl, haloalkoxy, amino, aminoalkyl, or a cycloalkyl group.

As used herein, the term "aryl" refers to a $C_{6-10}$ aromatic group which may be substituted (mono- or poly-) or unsubstituted. Typical examples include phenyl and naphthyl etc. Suitable substituents include, for example, hydroxy, alkyl, halo, alkoxy, haloalkyl, haloalkoxy, amino, aminoalkyl, or a cycloalkyl group.

As used herein, the term "heteroaryl" refers to an aryl group as defined above which contains one or more heteroatoms. Suitable heteroatoms will be apparent to those skilled in the art and include, for example, sulphur, nitrogen, oxygen, phosphorus and silicon. Suitable substituents include, for example, hydroxy, alkyl, halo, alkoxy, haloalkyl, haloalkoxy, amino, aminoalkyl, or a cycloalkyl group.

The term "linker" as used herein includes suitable substituents that can join a moiety, such as a chemical moiety, to the polypeptide, such as the polypeptide backbone. Thus, the linker and the chemical moiety become a substituent together. The moiety joined to the linker may be any suitable moiety. Examples include an albumin binding moiety, —(CH$_2$)$_s$—COOH, where s is an integer from 12 to 20. Other examples include albumin binding moieties such as —(CH$_2$)$_n$—CH$_3$, where s is an integer from 12 to 20, sulfonic moieties such as —(CH$_2$)$_s$—SO$_3$H, where s is an integer from 12 to 20, and tetrazoles such as —(CH$_2$)$_s$—CN$_4$H where s is an integer from 12 to 20.

In one embodiment the moiety joined to the linker is an albumin binding moiety.

For example, the linker can comprise one or two amino acids which at one end bind to the moiety—such as an albumin binding moiety—and at the other end bind to any available position on the polypeptide backbone.

In some embodiments, the linker provides a bridge or link between an amino group on the polypeptide backbone and an acyl group on the moiety—such as an albumin binding moiety.

The linker may be bound to, or near to, the N terminal amino acid residue. Preferably the linker is bound to the amino acid in position 1 of the amylin analogue.

Another example of a linker is a combination of at least one amino acid and an amine.

In an embodiment, preferably the amine is the group OEG, wherein the formula of OEG is shown below:

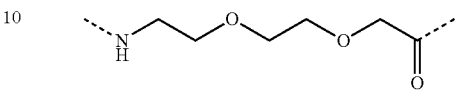

For some embodiments, preferably the linker is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser, -Gly-Ser-Ser, Ser-Ser, -Gly-Ser-Ser-γGlu, Ser-Ser-Gly-Ser-Ser-Gly and Ser-Ser-Gly-Ser-Ser-Gly-γGlu, γGlu-OEG, γGlu-2×OEG and OEG, preferably the linker is selected from γGlu, γGlu-γGlu, γGlu-OEG, γGlu-2×OEG and OEG, more preferably the linker is γGlu-γGlu.

The linker can contribute to and/or enhance the binding effect of the moiety (for example the albumin binding moiety), e.g. a linker comprising γGlu can enhance the albumin binding effect of the polypeptide.

Figure 3:
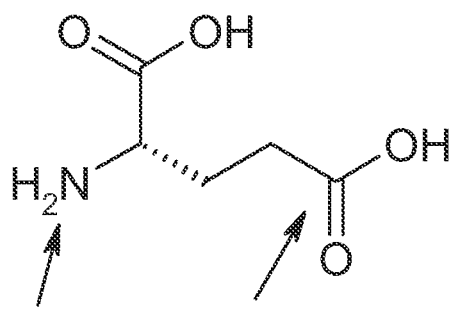
FIG. 3 presents a structure of gammaGlu.

By using the term "γGlu" or "gGlu" or "gammaGlu" or "gamma-L-Glu" is meant an amino acid with the following structure (also shown in FIG. 3):

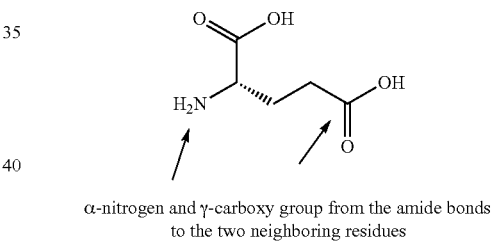

α-nitrogen and γ-carboxy group from the amide bonds to the two neighboring residues By using the term "γGlu-γGlu" is meant moiety with the following structure:

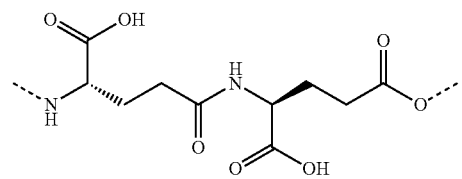

By using the term "γGlu-OEG" is meant a moiety with the following structure:

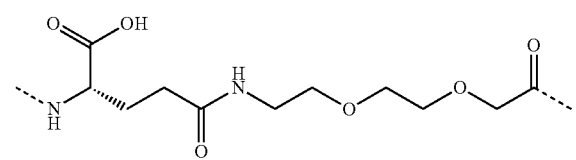

By using the term "γGlu-OEG-OEG" is meant moiety with the following structure:

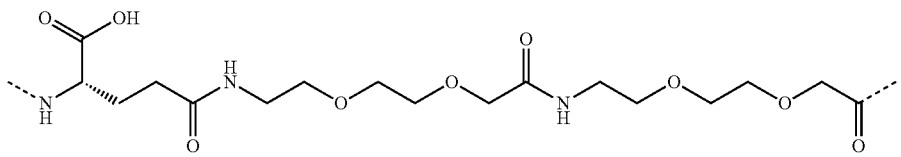

Figure 4:
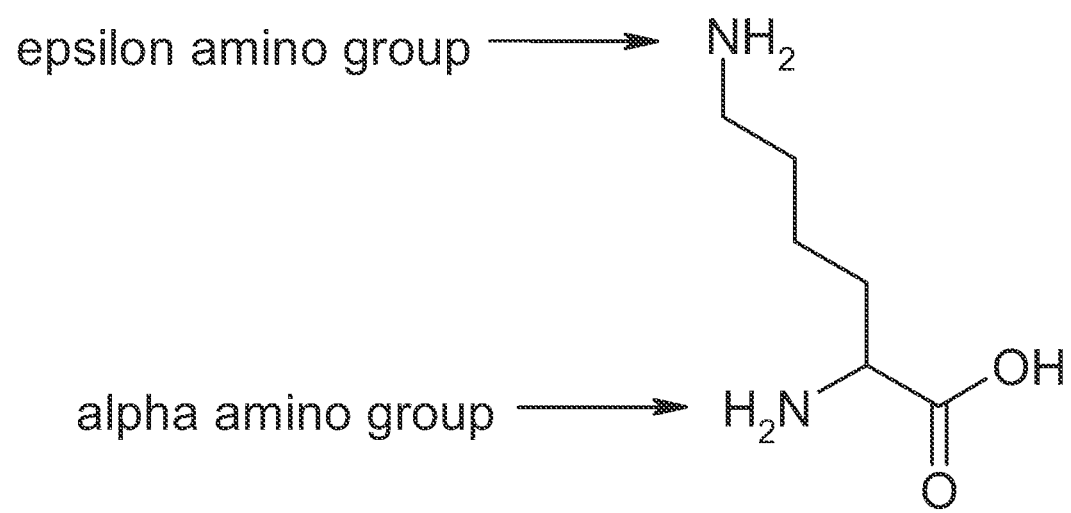
FIG. 4 presents a structure of epsilon amino group and alpha amino group.
Figure 5:
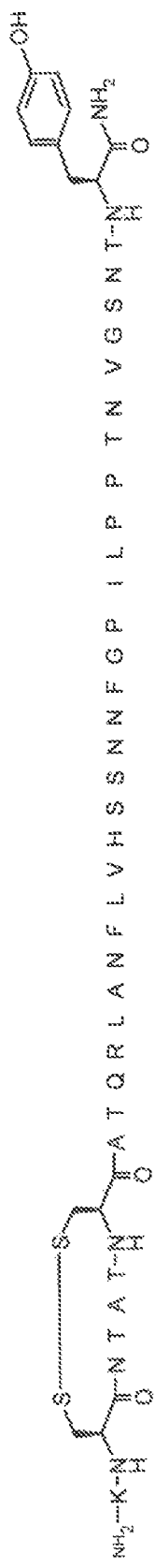
FIG. 5 presents a structure of pramlintide.
Figure 6:
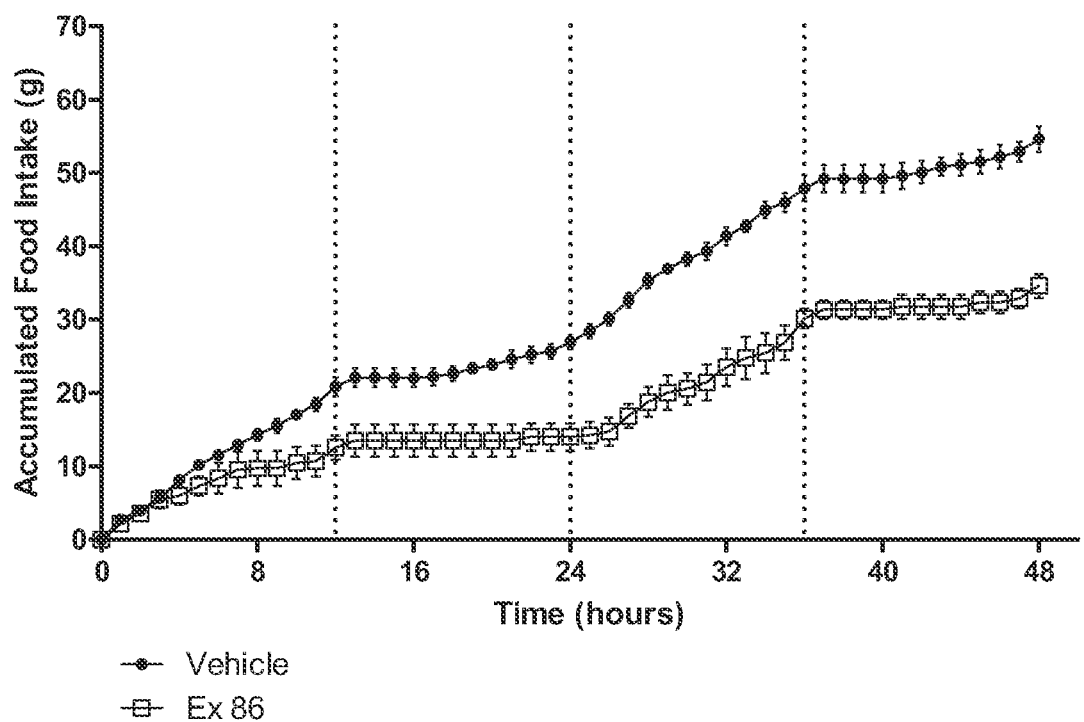
FIG. 6 Effect from single subcutaneous administration of example compound on plasma calcium in rats (ASSAY XI), food intake monitored over 48 hours after injecting vehicle or example 86 compound. The compound according to the present invention reduces food intake in rats, vehicle does not.
Figure 7:
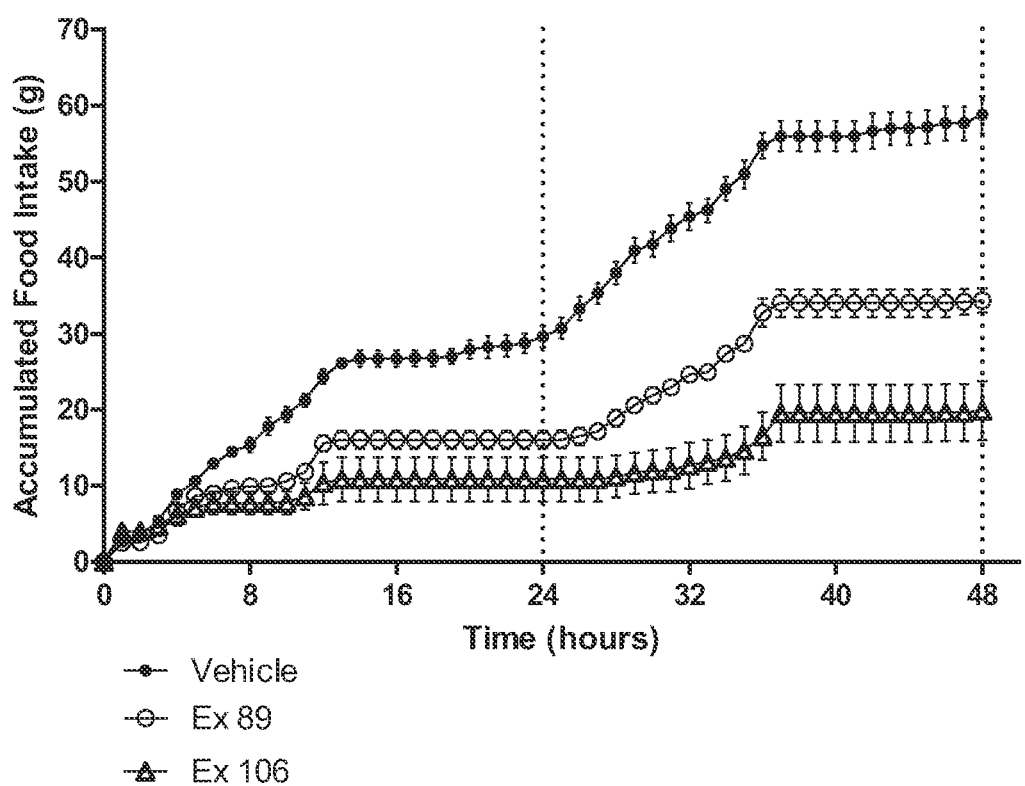
FIG. 7 Effect from single subcutaneous administration of example compound on plasma calcium in rats (ASSAY XI), food intake monitored over 48 hours after injecting vehicle or example 89 or example 106 compound. The compounds according to the present invention reduce food intake in rats, vehicle does not.
Figure 8:
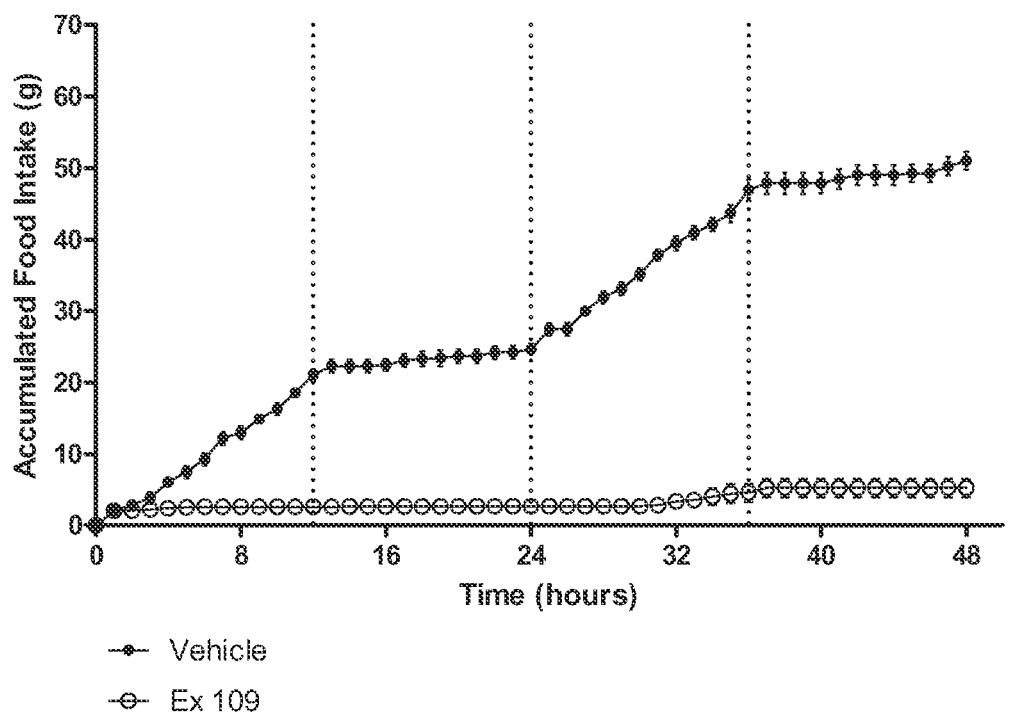
FIG. 8 Effect from single subcutaneous administration of example compound on plasma calcium in rats (ASSAY XI) on food intake in rats, food intake monitored over 48 hours after injecting vehicle or example 109. The compound according to the present invention reduces food intake in rats, vehicle does not.
Figure 9:
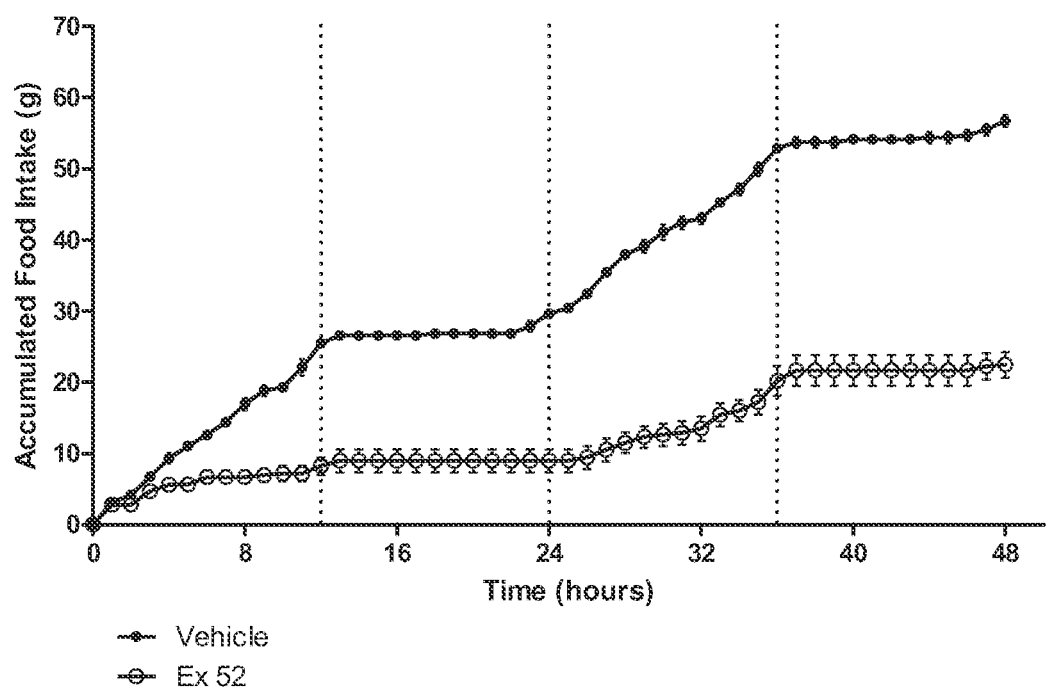
FIG. 9 Effect from single subcutaneous administration of example compound on plasma calcium in rats (ASSAY XI) on food intake in rats, food intake monitored over 48 hours after injecting vehicle or example 52. The compound according to the present invention reduces food intake in rats, vehicle does not.
Figure 10:
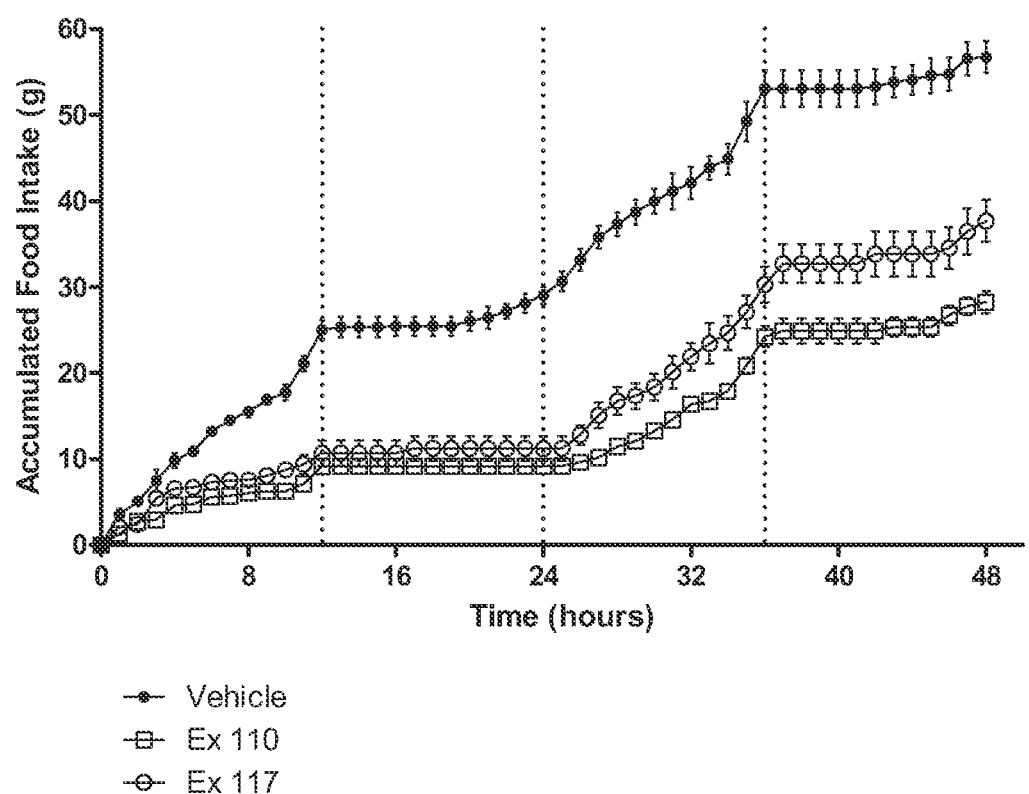
FIG. 10 Effect from single subcutaneous administration of example compound on plasma calcium in rats (ASSAY XI) on food intake in rats, food intake monitored over 48 hours after injecting vehicle or example 110 or example 117 compound. The compound according to the present invention reduces food intake in rats, vehicle does not.
Figure 11:
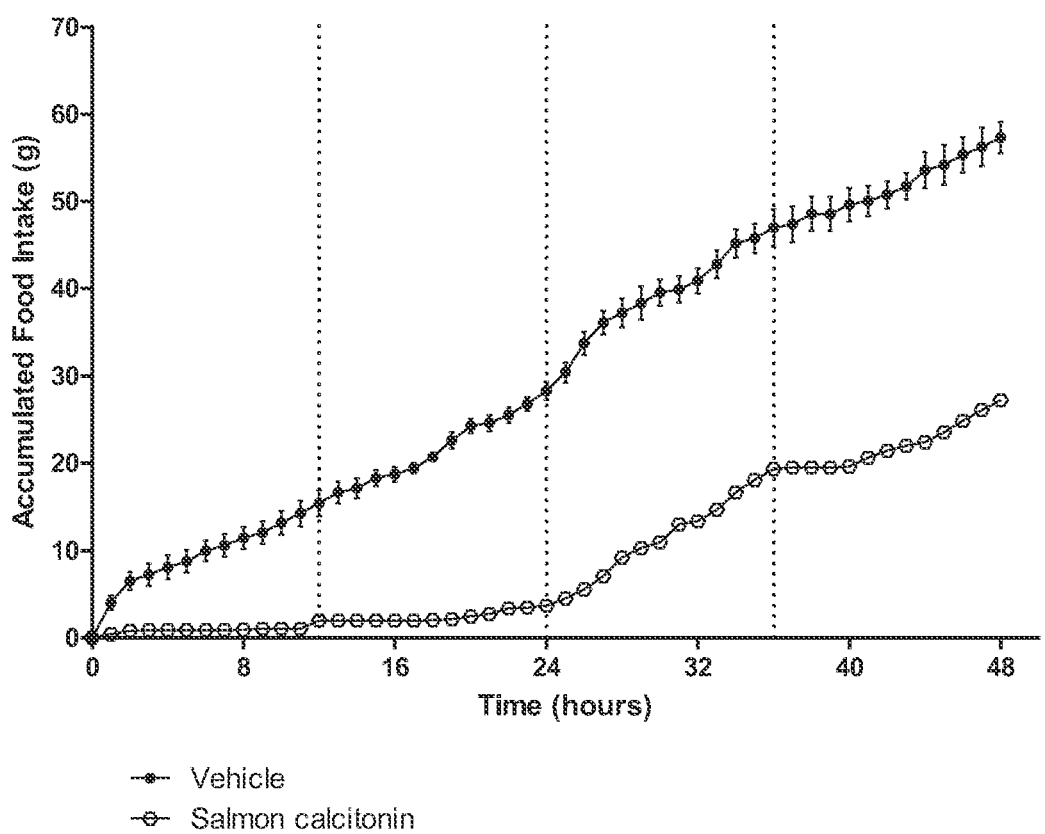
FIG. 11 Effect from single subcutaneous administration of example compound on plasma calcium in rats (ASSAY XI) on food intake in rats, food intake monitored over 48 hours after injecting vehicle or salmon calcitonin. Calcitonin reduces food intake in rats, vehicle does not.
Figure 12:
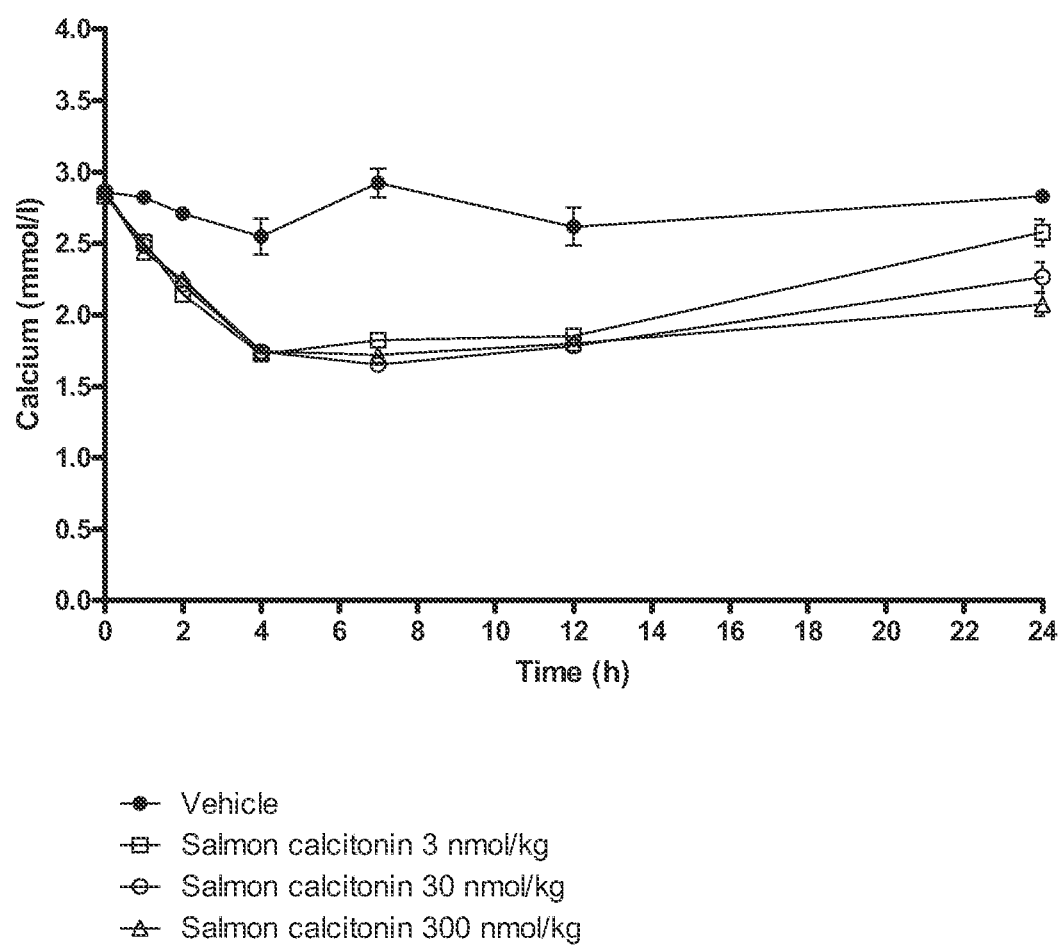
FIG. 12 Effect from single subcutaneous administration of example compound on plasma calcium in rats (ASSAY XII), calcium levels monitored over 24 hours after injecting vehicle or salmon calcitonin in 3 different doses. 3 nmol/kg calcitonin supresses calcium levels as effective as 30 nmol/kg and 300 nmol/kg calcitonin relative to vehicle calcium levels.
Figure 13:
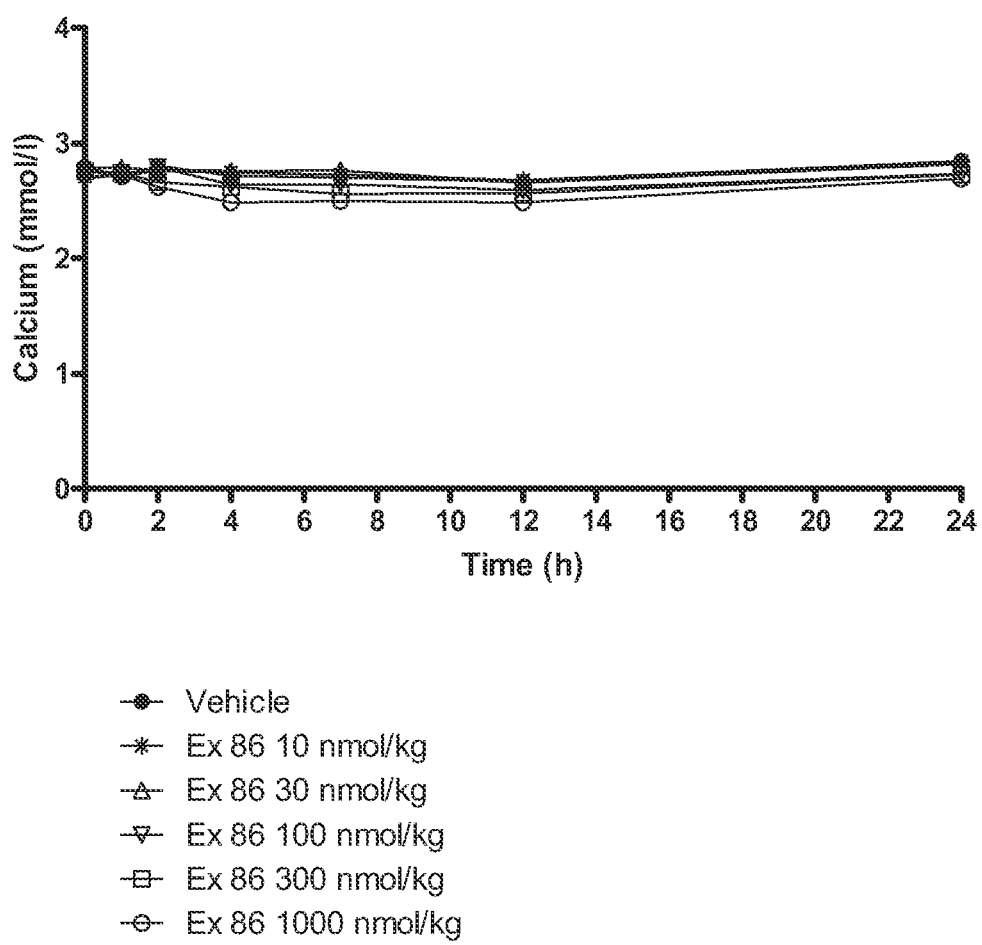
FIG. 13 Effect from single subcutaneous administration of example compound on plasma calcium in rats (ASSAY XII), calcium levels monitored over 24 hours after injecting vehicle or example 86 compound in increasing doses. None of the doses trigger a notable suppression of the calcium level relative to vehicle calcium levels.
Figure 14:
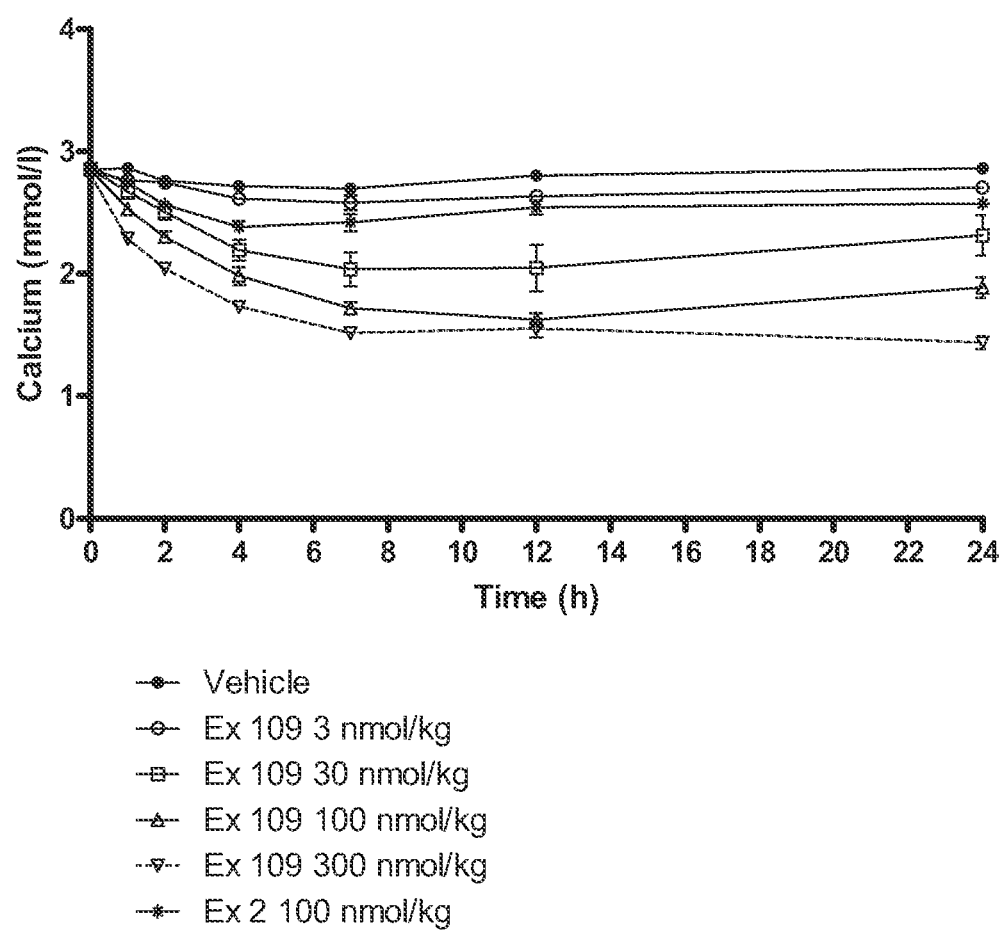
FIG. 14 Effect from single subcutaneous administration of example compound on plasma calcium in rats (ASSAY XII), calcium levels monitored over 24 hours after injecting vehicle or example 109 compound in increasing doses or 100 nmol/kg of example 2 compound. At 3 nmol/kg example 109 compound does not trigger a notable suppression of the calcium level relative to vehicle calcium levels. At 30 nmol/kg example 109 compound injection induces a minor suppression of the calcium level calcium level relative to vehicle calcium levels, however not as effective as calcitonin at the same concentration (see FIG. 7/11). At 100 and 300 nmol/kg example 109 compound induces a more pronounced suppression of the calcium level calcium level relative to vehicle calcium levels, which is comparable to the suppression of calcium levels seen by calcitonin at 3 nmol/kg. 100 nmol/kg of example 2 compound does not trigger a notable suppression of the calcium level relative to vehicle calcium levels not trigger a notable suppression of the calcium level relative to vehicle calcium levels.
Figure 15:
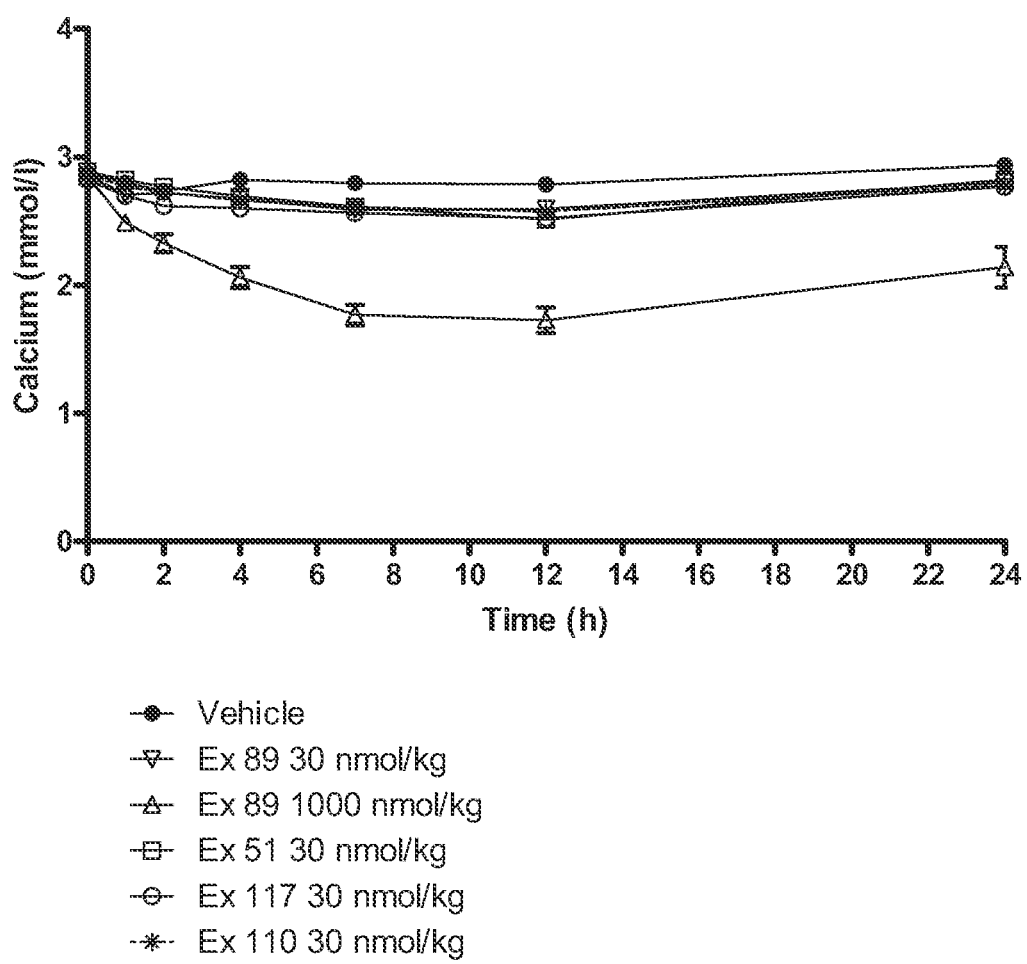
FIG. 15 Effect from single subcutaneous administration of example compound on plasma calcium in rats (ASSAY XII), calcium levels monitored over 24 hours after injecting vehicle or 30 nmol/kg example 51, 89, 110 or 117 compound or 1000 nmol/kg example 89 compound. None of the example compounds at 30 nmol/kg trigger a notable suppression of the calcium level relative to vehicle calcium levels 1000 nmol/kg example 89 compound induces a more pronounced suppression of the calcium level calcium level relative to vehicle calcium levels, which is comparable to the suppression of calcium levels seen by calcitonin at 3 nmol/kg.
Figure 16:
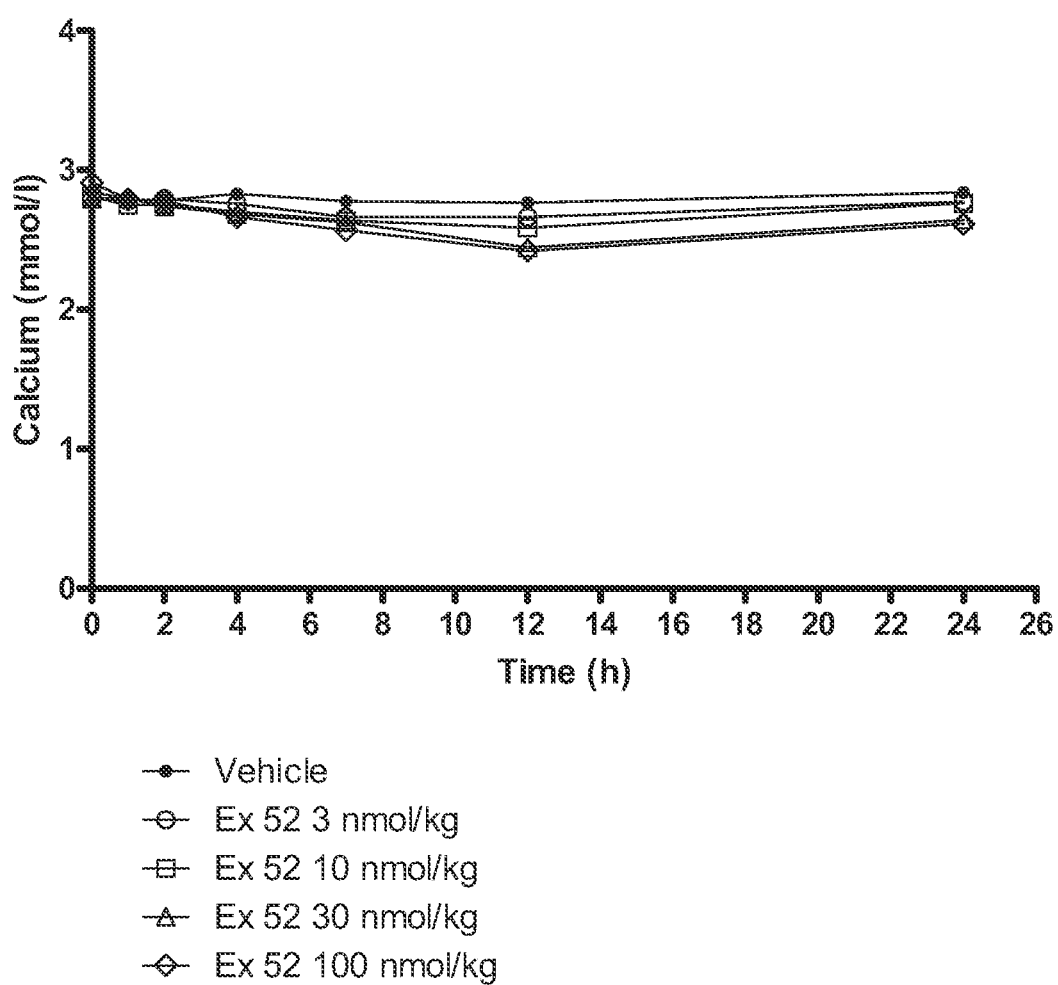
FIG. 16 Effect from single subcutaneous administration of example compound on plasma calcium in rats (ASSAY XII), calcium levels monitored over 24 hours after injecting vehicle or example 52 compounds in increasing doses. None of the doses trigger a notable suppression of the calcium level relative to vehicle calcium levels.

The term "epilson amino group" or "E-amino group", used herein in relation to lysine, refers to the amino group at the 6 position, using the IUPAC standard numbering conventions. The term "alpha amino group" or "α-amino group" refers to the amino group at the 2 position, using the IUPAC standard numbering conventions. We refer to the following structure (also shown in FIG. 4).

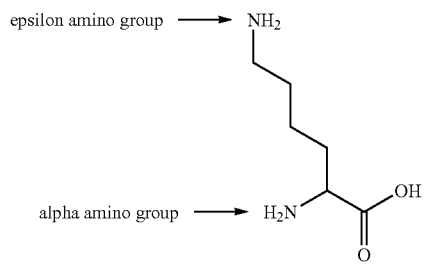

The term "albumin binding moiety" as used herein refers to any chemical group capable of binding to albumin, i.e. has albumin binding affinity. In one embodiment the albumin binding moiety is an acyl group.

In some embodiments, preferably the albumin binding moiety is an acyl group selected from:

(a) $CH_3(CH_2)_rCO$—, wherein r is an integer from 12 to 20;
(b) $HOOC(CH_2)_sCO$—, wherein s is an integer from 12 to 22.

"Albumin binding affinity" may be determined by several methods known within the art. In one method the compound to be measured is radiolabeled with e.g. $^{125}I$ or $^3H$ and incubated with immobilized albumin (Kurtzhals et. al., Biochem. J., 312, 725-731 (1995)). The binding of the compound relative to a standard is calculated. In another method a related compound is radiolabeled and its binding to albumin immobilized on e.g. SPA beads is competed by a dilution series of the compound to be measured. The $EC_{50}$ value for the competition is a measure of the affinity of the compound. In a third method, the receptor affinity or potency of a compound is measured at different concentrations of albumin, and the shift in relative affinity or potency of the compound as a function of albumin concentration reflects its affinity for albumin.

The polypeptides of the present invention exhibit good potency. The term "potency" is used to describe the effect of a given compound in assays where a sigmoidal relationship between log concentration and the effect of a compound has been established. Furthermore, the response should be variable from 0 to 100%. EC (effective concentration)$_{50}$ can be used to describe the concentration of a given compound yielding a response of 50% in the assay, such as in the functional assay.

The polypeptides of the present invention exhibit good activity. The term "activity" refers to the ability to reduce appetite and/or increase satiety. The activity can be measured by the ability to reduce appetite as e.g. described in the Assay (I) herein.

The polypeptides of the present invention exhibit good physical stability. The term "physical stability" of a polypeptide according to the invention, or a formulation thereof refers to the tendency of the polypeptide not to form biologically inactive and/or insoluble aggregates as a result of exposure to thermo-mechanical stresses and/or interaction with interfaces and surfaces that are destabilizing, such as hydrophobic surfaces and interfaces. Physical stability of the aqueous polypeptide formulations may be evaluated by means of visual inspection, ThT fibrillation assay (sometimes referred to as a ThT fibrillogenesis assay) and/or turbidity measurements as described elsewhere herein. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person.

The polypeptides of the present invention exhibit good chemical stability. The term "chemical stability" of a polypeptide according to the invention or of a formulation thereof refers to no chemical covalent changes in the polypeptide structure hence avoiding the formation of chemical degradation products with potentially less potency and/or potentially increased immunogenic properties compared to the parent (native) polypeptide structure. Various chemical degradation products can be formed depending on the type and nature of the parent polypeptide and the environment to which the polypeptide is exposed. Elimination of chemical degradation can most probably not be completely avoided and increasing amounts of chemical degradation products is often seen during storage and use of the polypeptide formulations as well-known by the person skilled in the art. Most polypeptides are prone to deamidation, a process in which the side chain amide group in glutaminyl or asparaginyl residues is hydrolysed to form a free carboxylic acid. Other degradations pathways involves formation of high molecular weight transformation products where two or more polypeptide molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the polypeptide formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

The term "stabilized formulation" refers to a formulation with increased physical stability, increased chemical stability or increased physical and chemical stability compared to an aqueous solution of the polypeptide.

DESCRIPTION OF THE INVENTION

General Embodiments

In one embodiment, the present invention relates to a polypeptide comprising an amino acid sequence which is an analogue of SEQ ID No: 1 wherein:
(a) said analogue comprises a proline residue at position 21;
wherein the amino acid sequence numbering of the analogue corresponds to the amino acid numbering sequence of SEQ ID No: 1;
optionally wherein (b) the polypeptide has an $IC_{50}$ in a human amylin receptor binding assay of about 1200 pM or less;
optionally wherein the polypeptide has at least one substituent attached to at least one of its amino acid residues.

In one specific embodiment, the present invention relates to a polypeptide comprising an amino acid sequence which is an analogue of SEQ ID No: 1 wherein:
(a) said analogue comprises a proline residue at position 21; and
(b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide comprising an amino acid sequence which is an analogue of SEQ ID No: 1 wherein:
(a) said analogue comprises a proline residue at position 21; and
(b) said analogue comprises a proline residue at position 27; and
(c) optionally wherein said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide comprising an amino acid sequence which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) optionally wherein said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide comprising an amino acid sequence which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) said analogue comprises an aspartic acid residue at position 14; and
(e) optionally wherein said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide comprising an amino acid sequence which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) said analogue comprises an aspartic acid residue at position 14; and
(e) said analogue comprises an arginine residue at position 35; and
(f) optionally wherein said polypeptide has an $IC_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide comprising an amino acid sequence which is an analogue of SEQ ID No: 1 of formula (I):

(I)
$Xaa_1$-Cys-Asn-Thr-Ala-Thr-Cys-Ala-Thr-Gln-Arg-Leu-

Ala-$Xaa_{14}$-Phe-Leu-$Xaa_{17}$-His-Ser-Ser-$Xaa_{21}$-Asn-Phe-

Gly-$Xaa_{25}$-$Xaa_{26}$-$Xaa_{27}$-$Xaa_{28}$-$Xaa_{29}$-Thr-$Xaa_{31}$-Val-Gly- $Xaa_{34}$-$Xaa_{35}$-Thr-$Xaa_{37}$;

wherein
$Xaa_1$ is independently selected from Ala, Cys, Glu, Gly, His, Arg, Ser and Lys;
$Xaa_{14}$ is independently selected from Asp, Glu, His, Asn, Arg, Gly, Ala, Ser, Lys, Thr and Cys;
$Xaa_{17}$ is independently selected from Arg and Val;
$Xaa_{21}$ is Pro;
$Xaa_{25}$ is independently selected from Pro and Ala;
$Xaa_{26}$ is independently selected from Pro and Ile;
$Xaa_{27}$ is independently selected from Pro and Leu;
$Xaa_{28}$ is independently selected from Pro and Ser;
$Xaa_{29}$ is independently selected from Pro and Ser;
$Xaa_{31}$ is independently selected from Pro and Asn;
$Xaa_{34}$ is independently selected from Pro, His, Lys, Arg and Ser Xaa$_{35}$ is independently selected from Asp, Arg, Glu, Lys, His and Asn;
Xaa$_{37}$ is independently selected from Pro and Tyr;
and where the C-terminal may optionally be derivatized;
and wherein said polypeptide has an IC$_{50}$ in a human amylin receptor binding assay of about 1200 pM or less.

In one embodiment, the present invention relates to a polypeptide which is an analogue of SEQ ID No: 1 wherein:
(a) said analogue comprises a proline residue at position 21;
wherein the amino acid sequence numbering of the analogue corresponds to the amino acid numbering sequence of SEQ ID No: 1;
optionally wherein (b) the polypeptide has an IC$_{50}$ in a human amylin receptor binding assay of about 1200 pM or less;
optionally wherein the polypeptide has at least one substituent attached to at least one of its amino acid residues.

In one specific embodiment, the present invention relates to a polypeptide which is an analogue of SEQ ID No: 1 wherein:
(a) said analogue comprises a proline residue at position 21; and
(b) said polypeptide has an IC$_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide which is an analogue of SEQ ID No: 1 wherein:
(a) said analogue comprises a proline residue at position 21; and
(b) said analogue comprises a proline residue at position 27; and
(c) optionally wherein said polypeptide has an IC$_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) optionally wherein said polypeptide has an IC$_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) said analogue comprises an aspartic acid residue at position 14; and
(e) optionally wherein said polypeptide has an IC$_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide which is an analogue of SEQ ID No: 1 wherein:
(a) said analogue comprises a proline residue at position 21; and
(b) said analogue comprises a proline residue at position 27; and
(c) said analogue comprises an arginine residue at position 17; and
(d) said analogue comprises an aspartic acid residue at position 14; and
(e) said analogue comprises an arginine residue at position 35; and
(f) optionally wherein said polypeptide has an IC$_{50}$ in a human amylin receptor binding assay of about 1200 pM or less;
wherein the amino acid sequence numbering of the analogue corresponds to the amino acid numbering sequence of SEQ ID No: 1.

In another embodiment, the present invention relates to a polypeptide which is an analogue of SEQ ID No: 1 of formula (I):

(I)
Xaa$_1$-Cys-Asn-Thr-Ala-Thr-Cys-Ala-Thr-Gln-Arg-Leu-

Ala-Xaa$_{14}$-Phe-Leu-Xaa$_{17}$-His-Ser-Ser-Xaa$_{21}$-Asn-Phe-

Gly-Xaa$_{25}$-Xaa$_{26}$-Xaa$_{27}$-Xaa$_{28}$-Xaa$_{29}$-Thr-Xaa$_{31}$-Val-Gly-

Xaa$_{34}$-Xaa$_{35}$-Thr-Xaa$_{37}$;

wherein
Xaa$_1$ is independently selected from Ala, Cys, Glu, Gly, His, Arg, Ser and Lys;
Xaa$_{14}$ is independently selected from Asp, Glu, His, Asn, Arg, Gly, Ala, Ser, Lys, Thr and Cys;
Xaa$_{17}$ is independently selected from Arg and Val;
Xaa$_{21}$ is Pro;
Xaa$_{25}$ is independently selected from Pro and Ala;
Xaa$_{26}$ is independently selected from Pro and Ile;
Xaa$_{27}$ is independently selected from Pro and Leu;
Xaa$_{28}$ is independently selected from Pro and Ser;
Xaa$_{29}$ is independently selected from Pro and Ser;
Xaa$_{31}$ is independently selected from Pro and Asn;
Xaa$_{34}$ is independently selected from Pro, His, Lys, Arg and Ser
Xaa$_{35}$ is independently selected from Asp, Arg, Glu, Lys, His and Asn;
Xaa$_{37}$ is independently selected from Pro and Tyr;
and where the C-terminal may optionally be derivatized;
and wherein said polypeptide has an IC$_{50}$ in a human amylin receptor binding assay of about 1200 pM or less.

Some Advantages

The polypeptides of the present invention exhibit improved physical stability.

The polypeptides of the present invention possess improved selectivity for amylin receptors over calcitonin receptors.

The polypeptides of the present invention possess improved selectivity for human amylin receptors over human calcitonin receptors.

Some Preferred Embodiments

A suitable human amylin receptor binding assay to determine the IC$_{50}$ is presented herein.

In one preferred embodiment, Xaa₂₁ is Pro. In one preferred embodiment, Xaa₂₁ is Pro and Xaa₂₇ is Pro. In one preferred embodiment Xaa₂₁ is Pro, Xaa₂₇ is Pro and Xaa₁₇ is Arg. In one preferred embodiment Xaa₂₁ is Pro, Xaa₂₇ is Pro, Xaa₁₇ is Arg and Xaa₁₄ is Asp. In one preferred embodiment Xaa₂₇ is Pro, Xaa₁₇ is Arg, Xaa₁₄ is Asp and Xaa₃₅ is Arg. In one preferred embodiment Xaa₂₁ is Pro, Xaa₂₇ is Pro, Xaa₁₇ is Arg, Xaa₁₄ is Asp and Xaa₃₅ is Arg. In one preferred embodiment Xaa₂₁ is Pro, Xaa₂₇ is Pro, Xaa₁₇ is Arg, and Xaa₃₄ is His. In one preferred embodiment Xaa₂₁ is Pro, Xaa₂₇ is Pro, Xaa₁₇ is Arg, Xaa₁₄ is Glu and Xaa₃₅ is Arg. In one preferred embodiment Xaa₂₁ is Pro, Xaa₂₇ is Pro, Xaa₁₇ is Arg, Xaa₁₄ is Glu, Xaa₃₄ is Pro and Xaa₃₅ is Glu. In one preferred embodiment Xaa₂₁ is Pro, Xaa₂₇ is Pro, Xaa₁₇ is Arg, Xaa₁₄ is Glu, Xaa₃₄ is Pro and Xaa₃₅ is His. In one preferred embodiment, Xaa₂₁ in a polypeptide according to this invention and formula (I) is Pro.

In one preferred embodiment, Xaa₂₁ in a polypeptide according to this invention and formula (I) is Pro and Xaa₂₇ in a polypeptide according to this invention and formula (I) is Pro. In one preferred embodiment Xaa₂₁ in a polypeptide according to this invention and formula (I) is Pro, Xaa₂₇ in a polypeptide according to this invention and formula (I) is Pro and Xaa₁₇ in a polypeptide according to this invention and formula (I) is Arg. In one preferred embodiment Xaa₂₁ in a polypeptide according to this invention and formula (I) is Pro, Xaa₂₇ in a polypeptide according to this invention and formula (I) is Pro, Xaa₁₇ in a polypeptide according to this invention and formula (I) is Arg and Xaa₁₄ in a polypeptide according to this invention and formula (I) is Asp. In one preferred embodiment Xaa₂₇ in a polypeptide according to this invention and formula (I) is Pro, Xaa₁₇ in a polypeptide according to this invention and formula (I) is Arg, Xaa₁₄ in a polypeptide according to this invention and formula (I) is Asp and Xaa₃₅ in a polypeptide according to this invention and formula (I) is Arg. In one preferred embodiment Xaa₂₁ in a polypeptide according to this invention and formula (I) is Pro, Xaa₂₇ in a polypeptide according to this invention and formula (I) is Pro, Xaa₁₇ is in a polypeptide according to this invention and formula (I) Arg, Xaa₁₄ in a polypeptide according to this invention and formula (I) is Asp and Xaa₃₅ in a polypeptide according to this invention and formula (I) is Arg. In one preferred embodiment Xaa₂₁ in a polypeptide according to this invention and formula (I) is Pro, Xaa₂₇ in a polypeptide according to this invention and formula (I) is Pro, Xaa₁₇ in a polypeptide according to this invention and formula (I) is Arg, and Xaa₃₄ in a polypeptide according to this invention and formula (I) is His. In one preferred embodiment Xaa₂₁ in a polypeptide according to this invention and formula (I) is Pro, Xaa₂₇ in a polypeptide according to this invention and formula (I) is Pro, Xaa₁₇ in a polypeptide according to this invention and formula (I) is Arg, Xaa₁₄ in a polypeptide according to this invention and formula (I) is Glu and Xaa₃₅ in a polypeptide according to this invention and formula (I) is Arg. In one preferred embodiment Xaa₂₁ is Pro, Xaa₂₇ in a polypeptide according to this invention and formula (I) is Pro, Xaa₁₇ in a polypeptide according to this invention and formula (I) is Arg, Xaa₁₄ in a polypeptide according to this invention and formula (I) is Glu, Xaa₃₄ in a polypeptide according to this invention and formula (I) is Pro and Xaa₃₅ in a polypeptide according to this invention and formula (I) is Glu. In one preferred embodiment Xaa₂₁ in a polypeptide according to this invention and formula (I) is Pro, Xaa₂₇ in a polypeptide according to this invention and formula (I) is Pro, Xaa₁₇ in a polypeptide according to this invention and formula (I) is Arg, Xaa₁₄ in a polypeptide according to this invention and formula (I) is Glu, Xaa₃₄ in a polypeptide according to this invention and formula (I) is Pro and Xaa₃₅ in a polypeptide according to this invention and formula (I) is His. In one embodiment the C-terminal may be derivatized. In one embodiment the C-terminal of an amylin peptide according to the present invention may be derivatized. The term "derivatized" as used herein means, that a substituent is attached to an amino acid in said human amylin, amylin analogue or amylin peptide as previously defined. Thus, when the C-terminal of an amylin peptide is derivatized, it is meant that a substituent is attached to this amylin peptides C-terminus.

In one embodiment the C-terminal is derivatized with an amide of formula (II):

$$C(O)NR^1R^2 \qquad (II)$$

wherein $R^1$ and $R^2$ are independently selected from H and alkyl. Preferably $R^1$ and $R^2$ are both H.

In one embodiment, polypeptides of the present invention may have a substituent attached to any available position on one or more of the amino acid residues. Examples of substituents include chemical moieties directly bound to one or more of the amino acid residues, or chemical moieties indirectly bound to one or more of the amino acid residues by means of a linker. Available points of attachment will be known to the skilled person. Examples of available attachment points include the N-terminal of the polypeptide, the C-terminal of the polypeptide, an epsilon-amino group of a Lysine residue, the hydroxyl group of a serine, tyrosine or threonine residue, the amide group of an asparagine or glutamine residue, the carboxyl group of an aspartic acid or glutamic acid residue, the thiol group of a cysteine residue. Preferably, the substituent is attached to the N-terminal of the polypeptide, or the epsilon amino group of a lysine residue.

The term "acylation" or "acylated" when used herein refers to a substituent which is attached by the formation of an amide bond between an amino group on the peptide/analogue and a carboxylic acid on the substituent.

For some embodiments, we have found that acylation in the epsilon amino group of Lys1 versus the alpha amino group surprisingly leads to an improvement in selectivity of about 1.5 to 5 fold. To illustrate this, pairs of analogues with identical polypeptide sequences but different acylation position can be compared. For example, we refer to any of: compound 18 vs compound 128, compound 16 vs compound 51, compound 8 vs compound 12, compound 21 vs compound 48, compound 39 vs compound 79, compound 71 vs compound 76.

In another embodiment the substitutent is attached to the N-terminal amino group of the polypeptide wherein the N-terminal amino acid residue corresponds to position 1 of the analogue of SEQ ID No: 1.

In another embodiment the substitutent is attached to the epilson amino group of a lysine residue in position 1 of analogue of SEQ ID No: 1.

In one embodiment, the substituent is selected from a hydrocarbyl substituent group, a hydroxyl group and a halogen atom. Examples of suitable halogen atoms include F, Cl, Br and I. Preferably, the substituent is a hydrocarbyl substituent group.

In another embodiment, the hydrocarbyl substituent group is an alkyl group, or a group of formula (III):

$$L_n\text{-}Y \qquad (III)$$

wherein
L is a linker;
n=0 or 1

Y is a chemical moiety—such as an albumin binding moiety.

In one embodiment the linker comprises 1 to 10 amino acids. The linker can further comprise amines.

Examples of suitable amines include:

C(O)—(CH$_2$)$_l$—O—[CH$_2$CH$_2$—O]$_m$—(CH$_2$)$_p$[NHC(O)—(CH$_2$)$_l$—O—[(CH$_2$)$_n$—O]$_m$—(CH$_2$)$_p$]$_q$—NH— wherein l, m, n, and p independently are 1-7, and q is 0-5.

For example the linker can comprise an amine selected from:

—C(O)—CH$_2$—O—CH$_2$—CH$_2$—O—CH$_2$—CH$_2$—NH—; and

—C(O)—CH$_2$—O—CH$_2$—CH$_2$—O—CH$_2$—CH$_2$—[NHC(O)—CH$_2$—O—CH$_2$—CH$_2$—O—CH$_2$—CH$_2$]$_1$—NH—; and

—C(O)—(CH$_2$)$_2$—O—[CH$_2$CH$_2$—O]$_7$—(CH$_2$)$_2$—NH—.

In another embodiment the linker is a combination of amino acid residues and the above mentioned amines, for example:

γGlu-C(O)—CH$_2$—O—CH$_2$—CH$_2$—O—CH$_2$—CH$_2$—[NHC(O)—CH$_2$—O—CH$_2$—CH$_2$—O—CH$_2$—CH$_2$—]$_1$—NH—; or

Arg-Arg-γGlu-C(O)—CH$_2$—O—CH$_2$—CH$_2$—O—CH$_2$—CH$_2$—[NHC(O)—CH$_2$—O—CH$_2$—CH$_2$—O—CH$_2$—CH$_2$—]$_1$—NH—.

In some embodiments, n=1 and L is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser, -Gly-Ser-Ser, Ser-Ser, -Gly-Ser-Ser-γGlu, Ser-Ser-Gly-Ser-Ser-Gly and Ser-Ser-Gly-Ser-Ser-Gly-γGlu, γGlu-OEG, γGlu-OEG-OEG and OEG.

In some embodiments, n=1 and L is selected from γGlu, γGlu-γGlu, γGlu-OEG, γGlu-OEG-OEG and OEG, more preferably the linker is γGlu-γGlu.

In another embodiment n=0; accordingly there is no linker between the amino acid residues of the polypeptide backbone and chemical moiety, Y i.e. Y is attached to an available position on the polypeptide backbone.

In one embodiment Y is an albumin binding moiety.

In one embodiment the albumin binding moiety is an acyl group.

Preferably the albumin binding moiety is HOOC(CH$_2$)$_s$CO—, wherein s is an integer from 12 to 22. More preferably s is an integer from 12 to 18. More preferably s is 16 to 18. More preferably s is 18.

In another embodiment the substituent group and/or group of formula (III) is selected from the following groups presented in Table 1.

TABLE 1

| Abbreviation | Substituent |
|---|---|
| C20diacid | (structure shown) |
| C20diacid-γGlu | (structure shown) |
| C20diacid-γGlu-γGlu | (structure shown) |
| | (structure shown) |
| C20diacid-γGlu-γGlu-γGlu | (structure shown) |

TABLE 1-continued

| Abbreviation | Substituent |
|---|---|
| C20diacid-OEG | (structure) |
| C20diacid-γGlu-OEG | (structure) |
| C20diacid-γGlu-OEG-OEG | (structure) |
| C18diacid-γGlu | (structure) |
| C16diacid-γGlu | (structure) |
| C14Diacid-γGlu | (structure) |

For embodiments that comprise an albumin binding moiety, the polypeptides of the present invention can exhibit a protracted pharmacokinetic profile and good pharmacodynamic properties. Therefore the polypeptides according to the present invention do not have to be injected as often as known amylin products.

Further the polypeptides of the invention give a reduction in food intake. The reduction in food intake is superior over the known amylin product (Pramlintide). Pram lintide reduces food intake by 25% after single subcutaneous 1000 nmol/kg injection in rats. In comparison the polypeptides according to the present invention trigger equivalent reductions in food intake in rats when administered in single subcutaneous doses considerable lower doses, which is demonstrated by data anf figures throughout this patent application.

In one embodiment the albumin binding moiety binds non-covalently to albumin. Preferably the albumin binding moiety has an albumin binding affinity towards human serum albumin that is below about 10 μM or below about 1 μM. In one embodiment the albumin binding moiety binds non-covalently to albumin. Preferably the albumin binding moiety has an albumin binding affinity towards human serum albumin that is below about 10 μM. In one embodiment the albumin binding moiety binds non-covalently to albumin. Preferably the albumin binding moiety has an albumin binding affinity towards human serum albumin that is below about 1 μM. In one embodiment the albumin binding moiety binds non-covalently to albumin. Preferably the albumin binding moiety has an albumin binding affinity towards human serum albumin that is below about 10 μM to below about 1 μM.

In one embodiment, the present invention concerns a polypeptide comprising an amino acid sequence which is an analogue of SEQ ID No: 1 wherein said analogue comprises a proline residue at position 21; wherein the amino acid sequence numbering of the analogue corresponds to the amino acid numbering sequence of SEQ ID No: 1.

In one embodiment, the present invention concerns a which is an analogue of SEQ ID No: 1 wherein said analogue comprises a proline residue at position 21; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 21 and which optionally further comprises substitutions or deletions relative to SEQ ID No: 1; wherein the amino acid sequence numbering of the analogue corresponds to the amino acid numbering sequence of SEQ ID No: 1.

In one embodiment, the present invention concerns a polypeptide comprising an amino acid sequence which is an analogue of SEQ ID No: 1 wherein said analogue comprises a proline residue at position 27; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 27; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 27 and which optionally further comprises substitutions or deletions relative to SEQ ID No: 1; wherein the amino acid sequence numbering of the analogue corresponds to the amino acid numbering sequence of SEQ ID No: 1.

In one embodiment, the present invention concerns a polypeptide comprising an amino acid sequence which is an analogue of SEQ ID No: 1 wherein said analogue comprises a proline residue at position 21 and a proline residue at position 27; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 21 and a proline residue at position 27; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 21 and a proline residue at position 27 and which optionally further comprises substitutions or deletions relative to SEQ ID No: 1; wherein the amino acid sequence numbering of the analogue corresponds to the amino acid numbering sequence of SEQ ID No: 1.

In one embodiment, the present invention concerns a polypeptide comprising an amino acid sequence which is an analogue of SEQ ID No: 1 wherein said analogue comprises a proline residue at position 21 and a proline residue at position 27 and an asparagine residue at position 14; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 21 and a proline residue at position 27 and an asparagine residue at position 14; wherein the amino acid sequence numbering of the analogue corresponds to the amino acid numbering sequence of SEQ ID No: 1. In one embodiment, the present invention concerns a which is an analogue of SEQ ID No: 1 wherein said analogue comprises a proline residue at position 21 and a proline residue at position 27 and an asparagine residue at position 14 and which optionally further comprises substitutions or deletions relative to SEQ ID No: 1; wherein the amino acid sequence numbering of the analogue corresponds to the amino acid numbering sequence of SEQ ID No: 1.

In one embodiment the polypeptide of the present invention comprises an analogue of SEQ ID NO: 1, wherein said polypeptide has an $IC_{50}$ in a human amylin receptor binding assay of about 1200 pM or less; preferably, the polypeptide of the present invention consists of an analogue of SEQ ID NO: 1 according to formula (I), as defined above, wherein said polypeptides have an $IC_{50}$ in a human amylin receptor binding assay of about 1200 pM or less. In one embodiment the polypeptide of the present invention is an analogue of SEQ ID NO: 1, wherein said polypeptide has an $IC_{50}$ in a human amylin receptor binding assay of about 1200 pM or less; preferably, the polypeptide of the present invention is an analogue of SEQ ID NO: 1 according to formula (I), as defined above, wherein said polypeptides have an $IC_{50}$ in a human amylin receptor binding assay of about 1200 pM or less. In one embodiment the polypeptide of the present invention is an analogue of SEQ ID NO: 1 optionally further comprising substitutions or deletion relative to SEQ ID NO: 1, wherein said polypeptide has an $IC_{50}$ in a human amylin receptor binding assay of about 1200 pM or less; preferably, the polypeptide of the present invention is an analogue of SEQ ID NO: 1 according to formula (I), as defined above, wherein said polypeptides have an $IC_{50}$ in a human amylin receptor binding assay of about 1200 pM or less. A suitable human amylin receptor binding assay to determine the $IC_{50}$ is presented herein.

In one embodiment the polypeptide of the present invention consists of an analogue of SEQ ID NO: 1, wherein said polypeptide has an $IC_{50}$ in a human amylin receptor binding assay of about 1200 pM or less; preferably, the polypeptide of the present invention consists of an analogue of SEQ ID NO: 1 according to formula (I), as defined above, wherein said polypeptides have an $IC_{50}$ in a human amylin receptor binding assay of about 1200 pM or less. A suitable human amylin receptor binding assay to determine the $IC_{50}$ is presented herein.

Preferably the polypeptide of the present invention has a solubility of at least 100 μM at pH 4 and a solubility of at least 100 μM at pH 7.5.

In one embodiment the polypeptide of the present invention is selected from the following compounds presented in Table 2 (below). Table 2 presents a list of compounds that have a hAmylinR IC50 value of less than 1200 pM. Further details regarding the compounds, such as IUPAC nomenclature, may be found in Table 14.

TABLE 2

| Example No. | Sequence modifications | Albumin binding moiety | Linker | Acylation sites |
|---|---|---|---|---|
| 1 | 14D, 17R, 21P, 26P, 35D | C20 diacid | 2xgGlu | 1K |
| 2 | 14D, 17R, 21P, 27P, 35D | C20 diacid | 2xgGlu | 1K |
| 3 | 14D, 17R, 22P, 26P, 35D | C20 diacid | 2xgGlu | 1K |

TABLE 2-continued

| Example No. | Sequence modifications | Albumin binding moiety | Linker | Acylation sites |
|---|---|---|---|---|
| 4 | 14E, 17R, 21P, 25P, 28P, 29P, 37P | C20 diacid | gGlu | N-terminal |
| 5 | 14E, 17R, 21P, 26P, 37P | C20 diacid | gGlu | N-terminal |
| 6 | 14E, 17R, 21P, 25P, 28P, 29P | C20 diacid | gGlu | N-terminal |
| 7 | 14E, 17R, 21P, 26P | C20 diacid | gGlu | N-terminal |
| 8 | 14E, 17R, 21P, 27P, 37P | C20 diacid | gGlu | N-terminal |
| 9 | 14E, 17R, 21P, 27P | C20 diacid | gGlu | N-terminal |
| 10 | 14D, 17R, 21P, 27P, 37P | C20 diacid | gGlu | N-terminal |
| 11 | 14E, 17R, 21P, 27P, 35D, 37P | C20 diacid | gGlu | N-terminal |
| 12 | 14E, 17R, 21P, 27P, 37P | C20 diacid | gGlu | 1K |
| 13 | 14E, 17R, 21P, 27P, 37P | C20 diacid | 2xgGlu | 1K |
| 14 | 14E, 17R, 21P, 27P, 37P | C20 diacid | 2xgGlu | N-terminal |
| 15 | 14E, 17R, 21P, 27P | C20 diacid | 2xgGlu | N-terminal |
| 16 | 14E, 17R, 21P, 27P, 35R | C20 diacid | gGlu | N-terminal |
| 17 | 14E, 17R, 21P, 27P, 34H | C20 diacid | gGlu | N-terminal |
| 18 | 14E, 17R, 21P, 27P, 35H | C20 diacid | gGlu | N-terminal |
| 19 | 14E, 17R, 21P, 27P | C20 diacid | gGlu-2xOEG | N-terminal |
| 20 | 14E, 17R, 21P, 27P, 37P | C20 diacid | gGlu-2xOEG | N-terminal |
| 21 | 17R, 21P, 27P | C20 diacid | gGlu | N-terminal |
| 22 | 14E, 17R, 21P, 27P, 35E | C20 diacid | gGlu | N-terminal |
| 23 | 17R, 21P, 27P, 35E | C20 diacid | gGlu | N-terminal |
| 24 | 17R, 21P, 27P | C20 diacid | gGlu-2xOEG | N-terminal |
| 25 | 17R, 21P, 27P, 35E | C20 diacid | gGlu-2xOEG | 1K |
| 26 | 17R, 21P, 27P, 35E | C20 diacid | gGlu-OEG | 1K |
| 27 | 17R, 21P, 27P, 35E | C20 diacid | gGlu | 1K |
| 28 | 17R, 21P, 27P, 31P, 35E | C20 diacid | gGlu | N-terminal |
| 29 | 17R, 21P, 27P, 34P, 35E | C20 diacid | gGlu | N-terminal |
| 30 | 14H, 17R, 21P, 27P, 35E | C20 diacid | gGlu | N-terminal |
| 31 | 14E, 17R, 21P, 27P, 31P | C20 diacid | gGlu | N-terminal |
| 32 | 14E, 17R, 21P, 27P, 34P | C20 diacid | gGlu | N-terminal |
| 33 | 14E, 17R, 21P, 28P, 35E | C20 diacid | gGlu | N-terminal |
| 34 | 17R, 21P, 27P, 35K | C20 diacid | gGlu | N-terminal |
| 35 | 17R, 21P, 27P, 35K | C20 diacid | gGlu | 1K |
| 36 | 14E, 17R, 21P, 27P, 34K | C20 diacid | gGlu | N-terminal |
| 37 | 14E, 17R, 21P, 27P, 29P | C20 diacid | gGlu | N-terminal |
| 38 | 17R, 21P, 27P, 35R | C20 diacid | gGlu-OEG | 1K |
| 39 | 17R, 21P, 27P, 34R | C20 diacid | gGlu | N-terminal |
| 40 | 17R, 21P, 27P, 34H | C20 diacid | gGlu | N-terminal |
| 41 | 17R, 21P, 27P | C20 diacid | gGlu-OEG | 1K |
| 42 | 17R, 21P, 27P | C20 diacid | none | 1K |
| 43 | 17R, 21P, 27P | C20 diacid | OEG | 1K |
| 44 | -1K, 1R, 17R, 21P, 27P, 35H | C20 diacid | gGlu | -1K |
| 45 | -1K, 1R, 17R, 21P, 27P, 35H | C20 diacid | gGlu-OEG | -1K |
| 46 | -1G, 1R, 17R, 21P, 27P | C20 diacid | gGlu | N-terminal |
| 47 | -1G, 1R, 17R, 21P, 27P, 35H | C20 diacid | gGlu | N-terminal |
| 48 | 17R, 21P, 27P | C20 diacid | gGlu | 1K |
| 49 | 17R, 21P, 27P, 31P | C20 diacid | gGlu-OEG | 1K |
| 50 | 17R, 21P, 27P, 34P | C20 diacid | gGlu-OEG | 1K |
| 51 | 14E, 17R, 21P, 27P, 35R | C20 diacid | gGlu | 1K |
| 52 | 14D, 17R, 21P, 27P, 35R | C20 diacid | 2xgGlu | 1K |
| 53 | 17R, 21P, 27P, 28P, 31P | C20 diacid | gGlu-OEG | 1K |
| 54 | 17R, 21P, 27P, 29P, 31P | C20 diacid | gGlu-OEG | 1K |
| 55 | 17R, 21P, 27P, 28P, 34P | C20 diacid | gGlu-OEG | 1K |
| 56 | 17R, 21P, 27P, 29P, 34P | C20 diacid | gGlu-OEG | 1K |
| 57 | 17R, 21P, 27P, 31P, 35H | C20 diacid | gGlu-OEG | 1K |
| 58 | 17R, 21P, 27P, 34P, 35H | C20 diacid | gGlu-OEG | 1K |
| 59 | 14D, 17R, 21K, 27P, 35D | C20 diacid | 2xgGlu | 21K |
| 60 | 17R, 21P, 27P, 35H | C20 diacid | gGlu | 1K |
| 61 | 14H, 17R, 21P, 27P, 31P | C20 diacid | gGlu-OEG | 1K |

TABLE 2-continued

| Example No. | Sequence modifications | Albumin binding moiety | Linker | Acylation sites |
|---|---|---|---|---|
| 62 | 14H, 17R, 21P, 27P, 31P | C20 diacid | gGlu | 1K |
| 63 | 14R, 17R, 21P, 27P, 31P | C20 diacid | gGlu | 1K |
| 64 | 14R, 17R, 21P, 27P, 31P | C20 diacid | gGlu-OEG | 1K |
| 65 | 14R, 17R, 21P, 27P, 34P | C20 diacid | gGlu | 1K |
| 66 | 14H, 17R, 21P, 27P, 35H | C20 diacid | gGlu | 1K |
| 67 | 14H, 17R, 21P, 27P, 34P | C20 diacid | gGlu | 1K |
| 68 | 14H, 17R, 21P, 27P, 34P | C20 diacid | gGlu-OEG | 1K |
| 69 | 14H, 17R, 21P, 27P | C20 diacid | gGlu-OEG | 1K |
| 70 | 14H, 17R, 21P, 27P | C20 diacid | gGlu | 1K |
| 71 | 14G, 17R, 21P, 27P, 31P | C20 diacid | gGlu-OEG | 1K |
| 72 | 14A, 17R, 21P, 27P, 31P | C20 diacid | gGlu-OEG | 1K |
| 73 | 14S, 17R, 21P, 27P, 31P | C20 diacid | gGlu-OEG | 1K |
| 74 | 14K, 17R, 21P, 27P, 31P | C20 diacid | gGlu-OEG | 1K |
| 75 | 14T, 17R, 21P, 27P, 31P | C20 diacid | gGlu-OEG | 1K |
| 76 | 17R, 21P, 27P, 34H | C20 diacid | gGlu-OEG | 1K |
| 77 | 17R, 21P, 27P, 34H | C20 diacid | gGlu | 1K |
| 78 | 17R, 21P, 27P, 34R | C20 diacid | gGlu-OEG | 1K |
| 79 | 17R, 21P, 27P, 34R | C20 diacid | gGlu | 1K |
| 80 | 14H, 17R, 21P, 27P, 34H | C20 diacid | gGlu-OEG | 1K |
| 81 | 14H, 17R, 21P, 27P, 34H | C20 diacid | gGlu | 1K |
| 82 | 14R, 17R, 21P, 27P | C20 diacid | gGlu-OEG | 1K |
| 83 | 14R, 17R, 21P, 27P | C20 diacid | gGlu | 1K |
| 84 | 14H, 17R, 21P, 27P, 34R | C20 diacid | gGlu-OEG | 1K |
| 85 | 14H, 17R, 21P, 27P, 34R | C20 diacid | gGlu | 1K |
| 86 | 17R, 21P, 27P, 34H | C20 diacid | 2xgGlu | 1K |
| 87 | 14E, 17R, 21P, 27P, 34H | C20 diacid | 2xgGlu | 1K |
| 88 | 14E, 17R, 21P, 27P, 34R | C20 diacid | 2xgGlu | 1K |
| 89 | 14E, 17R, 21P, 27P, 35R | C20 diacid | 2xgGlu | 1K |
| 90 | 14H, 17R, 21P, 27P | C20 diacid | OEG | 1K |
| 91 | 17R, 21P, 27P, 34H | C20 diacid | OEG | 1K |
| 92 | 14H, 17R, 21P, 27P | C20 diacid | 2xgGlu | 1K |
| 93 | 14A, 17R, 21P, 27P, 34H | C20 diacid | gGlu | 1K |
| 94 | 14A, 17R, 21P, 27P, 34P | C20 diacid | gGlu | 1K |
| 95 | 17R, 21P, 27P, 34R | C20 diacid | gGlu-2xOEG | 1K |
| 96 | 17R, 21P, 27P, 31P | C20 diacid | gGlu-2xOEG | 1K |
| 97 | 17R, 21P, 27P, 34H | C20 diacid | gGlu-2xOEG | 1K |
| 98 | 17R, 21P, 27P, 34P | C20 diacid | gGlu-2xOEG | 1K |
| 99 | −1G, 1R, 14H, 17R, 21P, 27P | C20 diacid | gGlu | N-terminal |
| 100 | −1G, 1R, 14H, 17R, 21P, 27P, 34H | C20 diacid | gGlu | N-terminal |
| 101 | −1G, 1R, 14A, 17R, 21P, 27P, 34H | C20 diacid | gGlu | N-terminal |
| 102 | −1G, 1R, 14H, 17R, 21P, 27P, 34P | C20 diacid | gGlu | N-terminal |
| 103 | −1G, 1R, 14A, 17R, 21P, 27P, 34P | C20 diacid | gGlu | N-terminal |
| 104 | 14E, 17R, 21P, 27P, 34H, 35E | C20 diacid | 2xgGlu | 1K |
| 105 | 14E, 17R, 21P, 27P, 34R, 35E | C20 diacid | 2xgGlu | 1K |
| 106 | 14E, 17R, 21P, 27P, 34P, 35E | C20 diacid | 2xgGlu | 1K |
| 107 | 14E, 17R, 21P, 27P, 34H, 35E | C20 diacid | gGlu | 1K |
| 108 | 14E, 17R, 21P, 27P, 34R, 35E | C20 diacid | gGlu | 1K |
| 109 | 14E, 17R, 21P, 27P, 34P, 35E | C20 diacid | gGlu | 1K |
| 110 | 14E, 17R, 21P, 27P, 34P, 35R | C20 diacid | 2xgGlu | 1K |
| 111 | 17R, 21P, 27P, 34H | C16 diacid | gGlu | 1K |
| 112 | 17R, 21P, 27P, 34H | C14 diacid | gGlu | 1K |
| 113 | 17R, 21P, 27P, 34H | C18 diacid | gGlu | 1K |
| 114 | 14E, 17R, 21P, 27P, 34P, 37P | C20 diacid | gGlu | 1K |
| 115 | 14H, 17R, 21P, 27P, 34P, 37P | C20 diacid | gGlu | 1K |
| 116 | 14H, 17R, 21P, 27P, 31P, 34P | C20 diacid | gGlu | 1K |
| 117 | 14E, 17R, 21P, 27P, 34P, 35R | C20 diacid | gGlu | 1K |
| 118 | 14E, 17R, 21P, 27P, 34P, 35H | C20 diacid | gGlu | 1K |
| 119 | 17R, 21P, 27P, 31P, 34P, 35R | C20 diacid | 2xgGlu | 1K |
| 120 | 14S, 17R, 21P, 27P, 34P, 35E | C20 diacid | 2xgGlu | 1K |

TABLE 2-continued

| Example No. | Sequence modifications | Albumin binding moiety | Linker | Acylation sites |
|---|---|---|---|---|
| 121 | 14E, 17R, 21P, 31P, 34P, 35E | C20 diacid | 2xgGlu | 1K |
| 122 | 14D, 17R, 21P, 27P, 34P, 35E | C20 diacid | 2xgGlu | 1K |
| 123 | 14D, 17R, 21P, 27P, 34P, 35E | C20 diacid | gGlu | 1K |
| 124 | 14E, 17R, 21P, 27P, 34P, 35H | C20 diacid | 2xgGlu | 1K |
| 125 | 14E, 17R, 21P, 27P, 34P, 35E, 37P | C20 diacid | 2xgGlu | 1K |
| 126 | 14E, 17R, 23P, 34P, 35E | C20 diacid | 2xgGlu | 1K |
| 127 | 14E, 17R, 21P, 27P, 34P, 37F | C20 diacid | 2xgGlu | 1K |
| 128 | 14E, 17R, 21P, 27P, 35H | C20 diacid | gGlu | 1K |
| 129 | 14D, 17R, 21P, 27P, 34P, 35R | C20 diacid | gGlu | 1K |
| 130 | 14D, 17R, 21P, 27P, 34P, 35R | C20 diacid | 2xgGlu | 1K |
| 131 | 14d, 17R, 21P, 27P, 35R | C20 diacid | 2xgGlu | 1K |
| 132 | 14D, 17R, 21P, 27P, 35R | none | none | |

In a further embodiment the polypeptide of the present invention is selected from the following compounds presented in Table 3 (below).

Table 3 presents compounds that have a hAmylinR IC50 value of less than 1200 pM and a ratio of hCT/hAmylin binding of at least 10. Further details regarding the compounds, such as IUPAC nomenclature, may be found in Table 14.

TABLE 3

| Example no. | Sequence modifications | Albumin binding moiety | Linker | Acylation sites |
|---|---|---|---|---|
| 1 | 14D, 17R, 21P, 26P, 35D | C20 diacid | 2xgGlu | 1K |
| 2 | 14D, 17R, 21P, 27P, 35D | C20 diacid | 2xgGlu | 1K |
| 3 | 14D, 17R, 22P, 26P, 35D | C20 diacid | 2xgGlu | 1K |
| 6 | 14E, 17R, 21P, 25P, 28P, 29P | C20 diacid | gGlu | N-terminal |
| 7 | 14E, 17R, 21P, 26P | C20 diacid | gGlu | N-terminal |
| 15 | 14E, 17R, 21P, 27P | C20 diacid | 2xgGlu | N-terminal |
| 16 | 14E, 17R, 21P, 27P, 35R | C20 diacid | gGlu | N-terminal |
| 17 | 14E, 17R, 21P, 27P, 34H | C20 diacid | gGlu | N-terminal |
| 19 | 14E, 17R, 21P, 27P | C20 diacid | gGlu-2xOEG | N-terminal |
| 21 | 17R, 21P, 27P | C20 diacid | gGlu | N-terminal |
| 22 | 14E, 17R, 21P, 27P, 35E | C20 diacid | gGlu | N-terminal |
| 23 | 17R, 21P, 27P, 35E | C20 diacid | gGlu | N-terminal |
| 24 | 17R, 21P, 27P | C20 diacid | gGlu-2xOEG | N-terminal |
| 25 | 17R, 21P, 27P, 35E | C20 diacid | gGlu-2xOEG | 1K |
| 26 | 17R, 21P, 27P, 35E | C20 diacid | gGlu-OEG | 1K |
| 27 | 17R, 21P, 27P, 35E | C20 diacid | gGlu | 1K |
| 28 | 17R, 21P, 27P, 31P, 35E | C20 diacid | gGlu | N-terminal |
| 29 | 17R, 21P, 27P, 34P, 35E | C20 diacid | gGlu | N-terminal |
| 30 | 14H, 17R, 21P, 27P, 35E | C20 diacid | gGlu | N-terminal |
| 31 | 14E, 17R, 21P, 27P, 31P | C20 diacid | gGlu | N-terminal |
| 32 | 14E, 17R, 21P, 27P, 34P | C20 diacid | gGlu | N-terminal |
| 34 | 17R, 21P, 27P, 35K | C20 diacid | gGlu | N-terminal |
| 35 | 17R, 21P, 27P, 35K | C20 diacid | gGlu | 1K |
| 36 | 14E, 17R, 21P, 27P, 34K | C20 diacid | gGlu | N-terminal |
| 38 | 17R, 21P, 27P, 35R | C20 diacid | gGlu-OEG | 1K |
| 39 | 17R, 21P, 27P, 34R | C20 diacid | gGlu | N-terminal |
| 40 | 17R, 21P, 27P, 34H | C20 diacid | gGlu | N-terminal |
| 41 | 17R, 21P, 27P | C20 diacid | gGlu-OEG | 1K |
| 42 | 17R, 21P, 27P | C20 diacid | none | 1K |
| 43 | 17R, 21P, 27P | C20 diacid | OEG | 1K |
| 44 | −1K, 1R, 17R, 21P, 27P, 35H | C20 diacid | gGlu | −1K |
| 45 | −1K, 1R, 17R, 21P, 27P, 35H | C20 diacid | gGlu-OEG | −1K |
| 46 | −1G, 1R, 17R, 21P, 27P | C20 diacid | gGlu | N-terminal |
| 47 | −1G, 1R, 17R, 21P, 27P, 35H | C20 diacid | gGlu | N-terminal |
| 48 | 17R, 21P, 27P | C20 diacid | gGlu | 1K |
| 49 | 17R, 21P, 27P, 31P | C20 diacid | gGlu-OEG | 1K |

TABLE 3-continued

| Example no. | Sequence modifications | Albumin binding moiety | Linker | Acylation sites |
|---|---|---|---|---|
| 50 | 17R, 21P, 27P, 34P | C20 diacid | gGlu-OEG | 1K |
| 51 | 14E, 17R, 21P, 27P, 35R | C20 diacid | gGlu | 1K |
| 52 | 14D, 17R, 21P, 27P, 35R | C20 diacid | 2xgGlu | 1K |
| 53 | 17R, 21P, 27P, 28P, 31P | C20 diacid | gGlu-OEG | 1K |
| 54 | 17R, 21P, 27P, 29P, 31P | C20 diacid | gGlu-OEG | 1K |
| 55 | 17R, 21P, 27P, 28P, 34P | C20 diacid | gGlu-OEG | 1K |
| 56 | 17R, 21P, 27P, 29P, 34P | C20 diacid | gGlu-OEG | 1K |
| 57 | 17R, 21P, 27P, 31P, 35H | C20 diacid | gGlu-OEG | 1K |
| 58 | 17R, 21P, 27P, 34P, 35H | C20 diacid | gGlu-OEG | 1K |
| 60 | 17R, 21P, 27P, 35H | C20 diacid | gGlu | 1K |
| 61 | 14H, 17R, 21P, 27P, 31P | C20 diacid | gGlu-OEG | 1K |
| 62 | 14H, 17R, 21P, 27P, 31P | C20 diacid | gGlu | 1K |
| 63 | 14R, 17R, 21P, 27P, 31P | C20 diacid | gGlu | 1K |
| 64 | 14R, 17R, 21P, 27P, 31P | C20 diacid | gGlu-OEG | 1K |
| 65 | 14R, 17R, 21P, 27P, 34P | C20 diacid | gGlu | 1K |
| 66 | 14H, 17R, 21P, 27P, 35H | C20 diacid | gGlu | 1K |
| 67 | 14H, 17R, 21P, 27P, 34P | C20 diacid | gGlu | 1K |
| 68 | 14H, 17R, 21P, 27P, 34P | C20 diacid | gGlu-OEG | 1K |
| 69 | 14H, 17R, 21P, 27P | C20 diacid | gGlu-OEG | 1K |
| 70 | 14H, 17R, 21P, 27P | C20 diacid | gGlu | 1K |
| 71 | 14G, 17R, 21P, 27P, 31P | C20 diacid | gGlu-OEG | 1K |
| 72 | 14A, 17R, 21P, 27P, 31P | C20 diacid | gGlu-OEG | 1K |
| 73 | 14S, 17R, 21P, 27P, 31P | C20 diacid | gGlu-OEG | 1K |
| 74 | 14K, 17R, 21P, 27P, 31P | C20 diacid | gGlu-OEG | 1K |
| 75 | 14T, 17R, 21P, 27P, 31P | C20 diacid | gGlu-OEG | 1K |
| 76 | 17R, 21P, 27P, 34H | C20 diacid | gGlu-OEG | 1K |
| 77 | 17R, 21P, 27P, 34H | C20 diacid | gGlu | 1K |
| 78 | 17R, 21P, 27P, 34R | C20 diacid | gGlu-OEG | 1K |
| 79 | 17R, 21P, 27P, 34R | C20 diacid | gGlu | 1K |
| 80 | 14H, 17R, 21P, 27P, 34H | C20 diacid | gGlu-OEG | 1K |
| 81 | 14H, 17R, 21P, 27P, 34H | C20 diacid | gGlu | 1K |
| 82 | 14R, 17R, 21P, 27P | C20 diacid | gGlu-OEG | 1K |
| 83 | 14R, 17R, 21P, 27P | C20 diacid | gGlu | 1K |
| 84 | 14H, 17R, 21P, 27P, 34R | C20 diacid | gGlu-OEG | 1K |
| 85 | 14H, 17R, 21P, 27P, 34R | C20 diacid | gGlu | 1K |
| 86 | 17R, 21P, 27P, 34H | C20 diacid | 2xgGlu | 1K |
| 87 | 14E, 17R, 21P, 27P, 34H | C20 diacid | 2xgGlu | 1K |
| 88 | 14E, 17R, 21P, 27P, 34R | C20 diacid | 2xgGlu | 1K |
| 89 | 14E, 17R, 21P, 27P, 35R | C20 diacid | 2xgGlu | 1K |
| 90 | 14H, 17R, 21P, 27P | C20 diacid | OEG | 1K |
| 91 | 17R, 21P, 27P, 34H | C20 diacid | OEG | 1K |
| 92 | 14H, 17R, 21P, 27P | C20 diacid | 2xgGlu | 1K |
| 93 | 14A, 17R, 21P, 27P, 34H | C20 diacid | gGlu | 1K |
| 94 | 14A, 17R, 21P, 27P, 34P | C20 diacid | gGlu | 1K |
| 95 | 17R, 21P, 27P, 34R | C20 diacid | gGlu-2xOEG | 1K |
| 96 | 17R, 21P, 27P, 31P | C20 diacid | gGlu-2xOEG | 1K |
| 97 | 17R, 21P, 27P, 34H | C20 diacid | gGlu-2xOEG | 1K |
| 98 | 17R, 21P, 27P, 34P | C20 diacid | gGlu-2xOEG | 1K |
| 99 | −1G, 1R, 14H, 17R, 21P, 27P | C20 diacid | gGlu | N-terminal |
| 100 | −1G, 1R, 14H, 17R, 21P, 27P, 34H | C20 diacid | gGlu | N-terminal |
| 101 | −1G, 1R, 14A, 17R, 21P, 27P, 34H | C20 diacid | gGlu | N-terminal |
| 102 | −1G, 1R, 14H, 17R, 21P, 27P, 34P | C20 diacid | gGlu | N-terminal |

TABLE 3-continued

| Example no. | Sequence modifications | Albumin binding moiety | Linker | Acylation sites |
|---|---|---|---|---|
| 103 | −1G, 1R, 14A, 17R, 21P, 27P, 34P | C20 diacid | gGlu | N-terminal |
| 104 | 14E, 17R, 21P, 27P, 34H, 35E | C20 diacid | 2xgGlu | 1K |
| 105 | 14E, 17R, 21P, 27P, 34R, 35E | C20 diacid | 2xgGlu | 1K |
| 106 | 14E, 17R, 21P, 27P, 34P, 35E | C20 diacid | 2xgGlu | 1K |
| 107 | 14E, 17R, 21P, 27P, 34H, 35E | C20 diacid | gGlu | 1K |
| 108 | 14E, 17R, 21P, 27P, 34R, 35E | C20 diacid | gGlu | 1K |
| 109 | 14E, 17R, 21P, 27P, 34P, 35E | C20 diacid | gGlu | 1K |
| 110 | 14E, 17R, 21P, 27P, 34P, 35R | C20 diacid | 2xgGlu | 1K |
| 111 | 17R, 21P, 27P, 34H | C16 diacid | gGlu | 1K |
| 112 | 17R, 21P, 27P, 34H | C14 diacid | gGlu | 1K |
| 113 | 17R, 21P, 27P, 34H | C18 diacid | gGlu | 1K |
| 116 | 14H, 17R, 21P, 27P, 31P, 34P | C20 diacid | gGlu | 1K |
| 117 | 14E, 17R, 21P, 27P, 34P, 35R | C20 diacid | gGlu | 1K |
| 118 | 14E, 17R, 21P, 27P, 34P, 35H | C20 diacid | gGlu | 1K |
| 119 | 17R, 21P, 27P, 31P, 34P, 35R | C20 diacid | 2xgGlu | 1K |
| 120 | 14S, 17R, 21P, 27P, 34P, 35E | C20 diacid | 2xgGlu | 1K |
| 121 | 14E, 17R, 21P, 31P, 34P, 35E | C20 diacid | 2xgGlu | 1K |
| 122 | 14D, 17R, 21P, 27P, 34P, 35E | C20 diacid | 2xgGlu | 1K |
| 123 | 14D, 17R, 21P, 27P, 34P, 35E | C20 diacid | gGlu | 1K |
| 124 | 14E, 17R, 21P, 27P, 34P, 35H | C20 diacid | 2xgGlu | 1K |
| 127 | 14E, 17R, 21P, 27P, 34P, 37F | C20 diacid | 2xgGlu | 1K |
| 128 | 14E, 17R, 21P, 27P, 35H | C20 diacid | gGlu | 1K |
| 129 | 14D, 17R, 21P, 27P, 34P, 35R | C20 diacid | gGlu | 1K |
| 130 | 14D, 17R, 21P, 27P, 34P, 35R | C20 diacid | 2xgGlu | 1K |
| 131 | 14d, 17R, 21P, 27P, 35R | C20 diacid | 2xgGlu | 1K |
| 132 | 14D, 17R, 21P, 27P, 35R | none | none | |

In this Table of compounds the term "sequence modifications" means modifications with respect to human amylin.

The polypeptides of the present invention may inhibit food intake, inhibit gastric emptying and glucagon secretion or other physiological effects as is known in the art.

The polypeptides of the present invention retain amylin binding. Amylin binding refers to the ability to bind to the amylin receptor, specifically to have an $IC_{50}$ of about 1200 pM or less in a human amylin binding assay. For example, the polypeptides of the invention can be tested for amylin binding using the Assay presented herein.

As demonstrated in the Examples section herein, the polypeptides presented above have an $IC_{50}$ in a human amylin receptor binding assay of about 1200 pM or less.

In one embodiment, the polypeptides of the present invention have an $IC_{50}$ of about 1200 pM (picomolar) or less in a human binding assay. In one embodiment, the polypeptides of the present invention have an $IC_{50}$ of 1100 pM or less in a human binding assay. In one embodiment, the polypeptides of the present invention have an $IC_{50}$ of 1000 pM or less in a human binding assay. In one embodiment, the polypeptides of the present invention have an $IC_{50}$ of 900 pM or less in a human binding assay. In one embodiment, the polypeptides of the present invention have an $IC_{50}$ of 800 pM or less in a human binding assay. In one embodiment, the polypeptides of the present invention have an $IC_{50}$ of 750 pM or less in a human binding assay. In one embodiment, the polypeptides of the present invention have an $IC_{50}$ of 700 pM or less in a human binding assay.

In one embodiment, the $IC_{50}$ is measured in a human binding Assay presented herein.

In one embodiment, the polypeptides of the present invention may exhibit selectivity for amylin receptors over calcitonin receptors. In one embodiment, the polypeptides of the present invention may exhibit selectivity for human amylin receptors over human calcitonin receptors.

For example, selectivity may be assessed by measuring the $IC_{50}$ in an amylin binding assay—such as that presented herein (e.g. Assay (V))—and measuring the $IC_{50}$ in a calcitonin binding assay—such as that presented herein (e.g. Assay (VII)) and then calculating the ratio of the two $IC_{50}$ values according to the equation below:

Selectivity=$IC_{50}$ in the calcitonin binding assay/$IC_{50}$ in the amylin binding assay In one embodiment, the polypeptides of the invention are more selective in amylin potency or binding assays than in calcitonin potency or binding assays.

The calcitonin and amylin binding or potency assays may use receptors from any species provided like is compared with like. The binding or potency assays may both use rat receptors or may both use human receptors, or combinations thereof. An example of a suitable human binding assay is presented herein. An example of a suitable human potency assay is presented herein. An example of a suitable rat binding assay is presented herein. An example of a suitable rat potency assay is presented herein.

In one embodiment, the polypeptides of the invention have a selectivity value of about at least 5 when both binding assays use human receptors. In one embodiment, the polypeptides of the invention have a selectivity value of about at least 10 when both binding assays use human receptors. In one embodiment, the polypeptides of the invention have a selectivity value of about at least 20 when both binding assays use human receptors. In one embodiment, the polypeptides of the invention have a selectivity value of about at least 30 when both binding assays use human receptors. In one embodiment, the polypeptides of the invention have a selectivity value of about at least 40 when both binding assays use human receptors. In one embodiment, the polypeptides of the invention have a selectivity value of about at least 50 when both binding assays use human receptors. In one embodiment, the polypeptides of the invention have a selectivity value of about at least 60 when both binding assays use human receptors. In one embodiment, the polypeptides of the invention have a selectivity value of about at least 70 when both binding assays use human receptors. In one embodiment, the polypeptides of the invention have a selectivity value of about at least 80 when both binding assays use human receptors.

In one embodiment, the polypeptides of the invention have a selectivity value of about at least 10 when both binding assays use rat receptors. In one embodiment, the polypeptides of the invention have a selectivity value of about at least 20 when both binding assays use rat receptors. In one embodiment, the polypeptides of the invention have a selectivity value of about at least 30 when both binding assays use rat receptors. In one embodiment, the polypeptides of the invention have a selectivity value of about at least 40 when both binding assays use rat receptors. In one embodiment, the polypeptides of the invention have a selectivity value of about at least 50 when both binding assays use rat receptors. In one embodiment, the polypeptides of the invention have a selectivity value of about at least 60 when both binding assays use rat receptors. In one embodiment, the polypeptides of the invention have a selectivity value of about at least 70 when both binding assays use rat receptors. In one embodiment, the polypeptides of the invention have a selectivity value of about at least 80 when both binding assays use rat receptors. In one embodiment, the polypeptides of the invention have a selectivity value of about at least 100 when both binding assays use rat receptors. In one embodiment, the polypeptides of the invention have a selectivity value of about at least 150 when both binding assays use rat receptors.

In one embodiment, the polypeptides of the invention have a selectivity value of about at least 200 when both binding assays use rat receptors. In one embodiment, the polypeptides of the invention have a selectivity value of about at least 300 when both binding assays use rat receptors. In one embodiment, the polypeptides of the invention have a selectivity value of about at least 400 when both binding assays use rat receptors. In one embodiment, the polypeptides of the invention have a selectivity value of about at least 450 when both binding assays use rat receptors.

In one embodiment, the polypeptides of the invention have a selectivity value of about at least 5 when both potency assays use human receptors.

In one embodiment, the polypeptides of the invention have a selectivity value of about at least 10 when both potency assays use human receptors.

In one embodiment, the polypeptides of the invention have a selectivity value of about at least 20 when both potency assays use human receptors.

In one embodiment, the polypeptides of the invention have a selectivity value of about at least 30 when both potency assays use human receptors.

In one embodiment, the polypeptides of the invention have a selectivity value of about at least 40 when both potency assays use human receptors.

For some embodiments, the polypeptide of the present invention has a protracted pharmacokinetic profile compared to pramlintide as measured by the Assay described herein.

For some embodiments, the polypeptide of the present invention has a plasma T½ of at least 30 hours. For some embodiments, the polypeptide of the present invention has a plasma T½ of at least 40 hours. For some embodiments, the polypeptide of the present invention has a plasma T½ of at least 50 hours. For some embodiments, the polypeptide of the present invention has a plasma T½ of at least 60 hours. For some embodiments, the polypeptide of the present invention has a plasma T½ of at least 70 hours. For some embodiments, the polypeptide of the present invention has a plasma T½ of at least 75 hours. For some embodiments, the polypeptide of the present invention has a plasma T½ of at least 80 hours. For some embodiments, the polypeptide of the present invention has a plasma T½ of at least 85 hours. For some embodiments, the polypeptide of the present invention has a plasma T½ of at least 90 hours. For some embodiments, the polypeptide of the present invention has a plasma T½ of at least 95 hours. For some embodiments, the polypeptide of the present invention has a plasma T½ of at least 100 hours.

Process

The production of polypeptides such as amylin or analogues thereof is well known in the art.

The polypeptides of the invention can thus be produced by classical polypeptide synthesis, e.g. solid phase polypeptide synthesis using t-Boc or Fmoc chemistry or other well established techniques, see e.g. Greene and Wuts, "Protective Groups in Organic Synthesis", John Wiley & Sons, 1999. The polypeptides may also be produced by a method which comprises culturing a host cell containing a DNA sequence encoding the polypeptide and capable of expressing the polypeptide in a suitable nutrient medium under conditions permitting the expression of the polypeptide. For polypeptides comprising non-natural amino acid residues, the recombinant cell should be modified such that the non-natural amino acids are incorporated into the polypeptide, for instance by use of tRNA mutants.

Pharmaceutical Compositions

In one embodiment the invention concerns a pharmaceutical composition comprising a polypeptide according of the invention, and a pharmaceutically acceptable excipient. The compositions are suited for parenteral administration.

In one embodiment the polypeptide is present in the formulation at a concentration of from about 0.1 mg/ml to about 25 mg/ml. In another embodiment, the polypeptide is present in the formulation at a concentration of from about 1 mg/ml to about 10 mg/ml.

In another embodiment, the formulation has a pH from 2.0 to 10.0. In another embodiment, the formulation has a pH from 2.0 to 7.0. In another embodiment, the formulation has a pH from 2.5 to 4.5. In another embodiment, the formulation has a pH from 3.5 to 4.5.

Pharmaceutical compositions containing a polypeptide according to the present invention may be prepared by conventional techniques, e.g. as described in Remington's *Pharmaceutical Sciences,* 1985 or in Remington: *The Science and Practice of Pharmacy,* $19^{th}$ edition, 1995.

The formulation may further comprise a buffer system, preservative(s), isotonicity agent(s), chelating agent(s), stabilizers and/or surfactants. The use of such excipients in pharmaceutical compositions is well-known to the skilled person. For convenience reference is made to Remington: *The Science and Practice of Pharmacy,* $19^{th}$ edition, 1995.

In one embodiment the pharmaceutical formulation is an aqueous formulation, i.e. formulation comprising water. Such formulation is typically a solution or a suspension. In a further embodiment of the invention the pharmaceutical formulation is an aqueous solution.

The term "aqueous formulation" is defined as a formulation comprising at least 50% w/w water.

Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use. In another embodiment the pharmaceutical formulation is a dried formulation (e.g. freeze-dried or spray-dried) ready for use without any prior dissolution.

By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

In a further embodiment of the invention the buffer is selected from the group consisting of acetate, carbonate, citrate, glycylglycine, histidine, glycine, lysine, arginine, dihydrogen phosphate, hydrogen phosphate, phosphate, and tris (hydroxymethyl)-aminomethan, bicine, tricine, malic acid, lactic acid, succinate, maleic acid, fumaric acid, tartaric acid, aspartic acid or mixtures thereof. Each one of these specific buffers constitutes an alternative embodiment of the invention.

In another embodiment of the invention the formulation further comprises a pharmaceutically acceptable preservative. In a further embodiment of the invention the formulation further comprises an isotonic agent, e.g. propylene glycol, mannitol or glycerol. In a further embodiment of the invention the formulation further comprises a chelating agent.

In another embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

Compositions of the invention are stabilized liquid pharmaceutical compositions whose therapeutically active components include a polypeptide that possibly exhibits aggregate formation during storage in liquid pharmaceutical formulations.

By "aggregate formation" is intended a physical interaction between the polypeptide molecules that results in formation of oligomers, which may remain soluble, or large visible aggregates that precipitate from the solution.

By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject.

The pharmaceutical compositions of the invention may further comprise an amount of an amino acid base sufficient to decrease aggregate formation by the polypeptide during storage of the composition.

By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids used in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with derivatives of these amino acids. Suitable arginine derivatives include, for example, aminoguanidine, ornithine and N-monoethyl L-arginine, suitable methionine derivatives include ethionine and buthionine and suitable cysteine derivatives include S-methyl-L cysteine. As with the other amino acids, the amino acid derivatives are incorporated into the compositions in either their free base form or their salt form. In a another embodiment of the invention the amino acids or amino acid derivatives thereof are used in a concentration, which is sufficient to prevent or delay aggregation of the protein.

In another embodiment of the invention the formulation further comprises a surfactant. In another embodiment of the invention the formulation further comprises protease inhibitors. The use of a protease inhibitor is particular useful in pharmaceutical compositions comprising zymogens of proteases in order to inhibit autocatalysis.

It is possible that other ingredients may be present in the polypeptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the derivative of an amylin analogue thereof increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of the derivative of an amylin analogue, using, for example a metered dose inhaler, dry powder inhaler and a nebulizer, all being devices well known to those skilled in the art.

Compositions of the current invention are useful in the formulation of controlled, sustained, protracting, retarded, and slow release drug delivery systems.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the derivative of an amylin analogue in the form of a nasal or pulmonal spray. As a still further option, the pharmaceutical compositions containing the polypeptide of the invention can also be adapted to transdermal administration, e.g. by needle-free injection or from a patch, optionally an iontophoretic patch, or transmucosal, e.g. buccal, administration.

The polypeptide of the invention can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (cf. Yu J, Chien Y W. ulmonary drug delivery: Physiologic and mechanistic embodiments. Crit. Rev Ther Drug Carr Sys 14(4) (1997) 395-453).

In one embodiment of the invention the pharmaceutical formulation comprising the polypeptide of the invention is stable for more than 6 weeks of usage and for more than 3 years of storage.

In another embodiment of the invention the pharmaceutical formulation comprising the polypeptide of the invention is stable for more than 4 weeks of usage and for more than 3 years of storage.

In another embodiment of the invention the pharmaceutical formulation comprising the derivative of an amylin analogue is stable for more than 4 weeks of usage and for more than two years of storage.

In another embodiment of the invention the pharmaceutical formulation comprising the derivative of an amylin analogue is stable for more than 2 weeks of usage and for more than two years of storage.

In one embodiment a process for preparing a pharmaceutical composition comprising the derivative according to the invention comprises mixing a derivative according to the invention with at least one pharmaceutically acceptable excipient.

Therapeutic Indications

In one embodiment the derivative according to the invention can be used as a medicament. In one embodiment the amylin derivative according to the invention can be used as a medicament. In one embodiment the amylin peptide according to the invention can be used as a medicament.

In one embodiment the derivative can be used as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers. In one embodiment the amylin derivative according to the invention can be used as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers. In one embodiment the amylin peptide according to the invention can be used as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one embodiment the medicament for delaying or preventing disease progression in type 2 diabetes.

In one embodiment the derivative can be used as a medicament for the treatment of or prevention of obesity. In one embodiment the amylin derivative according to the invention can be used as a medicament for the treatment of or prevention of obesity. In one embodiment the amylin peptide according to the invention can be used as a medicament for the treatment of or prevention of obesity.

In one embodiment the derivative can be used as a medicament for reduction of food intake. In one embodiment the amylin derivative according to the invention can be used as a medicament for reduction of food intake. In one embodiment the amylin peptide according to the invention can be used as a medicament for reduction of food intake In one embodiment the medicament can be used for decreasing food intake, decreasing β-cell apoptosis, increasing β-cell function and β-cell mass, and/or for restoring glucose sensitivity to β-cells.

In one embodiment the polypeptide according to the invention can be used for the preparation of a medicament.

In one embodiment the derivative can be used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one embodiment, the polypeptide can be used for the preparation of a medicament for delaying or preventing disease progression in type 2 diabetes.

In one embodiment the polypeptide can be used for the preparation of a medicament for decreasing food intake, decreasing β-cell apoptosis, increasing β-cell function and β-cell mass, and/or for restoring glucose sensitivity to β-cells.

In one embodiment the amylin polypeptide according to this invention reduces food intake in rats by 25% or more relative to vehicle within the first 24 hours after single subcutaneous injection of 3 nmol/kg of said derivative. In one embodiment the amylin polypeptide according to this invention reduces food intake in rats by more than 30% relative to vehicle within the first 24 hours after single subcutaneous injection of 3 nmol/kg of said derivative. In one embodiment the amylin polypeptide according to this invention reduces food intake in rats by more than 40% relative to vehicle within the first 24 hours after single subcutaneous injection of 3 nmol/kg of said derivative. In one embodiment the amylin polypeptide according to this invention reduces food intake in rats by more than 50% relative to vehicle within the first 24 hours after single subcutaneous injection of 3 nmol/kg of said derivative. In one embodiment the amylin polypeptide according to this invention reduces food intake in rats by more than 60% relative to vehicle within the first 24 hours after single subcutaneous injection of 3 nmol/kg of said derivative. In one embodiment the amylin polypeptide according to this invention reduces food intake in rats by more than 70% relative to vehicle within the first 24 hours after single subcutaneous injection of 3 nmol/kg of said derivative. In one embodiment the amylin polypeptide according to this invention reduces food intake in rats by more than 80% relative to vehicle within the first 24 hours after single subcutaneous injection of 3 nmol/kg of said derivative In one embodiment the amylin polypeptide according to this invention reduces food intake in rats by 25% or more relative to vehicle within the first 24 hours after single subcutaneous injection of 3 nmol/kg of said derivative.

In one embodiment the amylin polypeptide according to this invention reduces food intake in rats by more than 30% relative to vehicle within the first 24 hours after single subcutaneous injection of 3 nmol/kg of said derivative. In one embodiment the amylin polypeptide according to this invention reduces food intake in rats by more than 40% relative to vehicle within the first 24 hours after single subcutaneous injection of 3 nmol/kg of said derivative In one embodiment the amylin polypeptide according to this invention reduces food intake in rats by more than 50% relative to vehicle within the first 24 hours after single subcutaneous injection of 3 nmol/kg of said derivative. In one embodiment the amylin polypeptide according to this invention reduces food intake in rats by more than 60% relative to vehicle within the first 24 hours after single subcutaneous injection of 3 nmol/kg of said derivative. In one embodiment the amylin polypeptide according to this invention reduces food intake in rats by more than 70% relative to vehicle within the first 24 hours after single subcutaneous injection of 3 nmol/kg of said derivative. In one embodiment the amylin polypeptide according to this invention reduces food intake in rats by more than 80% relative to vehicle within the first 24 hours after single subcutaneous injection of 3 nmol/kg of said derivative In one embodiment the amylin polypeptide according to this invention reduces food intake in rats by more than 25% relative to vehicle within the first 24 hours after single subcutaneous injection of 30 nmol/kg of said derivative. In one embodiment the amylin polypeptide according to this invention reduces food intake in rats by more than 30% relative to vehicle within the first 24 hours after single subcutaneous injection of 30 nmol/kg of said derivative. In one embodiment the amylin polypeptide according to this invention reduces food intake in rats by more than 40% relative to vehicle within the first 24 hours after single subcutaneous injection of 30 nmol/kg of said derivative In one embodiment the amylin polypeptide according to this invention reduces food intake in rats by more than 50% relative to vehicle within the first 24 hours after single subcutaneous injection of 30 nmol/kg of said derivative. In one embodiment the amylin polypeptide according to this invention reduces food intake in rats by more than 60% relative to vehicle within the first 24 hours after single subcutaneous injection of 30 nmol/kg of said derivative. In one embodiment the amylin polypeptide according to this invention reduces food intake in rats by more than 70% relative to vehicle within the first 24 hours after single subcutaneous injection of 30 nmol/kg of said derivative. In one embodiment the amylin polypeptide according to this invention reduces food intake in rats by more than 80% relative to vehicle within the first 24 hours after single subcutaneous injection of 30 nmol/kg of said derivative. In one embodiment the amylin polypeptide according to this invention reduces food intake in rats by more than 90% relative to vehicle within the first 24 hours after single subcutaneous injection of 30 nmol/kg of said derivative. In one embodiment the amylin polypeptide according to this invention reduces food intake in rats by 100% relative to vehicle within the first 24 hours after single subcutaneous injection of 30 nmol/kg of said derivative Wherein a reduction of food intake by 100% relative to vehicle means that the rat does not eat.

In one embodiment the amylin polypeptide according to this invention reduces food intake in rats by more than 25% relative to vehicle within the 24 to 48 hours after single subcutaneous injection of 3 nmol/kg of said derivative. In one embodiment the amylin polypeptide according to this invention reduces food intake in rats by more than 30% relative to vehicle within the 24 to 48 hours after single subcutaneous injection of 3 nmol/kg of said derivative. In one embodiment the amylin polypeptide according to this invention reduces food intake in rats by more than 40% relative to vehicle within the 24 to 48 hours after single subcutaneous injection of 3 nmol/kg of said derivative In one embodiment the amylin polypeptide according to this invention reduces food intake in rats by more than 50% relative to vehicle within the 24 to 48 hours after single subcutaneous injection of 3 nmol/kg of said derivative. In one embodiment the amylin polypeptide according to this invention reduces food intake in rats by more than 60% relative to vehicle within the 24 to 48 hours after single subcutaneous injection of 3 nmol/kg of said derivative. In one embodiment the amylin polypeptide according to this invention reduces food intake in rats by more than 70% relative to vehicle within the 24 to 48 hours after single subcutaneous injection of 3 nmol/kg of said derivative. In one embodiment the amylin polypeptide according to this invention reduces food intake in rats by more than 80% relative to vehicle within the 24 to 48 hours after single subcutaneous injection of 3 nmol/kg of said derivative In one embodiment the amylin polypeptide according to this invention reduces food intake in rats by more than 25% relative to vehicle within the 24 to 48 hours after single subcutaneous injection of 30 nmol/kg of said derivative. In one embodiment the amylin polypeptide according to this invention reduces food intake in rats by more than 30% relative to vehicle within the 24 to 48 hours after single subcutaneous injection of 30 nmol/kg of said derivative. In one embodiment the amylin polypeptide according to this invention reduces food intake in rats by more than 40% relative to vehicle within the 24 to 48 hours after single subcutaneous injection of 30 nmol/kg of said derivative In one embodiment the amylin polypeptide according to this invention reduces food intake in rats by more than 50% relative to vehicle within the 24 to 48 hours after single subcutaneous injection of 30 nmol/kg of said derivative. In one embodiment the amylin polypeptide according to this invention reduces food intake in rats by more than 60% relative to vehicle within the 24 to 48 hours after single subcutaneous injection of 30 nmol/kg of said derivative. In one embodiment the amylin polypeptide according to this invention reduces food intake in rats by more than 70% relative to vehicle within the 24 to 48 hours after single subcutaneous injection of 30 nmol/kg of said derivative. In one embodiment the amylin polypeptide according to this invention reduces food intake in rats by more than 80% relative to vehicle within the 24 to 48 hours after single subcutaneous injection of 30 nmol/kg of said derivative. In one embodiment the amylin polypeptide according to this invention reduces food intake in rats by more than 90% relative to vehicle within the 24 to 48 hours after single subcutaneous injection of 30 nmol/kg of said derivative. In one embodiment the amylin polypeptide according to this invention reduces food intake in rats by 100% relative to vehicle within the 24 to 48 hours after single subcutaneous injection of 30 nmol/kg of said derivative Wherein a reduction of food intake by 100% relative to vehicle means that the rat does not eat.

In one embodiment the amylin polypeptide according to this invention reduces plasma calcium levels in rats by less than 30% relative to vehicle at any time after single subcutaneous injection of up to 30 nmol/kg. In one embodiment the amylin polypeptide according to this invention reduces plasma calcium levels in rats by less than 25% relative to vehicle at any time after single subcutaneous injection of up to 30 nmol/kg. In one embodiment the amylin polypeptide according to this invention reduces plasma calcium levels in rats by less than 20% relative to vehicle at any time after single subcutaneous injection up to 30 nmol/kg. In one embodiment the amylin polypeptide according to this invention reduces plasma calcium levels in rats by less than 15% relative to vehicle at any time after single subcutaneous injection of up to 30 nmol/kg.

In one embodiment the amylin polypeptide according to this invention reduces plasma calcium levels in rats by less than 10% relative to vehicle at any time after single subcutaneous injection of up to 30 nmol/kg. In one embodiment the amylin polypeptide according to this invention reduces plasma calcium levels in rats by less than 5% relative to vehicle at any time after single subcutaneous injection of up to 30 nmol/kg. In one embodiment the amylin polypeptide according to this invention reduces plasma calcium levels in rats by less than 1% relative to vehicle at any time after single subcutaneous injection of up to 30 nmol/kg.

In one embodiment the amylin polypeptide according to this invention reduces plasma calcium levels in rats by less than 30% relative to vehicle at any time after single subcutaneous injection of up to 1-30 nmol/kg. In one embodiment the amylin polypeptide according to this invention reduces plasma calcium levels in rats by less than 25% relative to vehicle at any time after single subcutaneous injection of up to 1-30 nmol/kg. In one embodiment the amylin polypeptide according to this invention reduces plasma calcium levels in rats by less than 20% relative to vehicle at any time after single subcutaneous injection up to 1-30 nmol/kg. In one embodiment the amylin polypeptide according to this invention reduces plasma calcium levels in rats by less than 15% relative to vehicle at any time after single subcutaneous injection of up to 1-30 nmol/kg. In one embodiment the amylin polypeptide according to this invention reduces plasma calcium levels in rats by less than 10% relative to vehicle at any time after single subcutaneous injection of up to 1-30 nmol/kg. In one embodiment the amylin polypeptide according to this invention reduces plasma calcium levels in rats by less than 5% relative to vehicle at any time after single subcutaneous injection of up to 1-30 nmol/kg. In one embodiment the amylin polypeptide according to this invention reduces plasma calcium levels in rats by less than 1% relative to vehicle at any time after single subcutaneous injection of up to 1-30 nmol/kg.

In one embodiment the amylin polypeptide according to this invention reduces plasma calcium levels in rats by less than 30% relative to vehicle at any time after single subcutaneous injection of up to 20-30 nmol/kg. In one embodiment the amylin polypeptide according to this invention reduces plasma calcium levels in rats by less than 25% relative to vehicle at any time after single subcutaneous injection of up to 20-30 nmol/kg. In one embodiment the amylin polypeptide according to this invention reduces plasma calcium levels in rats by less than 20% relative to vehicle at any time after single subcutaneous injection up to 20-30 nmol/kg. In one embodiment the amylin polypeptide according to this invention reduces plasma calcium levels in rats by less than 15% relative to vehicle at any time after single subcutaneous injection of up to 20-30 nmol/kg. In one embodiment the amylin polypeptide according to this invention reduces plasma calcium levels in rats by less than 10% relative to vehicle at any time after single subcutaneous injection of up to 20-30 nmol/kg. In one embodiment the amylin polypeptide according to this invention reduces plasma calcium levels in rats by less than 5% relative to vehicle at any time after single subcutaneous injection of up to 20-30 nmol/kg. In one embodiment the amylin polypeptide according to this invention reduces plasma calcium levels in rats by less than 1% relative to vehicle at any time after single subcutaneous injection of up to 20-30 nmol/kg.

In one embodiment the amylin polypeptide according to this invention reduces plasma calcium levels in rats by less than 30% relative to vehicle at any time after single subcutaneous injection of up to 3 nmol/kg. In one embodiment the amylin polypeptide according to this invention reduces plasma calcium levels in rats by less than 25% relative to vehicle at any time after single subcutaneous injection of up to 3 nmol/kg. In one embodiment the amylin polypeptide according to this invention reduces plasma calcium levels in rats by less than 20% relative to vehicle at any time after single subcutaneous injection up to 3 nmol/kg. In one embodiment the amylin polypeptide according to this invention reduces plasma calcium levels in rats by less than 15% relative to vehicle at any time after single subcutaneous injection of up to 3 nmol/kg. In one embodiment the amylin polypeptide according to this invention reduces plasma calcium levels in rats by less than 10% relative to vehicle at any time after single subcutaneous injection of up to 3 nmol/kg. In one embodiment the amylin polypeptide according to this invention reduces plasma calcium levels in rats by less than 5% relative to vehicle at any time after single subcutaneous injection of up to 3 nmol/kg. In one embodiment the amylin polypeptide according to this invention reduces plasma calcium levels in rats by less than 1% relative to vehicle at any time after single subcutaneous injection of up to 3 nmol/kg.

In one embodiment the amylin polypeptide according to this invention reduces plasma calcium levels in rats by less than 30% relative to vehicle at any time after single subcutaneous injection of up to 10 nmol/kg. In one embodiment the amylin polypeptide according to this invention reduces plasma calcium levels in rats by less than 25% relative to vehicle at any time after single subcutaneous injection of up to 10 nmol/kg. In one embodiment the amylin polypeptide according to this invention reduces plasma calcium levels in rats by less than 20% relative to vehicle at any time after single subcutaneous injection up to 10 nmol/kg. In one embodiment the amylin polypeptide according to this invention reduces plasma calcium levels in rats by less than 15% relative to vehicle at any time after single subcutaneous injection of up to 10 nmol/kg. In one embodiment the amylin polypeptide according to this invention reduces plasma calcium levels in rats by less than 10% relative to vehicle at any time after single subcutaneous injection of up to 10 nmol/kg. In one embodiment the amylin polypeptide according to this invention reduces plasma calcium levels in rats by less than 5% relative to vehicle at any time after single subcutaneous injection of up to 10 nmol/kg. In one embodiment the amylin polypeptide according to this invention reduces plasma calcium levels in rats by less than 1% relative to vehicle at any time after single subcutaneous injection of up to 10 nmol/kg.

In one embodiment the amylin polypeptide according to this invention reduces plasma calcium levels in rats by less than 30% relative to vehicle at any time after single subcutaneous injection of up to 15 nmol/kg. In one embodiment the amylin polypeptide according to this invention reduces plasma calcium levels in rats by less than 25% relative to vehicle at any time after single subcutaneous injection of up to 15 nmol/kg. In one embodiment the amylin polypeptide according to this invention reduces plasma calcium levels in rats by less than 20% relative to vehicle at any time after single subcutaneous injection up to 15 nmol/kg. In one embodiment the amylin polypeptide according to this invention reduces plasma calcium levels in rats by less than 15% relative to vehicle at any time after single subcutaneous injection of up to 15 nmol/kg. In one embodiment the amylin polypeptide according to this invention reduces plasma calcium levels in rats by less than 10% relative to vehicle at any time after single subcutaneous injection of up to 15 nmol/kg. In one embodiment the amylin polypeptide according to this invention reduces plasma calcium levels in rats by less than 5% relative to vehicle at any time after single subcutaneous injection of up to 15 nmol/kg. In one embodiment the amylin polypeptide according to this invention reduces plasma calcium levels in rats by less than 1% relative to vehicle at any time after single subcutaneous injection of up to 15 nmol/kg.

In one embodiment the amylin polypeptide according to this invention reduces plasma calcium levels in rats by less than 30% relative to vehicle at any time after single subcutaneous injection of up to 20 nmol/kg. In one embodiment the amylin polypeptide according to this invention reduces plasma calcium levels in rats by less than 25% relative to vehicle at any time after single subcutaneous injection of up to 20 nmol/kg. In one embodiment the amylin polypeptide according to this invention reduces plasma calcium levels in rats by less than 20% relative to vehicle at any time after single subcutaneous injection up to 20 nmol/kg. In one embodiment the amylin polypeptide according to this invention reduces plasma calcium levels in rats by less than 15% relative to vehicle at any time after single subcutaneous injection of up to 20 nmol/kg. In one embodiment the amylin polypeptide according to this invention reduces plasma calcium levels in rats by less than 10% relative to vehicle at any time after single subcutaneous injection of up to 20 nmol/kg. In one embodiment the amylin polypeptide according to this invention reduces plasma calcium levels in rats by less than 5% relative to vehicle at any time after single subcutaneous injection of up to 20 nmol/kg. In one embodiment the amylin polypeptide according to this invention reduces plasma calcium levels in rats by less than 1% relative to vehicle at any time after single subcutaneous injection of up to 20 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 30% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 25% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by more than 30% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 20% relative to vehicle at any time after single subcutaneous injection of 3 to 30 nmol/kg.

In one 25% or more relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by more than 30% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg.

In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 20% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 20% relative In one embodiment the amylin polypeptide according to this invention reduces food intake in rats by 25% or more relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by more than 30% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/ kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg In one embodiment the amylin polypeptide according to this invention reduces food intake in rats by more than 30% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg In one embodiment the amylin polypeptide according to this invention reduces food intake in rats by more than 30% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 15% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 15% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 15% relative In one embodiment the amylin polypeptide according to this invention reduces food intake in rats by 25% or more relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/ kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by more than 30% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 10% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 10% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 10% relative In one embodiment the amylin polypeptide according to this invention reduces food intake in rats by 25% or more relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by more than 30% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 5% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 5% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 5% relative In one embodiment the amylin polypeptide according to this invention reduces food intake in rats by more than 25% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg.

In one embodiment the amylin polypeptide according to this invention reduces food intake in rats by more than 325% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 3 nmol/kg and reduces plasma calcium levels in rats by less than 1% relative to vehicle at any time after single subcutaneous injection of 3 to 30 nmol/kg.

In one embodiment the amylin polypeptide according to this invention reduces food intake in rats by more than 30% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 3 nmol/kg and reduces plasma calcium levels in rats by less than 1% relative to vehicle at any time after single subcutaneous injection of 3 to 30 nmol/kg.

In one embodiment the amylin polypeptide according to this invention reduces food intake in rats by 25% or more relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 30% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the first 24 hours after single subcutaneous injection of 30 nmol/kg and reduces plasma calcium levels in rats by less than 1% relative to vehicle at any time after single subcutaneous injection of 3 to 30 nmol/kg.

In one embodiment the amylin polypeptide according to this invention reduces food intake in rats by 25% or more relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 30% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 40% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 50% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 60% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 70% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 80% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 90% relative to vehicle within the 24 to 48 hours after single subcutaneous injection of 30 nmol/kg and reduces plasma calcium levels in rats by less than 1% relative to vehicle at any time after single subcutaneous injection of 3 to 30 nmol/kg. In one embodiment the amylin polypeptide according to this invention reduces food intake in rats by more than 100% relative to vehicle within the 24 to 48 hours after single subcutaneous injection of 30 nmol/kg and reduces plasma calcium levels in rats by less than 1% relative The above embodiments are represented experimentally in table 15.

The treatment with a polypeptide according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, insulin derivative, insulin analogues, GLP-1, GLP-1 derivatives, GLP-1 analogues, oxyntomodulin derivatives, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the polypeptides according to the invention with one or more of the above-mentioned compounds and optionally one or more further pharmacologically active substances are considered to be within the scope of the present invention.

The invention will be further summarised but not limited in the paragraphs below:

1. A polypeptide selected from:
(i) a polypeptide comprising an amino acid sequence which is an analogue of SEQ ID No: 1 wherein:
  (a) said analogue comprises a proline residue at position 21;
  wherein the amino acid sequence numbering of the analogue corresponds to the amino acid numbering sequence of SEQ ID No: 1;
    optionally wherein (b) the polypeptide has an $IC_{50}$ in a human amylin receptor binding assay of about 1200 pM or less;
    optionally wherein the polypeptide has at least one substituent attached to at least one of its amino acid residues;
(ii) a polypeptide comprising an amino acid sequence which is an analogue of SEQ ID No: 1 wherein:
  (a) said analogue comprises a proline residue at position 21; and
  (b) said polypeptide has an $IC_{50}$ in a human amylin receptor binding assay of about 1200 pM or less;
  wherein the amino acid sequence numbering of the analogue corresponds to the amino acid numbering sequence of SEQ ID No: 1;
(iii) a polypeptide comprising an amino acid sequence which is an analogue of SEQ ID No: 1 wherein:
  (a) said analogue comprises a proline residue at position 21;
  wherein the amino acid sequence numbering of the analogue corresponds to the amino acid numbering sequence of SEQ ID No: 1; and
    wherein the polypeptide has at least one substituent attached to at least one of its amino acid residues; and
(iv) a polypeptide comprising an amino acid sequence which is an analogue of SEQ ID No: 1 wherein:
  (a) said analogue comprises a proline residue at position 21; and
  (b) said polypeptide has an $IC_{50}$ in a human amylin receptor binding assay of about 1200 pM or less;
  wherein the amino acid sequence numbering of the analogue corresponds to the amino acid numbering sequence of SEQ ID No: 1; and
    wherein the polypeptide has at least one substituent attached to at least one of its amino acid residues.

1A. A polypeptide selected from:
(i) a polypeptide according to SEQ ID No: 1 wherein:
  (a) said polypeptide comprises a proline residue at position 21;
  wherein the amino acid sequence numbering of the analogue corresponds to the amino acid numbering sequence of SEQ ID No: 1;
    optionally wherein (b) the polypeptide has an $IC_{50}$ in a human amylin receptor binding assay of about 1200 pM or less;
    optionally wherein the polypeptide has at least one substituent attached to at least one of its amino acid residues;
(ii) a polypeptide according to SEQ ID No: 1 wherein:
  (a) said polypeptide comprises a proline residue at position 21; and
  (b) said polypeptide has an $IC_{50}$ in a human amylin receptor binding assay of about 1200 pM or less;
  wherein the amino acid sequence numbering of the analogue corresponds to the amino acid numbering sequence of SEQ ID No: 1;
(iii) a polypeptide according to SEQ ID No: 1 wherein:
  (a) said polypeptide comprises a proline residue at position 21;
  wherein the amino acid sequence numbering of the analogue corresponds to the amino acid numbering sequence of SEQ ID No: 1; and
    wherein the polypeptide has at least one substituent attached to at least one of its amino acid residues; and
(iv) a polypeptide according to SEQ ID No: 1 wherein:
  (a) said polypeptide comprises a proline residue at position 21; and
  (b) said polypeptide has an $IC_{50}$ in a human amylin receptor binding assay of about 1200 pM or less;
  wherein the amino acid sequence numbering of the analogue corresponds to the amino acid numbering sequence of SEQ ID No: 1; and
wherein the polypeptide has at least one substituent attached to at least one of its amino acid residues.

1B. A polypeptide selected from:
(i) a polypeptide according to SEQ ID No: 1 having about a 10-fold or greater selectivity for binding to the human amylin receptor over binding to the human calcitonin receptor and wherein:
  (a) said polypeptide comprises a proline residue at position 21;
wherein the amino acid sequence numbering of the analogue corresponds to the amino acid numbering sequence of SEQ ID No: 1;
  optionally wherein (b) the polypeptide has an $IC_{50}$ in a human amylin receptor binding assay of about 1200 pM or less;
  optionally wherein the polypeptide has at least one substituent attached to at least one of its amino acid residues;
(ii) a polypeptide according to SEQ ID No: 1 having about a 10-fold or greater selectivity for binding to the human amylin receptor over binding to the human calcitonin receptor and wherein:
  (a) said polypeptide comprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1;
(iii) a polypeptide according to SEQ ID No: 1 having about a 10-fold or greater selectivity for binding to the human amylin receptor over binding to the human calcitonin receptor and wherein:
  (a) said polypeptide comprises a proline residue at position 21;
wherein the amino acid sequence numbering of the analogue corresponds to the amino acid numbering sequence of SEQ ID No: 1; and
  wherein the polypeptide has at least one substituent attached to at least one of its amino acid residues; and
(iv) a polypeptide according to SEQ ID No: 1 having about a 10-fold or greater selectivity for binding to the human amylin receptor over binding to the human calcitonin receptor and wherein:
  (a) said polypeptide comprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1; and
wherein the polypeptide has at least one substituent attached to at least one of its amino acid residues.

1C. A polypeptide selected from:
(i) an analogue of SEQ ID No: 1 wherein:
  (a) said analogue comprises a proline residue at position 21;
wherein the amino acid sequence numbering of the analogue corresponds to the amino acid numbering sequence of SEQ ID No: 1;
  optionally wherein (b) the polypeptide has an $IC_{50}$ in a human amylin receptor binding assay of about 1200 pM or less;
  optionally wherein the polypeptide has at least one substituent attached to at least one of its amino acid residues;
(ii) a polypeptide according to SEQ ID No: 1 wherein:
  (a) said analogue comprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1;
(iii) a polypeptide according to SEQ ID No: 1 wherein:
  (a) said analogue comprises a proline residue at position 21;
wherein the amino acid sequence numbering of the analogue corresponds to the amino acid numbering sequence of SEQ ID No: 1; and
  wherein the polypeptide has at least one substituent attached to at least one of its amino acid residues; and
(iv) a polypeptide according to SEQ ID No: 1 wherein:
  (a) said analoguecomprises a proline residue at position 21; and
  (b) said polypeptide has an $IC_{50}$ in a human amylin receptor binding assay of about 1200 pM or less;
wherein the amino acid sequence numbering of the analogue corresponds to the amino acid numbering sequence of SEQ ID No: 1; and
wherein the polypeptide has at least one substituent attached to at least one of its amino acid residues.

2. The polypeptide according to paragraph 1 which further has about a 10-fold or greater selectivity for binding to the human amylin receptor over binding to the human calcitonin receptor.

2A. The polypeptide according to paragraph 1 which further has about a 15-fold or greater selectivity for binding to the human amylin receptor over binding to the human calcitonin receptor.

2B. The polypeptide according to paragraph 1 which further has about a 20-fold or greater selectivity for binding to the human amylin receptor over binding to the human calcitonin receptor.

2C. The polypeptide according to paragraph 1 which further has about a 10 to 20-fold or greater selectivity for binding to the human amylin receptor over binding to the human calcitonin receptor.

3. The polypeptide according to any one of paragraphs 1 and 2 wherein the analogue comprises a proline or leucine residue at position 27, preferably proline.

4. The polypeptide according to any preceding paragraph wherein the analogue comprises a valine or arginine residue at position 17, preferably arginine.

5. The polypeptide according to any preceding paragraph wherein the analogue comprises an amino acid residue at position 1 selected from lysine, glycine and arginine; preferably lysine.

6. The polypeptide according to any preceding paragraph wherein the analogue comprises an amino acid residue at position 14 selected from aspartic acid, glutamic acid, histidine, asparagine, glycine, alanine, serine, lysine, threonine and cysteine; preferably selected from aspartic acid and glutamic acid; more preferably aspartic acid.

7. The polypeptide according to any preceding paragraph wherein the analogue comprises an amino acid residue at position 25 selected from proline and alanine; preferably alanine.

8. The polypeptide according to any preceding paragraph wherein the analogue comprises an amino acid residue at position 26 selected from proline and isoleucine, preferably isoleucine.

9. The polypeptide according to any preceding paragraph wherein the analogue comprises an amino acid residue at position 28 selected from proline and serine, preferably serine.

10. The polypeptide according to any preceding paragraph wherein the analogue comprises an amino acid residue at position 29 selected from proline or serine, preferably serine.

11. The polypeptide according to any preceding paragraph wherein the analogue comprises an amino acid residue at position 31 selected from proline and asparagine, preferably asparagine.

12. The polypeptide according to any preceding paragraph wherein the analogue comprises an amino acid residue at position 34 selected from proline, histidine, lysine, arginine and serine, preferably proline and serine, more preferably serine.

13. The polypeptide according to any preceding paragraph wherein the analogue comprises an amino acid residue at position 35 selected from aspartic acid, arginine, glutamic acid, lysine, histidine and asparagine, preferably asparagine and arginine, more preferably arginine.

14. The polypeptide according to any preceding paragraph wherein the analogue comprises an amino acid residue at position 37 selected from proline and tyrosine, preferably tyrosine.

15. The polypeptide according to any preceding paragraph wherein the analogue comprises an amino acid residue at position 14 which is aspartic acid, an amino acid residue at position 17 which is arginine, an amino acid residue at position 21 which is proline, an amino acid residue at position 27 which is proline and an amino acid residue at position 35 which is arginine.

15A. The polypeptide according to any of the paragraphs 1-14 (including the alternatives A, B, C) wherein the analogue comprises an amino acid residue at position 21 which is proline, an amino acid residue at position 27 which is proline and an amino acid residue at position 35 which is arginine.

15B. The polypeptide according to any of the paragraphs 1-14 (including the alternatives A, B, C) wherein the analogue comprises an amino acid residue at position 14 which is aspartic acid, an amino acid residue at position 21 which is proline, an amino acid residue at position 27 which is proline and an amino acid residue at position 35 which is arginine.

16. The polypeptide according any preceding paragraph wherein the analogue comprises the same amino acid residue at positions 2 to 13, 15 to 20, 22, 23, 24, 30, 32, 33 and 36 as the residues at positions 2 to 13, 15 to 20, 22, 23, 24, 30, 32, 33 and 36 of SEQ ID No: 1 respectively.

17. A polypeptide according to any one of paragraphs 1 and 2 comprising an analogue of SEQ ID No: 1 of formula (I):

(I)
Xaa$_1$-Cys-Asn-Thr-Ala-Thr-Cys-Ala-Thr-Gln-Arg-Leu-

Ala-Xaa$_{14}$-Phe-Leu-Xaa$_{17}$-His-Ser-Ser-Xaa$_{21}$-Asn-Phe-

Gly-Xaa$_{25}$-Xaa$_{26}$-Xaa$_{27}$-Xaa$_{28}$-Xaa$_{29}$-Thr-Xaa$_{31}$-Val-Gly-

Xaa$_{34}$-Xaa$_{35}$-Thr-Tyr;

wherein
Xaa$_1$ is independently selected from Gly, Arg and Lys;
Xaa$_{14}$ is independently selected from Asp, Glu, His, Arg, Gly, Ala, Ser, Lys, Thr and Cys;
Xaa$_{17}$ is independently selected from Arg and Val;
Xaa$_{21}$ is Pro;
Xaa$_{25}$ is independently selected from Pro and Ala;
Xaa$_{26}$ is independently selected from Pro and Ile;
Xaa$_{27}$ is independently selected from Pro and Leu;
Xaa$_{28}$ is independently selected from Pro and Ser;
Xaa$_{29}$ is independently selected from Pro and Ser;
Xaa$_{31}$ is independently selected from Pro and Asn;
Xaa$_{34}$ is independently selected from Pro, His, Lys, Arg and Ser
Xaa$_{35}$ is independently selected from Asp, Arg, Glu, Lys, His and Asn;
Xaa$_{37}$ is independently selected from Pro and Tyr;
and where the C-terminal may optionally be derivatized.

17A. A polypeptide according to any one of paragraphs 1 and 2 comprising an analogue of SEQ ID No: 1 of formula (I):

(I)
Xaa$_1$-Cys-Asn-Thr-Ala-Thr-Cys-Ala-Thr-Gln-Arg-Leu-

Ala-Xaa$_{14}$-Phe-Leu-Xaa$_{17}$-His-Ser-Ser-Xaa$_{21}$-Asn-Phe-

Gly-Xaa$_{25}$-Xaa$_{26}$-Xaa$_{27}$-Xaa$_{28}$-Xaa$_{29}$-Thr-Xaa$_{31}$-Val-Gly-

Xaa$_{34}$-Xaa$_{35}$-Thr-Xaa$_{37}$;

wherein
Xaa$_1$ is independently selected from Gly, Arg and Lys;
Xaa$_{14}$ is independently selected from Asp, Glu, His, Arg, Gly, Ala, Ser, Lys, Thr and Cys;
Xaa$_{17}$ is independently selected from Arg and Val;
Xaa$_{21}$ is Pro;
Xaa$_{25}$ is independently selected from Pro and Ala;
Xaa$_{26}$ is independently selected from Pro and Ile;
Xaa$_{27}$ is independently selected from Pro and Leu;
Xaa$_{28}$ is independently selected from Pro and Ser;
Xaa$_{29}$ is independently selected from Pro and Ser;
Xaa$_{31}$ is independently selected from Pro and Asn;
Xaa$_{34}$ is independently selected from Pro, His, Lys, Arg and Ser
Xaa$_{35}$ is independently selected from Asp, Arg, Glu, Lys, His and Asn;
Xaa$_{37}$ is independently selected from Pro and Tyr;
and where the C-terminal may optionally be derivatized.

18. A polypeptide according to any one of paragraphs 1 and 2 consisting of an analogue of SEQ ID No: 1 of formula (I) as defined in paragraph 17.

19. The polypeptide according to any one of paragraphs 17 and 18 wherein Xaa$_{27}$ is Pro.

20. The polypeptide according to any one of paragraphs 17 to 19 wherein Xaa$_{17}$ is Arg.

21. The polypeptide according to any one of paragraphs 17 to 20 wherein Xaa$_{37}$ is Tyr.

22. The polypeptide according to any one of paragraphs 17 to 21 wherein Xaa$_{14}$ is selected from Asp and Glu, preferably Asp.

23. The polypeptide according to any one of paragraphs 17 to 22 wherein Xaa$_{35}$ is selected from Asn and Arg, preferably Arg.

24. The polypeptide according to any one of paragraphs 17 to 23 wherein Xaa$_{34}$ is selected from Pro and Ser, preferably Ser.

25. The polypeptide according to any one of paragraphs 17 to 24 wherein Xaa$_1$ is Lys.

26. The polypeptide according to any one of paragraphs 17 to 25 wherein Xaa$_1$ is Lys, Xaa$_{14}$ is Asp, Xaa$_{17}$ is Arg, Xaa$_{21}$ is Pro, Xaa$_{25}$ is Ala, Xaa$_{26}$ is Ile, Xaa$_{27}$ is Pro, Xaa$_{28}$ is Ser, Xaa$_{29}$ is Ser, Xaa$_3$, is Asn, Xaa$_{34}$ is Ser, Xaa$_{35}$ is Asn, Xaa$_{27}$ is Tyr.

26A. The polypeptide according to any one of paragraphs 17 to 25 wherein Xaa$_1$ is Lys, Xaa$_{14}$ is Asp, Xaa$_{17}$ is Arg, Xaa$_{21}$ is Pro, Xaa$_{25}$ is Ala, Xaa$_{26}$ is Ile, Xaa$_{27}$ is Pro, Xaa$_{28}$ is Ser, Xaa$_{29}$ is Ser, Xaa$_{31}$ is Asn, Xaa$_{34}$ is Ser, Xaa$_{35}$ is Asn, Xaa$_{37}$ is Tyr.

27. The polypeptide according to any one of the preceding paragraphs comprising a C-terminal amide.

28. The polypeptide according to any one of the preceding paragraphs wherein at least one substituent is attached to one of the amino acid residues.

29. The polypeptide according to paragraph 28 wherein the substituent is selected from a hydrocarbyl group, a hydroxyl group and a halogen atom.

30. The polypeptide according to paragraphs 29 wherein the substituent group is of formula (II):

$$L_n\text{-}Y \quad (II)$$

wherein
L is a linker;
n=0 or 1
Y is an albumin binding moiety.

31. The polypeptide according to paragraph 30 wherein the albumin binding moiety is an acyl group selected from:
(a) $CH_3(CH_2)_rCO-$, wherein r is an integer from 12 to 20;
(b) $HOOC(CH_2)_sCO-$, wherein s is an integer from 12 to 22 or s is an integer from 12 to 18, or s is 16 to 18 or preferably s is 18.

32. The polypeptide according to any one of paragraphs 30 and 31 wherein the linker is selected from the group consisting of γGlu, γGlu-γGlu, γGlu-γGlu-γGlu, γGlu-γGlu-γGlu-γGlu, Glu, Glu-Glu, Glu-γGlu, Glu-Arg, Glu-Glu-Arg, His, His-His, His-γGlu, His-His-γGlu, Gly, Gly-γGlu, Ser, Ser-γGlu, D-Arg-D-Arg, Arg, Arg-Arg, Arg-Arg-γGlu, Ser-Ser, -Gly-Ser-Ser, Ser-Ser, -Gly-Ser-Ser-γGlu, Ser-Ser-Gly-Ser-Ser-Gly and Ser-Ser-Gly-Ser-Ser-Gly-γGlu, γGlu-OEG, γGlu-OEG-OEG and OEG, preferably the linker is selected from γGlu, γGlu-γGlu, γGlu-OEG, γGlu-OEG-OEG and OEG, more preferably the linker is γGlu-γGlu.

33. The polypeptide according to any one of paragraphs 29 to 32 wherein the substituent group is selected from the groups presented in Table 1 (presented earlier).

34. The polypeptide according to any one of paragraphs 28 to 33 wherein a substituent is attached to the α-amino group of the N-terminal amino acid residue or to a Lys residue.

35. The polypeptide according to any one of paragraphs 28 to 34 wherein a substituent is attached to the N-terminal amino acid residue or to a lysine residue via the &amino group, preferably the substituent is attached to a lysine residue via the &amino group.

36. The polypeptide according any one of paragraphs 28 to 35 wherein the substitutent is attached to a lysine residue at position 1 only.

37. The polypeptide according to paragraph 36 wherein the substituent is attached to the lysine residue either via the α-amino group or via the &amino group, preferably the substituent is attached to a lysine residue via the &amino group.

38. The polypeptide according to any preceding paragraphs selected from the group consisting of any of the polypeptides presented in Table 2 (presented earlier) or from the group consisting of any of the polypeptides presented in Table 3 (presented earlier) or from the group consisting of any of the polypeptides presented in Table 4 (presented later) or from the group consisting of any of the polypeptides presented in Table 5 (presented later) or from the group consisting of any of the polypeptides presented in Table 5a (presented later) or from the group consisting of any of the polypeptides presented in Table 6 (presented later) or from the group consisting of any of the polypeptides presented in Table 6a (presented later) or from the group consisting of any of the polypeptides presented in Table 7 (presented later) or from the group consisting of any of the polypeptides presented in Table 7a (presented later) or from the group consisting of any of the polypeptides presented in Table 7b (presented later) or from the group consisting of any of the polypeptides presented in Table 8 (presented later) or from the group consisting of any of the polypeptides presented in Table 9 (presented later) or from the group consisting of any of the polypeptides presented in Table 10 (presented later) or from the group consisting of any of the polypeptides presented in Table 11 (presented later) from the group consisting of any of the polypeptides presented in Table 12 (presented later) or from the group consisting of any of the polypeptides presented in Table 13 (presented later) or from the group consisting of any of the polypeptides presented in Table 14 (presented later).

38A. The polypeptide according to any of the preceding paragraphs selected from the group consisting of the polypeptides in Table 2 (presented earlier) or from the group consisting of any of the polypeptides presented in Table 3 (presented earlier) or from the group consisting of any of the polypeptides presented in Table 4 (presented later) or from the group consisting of any of the polypeptides presented in Table 4a (presented later) or from the group consisting of any of the polypeptides presented in Table 4b (presented later) or from the group consisting of any of the polypeptides presented in Table 4c (presented later) or from the group consisting of any of the polypeptides presented in Table 5 (presented later) or from the group consisting of any of the polypeptides presented in Table 5a (presented later) or from the group consisting of any of the polypeptides presented in Table 5b (presented later) or from the group consisting of any of the polypeptides presented in Table 5c (presented later) or from the group consisting of any of the polypeptides presented in Table 6 (presented later) or from the group consisting of any of the polypeptides presented in Table 6a (presented later) or from the group consisting of any of the polypeptides presented in Table 6b (presented later) or from the group consisting of any of the polypeptides presented in Table 6c (presented later) or from the group consisting of any of the polypeptides presented in Table 6d (presented later) or from the group consisting of any of the polypeptides presented in Table 6e (presented later) or from the group consisting of any of the polypeptides presented in Table 6f (presented later) or from the group consisting of any of the polypeptides presented in Table 6g (presented later) or from the group consisting of any of the polypeptides presented in Table 6h (presented later) or from the group consisting of any of the polypeptides presented in Table 6i (presented later) or from the group consisting of any of the polypeptides presented in Table 6j (presented later) or from the group consisting of any of the polypeptides presented in Table 6k (presented later) or from the group consisting of any of the polypeptides presented in Table 6l (presented later) or from the group consisting of any of the polypeptides presented in Table 6m (presented later) or from the group consisting of any of the polypeptides presented in Table 6n (presented later) or from the group consisting of any of the polypeptides presented in Table 6o (presented later) or from the group consisting of any of the polypeptides presented in Table 7 (presented later) or from the group consisting of any of the polypeptides presented in Table 7a (presented later) or from the group consisting of any of the polypeptides presented in Table 7b (presented later) or from the group consisting of any of the polypeptides presented in Table 7c (presented later) or from the group consisting of any of the polypeptides presented in Table 8 (presented later) or from the group consisting of any of the polypeptides presented in Table 8a (presented later) or from the group consisting of any of the polypeptides presented in Table 9 (presented later) or from the group consisting of any of the polypeptides presented in Table 9a (presented later) or from the group consisting of any of the polypeptides presented in Table 10 (presented later) or from the group consisting of any of the polypeptides presented in Table 11 (presented later) from the group consisting of any of the polypeptides presented in Table 12 (presented later) or from the group consisting of any of the polypeptides presented in Table 13 (presented later) or from the group consisting of any of the polypeptides presented in Table 14 (presented later).

39. The polypeptide according to any preceding paragraphs selected from the group consisting of any of the polypeptides presented in Table 5a (presented later) or from the group consisting of any of the polypeptides presented in Table 6a (presented later) or from the group consisting of any of the polypeptides presented in Table 7a (presented later) or from the group consisting of any of the polypeptides presented in Table 7b (presented later).

40. The polypeptide according to any one of the preceding paragraphs wherein said polypeptide is:
N-ε-1-{(S)-4-carboxy-4-[(S)-4-carboxy-4-(19-carboxynonadecanoylamino)butyrylamino]butyryl}-[Asp14,Arg17,Pro21,Pro27,Arg35]-human amylin. The amino acid sequence of said polypeptide is designated as SEQ ID NO: 4.

40A. The polypeptide according to any one of the preceding paragraphs wherein said polypeptide is:
$N^{\epsilon 1}$-[(4S)-4-carboxy-4-[[(4S)-4-carboxy-4-(19-carboxynonadecanoylamino)butanoyl]amino]butanoyl]-[Asp14,Arg17,Pro21,Pro27,Arg35]-h-amylin. The amino acid sequence of said polypeptide is designated as SEQ ID NO: 4.

41. A pharmaceutical composition comprising a polypeptide according to any of the preceding paragraphs and a pharmaceutically acceptable excipient.

42. The pharmaceutical composition according to paragraph 41, which is suited for parenteral administration.

43. A process for preparing a pharmaceutical composition according to paragraph 41 or paragraph 42 comprising mixing a polypeptide according to any preceding paragraph with at least one pharmaceutically acceptable excipient.

44. A polypeptide according to any of the preceding paragraphs for use as a medicament.

45. A polypeptide according to any one of the preceding paragraphs for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

46. A polypeptide according to any one of the preceding paragraphs for use in delaying or preventing disease progression in type 2 diabetes.

47. A polypeptide according to any one of the preceding paragraphs for use in preventing or treating obesity.

48. A polypeptide according to any one of the preceding paragraphs for use in decreasing food intake, decreasing β-cell apoptosis, increasing β-cell function and β-cell mass, and/or for restoring glucose sensitivity to β-cells.

49. A method of treating or preventing hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers by administering a polypeptide according to any preceding paragraph to an animal.

50. A method of delaying or preventing disease progression in type 2 diabetes by administering a polypeptide according to any preceding paragraph to an animal.

51. A method of decreasing food intake, decreasing β-cell apoptosis, increasing β-cell function and β-cell mass, and/or for restoring glucose sensitivity to β-cells by administering a polypeptide according to any preceding paragraph to an animal.

52. The invention according to any one of the preceding paragraphs wherein said polypeptide has an $IC_{50}$ in a human amylin receptor binding assay of about 1200 pM or less.

53. The invention according to any one of the preceding paragraphs wherein said polypeptide reduces food intake in rats by 25% or more relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg.

54. The invention according to any one of the preceding paragraphs wherein said polypeptide reduces food intake in rats by 25% or more relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg.

55. The invention according to any one of the preceding paragraphs wherein said polypeptide reduces food intake in rats by 30% or more relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg.

56. The invention according to any one of the preceding paragraphs wherein said polypeptide reduces food intake in rats by 25% or more relative to vehicle within the first 24 hours after single subcutaneous injection of 30 nmol/kg and reduces plasma calcium levels in rats by less than 30% relative to vehicle at any time after single subcutaneous injection of 3 to 30 nmol/kg.

57. The invention according to any one of the preceding paragraphs wherein said polypeptide reduces food intake in rats by 30% or more relative to vehicle within the first 24 hours after single subcutaneous injection of 30 nmol/kg and reduces plasma calcium levels in rats by less than 30% relative to vehicle at any time after single subcutaneous injection of 3 to 30 nmol/kg.

The invention will be further summarised but not limited in the paragraphs below:

1. A polypeptide which is an analogue of SEQ ID No: 1 having about a 10-fold or greater selectivity for binding to the human amylin receptor over binding to the human calcitonin receptor and wherein:

(a) said analogue of SEQ ID No: 1 comprises a proline residue at position 21;
wherein the amino acid sequence numbering of the analogue corresponds to the amino acid numbering sequence of SEQ ID No: 1; and
(b) wherein the polypeptide has at least one substituent attached to at least one of its amino acid residues and optionally
(c) wherein the polypeptide has an $IC_{50}$ in a human amylin receptor binding assay of about 1200 pM or less.

2. The polypeptide according to any one of paragraphs 1 and 2 wherein the analogue comprises a proline or leucine residue at position 27.

3. The polypeptide according to any one of paragraphs 1 and 2 wherein the analogue comprises a proline residue at position 27.

4. The polypeptide according any preceding paragraph wherein the analogue comprises an amino acid residue at position 14 which is aspartic acid, an amino acid residue at position 17 which is arginine, an amino acid residue at position 21 which is proline, an amino acid residue at position 27 which is proline and an amino acid residue at position 35 which is arginine.

5. A polypeptide according to any one of paragraphs 1 and 2 comprising an analogue of SEQ ID No: 1 according to formula (I):

(I)
Xaa$_1$-Cys-Asn-Thr-Ala-Thr-Cys-Ala-Thr-Gln-Arg-Leu-

Ala-Xaa$_{14}$-Phe-Leu-Xaa$_{17}$-His-Ser-Ser-Xaa$_{21}$-Asn-Phe-

Gly-Xaa$_{25}$-Xaa$_{26}$-Xaa$_{27}$-Xaa$_{28}$-Xaa$_{29}$-Thr-Xaa$_{31}$-Val-Gly-

Xaa$_{34}$-Xaa$_{35}$-Thr-Xaa$_{37}$;

wherein
Xaa$_1$ is independently selected from Ala, Cys, Glu, Gly, His, Arg, Ser and Lys;
Xaa$_{14}$ is independently selected from Asp, Glu, His, Asn, Arg, Gly, Ala, Ser, Lys, Thr and Cys;
Xaa$_{17}$ is independently selected from Arg and Val;
Xaa$_{21}$ is Pro;
Xaa$_{25}$ is independently selected from Pro and Ala;
Xaa$_{26}$ is independently selected from Pro and Ile;
Xaa$_{27}$ is independently selected from Pro and Leu;
Xaa$_{28}$ is independently selected from Pro and Ser;
Xaa$_{29}$ is independently selected from Pro and Ser;
Xaa$_{31}$ is independently selected from Pro and Asn;
Xaa$_{34}$ is independently selected from Pro, His, Lys, Arg and Ser
Xaa$_{35}$ is independently selected from Asp, Arg, Glu, Lys, His and Asn;
Xaa$_{37}$ is independently selected from Pro and Tyr;
and where the C-terminal may optionally be derivatized.

6. The polypeptide according to paragraph 5 wherein Xaa$_1$ is Lys, Xaa$_{14}$ is Asp, Xaa$_{17}$ is Arg, Xaa$_{21}$ is Pro, Xaa$_{25}$ is Ala, Xaa$_{26}$ is Ile, Xaa$_{27}$ is Pro, Xaa$_{28}$ is Ser, Xaa$_{29}$ is Ser, Xaa$_{31}$ is Asn, Xaa$_{34}$ is Ser, Xaa$_{35}$ is Asn, Xaa$_{37}$ is Tyr. (SEQ ID NO:3)

7. The polypeptide according to paragraph 7 wherein the substituent group is selected from any of the substituent groups presented in Table 1 (presented earlier).

8. The polypeptide according to any preceding paragraph wherein a substituent is attached to the α-amino group of the N-terminal amino acid residue or to a Lys residue or cysteine residue only.

9. The polypeptide according to any of the preceding paragraphs either selected from the group consisting of any of the polypeptides presented in Table 2 (presented earlier) or selected from the group consisting of any of the polypeptides presented in Table 3 (presented earlier).

10. The polypeptide according to any of the preceding paragraphs wherein the polypeptide is N-ϵ-1-{(S)-4-carboxy-4-[(S)-4-carboxy-4-(19-carboxynonadecanoylamino)butyrylamino]butyryl}-[Asp14,Arg17,Pro21,Pro27,Arg35]-human amylin.

11. A polypeptide according to any of the preceding paragraphs for use as a medicament.

12. A polypeptide according to any of the preceding paragraphs either for use in the treatment or prevention of hyperglycemia, type 2 diabetes, impaired glucose tolerance, type diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers and/or for use in decreasing food intake, decreasing n-cell apoptosis, increasing n-cell function and n-cell mass, and/or for restoring glucose sensitivity to n-cells.

13. The invention according to any one of the preceding paragraphs wherein said polypeptide reduces food intake in rats by 25% or more relative to vehicle within the first 24 hours after single subcutaneous injection of 3 nmol/kg and reduces plasma calcium levels in rats by less than 30% relative to vehicle at any time after single subcutaneous injection of 3 to 30 nmol/kg.

14. A pharmaceutical composition comprising a polypeptide according to any of the preceding paragraphs and a pharmaceutically acceptable excipient.

15. A process for preparing a pharmaceutical composition according to paragraph 14 comprising mixing a polypeptide according to any preceding paragraph with at least one pharmaceutically acceptable excipient.

The present invention will now be described only by way of examples.

EXAMPLES

Abbreviations

Some of the abbreviations used in the Examples are as follows:
Acm: acetamidomethyl
HATU: (O-(7-azabenzotriazol-1-yl)-1,1,3,3-tetramethyluronium hexafluorophosphate)
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl
Mtt: 4-methyltrityl
DCM: dichloromethane
TIPS: triisopropylsilane
TFA: trifluoroacetic acid
NMP: 1-Methyl-pyrrolidin-2-one
HOAt: 1-Hydroxy-7-azabenzotriazole
DIC: Diisopropylcarbodiimide
Trt: triphenylmethyl
Assays
In the following examples reference is made to the following Assays:
ASSAY (I)—Experimental protocol for efficacy testing on appetite using an ad libitum fed rat model
ASSAY (II)a—Functional assay—Human calcitonin and amylin receptor assay
ASSAY (II)b—Functional assay—Rat calcitonin and rat amylin receptor assays
ASSAY (III)—ThT fibrillation assays for the assessment of physical stability of protein formulations
ASSAY (IV)—Determination of solubility
ASSAY (V)—Determination of binding to the human amylin receptor
ASSAY (VI)—Determination of the binding to the rat amylin receptor
ASSAY (VII)—Determination of binding to the human calcitonin receptor
ASSAY (VIII)—Determination of binding to the rat calcitonin receptor
ASSAY (IX)— pK—Determination of T½ in mini-pig
ASSAY (X)—pK—Determination of T½ in rat
ASSAY (XI)—Effect from single subcutaneous administration of analogue on plasma calcium in rats
ASSAY (XII)—Effect from single subcutaneous administration of analogue on plasma calcium in rats Assay (I)— Experimental Protocol for Efficacy Testing on Appetite Using an Ad Libitum Fed Rat MODEL Sprague Dawley (SD) rats from Taconic Europe, Denmark are used for the experiments. The rats have a body weight 200-250 g at the start of experiment. The rats arrive at least 10-14 days before start of experiment to allow acclimatization to experimental settings. During this period the animals are handled at least 2 times. After arrival rats are housed individually for one week in a reversed light/dark phase (meaning that lights are off during daytime and on during nighttime) for two weeks. Since rats are normally active and eat their major part of their daily food intake during the dark period, rats are dosed in the morning right before lights are turned off. This set-up results in the lowest data variation and highst test sensitivity. The experiment is conducted in the rats' home cages and rats have free access to food and water throughout the acclimatization period and the experiment period. Each dose of derivative is tested in a group of 5-8 rats. A vehicle group of 6-8 rats is included in each set of testing. Rats are dosed once according to body weight with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by online registration or manually every hour for 7 hours, and then after 24 h and sometimes 48 h. At the end of the experimental session, the animals are euthanized.

The individual data are recorded in Microsoft excel sheets. Outliers are excluded after applying the Grubbs statistical evaluation test for outliers, and the result is presented graphically using the GraphPad Prism program.

Assay (II)—Functional Assays
Assay (II)a—Human Calcitonin and Amylin Receptor Assay
1. Luciferase Assay Outline Activation of calcitonin and amylin (coexpression of calcitonin receptor and receptor activity modifying proteins (RAMP)) receptors lead to increased intracellular concentrations of cAMP. Consequently, transcription is activated by promoters containing multiple copies of the cAMP response element (CRE). It is thus possible to measure amylin activity by the use of a CRE luciferase reporter gene introduced into BHK cells also expressing calcitonin or amylin receptors.

2. Construction of Calcitonin (a)- and Amylin 3(a)-Receptor/ CRE-Luc Cell Line.

A BHK570 cell line was stably transfected with the human calcitonin receptor and a CRE-responsive luciferase reporter gene. The cell line was further transfected with RAMP-3, using standard methods. This turns the calcitonin receptor into an amylin 3(a) receptor. Methotrexate, Neomycin, and Hygromycin are selection markers for luciferase, the calcitonin receptor, and RAMP-3, respectively.

3. Luciferase Assays

To perform activity assays, BHK calcitonin (a) receptor- or amylin 3(a)-receptor/CRE-luc cells were seeded in white 96 well culture plates at a density of about 20.000 cells/well. The cells were in 100 µl growth medium (DMEM with 10% FBS, 1% Pen/Strep, 1 mM Na-pyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glutamax™, 10% FBS, and 10 mM Hepes, pH 7.4). Further, 50 µl/well of standard or sample in assay buffer were added. After 3 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was measured on a TopCounter (Packard) in SPC (single photon counting) mode.

Assay (II)b—Rat Calcitonin and Rat Amylin Receptor Assays
cAMP Assay Outline

Activation of calcitonin and amylin (coexpression of calcitonin receptor and receptor activity modifying proteins (RAMP)) receptors lead to increased intracellular concentrations of cAMP. In order to quantify the cAMP levels in transiently transfected cells the Adenylyl Cyclase Activation FlashPlate® Assay from Perkin Elmer was used. The basic principle of the FlashPlate® Assay is a competition between radioactive and non-radioactive cAMP generated by the cells for a fixed number of binding sites.

Construction of Rat Calcitonin(a)- and Rat Amylin 3(a)-Receptor Cells.

BHK tk'ts 13 cells were transiently transfected with either rat calcitonin (a) receptor or amylin 3 (a) receptor (rat calcitonin (a) receptor+rat RAMP3) using FuGENE® 6 (Roche), according to the manufacturers recommendations.

cAMP Assay 24 hours after transient transfection the cells (rat calcitonin (a)- or rat amylin 3(a)-receptor cells) were added (100.000 cells/well) to the 96 well FlashPlates® with samples or standard in FlashPlate stimulation buffer with IBMX and incubated for 30 min. Detection mix was created according to manufacturers protocol and scintillation measured after 3 h of incubation on TopCounter™ (Packard).

Assay (III)—ThT Fibrillation Assays for the Assessment of Physical Stability of Protein Formulations Low physical stability of a polypeptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 09, 274-284].

The time course for fibril formation can be described by a sigmoidal curve with the following expression [Nielsen et al. (2001) Biochemistry 40, 6036-6046];

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the polypeptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and $HClO_4$ or HCl. Thioflavin T was added to the samples from a stock solution in $H_2O$ to a final concentration of 1 µM.

Sample aliquots of 200 µl were placed in a 96 well microtiter plate (Packard OptiPlate™96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader or Varioskan platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the samples and shown with the standard deviation at various time points.

Measurement of Initial and Final Concentrations

The polypeptide concentration in each of the tested formulations were measured both before application in the ThT fibrillation assay ("Initial") and after completion of the ThT fibrillation ("After ThT assay"). Concentrations were determined by reverse HPLC methods using a pramlintide standard as a reference. Before measurement after completion 150 µl was collected from each of the replica and transferred to an Eppendorf tube. These were centrifuged at 30000 G for 40 mins. The supernatants were filtered through a 0.22 µm filter before application on the HPLC system.

Assay (IV)—Determination of Solubility

The polypeptide was dissolved in water at ~500 nmol/ml and mixed 1:1 with a series of buffers (100 mM glycylglycine pH 3.0, 100 mM glycylglycine pH 4.0, 100 mM glycylglycine pH 5.0, 100 mM bistrispropane pH 6.0, 100 mM bistrispropane pH 6.5, 100 mM bistrispropane pH 7.0, 100 mM bistrispropane pH 7.5, 100 mM bistrispropane pH 8.0). After 18 hours at room temperature the samples were centrifuged and the polypeptide concentration determined by UPLC.

Assay (V)—Determination of Binding to the Human Amylin Receptor

The binding assay was performed using scintillation proximity assay (SPA) beads (RPNQ0001) from PerkinElmer and cell membranes from the Amylin 3(a)/CRE-luc cells (as described in Assay (II)) were used. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized (ultrathurrax) in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was measured (BCA protein Assay, Pierce). The homogenate was kept cold during the whole procedure. The membranes were kept at −80° C. until use. The assay was performed in a 384 well Optiplate (PerkinElmer) in a total volume of 40 ul. Membranes were mixed with SPA beads. Final concentration of membranes 35 ng/µL final and SPA beads was 0.05 mg/well. Test-compounds were dissolved in DMSO and further diluted in assay buffer (50 mM Hepes, pH 7.4, 1 mM CaCl2, 5 mM $MgCl_2$, 0.1% OA and 0.02% Tween20). Radioligand $^{125}$I-rat amylin (NEX448 PerkinElmer) was dissolved in assay buffer and added to the Optiplate at a final concentration of 50 pM/well (approx. 20.000 cpm/10 ul). The final mixture was incubated with shaking at 400 rpm for 120 min at 25° C. prior to centrifugation (1500 rpm, 10 min). Samples were analyzed on TopCounter™ (Packard). The $IC_{50}$ was calculated using (one site binding competition analysis) GraphPad Prism5 as a measure of receptor affinity.

Assay (VI)—Determination of the Binding to the Rat Amylin Receptor

The assay was performed as described above (Assay (V)—Determination of binding to the human amylin receptor) with the exception that we used membranes prepared from BHK tk'ts 13 cells that were transiently transfected with the rat calcitonin receptor rat RAMP 3 at an equimolar ratio (1:2). The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

Assay (VII)—Determination of binding to the human calcitonin receptor

The binding assay was performed using scintillation proximity assay (SPA) beads (RPNQ0001) from PerkinElmer and cell membranes prepared from a BHK tk'ts 13 cell line was stably transfected with the human calcitonin receptor and a CRE-responsive luciferase reporter gene. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized (Ultrathurrax) in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was measured (BCA protein Assay, Pierce). The homogenate was kept cold during the whole procedure. The membranes were kept at −80° C. until use. Assay was performed in a 384 well Optiplate (PerkinElmer) in a total volume of 40 ul. Membranes were mixed with SPA beads. Final concentration of membranes 35 ng/µL final and Final concentration of SPA beads was 0.05 mg/well. Test-compounds were dissolved in DMSO and further diluted in assay buffer (50 mM Hepes, pH 7.4, 1 mM CaCl2, 5 mM $MgCl_2$, 0.1% OA and 0.02% Tween20). Radioligand $^{125}$I-Calcitonin (NEX422 PerkinElmer) was dissolved in assay buffer and added to the Optiplate at a final concentration of 75 pM/well (approx. 30.000 cpm/10 ul). The final mixture was incubated for 120 min with shaking at 400 rpm at 25° C. prior to centrifugation (1500 rpm, 10 min). Samples were analyzed on TopCounter™ (Packard). The $I_{50}$ was calculated using (one site binding competition analysis) GraphPad Prism5 as a measure of receptor affinity.

Assay (VIII)—Determination of Binding to the Rat Calcitonin Receptor

The assay was performed as described above (Assay (VII)—Determination of binding to the human calcitonin receptor) with the exception that we used membranes prepared from BHK tk'ts 13 cells that were transiently transfected with the rat calcitonin receptor. The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

Assay (IX)—pK—Determination of T½ in Mini-Pig

T½ is the terminal half-life=ln $2/\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in male Göttingen mini-pigs from Ellegaard Göttingen Minipigs ApS and the principles of laboratory animal care are followed.

An acclimatisation period of approximately 6-10 days was allowed before the animals entered the study. At start of the acclimatisation period the mini-pigs were about 5 to 12 months old and in the weight range of 7-35 kg. The mini-pigs had two central venous catheters inserted which were used for blood sampling.

The studies were conducted in an animal room which was illuminated to give a cycle of approx 12 hours light and 12 hours darkness. The animals were housed individually.

The animals had free access to domestic quality drinking water during the study, but were typically fasted from overnight before dosing until approx 6-12 hours after dosing. The animals were weighed on arrival and on the days of dosing.

In the present studies the test substances were administered subcutaneously in approx 2 nmol/kg dose. The animals received a single subcutaneous injection. The subcutaneous injection was given on the right side of the neck, approximately 5-7 cm from the ear and 7-9 cm from the middle of the neck. The injections were given with a stopper on the needle, allowing approx 0.5 cm of the needle to be introduced. Each test substance was given to typically three but in some cases two or four animals.

A full plasma concentration-time profile, employing 12-16 sampling points, was obtained from each animal. In example blood samples were collected according to the following schedule: After subcutaneous administration:

Predose (0), 0.5, 1, 2, 4, 6, 8, 12, 24, 48, 72, 96, 120, 168 and 240 hours after injection.

In some cases also additional blood samples up to 288 hours post injection were taken.

At each sampling time, 0.5 to 2 ml of blood was drawn from each animal. The blood samples were taken via the central venous catheter.

The blood samples were collected into EDTA test tubes (i.e. Sarstedt Micro tube 1.3 mL K3E). Blood samples were kept on ice for max 20 min. before centrifugation. Plasma was separated using centrifugation (i.e. at 4° C., 10 min., 1500 G) and was immediately transferred to Micronic tubes. Approximately 200 µl plasma was transferred to each Micronic tube.

The plasma was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln $2/\lambda_z$ and was determined from $\lambda_z$ the first order rate constant associated with the terminal (log-linear) portion of the curve, estimated by linear regression of time vs. log concentration.

ELISA Plasma Assay for Amylin Quantification

The human amylin ELISA is a monoclonal antibody-based sandwich immunoassay for determining amylin levels in human plasma. The capture antibody recognizes human amylin, amylin acid (deamidated amylin), a 1-20 fragment of amylin, but not reduced amylin. The detection antibody binds to reduced or unreduced human amylin but not amylin acid and is complexed with streptavidin-alkaline phosphatase. The substrate, 4-methylumbelliferyl phosphate, is applied to the completed sandwich and the fluorescent signal, monitored at 355 nm/460 nm, is proportional to the amount of amylin present in the sample.

MS-Method for Amylin Quantification

40 µl plasma is diluted with 120 µl 66.67% EtOH+1% HCOOH and mixed. Centrifuged for 20 min. at 13000 rpm, 4° C. The supernatant is analyzed by an LC-MS method on a Sciex API 3000 and quantitated with a standard made up in plasma Assay (X)—pK—Determination of T½ in Rat T½ is the terminal half-life=ln $2/\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in Sprague Dawley male rats, from Taconic Europe and the principles of laboratory animal care are followed.

An acclimatisation period of approximately 7 days was allowed before the animals entered the study. At start of the acclimatisation period the rats were in the weight range of 300-400 g. The rats had permanent catheters inserted in a. carotis which were used for blood sampling.

The studies were conducted in an animal room which was illuminated to give a cycle of approx 12 hours light and 12 hours darkness. The animals were housed individually due to the catheters and had food and water ad lib. The animals were weighed on the days of dosing.

In the present studies the test substances were administered subcutaneously in approx 20 nmol/kg dose. The animals received a single subcutaneous injection to the neck using a 25 G needle with syringe. Each test substance was given to typically three but in some cases two or four animals.

A full plasma concentration-time profile, employing 8-10 sampling points, was obtained from each animal. In example blood samples were collected according to the following schedule: After subcutaneous administration:

Predose (0), 0.5, 1, 1.5, 2, 4, 6, 12, 24, 48 and 72 hours after injection.

At each sampling time, 0.08 to 0.10 ml of blood was drawn from each animal. The blood samples were taken via the catheter.

The blood samples were collected into EDTA test tubes. Blood samples were kept on ice for max 20 min. before centrifugation. Plasma was separated using centrifugation (i.e. at 4° C., 10 min., 1500 G) and was immediately transferred to Micronic tubes or PCR plates. Approximately 40 µl plasma was transferred and was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln 2/$\lambda_z$ and was determined from $\lambda_z$ the first order rate constant associated with the terminal (log-linear) portion of the curve, estimated by linear regression of time vs. log concentration.

Assay (XI)—Effect from Single Subcutaneous Administration of Analogue on Plasma Calcium in Rats Male Sprague-Dawley rats (Taconic Europe, ~250 g at test date) were acclimatized to reversed day light cycle (lights on from 10 PM to 10 AM) and single housing in online food intake monitoring system (Ellegaard MBRose, Denmark) prior to study start. Rats were divided in groups of five and subcutaneously dosed with test compound (30 nmol/kg) and food intake was monitored for 48 hours hereafter. Data are illustrated in graphs as mean±SEM. Reduction of food intake from administration of the compound is positively correlated to the binding of the compound to the amylin receptor.

Assay (XII)—Effect from Single Subcutaneous Administration of Analogue on Plasma Calcium in Rats Male Wistar rats (Taconic Europe, ~250 g at test date) were acclimatized to handling prior to the study. Rats were divided in groups of five and subcutaneously dosed with test compound at time=0. At time T=−15 min; 1 h, 2 h, 4 h, 7 h, 12 h, and 24 h a blood sample was obtained and heparin stabilized plasma was analysed for total calcium (Cobas, Hitachi). Data are illustrated in graphs as mean±SEM.

Preparations

The polypeptide sequences were prepared according to the below-mentioned polypeptide synthesis and the compounds as presented in the Tables (e.g. Table 2 or Table 3) were prepared according to the below-mentioned synthesis.

One method of polypeptide synthesis was by Fmoc chemistry on a microwave-based Liberty polypeptide synthesizer (CEM Corp., North Carolina). The resin was Tentagel S RAM with a loading of about 0.25 mmol/g or PAL-ChemMatrix with a loading of about 0.43 mmol/g. The coupling chemistry was DIC/HOAt in NMP using amino acid solutions of 0.3 M in NMP and a molar excess of 6-8 fold. Coupling conditions was 5 minutes at up to 70° C. Deprotection was with 5% piperidine in NMP at up to 70° C. The protected amino acids used were standard Fmoc-amino acids (supplied from e.g. Anaspec or Novabiochem) dissolved at 0.3 M in NMP containing 0.3 M HOAt.

Another method of polypeptide synthesis was by Fmoc chemistry on a Prelude polypeptide synthesizer (Protein Technologies, Arizona). The resin was Tentagel S RAM with a loading of about 0.25 mmol/g or PAL-Chem Matrix with a loading of about 0.43 mmol/g. The coupling chemistry was DIC/HOAt in NMP using amino acid solutions of 0.3 M in NMP and a molar excess of 6-8 fold. Coupling conditions was single or double couplings for 1 or 2 hours at room temperature. Deprotection was with 20% piperidine in NMP. The protected amino acids used were standard Fmoc-amino acids (supplied from e.g. Anaspec or Novabiochem) dissolved at 0.3 M in NMP containing 0.3 M HOAt.

Another method of polypeptide synthesis was on an Applied Biosystems 433 polypeptide synthesizer in 0.25 mmol or 1.0 mmol scale using the manufacturer supplied FastMoc UV protocols which employ HBTU or HATU mediated couplings in NMP, and UV monitoring of the deprotection of the Fmoc protection group. The starting resin used for the synthesis of the polypeptide amides was Rink-Amide resin. The protected amino acid derivatives used were standard Fmoc-amino acids (supplied from e.g. Anaspec, or Novabiochem) supplied in preweighed cartridges suitable for the AB1433A synthesizer.

When a chemical modification of a lysine side chain was desired, the lysine was incorporated as Lys(Mtt) and the N-terminal amino acid was either incorporated into the sequence as a Boc-amino acid or, if the N-terminal amino acid was incorporated as an Fmoc-amino acid, the Fmoc group was removed and the N-terminal was protected by treatment with 6 equivalents of Boc-carbonate and 6 equivalents of DIPEA in NMP for 30 minutes. The resin was washed with NMP and DCM and the Mtt group was removed by suspending the resin in neat hexafluoroisopropanol for 20 minutes followed by washing with DCM and NMP. The chemical modification of the lysine was performed by adding one or more of the building blocks listed below by the same methods as used for the polypeptide synthesis, i.e. by one or more automated steps on the Liberty or the ABI 433 or by one or more manual coupling steps at room temperature. After synthesis the resin was washed with DCM and dried, and the polypeptide was cleaved from the resin by a 2 hour treatment with TFA/TIPS/water (92.5/5/2.5 or 95/2.5/2.5) followed by precipitation with 4 volumes of diethylether, further washing with diethylether and drying. If the polypeptide contained cysteines protected with Acm groups, the polypeptide was redissolved in water at 2-5 mg/ml, pH adjusted to below 4, and the disulfide bridge formed by treatment with 4 eq. of iodine (2% w/v in methanol) for 15 minutes. Alternatively, the disulfide bridge was formed on the resin by using Trt as the protecting group for cysteine and treating with 10 equivalents of iodine in NMP for 1 hour. In this case the crude polypeptide was purified directly after cleavage and diethyl-ether precipitation.

Purification: The crude polypeptide was purified by semi-preparative HPLC on a 20 mm×250 mm column packed with either 5µ or 7µ C-18 silica. Polypeptide solutions were pumped onto the HPLC column and precipitated polypeptides were dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The polypeptide containing fractions were collected. The purified polypeptide was lyophilized after dilution of the eluate with water.

For analysis of HPLC-fractions and final product RP-HPLC analysis was performed using UV detection at 214 nm and e.g. a Vydac 218TP54 4.6 mm×250 mm 5µ C-18 silica column (The Separations Group, Hesperia, USA) and eluted at e.g. 1 ml/min at 42° C. Most often one of four different elution conditions was used:

A1: Equilibration of the column with a buffer consisting of 0.1 M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% TFA/$H_2O$ and elution by a gradient of 0% $CH_3CN$/0.1% TFA/$H_2O$ to 60% $CH_3CN$/0.1% TFA/$H_2O$ during 50 min.

B6: Equilibration of the column with 0.1% TFA/$H_2O$ and elution by a gradient of 0% $CH_3CN$/0.1% TFA/$H_2O$ to 90% $CH_3CN$/0.1% TFA/$H_2O$ during 50 min.

Alternatively the RP-HPLC analysis was performed using UV detection at 214 nm and a Symmetry300, 3.6 mm×150 mm, 3.5 g C-18 silica column (Waters) which was eluted at 1 ml/min at 42° C.

B4: Equilibration of the column with 0.05% TFA/H$_2$O and elution by a gradient of 5% CH$_3$CN/0.05% TFA/H$_2$O to 95% CH$_3$CN/0.05% TFA/H$_2$O during 15 min.

The identity of the polypeptide was confirmed by MALDI-MS on a Bruker Microflex.

The polypeptides prepared are shown in Table 2 (presented earlier):

Binding to Human Amylin Receptors

The in vitro data regarding binding to human amylin receptors are shown in Table 4 (below).

Table 4 discloses compounds that have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 4

| Example no. | Sequence modifications | hAmylin-R bind IC50 (pM) |
| --- | --- | --- |
| 1 | 14D, 17R, 21P, 26P, 35D | 1177 |
| 2 | 14D, 17R, 21P, 27P, 35D | 411 |
| 3 | 14D, 17R, 22P, 26P, 35D | 1131 |
| 4 | 14E, 17R, 21P, 25P, 28P, 29P, 37P | 321 |
| 5 | 14E, 17R, 21P, 26P, 37P | 374 |
| 6 | 14E, 17R, 21P, 25P, 28P, 29P | 996 |
| 7 | 14E, 17R, 21P, 26P | 674 |
| 8 | 14E, 17R, 21P, 27P, 37P | 72 |
| 9 | 14E, 17R, 21P, 27P | 143 |
| 10 | 14D, 17R, 21P, 27P, 37P | 82 |
| 11 | 14E, 17R, 21P, 27P, 35D, 37P | 105 |
| 12 | 14E, 17R, 21P, 27P, 37P | 142 |
| 13 | 14E, 17R, 21P, 27P, 37P | 264 |
| 14 | 14E, 17R, 21P, 27P, 37P | 196 |
| 15 | 14E, 17R, 21P, 27P | 597 |
| 16 | 14E, 17R, 21P, 27P, 35R | 894 |
| 17 | 14E, 17R, 21P, 27P, 34H | 878 |
| 18 | 14E, 17R, 21P, 27P, 35H | 554 |
| 19 | 14E, 17R, 21P, 27P | 556 |
| 20 | 14E, 17R, 21P, 27P, 37P | 217 |
| 21 | 17R, 21P, 27P | 585 |
| 22 | 14E, 17R, 21P, 27P, 35E | 794 |
| 23 | 17R, 21P, 27P, 35E | 871 |
| 24 | 17R, 21P, 27P | 1138 |
| 25 | 17R, 21P, 27P, 35E | 768 |
| 26 | 17R, 21P, 27P, 35E | 532 |
| 27 | 17R, 21P, 27P, 35E | 837 |
| 28 | 17R, 21P, 27P, 31P, 35E | 610 |
| 29 | 17R, 21P, 27P, 34P, 35E | 577 |
| 30 | 14H, 17R, 21P, 27P, 35E | 919 |
| 31 | 14E, 17R, 21P, 27P, 31P | 204 |
| 32 | 14E, 17R, 21P, 27P, 34P | 100 |
| 33 | 14E, 17R, 21P, 28P, 35E | 915 |
| 34 | 17R, 21P, 27P, 35K | 1139 |
| 35 | 17R, 21P, 27P, 35K | 970 |
| 36 | 14E, 17R, 21P, 27P, 34K | 403 |
| 37 | 14E, 17R, 21P, 27P, 29P | 970 |
| 38 | 17R, 21P, 27P, 35R | 249 |
| 39 | 17R, 21P, 27P, 34R | 665 |
| 40 | 17R, 21P, 27P, 34H | 549 |
| 41 | 17R, 21P, 27P | 427 |
| 42 | 17R, 21P, 27P | 264 |
| 43 | 17R, 21P, 27P | 76 |
| 44 | -1K, 1R, 17R, 21P, 27P, 35H | 275 |
| 45 | -1K, 1R, 17R, 21P, 27P, 35H | 552 |
| 46 | -1G, 1R, 17R, 21P, 27P | 195 |
| 47 | -1G, 1R, 17R, 21P, 27P, 35H | 344 |
| 48 | 17R, 21P, 27P | 443 |
| 49 | 17R, 21P, 27P, 31P | 1191 |
| 50 | 17R, 21P, 27P, 34P | 38 |
| 51 | 14E, 17R, 21P, 27P, 35R | 828 |
| 52 | 14D, 17R, 21P, 27P, 35R | 697 |
| 53 | 17R, 21P, 27P, 28P, 31P | 52 |
| 54 | 17R, 21P, 27P, 29P, 31P | 30 |
| 55 | 17R, 21P, 27P, 28P, 34P | 42 |
| 56 | 17R, 21P, 27P, 29P, 34P | 49 |
| 57 | 17R, 21P, 27P, 31P, 35H | 115 |
| 58 | 17R, 21P, 27P, 34P, 35H | 88 |
| 59 | 14D, 17R, 21K, 27P, 35D | 1193 |
| 60 | 17R, 21P, 27P, 35H | 695 |
| 61 | 14H, 17R, 21P, 27P, 31P | 122 |
| 62 | 14H, 17R, 21P, 27P, 31P | 98 |
| 63 | 14R, 17R, 21P, 27P, 31P | 825 |
| 64 | 14R, 17R, 21P, 27P, 31P | 444 |
| 65 | 14R, 17R, 21P, 27P, 34P | 649 |
| 66 | 14H, 17R, 21P, 27P, 35H | 396 |
| 67 | 14H, 17R, 21P, 27P, 34P | 90 |
| 68 | 14H, 17R, 21P, 27P, 34P | 88 |
| 69 | 14H, 17R, 21P, 27P | 133 |
| 70 | 14H, 17R, 21P, 27P | 169 |
| 71 | 14G, 17R, 21P, 27P, 31P | 48 |
| 72 | 14A, 17R, 21P, 27P, 31P | 172 |
| 73 | 14S, 17R, 21P, 27P, 31P | 104 |
| 74 | 14K, 17R, 21P, 27P, 31P | 791 |
| 75 | 14T, 17R, 21P, 27P, 31P | 666 |
| 76 | 17R, 21P, 27P, 34H | 215 |
| 77 | 17R, 21P, 27P, 34H | 428 |
| 78 | 17R, 21P, 27P, 34R | 602 |
| 79 | 17R, 21P, 27P, 34R | 790 |
| 80 | 14H, 17R, 21P, 27P, 34H | 290 |
| 81 | 14H, 17R, 21P, 27P, 34H | 271 |
| 82 | 14R, 17R, 21P, 27P | 636 |
| 83 | 14R, 17R, 21P, 27P | 939 |
| 84 | 14H, 17R, 21P, 27P, 34R | 743 |
| 85 | 14H, 17R, 21P, 27P, 34R | 876 |
| 86 | 17R, 21P, 27P, 34H | 833 |
| 87 | 14E, 17R, 21P, 27P, 34H | 633 |
| 88 | 14E, 17R, 21P, 27P, 34R | 750 |
| 89 | 14E, 17R, 21P, 27P, 35R | 1160 |
| 90 | 14H, 17R, 21P, 27P | 61 |
| 91 | 17R, 21P, 27P, 34H | 119 |
| 92 | 14H, 17R, 21P, 27P | 179 |
| 93 | 14A, 17R, 21P, 27P, 34H | 176 |
| 94 | 14A, 17R, 21P, 27P, 34P | 148 |
| 95 | 17R, 21P, 27P, 34R | 967 |
| 96 | 17R, 21P, 27P, 31P | 166 |
| 97 | 17R, 21P, 27P, 34H | 568 |
| 98 | 17R, 21P, 27P, 34P | 91 |
| 99 | -1G, 1R, 14H, 17R, 21P, 27P | 348 |
| 100 | -1G, 1R, 14H, 17R, 21P, 27P, 34H | 1015 |
| 101 | -1G, 1R, 14A, 17R, 21P, 27P, 34H | 426 |
| 102 | -1G, 1R, 14H, 17R, 21P, 27P, 34P | 217 |
| 103 | -1G, 1R, 14A, 17R, 21P, 27P, 34P | 114 |
| 104 | 14E, 17R, 21P, 27P, 34H, 35E | 525 |
| 105 | 14E, 17R, 21P, 27P, 34R, 35E | 957 |
| 106 | 14E, 17R, 21P, 27P, 34P, 35E | 121 |
| 107 | 14E, 17R, 21P, 27P, 34H, 35E | 387 |
| 108 | 14E, 17R, 21P, 27P, 34R, 35E | 232 |
| 109 | 14E, 17R, 21P, 27P, 34P, 35E | 140 |
| 110 | 14E, 17R, 21P, 27P, 34P, 35R | 326 |
| 111 | 17R, 21P, 27P, 34H | 580 |
| 112 | 17R, 21P, 27P, 34H | 1037 |
| 113 | 17R, 21P, 27P, 34H | 382 |
| 114 | 14E, 17R, 21P, 27P, 34P, 37P | 214 |
| 115 | 14H, 17R, 21P, 27P, 34P, 37P | 131 |
| 116 | 14H, 17R, 21P, 27P, 31P, 34P | 82 |
| 117 | 14E, 17R, 21P, 27P, 34P, 35R | 163 |
| 118 | 14E, 17R, 21P, 27P, 34P, 35H | 179 |
| 119 | 17R, 21P, 27P, 31P, 34P, 35R | 880 |
| 120 | 14S, 17R, 21P, 27P, 34P, 35E | 76 |
| 121 | 14E, 17R, 21P, 31P, 34P, 35E | 69 |
| 122 | 14D, 17R, 21P, 27P, 34P, 35E | 172 |
| 123 | 14D, 17R, 21P, 27P, 34P, 35E | 196 |
| 124 | 14E, 17R, 21P, 27P, 34P, 35H | 377 |
| 125 | 14E, 17R, 21P, 27P, 34P, 35E, 37P | 533 |
| 126 | 14E, 17R, 23P, 34P, 35E | 1187 |

TABLE 4-continued

| Example no. | Sequence modifications | hAmylin-R bind IC50 (pM) |
|---|---|---|
| 127 | 14E, 17R, 21P, 27P, 34P, 37F | 152 |
| 128 | 14E, 17R, 21P, 27P, 35H | 992 |
| 129 | 14D, 17R, 21P, 27P, 34P, 35R | 281 |
| 130 | 14D, 17R, 21P, 27P, 34P, 35R | 453 |
| 131 | 14d, 17R, 21P, 27P, 35R | 365 |
| 132 | 14D, 17R, 21P, 27P, 35R | 266 |

TABLE 4a

| Example no. | Sequence modifications | hAmylin-R bind IC50 (pM) |
|---|---|---|
| 2 | 14D, 17R, 21P, 27P, 35D | 411 |
| 4 | 14E, 17R, 21P, 25P, 28P, 29P, 37P | 321 |
| 5 | 14E, 17R, 21P, 26P, 37P | 374 |
| 6 | 14E, 17R, 21P, 25P, 28P, 29P | 996 |
| 7 | 14E, 17R, 21P, 26P | 674 |
| 8 | 14E, 17R, 21P, 27P, 37P | 72 |
| 9 | 14E, 17R, 21P, 27P | 143 |
| 10 | 14D, 17R, 21P, 27P, 37P | 82 |
| 11 | 14E, 17R, 21P, 27P, 35D, 37P | 105 |
| 12 | 14E, 17R, 21P, 27P, 37P | 142 |
| 13 | 14E, 17R, 21P, 27P, 37P | 264 |
| 14 | 14E, 17R, 21P, 27P, 37P | 196 |
| 15 | 14E, 17R, 21P, 27P | 597 |
| 16 | 14E, 17R, 21P, 27P, 35R | 894 |
| 17 | 14E, 17R, 21P, 27P, 34H | 878 |
| 18 | 14E, 17R, 21P, 27P, 35H | 554 |
| 19 | 14E, 17R, 21P, 27P | 556 |
| 20 | 14E, 17R, 21P, 27P, 37P | 217 |
| 21 | 17R, 21P, 27P | 585 |
| 22 | 14E, 17R, 21P, 27P, 35E | 794 |
| 23 | 17R, 21P, 27P, 35E | 871 |
| 25 | 17R, 21P, 27P, 35E | 768 |
| 26 | 17R, 21P, 27P, 35E | 532 |
| 27 | 17R, 21P, 27P, 35E | 837 |
| 28 | 17R, 21P, 27P, 31P, 35E | 610 |
| 29 | 17R, 21P, 27P, 34R, 35E | 577 |
| 30 | 14H, 17R, 21P, 27P, 35E | 919 |
| 31 | 14E, 17R, 21P, 27P, 31P | 204 |
| 32 | 14E, 17R, 21P, 27P, 34P | 100 |
| 33 | 14E, 17R, 21P, 28P, 35E | 915 |
| 35 | 17R, 21P, 27P, 35K | 970 |
| 36 | 14E, 17R, 21P, 27P, 34K | 403 |
| 37 | 14E, 17R, 21P, 27P, 29P | 970 |
| 38 | 17R, 21P, 27P, 35R | 249 |
| 39 | 17R, 21P, 27P, 34R | 665 |
| 40 | 17R, 21P, 27P, 34H | 549 |
| 41 | 17R, 21P, 27P | 427 |
| 42 | 17R, 21P, 27P | 264 |
| 43 | 17R, 21P, 27P | 76 |
| 44 | -1K, 1R, 17R, 21P, 27P, 35H | 275 |
| 45 | -1K, 1R, 17R, 21P, 27P, 35H | 552 |
| 46 | -1G, 1R, 17R, 21P, 27P | 195 |
| 47 | -1G, 1R, 17R, 21P, 27P, 35H | 344 |
| 48 | 17R, 21P, 27P | 443 |
| 50 | 17R, 21P, 27P, 34P | 38 |
| 51 | 14E, 17R, 21P, 27P, 35R | 828 |
| 52 | 14D, 17R, 21P, 27P, 35R | 697 |
| 53 | 17R, 21P, 27P, 28P, 31P | 52 |
| 54 | 17R, 21P, 27P, 29P, 31P | 30 |
| 55 | 17R, 21P, 27P, 28P, 34P | 42 |
| 56 | 17R, 21P, 27P, 29P, 34P | 49 |
| 57 | 17R, 21P, 27P, 31P, 35H | 115 |
| 58 | 17R, 21P, 27P, 34P, 35H | 88 |
| 60 | 17R, 21P, 27P, 35H | 695 |
| 61 | 14H, 17R, 21P, 27P, 31P | 122 |
| 62 | 14H, 17R, 21P, 27P, 31P | 98 |
| 63 | 14R, 17R, 21P, 27P, 31P | 825 |
| 64 | 14R, 17R, 21P, 27P, 31P | 444 |
| 65 | 14R, 17R, 21P, 27P, 34P | 649 |
| 66 | 14H, 17R, 21P, 27P, 35H | 396 |
| 67 | 14H, 17R, 21P, 27P, 34P | 90 |
| 68 | 14H, 17R, 21P, 27P, 34P | 88 |

TABLE 4a-continued

| Example no. | Sequence modifications | hAmylin-R bind IC50 (pM) |
|---|---|---|
| 69 | 14H, 17R, 21P, 27P | 133 |
| 70 | 14H, 17R, 21P, 27P | 169 |
| 71 | 14G, 17R, 21P, 27P, 31P | 48 |
| 72 | 14A, 17R, 21P, 27P, 31P | 172 |
| 73 | 14S, 17R, 21P, 27P, 31P | 104 |
| 74 | 14K, 17R, 21P, 27P, 31P | 791 |
| 75 | 14T, 17R, 21P, 27P, 31P | 666 |
| 76 | 17R, 21P, 27P, 34H | 215 |
| 77 | 17R, 21P, 27P, 34H | 428 |
| 78 | 17R, 21P, 27P, 34R | 602 |
| 79 | 17R, 21P, 27P, 34R | 790 |
| 80 | 14H, 17R, 21P, 27P, 34H | 290 |
| 81 | 14H, 17R, 21P, 27P, 34H | 271 |
| 82 | 14R, 17R, 21P, 27P | 636 |
| 83 | 14R, 17R, 21P, 27P | 939 |
| 84 | 14H, 17R, 21P, 27P, 34R | 743 |
| 85 | 14H, 17R, 21P, 27P, 34R | 876 |
| 86 | 17R, 21P, 27P, 34H | 833 |
| 87 | 14E, 17R, 21P, 27P, 34H | 633 |
| 88 | 14E, 17R, 21P, 27P, 34R | 750 |
| 90 | 14H, 17R, 21P, 27P | 61 |
| 91 | 17R, 21P, 27P, 34H | 119 |
| 92 | 14H, 17R, 21P, 27P | 179 |
| 93 | 14A, 17R, 21P, 27P, 34H | 176 |
| 94 | 14A, 17R, 21P, 27P, 34P | 148 |
| 95 | 17R, 21P, 27P, 34R | 967 |
| 96 | 17R, 21P, 27P, 31P | 166 |
| 97 | 17R, 21P, 27P, 34H | 568 |
| 98 | 17R, 21P, 27P, 34P | 91 |
| 99 | -1G, 1R, 14H, 17R, 21P, 27P | 348 |
| 101 | -1G, 1R, 14A, 17R, 21P, 27P, 34H | 426 |
| 102 | -1G, 1R, 14H, 17R, 21P, 27P, 34P | 217 |
| 103 | -1G, 1R, 14A, 17R, 21P, 27P, 34P | 114 |
| 104 | 14E, 17R, 21P, 27P, 34H, 35E | 525 |
| 105 | 14E, 17R, 21P, 27P, 34R, 35E | 957 |
| 106 | 14E, 17R, 21P, 27P, 34P, 35E | 121 |
| 107 | 14E, 17R, 21P, 27P, 34H, 35E | 387 |
| 108 | 14E, 17R, 21P, 27P, 34R, 35E | 232 |
| 109 | 14E, 17R, 21P, 27P, 34P, 35E | 140 |
| 110 | 14E, 17R, 21P, 27P, 34P, 35R | 326 |
| 111 | 17R, 21P, 27P, 34H | 580 |
| 113 | 17R, 21P, 27P, 34H | 382 |
| 114 | 14E, 17R, 21P, 27P, 34P, 37P | 214 |
| 115 | 14H, 17R, 21P, 27P, 34P, 37P | 131 |
| 116 | 14H, 17R, 21P, 27P, 31P, 34P | 82 |
| 117 | 14E, 17R, 21P, 27P, 34P, 35R | 163 |
| 118 | 14E, 17R, 21P, 27P, 34P, 35H | 179 |
| 119 | 17R, 21P, 27P, 31P, 34P, 35R | 880 |
| 120 | 14S, 17R, 21P, 27P, 34P, 35E | 76 |
| 121 | 14E, 17R, 21P, 31P, 34P, 35E | 69 |
| 122 | 14D, 17R, 21P, 27P, 34P, 35E | 172 |
| 123 | 14D, 17R, 21P, 27P, 34P, 35E | 196 |
| 124 | 14E, 17R, 21P, 27P, 34P, 35H | 377 |
| 125 | 14E, 17R, 21P, 27P, 34P, 35E, 37P | 533 |
| 127 | 14E, 17R, 21P, 27P, 34P, 37F | 152 |
| 128 | 14E, 17R, 21P, 27P, 35H | 992 |
| 129 | 14D, 17R, 21P, 27P, 34P, 35R | 281 |
| 130 | 14D, 17R, 21P, 27P, 34P, 35R | 453 |
| 131 | 14d, 17R, 21P, 27P, 35R | 365 |
| 132 | 14D, 17R, 21P, 27P, 35R | 266 |

TABLE 4b

| Example no. | Sequence modifications | hAmylin-R bind IC50 (pM) |
|---|---|---|
| 2 | 14D, 17R, 21P, 27P, 35D | 411 |
| 4 | 14E, 17R, 21P, 25P, 28P, 29P, 37P | 321 |
| 5 | 14E, 17R, 21P, 26P, 37P | 374 |
| 7 | 14E, 17R, 21P, 26P | 674 |
| 8 | 14E, 17R, 21P, 27P, 37P | 72 |
| 9 | 14E, 17R, 21P, 27P | 143 |
| 10 | 14D, 17R, 21P, 27P, 37P | 82 |
| 11 | 14E, 17R, 21P, 27P, 35D, 37P | 105 |

TABLE 4b-continued

| Example no. | Sequence modifications | hAmylin-R bind IC50 (pM) |
|---|---|---|
| 12 | 14E, 17R, 21P, 27P, 37P | 142 |
| 13 | 14E, 17R, 21P, 27P, 37P | 264 |
| 14 | 14E, 17R, 21P, 27P, 37P | 196 |
| 15 | 14E, 17R, 21P, 27P | 597 |
| 18 | 14E, 17R, 21P, 27P, 35H | 554 |
| 19 | 14E, 17R, 21P, 27P | 556 |
| 20 | 14E, 17R, 21P, 27P, 37P | 217 |
| 21 | 17R, 21P, 27P | 585 |
| 22 | 14E, 17R, 21P, 27P, 35E | 794 |
| 25 | 17R, 21P, 27P, 35E | 768 |
| 26 | 17R, 21P, 27P, 35E | 532 |
| 28 | 17R, 21P, 27P, 31P, 35E | 610 |
| 29 | 17R, 21P, 27P, 34P, 35E | 577 |
| 31 | 14E, 17R, 21P, 27P, 31P | 204 |
| 32 | 14E, 17R, 21P, 27P, 34P | 100 |
| 36 | 14E, 17R, 21P, 27P, 34K | 403 |
| 38 | 17R, 21P, 27P, 35R | 249 |
| 39 | 17R, 21P, 27P, 34R | 665 |
| 40 | 17R, 21P, 27P, 34H | 549 |
| 41 | 17R, 21P, 27P | 427 |
| 42 | 17R, 21P, 27P | 264 |
| 43 | 17R, 21P, 27P | 76 |
| 44 | −1K, 1R, 17R, 21P, 27P, 35H | 275 |
| 45 | −1K, 1R, 17R, 21P, 27P, 35H | 552 |
| 46 | −1G, 1R, 17R, 21P, 27P | 195 |
| 47 | −1G, 1R, 17R, 21P, 27P, 35H | 344 |
| 48 | 17R, 21P, 27P | 443 |
| 50 | 17R, 21P, 27P, 34P | 38 |
| 52 | 14D, 17R, 21P, 27P, 35R | 697 |
| 53 | 17R, 21P, 27P, 28P, 31P | 52 |
| 54 | 17R, 21P, 27P, 29P, 31P | 30 |
| 55 | 17R, 21P, 27P, 28P, 34P | 42 |
| 56 | 17R, 21P, 27P, 29P, 34P | 49 |
| 57 | 17R, 21P, 27P, 31P, 35H | 115 |
| 58 | 17R, 21P, 27P, 34P, 35H | 88 |
| 60 | 17R, 21P, 27P, 35H | 695 |
| 61 | 14H, 17R, 21P, 27P, 31P | 122 |
| 62 | 14H, 17R, 21P, 27P, 31P | 98 |
| 64 | 14R, 17R, 21P, 27P, 31P | 444 |
| 65 | 14R, 17R, 21P, 27P, 34P | 649 |
| 66 | 14H, 17R, 21P, 27P, 35H | 396 |
| 67 | 14H, 17R, 21P, 27P, 34P | 90 |
| 68 | 14H, 17R, 21P, 27P, 34P | 88 |
| 69 | 14H, 17R, 21P, 27P | 133 |
| 70 | 14H, 17R, 21P, 27P | 169 |
| 71 | 14G, 17R, 21P, 27P, 31P | 48 |
| 72 | 14A, 17R, 21P, 27P, 31P | 172 |
| 73 | 14S, 17R, 21P, 27P, 31P | 104 |
| 74 | 14K, 17R, 21P, 27P, 31P | 791 |
| 75 | 14T, 17R, 21P, 27P, 31P | 666 |
| 76 | 17R, 21P, 27P, 34H | 215 |
| 77 | 17R, 21P, 27P, 34H | 428 |
| 78 | 17R, 21P, 27P, 34R | 602 |
| 79 | 17R, 21P, 27P, 34R | 790 |
| 80 | 14H, 17R, 21P, 27P, 34H | 290 |
| 81 | 14H, 17R, 21P, 27P, 34H | 271 |
| 82 | 14R, 17R, 21P, 27P | 636 |
| 84 | 14H, 17R, 21P, 27P, 34R | 743 |
| 87 | 14E, 17R, 21P, 27P, 34H | 633 |
| 88 | 14E, 17R, 21P, 27P, 34R | 750 |
| 90 | 14H, 17R, 21P, 27P | 61 |
| 91 | 17R, 21P, 27P, 34H | 119 |
| 92 | 14H, 17R, 21P, 27P | 179 |
| 93 | 14A, 17R, 21P, 27P, 34H | 176 |
| 94 | 14A, 17R, 21P, 27P, 34P | 148 |
| 96 | 17R, 21P, 27P, 31P | 166 |
| 97 | 17R, 21P, 27P, 34H | 568 |
| 98 | 17R, 21P, 27P, 34P | 91 |
| 99 | −1G, 1R, 14H, 17R, 21P, 27P | 348 |
| 101 | −1G, 1R, 14A, 17R, 21P, 27P, 34H | 426 |
| 102 | −1G, 1R, 14H, 17R, 21P, 27P, 34P | 217 |
| 103 | −1G, 1R, 14A, 17R, 21P, 27P, 34P | 114 |
| 104 | 14E, 17R, 21P, 27P, 34H, 35E | 525 |
| 105 | 14E, 17R, 21P, 27P, 34R, 35E | 957 |
| 106 | 14E, 17R, 21P, 27P, 34P, 35E | 121 |
| 107 | 14E, 17R, 21P, 27P, 34H, 35E | 387 |
| 108 | 14E, 17R, 21P, 27P, 34R, 35E | 232 |
| 109 | 14E, 17R, 21P, 27P, 34P, 35E | 140 |
| 110 | 14E, 17R, 21P, 27P, 34P, 35R | 326 |
| 111 | 17R, 21P, 27P, 34H | 580 |
| 113 | 17R, 21P, 27P, 34H | 382 |
| 114 | 14E, 17R, 21P, 27P, 34P, 37P | 214 |
| 115 | 14H, 17R, 21P, 27P, 34P, 37P | 131 |
| 116 | 14H, 17R, 21P, 27P, 31P, 34P | 82 |
| 117 | 14E, 17R, 21P, 27P, 34P, 35R | 163 |
| 118 | 14E, 17R, 21P, 27P, 34P, 35H | 179 |
| 120 | 14S, 17R, 21P, 27P, 34P, 35E | 76 |
| 121 | 14E, 17R, 21P, 31P, 34P, 35E | 69 |
| 122 | 14D, 17R, 21P, 27P, 34P, 35E | 172 |
| 123 | 14D, 17R, 21P, 27P, 34P, 35E | 196 |
| 124 | 14E, 17R, 21P, 27P, 34P, 35H | 377 |
| 125 | 14E, 17R, 21P, 27P, 34P, 35E, 37P | 533 |
| 127 | 14E, 17R, 21P, 27P, 34P, 37F | 152 |
| 129 | 14D, 17R, 21P, 27P, 34P, 35R | 281 |
| 130 | 14D, 17R, 21P, 27P, 34P, 35R | 453 |
| 131 | 14d, 17R, 21P, 27P, 35R | 365 |
| 132 | 14D, 17R, 21P, 27P, 35R | 266 |

TABLE 4c

| Example no. | Sequence modifications | hAmylin-R bind IC50 (pM) |
|---|---|---|
| 2 | 14D, 17R, 21P, 27P, 35D | 411 |
| 4 | 14E, 17R, 21P, 25P, 28P, 29P, 37P | 321 |
| 5 | 14E, 17R, 21P, 26P, 37P | 374 |
| 8 | 14E, 17R, 21P, 27P, 37P | 72 |
| 9 | 14E, 17R, 21P, 27P | 143 |
| 10 | 14D, 17R, 21P, 27P, 37P | 82 |
| 11 | 14E, 17R, 21P, 27P, 35D, 37P | 105 |
| 12 | 14E, 17R, 21P, 27P, 37P | 142 |
| 13 | 14E, 17R, 21P, 27P, 37P | 264 |
| 14 | 14E, 17R, 21P, 27P, 37P | 196 |
| 15 | 14E, 17R, 21P, 27P | 597 |
| 18 | 14E, 17R, 21P, 27P, 35H | 554 |
| 19 | 14E, 17R, 21P, 27P | 556 |
| 20 | 14E, 17R, 21P, 27P, 37P | 217 |
| 21 | 17R, 21P, 27P | 585 |
| 26 | 17R, 21P, 27P, 35E | 532 |
| 29 | 17R, 21P, 27P, 34P, 35E | 577 |
| 31 | 14E, 17R, 21P, 27P, 31P | 204 |
| 32 | 14E, 17R, 21P, 27P, 34P | 100 |
| 36 | 14E, 17R, 21P, 27P, 34K | 403 |
| 38 | 17R, 21P, 27P, 35R | 249 |
| 40 | 17R, 21P, 27P, 34H | 549 |
| 41 | 17R, 21P, 27P | 427 |
| 42 | 17R, 21P, 27P | 264 |
| 43 | 17R, 21P, 27P | 76 |
| 44 | −1K, 1R, 17R, 21P, 27P, 35H | 275 |
| 45 | −1K, 1R, 17R, 21P, 27P, 35H | 552 |
| 46 | −1G, 1R, 17R, 21P, 27P | 195 |
| 47 | −1G, 1R, 17R, 21P, 27P, 35H | 344 |
| 48 | 17R, 21P, 27P | 443 |
| 50 | 17R, 21P, 27P, 34P | 38 |
| 53 | 17R, 21P, 27P, 28P, 31P | 52 |
| 54 | 17R, 21P, 27P, 29P, 31P | 30 |
| 55 | 17R, 21P, 27P, 28P, 34P | 42 |
| 56 | 17R, 21P, 27P, 29P, 34P | 49 |
| 57 | 17R, 21P, 27P, 31P, 35H | 115 |
| 58 | 17R, 21P, 27P, 34P, 35H | 88 |
| 61 | 14H, 17R, 21P, 27P, 31P | 122 |
| 62 | 14H, 17R, 21P, 27P, 31P | 98 |
| 64 | 14R, 17R, 21P, 27P, 31P | 444 |
| 65 | 14R, 17R, 21P, 27P, 34P | 649 |
| 66 | 14H, 17R, 21P, 27P, 35H | 396 |
| 67 | 14H, 17R, 21P, 27P, 34P | 90 |
| 68 | 14H, 17R, 21P, 27P, 34P | 88 |
| 69 | 14H, 17R, 21P, 27P | 133 |
| 70 | 14H, 17R, 21P, 27P | 169 |
| 71 | 14G, 17R, 21P, 27P, 31P | 48 |
| 72 | 14A, 17R, 21P, 27P, 31P | 172 |

TABLE 4c-continued

| Example no. | Sequence modifications | hAmylin-R bind IC50 (pM) |
|---|---|---|
| 73 | 14S, 17R, 21P, 27P, 31P | 104 |
| 76 | 17R, 21P, 27P, 34H | 215 |
| 77 | 17R, 21P, 27P, 34H | 428 |
| 78 | 17R, 21P, 27P, 34R | 602 |
| 80 | 14H, 17R, 21P, 27P, 34H | 290 |
| 81 | 14H, 17R, 21P, 27P, 34H | 271 |
| 82 | 14R, 17R, 21P, 27P | 636 |
| 87 | 14E, 17R, 21P, 27P, 34H | 633 |
| 88 | 14E, 17R, 21P, 27P, 34R | 750 |
| 90 | 14H, 17R, 21P, 27P | 61 |
| 91 | 17R, 21P, 27P, 34H | 119 |
| 92 | 14H, 17R, 21P, 27P | 179 |
| 93 | 14A, 17R, 21P, 27P, 34H | 176 |
| 94 | 14A, 17R, 21P, 27P, 34P | 148 |
| 96 | 17R, 21P, 27P, 31P | 166 |
| 97 | 17R, 21P, 27P, 34H | 568 |
| 98 | 17R, 21P, 27P, 34P | 91 |
| 99 | −1G, 1R, 14H, 17R, 21P, 27P | 348 |
| 101 | −1G, 1R, 14A, 17R, 21P, 27P, 34H | 426 |
| 102 | −1G, 1R, 14H, 17R, 21P, 27P, 34P | 217 |
| 103 | −1G, 1R, 14A, 17R, 21P, 27P, 34P | 114 |
| 104 | 14E, 17R, 21P, 27P, 34H, 35E | 525 |
| 105 | 14E, 17R, 21P, 27P, 34R, 35E | 957 |
| 106 | 14E, 17R, 21P, 27P, 34P, 35E | 121 |
| 107 | 14E, 17R, 21P, 27P, 34H, 35E | 387 |
| 108 | 14E, 17R, 21P, 27P, 34R, 35E | 232 |
| 109 | 14E, 17R, 21P, 27P, 34P, 35E | 140 |
| 110 | 14E, 17R, 21P, 27P, 34P, 35R | 326 |
| 111 | 17R, 21P, 27P, 34H | 580 |
| 113 | 17R, 21P, 27P, 34H | 382 |
| 114 | 14E, 17R, 21P, 27P, 34P, 37P | 214 |
| 115 | 14H, 17R, 21P, 27P, 34P, 37P | 131 |
| 116 | 14H, 17R, 21P, 27P, 31P, 34P | 82 |
| 117 | 14E, 17R, 21P, 27P, 34P, 35R | 163 |
| 118 | 14E, 17R, 21P, 27P, 34P, 35H | 179 |
| 120 | 14S, 17R, 21P, 27P, 34P, 35E | 76 |
| 121 | 14E, 17R, 21P, 31P, 34P, 35E | 69 |
| 122 | 14D, 17R, 21P, 27P, 34P, 35E | 172 |
| 123 | 14D, 17R, 21P, 27P, 34P, 35E | 196 |
| 124 | 14E, 17R, 21P, 27P, 34P, 35H | 377 |
| 125 | 14E, 17R, 21P, 27P, 34P, 35E, 37P | 533 |
| 127 | 14E, 17R, 21P, 27P, 34P, 37F | 152 |
| 129 | 14D, 17R, 21P, 27P, 34P, 35R | 281 |
| 130 | 14D, 17R, 21P, 27P, 34P, 35R | 453 |
| 131 | 14d, 17R, 21P, 27P, 35R | 365 |
| 132 | 14D, 17R, 21P, 27P, 35R | 266 |

Binding to Human Amylin Receptors and Human Calcitonin Receptors

The in vitro data regarding binding to human amylin receptors and human calcitonin receptors and the corresponding selectivity values are shown in Table 5 (below).

Table 5 presents compounds that have a hAmylinR IC50 value of less than 1200 pM and a ratio of hCT/hAmylin binding of less than or at least 10. The preferred compounds—which have a ratio of hCT/hAmylin binding of at least 10—are presented in Table 5a (below). Details of the albumin binding moiety, linker and acylation sites have been removed from these Tables. For full structural information please consult the entry with a corresponding compound number in Table 2. Further details regarding the compounds, such as IUPAC nomenclature, may be found in Table 14.

TABLE 5

| Example no. | Sequence modifications | hAmylin-R bind IC50 (pM) | hCTR bind IC50 (pM) | Ratio hCT/hAmylin binding |
|---|---|---|---|---|
| 1 | 14D, 17R, 21P, 26P, 35D | 1177 | 32473 | 27.6 |
| 2 | 14D, 17R, 21P, 27P, 35D | 411 | 19538 | 47.5 |
| 3 | 14D, 17R, 22P, 26P, 35D | 1131 | 19505 | 17.3 |
| 4 | 14E, 17R, 21P, 25P, 28P, 29P, 37P | 321 | 688 | 2.1 |
| 5 | 14E, 17R, 21P, 26P, 37P | 374 | 537 | 1.4 |
| 6 | 14E, 17R, 21P, 25P, 28P, 29P | 996 | 19950 | 20.0 |
| 7 | 14E, 17R, 21P, 26P | 674 | 11140 | 16.5 |
| 8 | 14E, 17R, 21P, 27P, 37P | 72 | 38 | 0.5 |
| 9 | 14E, 17R, 21P, 27P | 143 | 1142 | 8.0 |
| 10 | 14D, 17R, 21P, 27P, 37P | 82 | 99 | 1.2 |
| 11 | 14E, 17R, 21P, 27P, 35D, 37P | 105 | 101 | 1.0 |
| 12 | 14E, 17R, 21P, 27P, 37P | 142 | 353 | 2.5 |
| 13 | 14E, 17R, 21P, 27P, 37P | 264 | 305 | 1.2 |
| 14 | 14E, 17R, 21P, 27P, 37P | 196 | 432 | 2.2 |
| 15 | 14E, 17R, 21P, 27P | 597 | 15510 | 26.0 |
| 16 | 14E, 17R, 21P, 27P, 35R | 894 | 17070 | 19.1 |
| 17 | 14E, 17R, 21P, 27P, 34H | 878 | 10940 | 12.5 |
| 18 | 14E, 17R, 21P, 27P, 35H | 554 | 5087 | 9.2 |
| 19 | 14E, 17R, 21P, 27P | 556 | 20390 | 36.7 |
| 20 | 14E, 17R, 21P, 27P, 37P | 217 | 787 | 3.6 |
| 21 | 17R, 21P, 27P | 585 | 14240 | 24.4 |
| 22 | 14E, 17R, 21P, 27P, 35E | 794 | 9729 | 12.3 |
| 23 | 17R, 21P, 27P, 35E | 871 | 21810 | 25.0 |
| 24 | 17R, 21P, 27P | 1138 | 102400 | 90.0 |
| 25 | 17R, 21P, 27P, 35E | 768 | 43390 | 56.5 |
| 26 | 17R, 21P, 27P, 35E | 532 | 25265 | 47.5 |
| 27 | 17R, 21P, 27P, 35E | 837 | 34545 | 41.3 |
| 28 | 17R, 21P, 27P, 31P, 35E | 610 | 12522 | 20.5 |
| 29 | 17R, 21P, 27P, 34P, 35E | 577 | 8006 | 13.9 |
| 30 | 14H, 17R, 21P, 27P, 35E | 919 | 21650 | 23.6 |
| 31 | 14E, 17R, 21P, 27P, 31P | 204 | 3259 | 16.0 |
| 32 | 14E, 17R, 21P, 27P, 34P | 100 | 1088 | 10.9 |
| 33 | 14E, 17R, 21P, 28P, 35E | 915 | 3606 | 3.9 |
| 34 | 17R, 21P, 27P, 35K | 1139 | 73390 | 64.4 |
| 35 | 17R, 21P, 27P, 35K | 970 | 48750 | 50.3 |
| 36 | 14E, 17R, 21P, 27P, 34K | 403 | 6305 | 15.7 |

TABLE 5-continued

| Example no. | Sequence modifications | hAmylin-R bind IC50 (pM) | hCTR bind IC50 (pM) | Ratio hCT/hAmylin binding |
|---|---|---|---|---|
| 37 | 14E, 17R, 21P, 27P, 29P | 970 | 2184 | 2.3 |
| 38 | 17R, 21P, 27P, 35R | 249 | 21170 | 84.9 |
| 39 | 17R, 21P, 27P, 34R | 665 | 19280 | 29.0 |
| 40 | 17R, 21P, 27P, 34H | 549 | 17057 | 31.1 |
| 41 | 17R, 21P, 27P | 427 | 21310 | 49.9 |
| 42 | 17R, 21P, 27P | 264 | 8105 | 30.7 |
| 43 | 17R, 21P, 27P | 76 | 2636 | 34.7 |
| 44 | -1K, 1R, 17R, 21P, 27P, 35H | 275 | 4872 | 17.7 |
| 45 | -1K, 1R, 17R, 21P, 27P, 35H | 552 | 14790 | 26.8 |
| 46 | -1G, 1R, 17R, 21P, 27P | 195 | 9530 | 48.9 |
| 47 | -1G, 1R, 17R, 21P, 27P, 35H | 344 | 15460 | 44.9 |
| 48 | 17R, 21P, 27P | 443 | 30870 | 69.7 |
| 49 | 17R, 21P, 27P, 31P | 1191 | 12861 | 10.8 |
| 50 | 17R, 21P, 27P, 34P | 38 | 1380 | 36.0 |
| 51 | 14E, 17R, 21P, 27P, 35R | 828 | 31065 | 37.5 |
| 52 | 14D, 17R, 21P, 27P, 35R | 697 | 56874 | 81.6 |
| 53 | 17R, 21P, 27P, 28P, 31P | 52 | 5383 | 103.5 |
| 54 | 17R, 21P, 27P, 29P, 31P | 30 | 4382 | 146.1 |
| 55 | 17R, 21P, 27P, 28P, 34P | 42 | 2175 | 51.8 |
| 56 | 17R, 21P, 27P, 29P, 34P | 49 | 2088 | 42.6 |
| 57 | 17R, 21P, 27P, 31P, 35H | 115 | 15300 | 133.0 |
| 58 | 17R, 21P, 27P, 34P, 35H | 88 | 9626 | 109.4 |
| 59 | 14D, 17R, 21K, 27P, 35D | 1193 | 5143 | 4.3 |
| 60 | 17R, 21P, 27P, 35H | 695 | 31410 | 45.2 |
| 61 | 14H, 17R, 21P, 27P, 31P | 122 | 8111 | 66.7 |
| 62 | 14H, 17R, 21P, 27P, 31P | 98 | 6174 | 63.0 |
| 63 | 14R, 17R, 21P, 27P, 31P | 825 | 129600 | 157.1 |
| 64 | 14R, 17R, 21P, 27P, 31P | 444 | 55970 | 126.1 |
| 65 | 14R, 17R, 21P, 27P, 34P | 649 | 53461 | 82.4 |
| 66 | 14H, 17R, 21P, 27P, 35H | 396 | 18020 | 45.5 |
| 67 | 14H, 17R, 21P, 27P, 34P | 90 | 4633 | 51.6 |
| 68 | 14H, 17R, 21P, 27P, 34P | 88 | 5664 | 64.4 |
| 69 | 14H, 17R, 21P, 27P | 133 | 8680 | 65.3 |
| 70 | 14H, 17R, 21P, 27P | 169 | 10280 | 60.8 |
| 71 | 14G, 17R, 21P, 27P, 31P | 48 | 1535 | 32.0 |
| 72 | 14A, 17R, 21P, 27P, 31P | 172 | 42410 | 246.6 |
| 73 | 14S, 17R, 21P, 27P, 31P | 104 | 5377 | 51.7 |
| 74 | 14K, 17R, 21P, 27P, 31P | 791 | 79875 | 101.0 |
| 75 | 14T, 17R, 21P, 27P, 31P | 666 | 60870 | 91.4 |
| 76 | 17R, 21P, 27P, 34H | 215 | 17207 | 80.0 |
| 77 | 17R, 21P, 27P, 34H | 428 | 50664 | 118.4 |
| 78 | 17R, 21P, 27P, 34R | 602 | 36550 | 60.7 |
| 79 | 17R, 21P, 27P, 34R | 790 | 36390 | 46.1 |
| 80 | 14H, 17R, 21P, 27P, 34H | 290 | 19760 | 68.1 |
| 81 | 14H, 17R, 21P, 27P, 34H | 271 | 23640 | 87.2 |
| 82 | 14R, 17R, 21P, 27P | 636 | 88760 | 139.6 |
| 83 | 14R, 17R, 21P, 27P | 939 | 136700 | 145.6 |
| 84 | 14H, 17R, 21P, 27P, 34R | 743 | 88860 | 119.6 |
| 85 | 14H, 17R, 21P, 27P, 34R | 876 | 80420 | 91.8 |
| 86 | 17R, 21P, 27P, 34H | 833 | 132723 | 159.3 |
| 87 | 14E, 17R, 21P, 27P, 34H | 633 | 22523 | 35.6 |
| 88 | 14E, 17R, 21P, 27P, 34R | 750 | 34870 | 46.5 |
| 89 | 14E, 17R, 21P, 27P, 35R | 1160 | 32510 | 28.0 |
| 90 | 14H, 17R, 21P, 27P | 61 | 2574 | 42.2 |
| 91 | 17R, 21P, 27P, 34H | 119 | 12000 | 100.8 |
| 92 | 14H, 17R, 21P, 27P | 179 | 25960 | 145.0 |
| 93 | 14A, 17R, 21P, 27P, 34H | 176 | 17780 | 101.0 |
| 94 | 14A, 17R, 21P, 27P, 34P | 148 | 6857 | 46.3 |
| 95 | 17R, 21P, 27P, 34R | 967 | 61280 | 63.4 |
| 96 | 17R, 21P, 27P, 31P | 166 | 13210 | 79.6 |
| 97 | 17R, 21P, 27P, 34H | 568 | 58920 | 103.7 |
| 98 | 17R, 21P, 27P, 34P | 91 | 6739 | 74.1 |
| 99 | -1G, 1R, 14H, 17R, 21P, 27P | 348 | 34950 | 100.4 |
| 100 | -1G, 1R, 14H, 17R, 21P, 27P, 34H | 1015 | 66275 | 65.3 |
| 101 | -1G, 1R, 14A, 17R, 21P, 27P, 34H | 426 | 29175 | 68.6 |
| 102 | -1G, 1R, 14H, 17R, 21P, 27P, 34P | 217 | 7865 | 36.2 |
| 103 | -1G, 1R, 14A, 17R, 21P, 27P, 34P | 114 | 3004 | 26.5 |
| 104 | 14E, 17R, 21P, 27P, 34H, 35E | 525 | 15245 | 29.1 |
| 105 | 14E, 17R, 21P, 27P, 34R, 35E | 957 | 14099 | 14.7 |
| 106 | 14E, 17R, 21P, 27P, 34P, 35E | 121 | 2135 | 17.6 |
| 107 | 14E, 17R, 21P, 27P, 34H, 35E | 387 | 4283 | 11.1 |
| 108 | 14E, 17R, 21P, 27P, 34R, 35E | 232 | 6623 | 28.5 |
| 109 | 14E, 17R, 21P, 27P, 34P, 35E | 140 | 1861 | 13.3 |
| 110 | 14E, 17R, 21P, 27P, 34P, 35R | 326 | 17455 | 53.6 |
| 111 | 17R, 21P, 27P, 34H | 580 | 10750 | 18.5 |
| 112 | 17R, 21P, 27P, 34H | 1037 | 24320 | 23.5 |

TABLE 5-continued

| Example no. | Sequence modifications | hAmylin-R bind IC50 (pM) | hCTR bind IC50 (pM) | Ratio hCT/hAmylin binding |
|---|---|---|---|---|
| 113 | 17R, 21P, 27P, 34H | 382 | 22690 | 59.4 |
| 114 | 14E, 17R, 21P, 27P, 34P, 37P | 214 | 117 | 0.5 |
| 115 | 14H, 17R, 21P, 27P, 34P, 37P | 131 | 157 | 1.2 |
| 116 | 14H, 17R, 21P, 27P, 31P, 34P | 82 | 2036 | 24.8 |
| 117 | 14E, 17R, 21P, 27P, 34P, 35R | 163 | 6298 | 38.6 |
| 118 | 14E, 17R, 21P, 27P, 34P, 35H | 179 | 3801 | 21.2 |
| 119 | 17R, 21P, 27P, 31P, 34P, 35R | 880 | 42770 | 48.6 |
| 120 | 14S, 17R, 21P, 27P, 34P, 35E | 76 | 3439 | 45.3 |
| 121 | 14E, 17R, 21P, 31P, 34P, 35E | 69 | 1561 | 22.6 |
| 122 | 14D, 17R, 21P, 27P, 34P, 35E | 172 | 8565 | 49.8 |
| 123 | 14D, 17R, 21P, 27P, 34P, 35E | 196 | 3273 | 16.7 |
| 124 | 14E, 17R, 21P, 27P, 34P, 35H | 377 | 10314 | 27.3 |
| 125 | 14E, 17R, 21P, 27P, 34P, 35E, 37P | 533 | 226 | 0.4 |
| 126 | 14E, 17R, 23P, 34P, 35E | 1187 | 9294 | 7.8 |
| 127 | 14E, 17R, 21P, 27P, 34P, 37F | 152 | 2733 | 18.0 |
| 128 | 14E, 17R, 21P, 27P, 35H | 992 | 26140 | 26.4 |
| 129 | 14D, 17R, 21P, 27P, 34P, 35R | 281 | 42470 | 151.1 |
| 130 | 14D, 17R, 21P, 27P, 34P, 35R | 453 | 126850 | 280.0 |
| 131 | 14d, 17R, 21P, 27P, 35R | 365 | 111900 | 306.6 |
| 132 | 14D, 17R, 21P, 27P, 35R | 266 | 7504 | 28.2 |

TABLE 5a

| Example no. | Sequence modifications | hAmylin-R bind IC50 (pM) | hCTR bind IC50 (pM) | Ratio hCT/hAmylin binding |
|---|---|---|---|---|
| 1 | 14D, 17R, 21P, 26P, 35D | 1177 | 32473 | 27.6 |
| 2 | 14D, 17R, 21P, 27P, 35D | 411 | 19538 | 47.5 |
| 3 | 14D, 17R, 22P, 26P, 35D | 1131 | 19505 | 17.3 |
| 6 | 14E, 17R, 21P, 25P, 28P, 29P | 996 | 19950 | 20.0 |
| 7 | 14E, 17R, 21P, 26P | 674 | 11140 | 16.5 |
| 15 | 14E, 17R, 21P, 27P | 597 | 15510 | 26.0 |
| 16 | 14E, 17R, 21P, 27P, 35R | 894 | 17070 | 19.1 |
| 17 | 14E, 17R, 21P, 27P, 34H | 878 | 10940 | 12.5 |
| 19 | 14E, 17R, 21P, 27P | 556 | 20390 | 36.7 |
| 21 | 17R, 21P, 27P | 585 | 14240 | 24.4 |
| 22 | 14E, 17R, 21P, 27P, 35E | 794 | 9729 | 12.3 |
| 23 | 17R, 21P, 27P, 35E | 871 | 21810 | 25.0 |
| 24 | 17R, 21P, 27P | 1138 | 102400 | 90.0 |
| 25 | 17R, 21P, 27P, 35E | 768 | 43390 | 56.5 |
| 26 | 17R, 21P, 27P, 35E | 532 | 25265 | 47.5 |
| 27 | 17R, 21P, 27P, 35E | 837 | 34545 | 41.3 |
| 28 | 17R, 21P, 27P, 31P, 35E | 610 | 12522 | 20.5 |
| 29 | 17R, 21P, 27P, 34P, 35E | 577 | 8006 | 13.9 |
| 30 | 14H, 17R, 21P, 27P, 35E | 919 | 21650 | 23.6 |
| 31 | 14E, 17R, 21P, 27P, 31P | 204 | 3259 | 16.0 |
| 32 | 14E, 17R, 21P, 27P, 34P | 100 | 1088 | 10.9 |
| 34 | 17R, 21P, 27P, 35K | 1139 | 73390 | 64.4 |
| 35 | 17R, 21P, 27P, 35K | 970 | 48750 | 50.3 |
| 36 | 14E, 17R, 21P, 27P, 34K | 403 | 6305 | 15.7 |
| 38 | 17R, 21P, 27P, 35R | 249 | 21170 | 84.9 |
| 39 | 17R, 21P, 27P, 34R | 665 | 19280 | 29.0 |
| 40 | 17R, 21P, 27P, 34H | 549 | 17057 | 31.1 |
| 41 | 17R, 21P, 27P | 427 | 21310 | 49.9 |
| 42 | 17R, 21P, 27P | 264 | 8105 | 30.7 |
| 43 | 17R, 21P, 27P | 76 | 2636 | 34.7 |
| 44 | −1K, 1R, 17R, 21P, 27P, 35H | 275 | 4872 | 17.7 |
| 45 | −1K, 1R, 17R, 21P, 27P, 35H | 552 | 14790 | 26.8 |
| 46 | −1G, 1R, 17R, 21P, 27P | 195 | 9530 | 48.9 |
| 47 | −1G, 1R, 17R, 21P, 27P, 35H | 344 | 15460 | 44.9 |
| 48 | 17R, 21P, 27P | 443 | 30870 | 69.7 |
| 49 | 17R, 21P, 27P, 31P | 1191 | 12861 | 10.8 |
| 50 | 17R, 21P, 27P, 34P | 38 | 1380 | 36.0 |
| 51 | 14E, 17R, 21P, 27P, 35R | 828 | 31065 | 37.5 |
| 52 | 14D, 17R, 21P, 27P, 35R | 697 | 56874 | 81.6 |
| 53 | 17R, 21P, 27P, 28P, 31P | 52 | 5383 | 103.5 |
| 54 | 17R, 21P, 27P, 29P, 31P | 30 | 4382 | 146.1 |
| 55 | 17R, 21P, 27P, 28P, 34P | 42 | 2175 | 51.8 |
| 56 | 17R, 21P, 27P, 29P, 34P | 49 | 2088 | 42.6 |
| 57 | 17R, 21P, 27P, 31P, 35H | 115 | 15300 | 133.0 |
| 58 | 17R, 21P, 27P, 34P, 35H | 88 | 9626 | 109.4 |
| 60 | 17R, 21P, 27P, 35H | 695 | 31410 | 45.2 |

TABLE 5a-continued

| Example no. | Sequence modifications | hAmylin-R bind IC50 (pM) | hCTR bind IC50 (pM) | Ratio hCT/hAmylin binding |
|---|---|---|---|---|
| 61 | 14H, 17R, 21P, 27P, 31P | 122 | 8111 | 66.7 |
| 62 | 14H, 17R, 21P, 27P, 31P | 98 | 6174 | 63.0 |
| 63 | 14R, 17R, 21P, 27P, 31P | 825 | 129600 | 157.1 |
| 64 | 14R, 17R, 21P, 27P, 31P | 444 | 55970 | 126.1 |
| 65 | 14R, 17R, 21P, 27P, 34P | 649 | 53461 | 82.4 |
| 66 | 14H, 17R, 21P, 27P, 35H | 396 | 18020 | 45.5 |
| 67 | 14H, 17R, 21P, 27P, 34P | 90 | 4633 | 51.6 |
| 68 | 14H, 17R, 21P, 27P, 34P | 88 | 5664 | 64.4 |
| 69 | 14H, 17R, 21P, 27P | 133 | 8680 | 65.3 |
| 70 | 14H, 17R, 21P, 27P | 169 | 10280 | 60.8 |
| 71 | 14G, 17R, 21P, 27P, 31P | 48 | 1535 | 32.0 |
| 72 | 14A, 17R, 21P, 27P, 31P | 172 | 42410 | 246.6 |
| 73 | 14S, 17R, 21P, 27P, 31P | 104 | 5377 | 51.7 |
| 74 | 14K, 17R, 21P, 27P, 31P | 791 | 79875 | 101.0 |
| 75 | 14T, 17R, 21P, 27P, 31P | 666 | 60870 | 91.4 |
| 76 | 17R, 21P, 27P, 34H | 215 | 17207 | 80.0 |
| 77 | 17R, 21P, 27P, 34H | 428 | 50664 | 118.4 |
| 78 | 17R, 21P, 27P, 34R | 602 | 36550 | 60.7 |
| 79 | 17R, 21P, 27P, 34R | 790 | 36390 | 46.1 |
| 80 | 14H, 17R, 21P, 27P, 34H | 290 | 19760 | 68.1 |
| 81 | 14H, 17R, 21P, 27P, 34H | 271 | 23640 | 87.2 |
| 82 | 14R, 17R, 21P, 27P | 636 | 88760 | 139.6 |
| 83 | 14R, 17R, 21P, 27P | 939 | 136700 | 145.6 |
| 84 | 14H, 17R, 21P, 27P, 34R | 743 | 88860 | 119.6 |
| 85 | 14H, 17R, 21P, 27P, 34R | 876 | 80420 | 91.8 |
| 86 | 17R, 21P, 27P, 34H | 833 | 132723 | 159.3 |
| 87 | 14E, 17R, 21P, 27P, 34H | 633 | 22523 | 35.6 |
| 88 | 14E, 17R, 21P, 27P, 34R | 750 | 34870 | 46.5 |
| 89 | 14E, 17R, 21P, 27P, 35R | 1160 | 32510 | 28.0 |
| 90 | 14H, 17R, 21P, 27P | 61 | 2574 | 42.2 |
| 91 | 17R, 21P, 27P, 34H | 119 | 12000 | 100.8 |
| 92 | 14H, 17R, 21P, 27P | 179 | 25960 | 145.0 |
| 93 | 14A, 17R, 21P, 27P, 34H | 176 | 17780 | 101.0 |
| 94 | 14A, 17R, 21P, 27P, 34P | 148 | 6857 | 46.3 |
| 95 | 17R, 21P, 27P, 34R | 967 | 61280 | 63.4 |
| 96 | 17R, 21P, 27P, 31P | 166 | 13210 | 79.6 |
| 97 | 17R, 21P, 27P, 34H | 568 | 58920 | 103.7 |
| 98 | 17R, 21P, 27P, 34P | 91 | 6739 | 74.1 |
| 99 | −1G, 1R, 14H, 17R, 21P, 27P | 348 | 34950 | 100.4 |
| 100 | −1G, 1R, 14H, 17R, 21P, 27P, 34H | 1015 | 66275 | 65.3 |
| 101 | −1G, 1R, 14A, 17R, 21P, 27P, 34H | 426 | 29175 | 68.6 |
| 102 | −1G, 1R, 14H, 17R, 21P, 27P, 34P | 217 | 7865 | 36.2 |
| 103 | −1G, 1R, 14A, 17R, 21P, 27P, 34P | 114 | 3004 | 26.5 |
| 104 | 14E, 17R, 21P, 27P, 34H, 35E | 525 | 15245 | 29.1 |
| 105 | 14E, 17R, 21P, 27P, 34R, 35E | 957 | 14099 | 14.7 |
| 106 | 14E, 17R, 21P, 27P, 34P, 35E | 121 | 2135 | 17.6 |
| 107 | 14E, 17R, 21P, 27P, 34H, 35E | 387 | 4283 | 11.1 |
| 108 | 14E, 17R, 21P, 27P, 34R, 35E | 232 | 6623 | 28.5 |
| 109 | 14E, 17R, 21P, 27P, 34P, 35E | 140 | 1861 | 13.3 |
| 110 | 14E, 17R, 21P, 27P, 34P, 35R | 326 | 17455 | 53.6 |
| 111 | 17R, 21P, 27P, 34H | 580 | 10750 | 18.5 |
| 112 | 17R, 21P, 27P, 34H | 1037 | 24320 | 23.5 |
| 113 | 17R, 21P, 27P, 34H | 382 | 22690 | 59.4 |
| 116 | 14H, 17R, 21P, 27P, 31P, 34P | 82 | 2036 | 24.8 |
| 117 | 14E, 17R, 21P, 27P, 34P, 35R | 163 | 6298 | 38.6 |
| 118 | 14E, 17R, 21P, 27P, 34P, 35H | 179 | 3801 | 21.2 |
| 119 | 17R, 21P, 27P, 31P, 34P, 35R | 880 | 42770 | 48.6 |
| 120 | 14S, 17R, 21P, 27P, 34P, 35E | 76 | 3439 | 45.3 |
| 121 | 14E, 17R, 21P, 31P, 34P, 35E | 69 | 1561 | 22.6 |
| 122 | 14D, 17R, 21P, 27P, 34P, 35E | 172 | 8565 | 49.8 |
| 123 | 14D, 17R, 21P, 27P, 34P, 35E | 196 | 3273 | 16.7 |
| 124 | 14E, 17R, 21P, 27P, 34P, 35H | 377 | 10314 | 27.3 |
| 127 | 14E, 17R, 21P, 27P, 34P, 37F | 152 | 2733 | 18.0 |
| 128 | 14E, 17R, 21P, 27P, 35H | 992 | 26140 | 26.4 |
| 129 | 14D, 17R, 21P, 27P, 34P, 35R | 281 | 42470 | 151.1 |
| 130 | 14D, 17R, 21P, 27P, 34P, 35R | 453 | 126850 | 280.0 |
| 131 | 14d, 17R, 21P, 27P, 35R | 365 | 111900 | 306.6 |
| 132 | 14D, 17R, 21P, 27P, 35R | 266 | 7504 | 28.2 |

TABLE 5b

| Example no. | Sequence modifications | hAmylin-R bind IC50 (pM) | hCTR bind IC50 (pM) | Ratio hCT/hAmylin binding |
|---|---|---|---|---|
| 1 | 14D, 17R, 21P, 26P, 35D | 1177 | 32473 | 27.6 |
| 2 | 14D, 17R, 21P, 27P, 35D | 411 | 19538 | 47.5 |
| 3 | 14D, 17R, 22P, 26P, 35D | 1131 | 19505 | 17.3 |
| 6 | 14E, 17R, 21P, 25P, 28P, 29P | 996 | 19950 | 20.0 |
| 7 | 14E, 17R, 21P, 26P | 674 | 11140 | 16.5 |
| 15 | 14E, 17R, 21P, 27P | 597 | 15510 | 26.0 |
| 16 | 14E, 17R, 21P, 27P, 35R | 894 | 17070 | 19.1 |
| 19 | 14E, 17R, 21P, 27P | 556 | 20390 | 36.7 |
| 21 | 17R, 21P, 27P | 585 | 14240 | 24.4 |
| 23 | 17R, 21P, 27P, 35E | 871 | 21810 | 25.0 |
| 24 | 17R, 21P, 27P | 1138 | 102400 | 90.0 |
| 25 | 17R, 21P, 27P, 35E | 768 | 43390 | 56.5 |
| 26 | 17R, 21P, 27P, 35E | 532 | 25265 | 47.5 |
| 27 | 17R, 21P, 27P, 35E | 837 | 34545 | 41.3 |
| 28 | 17R, 21P, 27P, 31P, 35E | 610 | 12522 | 20.5 |
| 30 | 14H, 17R, 21P, 27P, 35E | 919 | 21650 | 23.6 |
| 31 | 14E, 17R, 21P, 27P, 31P | 204 | 3259 | 16.0 |
| 34 | 17R, 21P, 27P, 35K | 1139 | 73390 | 64.4 |
| 35 | 17R, 21P, 27P, 35K | 970 | 48750 | 50.3 |
| 36 | 14E, 17R, 21P, 27P, 34K | 403 | 6305 | 15.7 |
| 38 | 17R, 21P, 27P, 35R | 249 | 21170 | 84.9 |
| 39 | 17R, 21P, 27P, 34R | 665 | 19280 | 29.0 |
| 40 | 17R, 21P, 27P, 34H | 549 | 17057 | 31.1 |
| 41 | 17R, 21P, 27P | 427 | 21310 | 49.9 |
| 42 | 17R, 21P, 27P | 264 | 8105 | 30.7 |
| 43 | 17R, 21P, 27P | 76 | 2636 | 34.7 |
| 44 | −1K, 1R, 17R, 21P, 27P, 35H | 275 | 4872 | 17.7 |
| 45 | −1K, 1R, 17R, 21P, 27P, 35H | 552 | 14790 | 26.8 |
| 46 | −1G, 1R, 17R, 21P, 27P | 195 | 9530 | 48.9 |
| 47 | −1G, 1R, 17R, 21P, 27P, 35H | 344 | 15460 | 44.9 |
| 48 | 17R, 21P, 27P | 443 | 30870 | 69.7 |
| 50 | 17R, 21P, 27P, 34P | 38 | 1380 | 36.0 |
| 51 | 14E, 17R, 21P, 27P, 35R | 828 | 31065 | 37.5 |
| 52 | 14D, 17R, 21P, 27P, 35R | 697 | 56874 | 81.6 |
| 53 | 17R, 21P, 27P, 28P, 31P | 52 | 5383 | 103.5 |
| 54 | 17R, 21P, 27P, 29P, 31P | 30 | 4382 | 146.1 |
| 55 | 17R, 21P, 27P, 28P, 34P | 42 | 2175 | 51.8 |
| 56 | 17R, 21P, 27P, 29P, 34P | 49 | 2088 | 42.6 |
| 57 | 17R, 21P, 27P, 31P, 35H | 115 | 15300 | 133.0 |
| 58 | 17R, 21P, 27P, 34P, 35H | 88 | 9626 | 109.4 |
| 60 | 17R, 21P, 27P, 35H | 695 | 31410 | 45.2 |
| 61 | 14H, 17R, 21P, 27P, 31P | 122 | 8111 | 66.7 |
| 62 | 14H, 17R, 21P, 27P, 31P | 98 | 6174 | 63.0 |
| 63 | 14R, 17R, 21P, 27P, 31P | 825 | 129600 | 157.1 |
| 64 | 14R, 17R, 21P, 27P, 31P | 444 | 55970 | 126.1 |
| 65 | 14R, 17R, 21P, 27P, 34P | 649 | 53461 | 82.4 |
| 66 | 14H, 17R, 21P, 27P, 35H | 396 | 18020 | 45.5 |
| 67 | 14H, 17R, 21P, 27P, 34P | 90 | 4633 | 51.6 |
| 68 | 14H, 17R, 21P, 27P, 34P | 88 | 5664 | 64.4 |
| 69 | 14H, 17R, 21P, 27P | 133 | 8680 | 65.3 |
| 70 | 14H, 17R, 21P, 27P | 169 | 10280 | 60.8 |
| 71 | 14G, 17R, 21P, 27P, 31P | 48 | 1535 | 32.0 |
| 72 | 14A, 17R, 21P, 27P, 31P | 172 | 42410 | 246.6 |
| 73 | 14S, 17R, 21P, 27P, 31P | 104 | 5377 | 51.7 |
| 74 | 14K, 17R, 21P, 27P, 31P | 791 | 79875 | 101.0 |
| 75 | 14T, 17R, 21P, 27P, 31P | 666 | 60870 | 91.4 |
| 76 | 17R, 21P, 27P, 34H | 215 | 17207 | 80.0 |
| 77 | 17R, 21P, 27P, 34H | 428 | 50664 | 118.4 |
| 78 | 17R, 21P, 27P, 34R | 602 | 36550 | 60.7 |
| 79 | 17R, 21P, 27P, 34R | 790 | 36390 | 46.1 |
| 80 | 14H, 17R, 21P, 27P, 34H | 290 | 19760 | 68.1 |
| 81 | 14H, 17R, 21P, 27P, 34H | 271 | 23640 | 87.2 |
| 82 | 14R, 17R, 21P, 27P | 636 | 88760 | 139.6 |
| 83 | 14R, 17R, 21P, 27P | 939 | 136700 | 145.6 |
| 84 | 14H, 17R, 21P, 27P, 34R | 743 | 88860 | 119.6 |
| 85 | 14H, 17R, 21P, 27P, 34R | 876 | 80420 | 91.8 |
| 86 | 17R, 21P, 27P, 34H | 833 | 132723 | 159.3 |
| 87 | 14E, 17R, 21P, 27P, 34H | 633 | 22523 | 35.6 |
| 88 | 14E, 17R, 21P, 27P, 34R | 750 | 34870 | 46.5 |
| 89 | 14E, 17R, 21P, 27P, 35R | 1160 | 32510 | 28.0 |
| 90 | 14H, 17R, 21P, 27P | 61 | 2574 | 42.2 |
| 91 | 17R, 21P, 27P, 34H | 119 | 12000 | 100.8 |
| 92 | 14H, 17R, 21P, 27P | 179 | 25960 | 145.0 |
| 93 | 14A, 17R, 21P, 27P, 34H | 176 | 17780 | 101.0 |
| 94 | 14A, 17R, 21P, 27P, 34P | 148 | 6857 | 46.3 |
| 95 | 17R, 21P, 27P, 34R | 967 | 61280 | 63.4 |

TABLE 5b-continued

| Example no. | Sequence modifications | hAmylin-R bind IC50 (pM) | hCTR bind IC50 (pM) | Ratio hCT/hAmylin binding |
|---|---|---|---|---|
| 96 | 17R, 21P, 27P, 31P | 166 | 13210 | 79.6 |
| 97 | 17R, 21P, 27P, 34H | 568 | 58920 | 103.7 |
| 98 | 17R, 21P, 27P, 34P | 91 | 6739 | 74.1 |
| 99 | -1G, 1R, 14H, 17R, 21P, 27P | 348 | 34950 | 100.4 |
| 100 | -1G, 1R, 14H, 17R, 21P, 27P, 34H | 1015 | 66275 | 65.3 |
| 101 | -1G, 1R, 14A, 17R, 21P, 27P, 34H | 426 | 29175 | 68.6 |
| 102 | -1G, 1R, 14H, 17R, 21P, 27P, 34P | 217 | 7865 | 36.2 |
| 103 | -1G, 1R, 14A, 17R, 21P, 27P, 34P | 114 | 3004 | 26.5 |
| 104 | 14E, 17R, 21P, 27P, 34H, 35E | 525 | 15245 | 29.1 |
| 106 | 14E, 17R, 21P, 27P, 34P, 35E | 121 | 2135 | 17.6 |
| 108 | 14E, 17R, 21P, 27P, 34R, 35E | 232 | 6623 | 28.5 |
| 109 | 14E, 17R, 21P, 27P, 34P, 35E | 140 | 1861 | 13.3 |
| 110 | 14E, 17R, 21P, 27P, 34P, 35R | 326 | 17455 | 53.6 |
| 111 | 17R, 21P, 27P, 34H | 580 | 10750 | 18.5 |
| 112 | 17R, 21P, 27P, 34H | 1037 | 24320 | 23.5 |
| 113 | 17R, 21P, 27P, 34H | 382 | 22690 | 59.4 |
| 116 | 14H, 17R, 21P, 27P, 31P, 34P | 82 | 2036 | 24.8 |
| 117 | 14E, 17R, 21P, 27P, 34P, 35R | 163 | 6298 | 38.6 |
| 118 | 14E, 17R, 21P, 27P, 34P, 35H | 179 | 3801 | 21.2 |
| 119 | 17R, 21P, 27P, 31P, 34P, 35R | 880 | 42770 | 48.6 |
| 120 | 14S, 17R, 21P, 27P, 34P, 35E | 76 | 3439 | 45.3 |
| 121 | 14E, 17R, 21P, 31P, 34P, 35E | 69 | 1561 | 22.6 |
| 122 | 14D, 17R, 21P, 27P, 34P, 35E | 172 | 8565 | 49.8 |
| 123 | 14D, 17R, 21P, 27P, 34P, 35E | 196 | 3273 | 16.7 |
| 124 | 14E, 17R, 21P, 27P, 34P, 35H | 377 | 10314 | 27.3 |
| 127 | 14E, 17R, 21P, 27P, 34P, 37F | 152 | 2733 | 18.0 |
| 128 | 14E, 17R, 21P, 27P, 35H | 992 | 26140 | 26.4 |
| 129 | 14D, 17R, 21P, 27P, 34P, 35R | 281 | 42470 | 151.1 |
| 130 | 14D, 17R, 21P, 27P, 34P, 35R | 453 | 126850 | 280.0 |
| 131 | 14d, 17R, 21P, 27P, 35R | 365 | 111900 | 306.6 |
| 132 | 14D, 17R, 21P, 27P, 35R | 266 | 7504 | 28.2 |

TABLE 5c

| Example no. | Sequence modifications | hAmylin-R bind IC50 (pM) | hCTR bind IC50 (pM) | Ratio hCT/hAmylin binding |
|---|---|---|---|---|
| 1 | 14D, 17R, 21P, 26P, 35D | 1177 | 32473 | 27.6 |
| 2 | 14D, 17R, 21P, 27P, 35D | 411 | 19538 | 47.5 |
| 6 | 14E, 17R, 21P, 25P, 28P, 29P | 996 | 19950 | 20.0 |
| 15 | 14E, 17R, 21P, 27P | 597 | 15510 | 26.0 |
| 19 | 14E, 17R, 21P, 27P | 556 | 20390 | 36.7 |
| 21 | 17R, 21P, 27P | 585 | 14240 | 24.4 |
| 23 | 17R, 21P, 27P, 35E | 871 | 21810 | 25.0 |
| 24 | 17R, 21P, 27P | 1138 | 102400 | 90.0 |
| 25 | 17R, 21P, 27P, 35E | 768 | 43390 | 56.5 |
| 26 | 17R, 21P, 27P, 35E | 532 | 25265 | 47.5 |
| 27 | 17R, 21P, 27P, 35E | 837 | 34545 | 41.3 |
| 28 | 17R, 21P, 27P, 31P, 35E | 610 | 12522 | 20.5 |
| 30 | 14H, 17R, 21P, 27P, 35E | 919 | 21650 | 23.6 |
| 34 | 17R, 21P, 27P, 35K | 1139 | 73390 | 64.4 |
| 35 | 17R, 21P, 27P, 35K | 970 | 48750 | 50.3 |
| 38 | 17R, 21P, 27P, 35R | 249 | 21170 | 84.9 |
| 39 | 17R, 21P, 27P, 34R | 665 | 19280 | 29.0 |
| 40 | 17R, 21P, 27P, 34H | 549 | 17057 | 31.1 |
| 41 | 17R, 21P, 27P | 427 | 21310 | 49.9 |
| 42 | 17R, 21P, 27P | 264 | 8105 | 30.7 |
| 43 | 17R, 21P, 27P | 76 | 2636 | 34.7 |
| 45 | -1K, 1R, 17R, 21P, 27P, 35H | 552 | 14790 | 26.8 |
| 46 | -1G, 1R, 17R, 21P, 27P | 195 | 9530 | 48.9 |
| 47 | -1G, 1R, 17R, 21P, 27P, 35H | 344 | 15460 | 44.9 |
| 48 | 17R, 21P, 27P | 443 | 30870 | 69.7 |
| 50 | 17R, 21P, 27P, 34P | 38 | 1380 | 36.0 |
| 51 | 14E, 17R, 21P, 27P, 35R | 828 | 31065 | 37.5 |
| 52 | 14D, 17R, 21P, 27P, 35R | 697 | 56874 | 81.6 |
| 53 | 17R, 21P, 27P, 28P, 31P | 52 | 5383 | 103.5 |
| 54 | 17R, 21P, 27P, 29P, 31P | 30 | 4382 | 146.1 |
| 55 | 17R, 21P, 27P, 28P, 34P | 42 | 2175 | 51.8 |
| 56 | 17R, 21P, 27P, 29P, 34P | 49 | 2088 | 42.6 |
| 57 | 17R, 21P, 27P, 31P, 35H | 115 | 15300 | 133.0 |
| 58 | 17R, 21P, 27P, 34P, 35H | 88 | 9626 | 109.4 |
| 60 | 17R, 21P, 27P, 35H | 695 | 31410 | 45.2 |

TABLE 5c-continued

| Example no. | Sequence modifications | hAmylin-R bind IC50 (pM) | hCTR bind IC50 (pM) | Ratio hCT/ hAmylin binding |
|---|---|---|---|---|
| 61 | 14H, 17R, 21P, 27P, 31P | 122 | 8111 | 66.7 |
| 62 | 14H, 17R, 21P, 27P, 31P | 98 | 6174 | 63.0 |
| 63 | 14R, 17R, 21P, 27P, 31P | 825 | 129600 | 157.1 |
| 64 | 14R, 17R, 21P, 27P, 31P | 444 | 55970 | 126.1 |
| 65 | 14R, 17R, 21P, 27P, 34P | 649 | 53461 | 82.4 |
| 66 | 14H, 17R, 21P, 27P, 35H | 396 | 18020 | 45.5 |
| 67 | 14H, 17R, 21P, 27P, 34P | 90 | 4633 | 51.6 |
| 68 | 14H, 17R, 21P, 27P, 34P | 88 | 5664 | 64.4 |
| 69 | 14H, 17R, 21P, 27P | 133 | 8680 | 65.3 |
| 70 | 14H, 17R, 21P, 27P | 169 | 10280 | 60.8 |
| 71 | 14G, 17R, 21P, 27P, 31P | 48 | 1535 | 32.0 |
| 72 | 14A, 17R, 21P, 27P, 31P | 172 | 42410 | 246.6 |
| 73 | 14S, 17R, 21P, 27P, 31P | 104 | 5377 | 51.7 |
| 74 | 14K, 17R, 21P, 27P, 31P | 791 | 79875 | 101.0 |
| 75 | 14T, 17R, 21P, 27P, 31P | 666 | 60870 | 91.4 |
| 76 | 17R, 21P, 27P, 34H | 215 | 17207 | 80.0 |
| 77 | 17R, 21P, 27P, 34H | 428 | 50664 | 118.4 |
| 78 | 17R, 21P, 27P, 34R | 602 | 36550 | 60.7 |
| 79 | 17R, 21P, 27P, 34R | 790 | 36390 | 46.1 |
| 80 | 14H, 17R, 21P, 27P, 34H | 290 | 19760 | 68.1 |
| 81 | 14H, 17R, 21P, 27P, 34H | 271 | 23640 | 87.2 |
| 82 | 14R, 17R, 21P, 27P | 636 | 88760 | 139.6 |
| 83 | 14R, 17R, 21P, 27P | 939 | 136700 | 145.6 |
| 84 | 14H, 17R, 21P, 27P, 34R | 743 | 88860 | 119.6 |
| 85 | 14H, 17R, 21P, 27P, 34R | 876 | 80420 | 91.8 |
| 86 | 17R, 21P, 27P, 34H | 833 | 132723 | 159.3 |
| 87 | 14E, 17R, 21P, 27P, 34H | 633 | 22523 | 35.6 |
| 88 | 14E, 17R, 21P, 27P, 34R | 750 | 34870 | 46.5 |
| 89 | 14E, 17R, 21P, 27P, 35R | 1160 | 32510 | 28.0 |
| 90 | 14H, 17R, 21P, 27P | 61 | 2574 | 42.2 |
| 91 | 17R, 21P, 27P, 34H | 119 | 12000 | 100.8 |
| 92 | 14H, 17R, 21P, 27P | 179 | 25960 | 145.0 |
| 93 | 14A, 17R, 21P, 27P, 34H | 176 | 17780 | 101.0 |
| 94 | 14A, 17R, 21P, 27P, 34P | 148 | 6857 | 46.3 |
| 95 | 17R, 21P, 27P, 34R | 967 | 61280 | 63.4 |
| 96 | 17R, 21P, 27P, 31P | 166 | 13210 | 79.6 |
| 97 | 17R, 21P, 27P, 34H | 568 | 58920 | 103.7 |
| 98 | 17R, 21P, 27P, 34P | 91 | 6739 | 74.1 |
| 99 | −1G, 1R, 14H, 17R, 21P, 27P | 348 | 34950 | 100.4 |
| 100 | −1G, 1R, 14H, 17R, 21P, 27P, 34H | 1015 | 66275 | 65.3 |
| 101 | −1G, 1R, 14A, 17R, 21P, 27P, 34H | 426 | 29175 | 68.6 |
| 102 | −1G, 1R, 14H, 17R, 21P, 27P, 34P | 217 | 7865 | 36.2 |
| 103 | −1G, 1R, 14A, 17R, 21P, 27P, 34P | 114 | 3004 | 26.5 |
| 104 | 14E, 17R, 21P, 27P, 34H, 35E | 525 | 15245 | 29.1 |
| 108 | 14E, 17R, 21P, 27P, 34R, 35E | 232 | 6623 | 28.5 |
| 109 | 14E, 17R, 21P, 27P, 34P, 35E | 140 | 1861 | 13.3 |
| 110 | 14E, 17R, 21P, 27P, 34P, 35R | 326 | 17455 | 53.6 |
| 111 | 17R, 21P, 27P, 34H | 580 | 10750 | 18.5 |
| 112 | 17R, 21P, 27P, 34H | 1037 | 24320 | 23.5 |
| 113 | 17R, 21P, 27P, 34H | 382 | 22690 | 59.4 |
| 116 | 14H, 17R, 21P, 27P, 31P, 34P | 82 | 2036 | 24.8 |
| 117 | 14E, 17R, 21P, 27P, 34P, 35R | 163 | 6298 | 38.6 |
| 118 | 14E, 17R, 21P, 27P, 34P, 35H | 179 | 3801 | 21.2 |
| 119 | 17R, 21P, 27P, 31P, 34P, 35R | 880 | 42770 | 48.6 |
| 120 | 14S, 17R, 21P, 27P, 34P, 35E | 76 | 3439 | 45.3 |
| 121 | 14E, 17R, 21P, 31P, 34P, 35E | 69 | 1561 | 22.6 |
| 122 | 14D, 17R, 21P, 27P, 34P, 35E | 172 | 8565 | 49.8 |
| 124 | 14E, 17R, 21P, 27P, 34P, 35H | 377 | 10314 | 27.3 |
| 128 | 14E, 17R, 21P, 27P, 35H | 992 | 26140 | 26.4 |
| 129 | 14D, 17R, 21P, 27P, 34P, 35R | 281 | 42470 | 151.1 |
| 130 | 14D, 17R, 21P, 27P, 34P, 35R | 453 | 126850 | 280.0 |
| 131 | 14d, 17R, 21P, 27P, 35R | 365 | 111900 | 306.6 |
| 132 | 14D, 17R, 21P, 27P, 35R | 266 | 7504 | 28.2 |

Human Amylin Receptor Potency and Human Calcitonin Receptor Potency

The in vitro data regarding human amylin receptor potency and human calcitonin receptor potency (measured as described in assay (II)) and the corresponding selectivity values are shown in Table 6. For ease of reference, the human binding data are also included.

Table 6 discloses compounds that have a hAmylinR IC$_{50}$ value of less than 1200 pM and indicates values for human functional selectivity of at least 5 or less than 5. Preferred compounds have a hAmylinR IC50 value of less than 1200 pM and a human functional selectivity of at least 5. For ease of reference, these preferred compounds are presented in Table 6a. In one embodiment the amylin polypeptide according to the present invention is selected from the compounds presented in table 6. In one embodiment the amylin polypeptide according to the present invention is selected from the compounds presented in table 6a. In one embodiment the amylin polypeptide according to the present invention is selected from the compounds presented in table 6b. In one embodiment the amylin polypeptide according to the present invention is selected from the compounds presented in table 6c. In one embodiment the amylin polypeptide according to the present invention is selected from the compounds presented in table 6d. In one embodiment the amylin polypeptide according to the present invention is selected from the compounds presented in table 6e. In one embodiment the amylin polypeptide according to the present invention is selected from the compounds presented in table 6f. In one embodiment the amylin polypeptide according to the present invention is selected from the compounds presented in table 6g. In one embodiment the amylin polypeptide according to the present invention is selected from the compounds presented in table 6h. In one embodiment the amylin polypeptide according to the present invention is selected from the compounds presented in table 6i. In one embodiment the amylin polypeptide according to the present invention is selected from the compounds presented in table 6j. In one embodiment the amylin polypeptide according to the present invention is selected from the compounds presented in table 6k. In one embodiment the amylin polypeptide according to the present invention is selected from the compounds presented in table 6l. In one embodiment the amylin polypeptide according to the present invention is selected from the compounds presented in table 6m. In one embodiment the amylin polypeptide according to the present invention is selected from the compounds presented in table 6n. In one embodiment the amylin polypeptide according to the present invention is selected from the compounds presented in table 6o.

In one embodiment the amylin polypeptide according to the present invention is selected from the compounds which are in common between the presented compounds of in table 6 and table 4. In one embodiment the amylin polypeptide according to the present invention is selected from the compounds which are in common between the presented compounds of in table 6 and table 4a. In one embodiment the amylin polypeptide according to the present invention is selected from the compounds which are in common between the presented compounds of in table 6 and table 4b. In one embodiment the amylin polypeptide according to the present invention is selected from the compounds which are in common between the presented compounds of in table 6 and table 4a. In one embodiment the amylin polypeptide according to the present invention is selected from the compounds which are in common between the presented compounds of in table 6 and table 4c. In one embodiment the amylin polypeptide according to the present invention is selected from the compounds which are in common between the presented compounds of in table 6 and table 5. In one embodiment the amylin polypeptide according to the present invention is selected from the compounds which are in common between the presented compounds of in table 6 and table 5a. In one embodiment the amylin polypeptide according to the present invention is selected from the compounds which are in common between the presented compounds of in table 6 and table 5b. In one embodiment the amylin polypeptide according to the present invention is selected from the compounds which are in common between the presented compounds of in table 6 and table 5c. In one embodiment the amylin polypeptide according to the present invention is selected from the compounds which are in common between the presented compounds of in table 6 and table 8. In one embodiment the amylin polypeptide according to the present invention is selected from the compounds which are in common between the presented compounds of in table 6 and table 8a. In one embodiment the amylin polypeptide according to the present invention is selected from the compounds which are in common between the presented compounds of in table 6 and table 9. In one embodiment the amylin polypeptide according to the present invention is selected from the compounds which are in common between the presented compounds of in table 6 and table 9a.

In one embodiment the amylin polypeptide according to the present invention is selected from the compounds which are in common between the presented compounds of in table 6a and table 4. In one embodiment the amylin polypeptide according to the present invention is selected from the compounds which are in common between the presented compounds of in table 6a and table 4a. In one embodiment the amylin polypeptide according to the present invention is selected from the compounds which are in common between the presented compounds of in table 6a and table 4b. In one embodiment the amylin polypeptide according to the present invention is selected from the compounds which are in common between the presented compounds of in table 6a and table 4a. In one embodiment the amylin polypeptide according to the present invention is selected from the compounds which are in common between the presented compounds of in table 6a and table 4c. In one embodiment the amylin polypeptide according to the present invention is selected from the compounds which are in common between the presented compounds of in table 6a and table 5. In one embodiment the amylin polypeptide according to the present invention is selected from the compounds which are in common between the presented compounds of in table 6a and table 5a. In one embodiment the amylin polypeptide according to the present invention is selected from the compounds which are in common between the presented compounds of in table 6a and table 5b. In one embodiment the amylin polypeptide according to the present invention is selected from the compounds which are in common between the presented compounds of in table 6a and table 5c. In one embodiment the amylin polypeptide according to the present invention is selected from the compounds which are in common between the presented compounds of in table 6a and table 8. In one embodiment the amylin polypeptide according to the present invention is selected from the compounds which are in common between the presented compounds of in table 6a and table 8a. In one embodiment the amylin polypeptide according to the present invention is selected from the compounds which are in common between the presented compounds of in table 6a and table 9. In one embodiment the amylin polypeptide according to the present invention is selected from the compounds which are in common between the presented compounds of in table 6a and table 9a.

In one embodiment the amylin polypeptide according to the present invention is selected from the compounds which are in common between the presented compounds of in table 6b and table 4. In one embodiment the amylin polypeptide according to the present invention is selected from the compounds which are in common between the presented compounds of in table 6b and table 4a. In one embodiment the amylin polypeptide according to the present invention is selected from the compounds which are in common between the presented compounds of in table 6 band table 4b. In one embodiment the amylin polypeptide according to the present invention is selected from the compounds which are in common between the presented compounds of in table 6b and table 4a. In one embodiment the amylin polypeptide according to the present invention is selected from the compounds which are in common between the presented compounds of in table 6b and table 4c. In one embodiment the amylin polypeptide according to the present invention is selected from the compounds which are in common between the presented compounds of in table 6b and table 5. In one embodiment the amylin polypeptide according to the present invention is selected from the compounds which are in common between the presented compounds of in table 6b and table 5a. In one embodiment the amylin polypeptide according to the present invention is selected from the compounds which are in common between the presented compounds of in table 6b and table 5b. In one embodiment the amylin polypeptide according to the present invention is selected from the compounds which are in common between the presented compounds of in table 6b and table 5c. In one embodiment the amylin polypeptide according to the present invention is selected from the compounds which are in common between the presented compounds of in table 6b and table 8. In one embodiment the amylin polypeptide according to the present invention is selected from the compounds which are in common between the presented compounds of in table 6b and table 8a. In one embodiment the amylin polypeptide according to the present invention is selected from the compounds which are in common between the presented compounds of in table 6b and table 9. In one embodiment the amylin polypeptide according to the present invention is selected from the compounds which are in common between the presented compounds of in table 6b and table 9a.

In one embodiment the amylin polypeptide according to the present invention is selected from the compounds which are in common between the presented compounds of in table 6c and table 4. In one embodiment the amylin polypeptide according to the present invention is selected from the compounds which are in common between the presented compounds of in table 6c and table 4a. In one embodiment the amylin polypeptide according to the present invention is selected from the compounds which are in common between the presented compounds of in table 6c and table 4b. In one embodiment the amylin polypeptide according to the present invention is selected from the compounds which are in common between the presented compounds of in table 6c and table 4a. In one embodiment the amylin polypeptide according to the present invention is selected from the compounds which are in common between the presented compounds of in table 6c and table 4c. In one embodiment the amylin polypeptide according to the present invention is selected from the compounds which are in common between the presented compounds of in table 6c and table 5. In one embodiment the amylin polypeptide according to the present invention is selected from the compounds which are in common between the presented compounds of in table 6c and table 5a. In one embodiment the amylin polypeptide according to the present invention is selected from the compounds which are in common between the presented compounds of in table 6c and table 5b. In one embodiment the amylin polypeptide according to the present invention is selected from the compounds which are in common between the presented compounds of in table 6c and table 5c. In one embodiment the amylin polypeptide according to the present invention is selected from the compounds which are in common between the presented compounds of in table 6b and table 8. In one embodiment the amylin polypeptide according to the present invention is selected from the compounds which are in common between the presented compounds of in table 6b and table 8a. In one embodiment the amylin polypeptide according to the present invention is selected from the compounds which are in common between the presented compounds of in table 6b and table 9. In one embodiment the amylin polypeptide according to the present invention is selected from the compounds which are in common between the presented compounds of in table 6b and table 9a.

In one embodiment the amylin polypeptide according to the present invention is selected from the compounds which are in common between the presented compounds of in table 6d and table 4. In one embodiment the amylin polypeptide according to the present invention is selected from the compounds which are in common between the presented compounds of in table 6d and table 4a. In one embodiment the amylin polypeptide according to the present invention is selected from the compounds which are in common between the presented compounds of in table 6d and table 4b. In one embodiment the amylin polypeptide according to the present invention is selected from the compounds which are in common between the presented compounds of in table 6d and table 4a. In one embodiment the amylin polypeptide according to the present invention is selected from the compounds which are in common between the presented compounds of in table 6d and table 4c. In one embodiment the amylin polypeptide according to the present invention is selected from the compounds which are in common between the presented compounds of in table 6d and table 5. In one embodiment the amylin polypeptide according to the present invention is selected from the compounds which are in common between the presented compounds of in table 6d and table 5a. In one embodiment the amylin polypeptide according to the present invention is selected from the compounds which are in common between the presented compounds of in table 6d and table 5b. In one embodiment the amylin polypeptide according to the present invention is selected from the compounds which are in common between the presented compounds of in table 6d and table 5c. In one embodiment the amylin polypeptide according to the present invention is selected from the compounds which are in common between the presented compounds of in table 6c and table 8. In one embodiment the amylin polypeptide according to the present invention is selected from the compounds which are in common between the presented compounds of in table 6c and table 8a. In one embodiment the amylin polypeptide according to the present invention is selected from the compounds which are in common between the presented compounds of in table 6c and table 9. In one embodiment the amylin polypeptide according to the present invention is selected from the compounds which are in common between the presented compounds of in table 6c and table 9a.

In one embodiment the amylin polypeptide according to the present invention is selected from the compounds which are in common between the presented compounds of in table 6e and table 4. In one embodiment the amylin polypeptide according to the present invention is selected from the compounds which are in common between the presented compounds of in table 6e and table 4a. In one embodiment the amylin polypeptide according to the present invention is selected from the compounds which are in common between the presented compounds of in table 6e and table 4b. In one embodiment the amylin polypeptide according to the present invention is selected from the compounds which are in common between the presented compounds of in table 6e and table 4a. In one embodiment the amylin polypeptide according to the present invention is selected from the compounds which are in common between the presented compounds of in table 6e and table 4c. In one embodiment the amylin polypeptide according to the present invention is selected from the compounds which are in common between the presented compounds of in table 6e and table 5. In one embodiment the amylin polypeptide according to the present invention is selected from the compounds which are in common between the presented compounds of in table 6e and table 5a. In one embodiment the amylin polypeptide according to the present invention is selected from the compounds which are in common between the presented compounds of in table 6e and table 5b. In one embodiment the amylin polypeptide according to the present invention is selected from the compounds which are in common between the presented compounds of in table 6e and table 5c. In one embodiment the amylin polypeptide according to the present invention is selected from the compounds which are in common between the presented compounds of in table 6e and table 8. In one embodiment the amylin polypeptide according to the present invention is selected from the compounds which are in common between the presented compounds of in table 6e and table 8a. In one embodiment the amylin polypeptide according to the present invention is selected from the compounds which are in common between the presented compounds of in table 6e and table 9. In one embodiment the amylin polypeptide according to the present invention is selected from the compounds which are in common between the presented compounds of in table 6e and table 9a.

In one embodiment the amylin polypeptide according to the present invention is selected from the compounds which are in common between the presented compounds of in table 6f and table 4. In one embodiment the amylin polypeptide according to the present invention is selected from the compounds which are in common between the presented compounds of in table 6f and table 4a. In one embodiment the amylin polypeptide according to the present invention is selected from the compounds which are in common between the presented compounds of in table 6f and table 4b. In one embodiment the amylin polypeptide according to the present invention is selected from the compounds which are in common between the presented compounds of in table 6f and table 4a. In one embodiment the amylin polypeptide according to the present invention is selected from the compounds which are in common between the presented compounds of in table 6f and table 4c. In one embodiment the amylin polypeptide according to the present invention is selected from the compounds which are in common between the presented compounds of in table 6f and table 5. In one embodiment the amylin polypeptide according to the present invention is selected from the compounds which are in common between the presented compounds of in table 6f and table 5a. In one embodiment the amylin polypeptide according to the present invention is selected from the compounds which are in common between the presented compounds of in table 6f and table 5b. In one embodiment the amylin polypeptide according to the present invention is selected from the compounds which are in common between the presented compounds of in table 6f and table 5c. In one embodiment the amylin polypeptide according to the present invention is selected from the compounds which are in common between the presented compounds of in table 6f and table 8. In one embodiment the amylin polypeptide according to the present invention is selected from the compounds which are in common between the presented compounds of in table 6f and table 8a. In one embodiment the amylin polypeptide according to the present invention is selected from the compounds which are in common between the presented compounds of in table 6f and table 9. In one embodiment the amylin polypeptide according to the present invention is selected from the compounds which are in common between the presented compounds of in table 6f and table 9a.

In one embodiment the amylin polypeptide according to the present invention is selected from the compounds which are in common between the presented compounds of in table 6g and table 4. In one embodiment the amylin polypeptide according to the present invention is selected from the compounds which are in common between the presented compounds of in table 6g and table 4a. In one embodiment the amylin polypeptide according to the present invention is selected from the compounds which are in common between the presented compounds of in table 6g and table 4b. In one embodiment the amylin polypeptide according to the present invention is selected from the compounds which are in common between the presented compounds of in table 6g and table 4a. In one embodiment the amylin polypeptide according to the present invention is selected from the compounds which are in common between the presented compounds of in table 6g and table 4c. In one embodiment the amylin polypeptide according to the present invention is selected from the compounds which are in common between the presented compounds of in table 6g and table 5. In one embodiment the amylin polypeptide according to the present invention is selected from the compounds which are in common between the presented compounds of in table 6g and table 5a. In one embodiment the amylin polypeptide according to the present invention is selected from the compounds which are in common between the presented compounds of in table 6g and table 5b. In one embodiment the amylin polypeptide according to the present invention is selected from the compounds which are in common between the presented compounds of in table 6g and table 5c. In one embodiment the amylin polypeptide according to the present invention is selected from the compounds which are in common between the presented compounds of in table 6g and table 8. In one embodiment the amylin polypeptide according to the present invention is selected from the compounds which are in common between the presented compounds of in table 6g and table 8a. In one embodiment the amylin polypeptide according to the present invention is selected from the compounds which are in common between the presented compounds of in table 6g and table 9. In one embodiment the amylin polypeptide according to the present invention is selected from the compounds which are in common between the presented compounds of in table 6g and table 9a.

In one embodiment the amylin polypeptide according to the present invention is selected from the compounds which are in common between the presented compounds of in table 6h and table 4. In one embodiment the amylin polypeptide according to the present invention is selected from the compounds which are in common between the presented compounds of in table 6h and table 4a. In one embodiment the amylin polypeptide according to the present invention is selected from the compounds which are in common between the presented compounds of in table 6h and table 4b. In one embodiment the amylin polypeptide according to the present invention is selected from the compounds which are in common between the presented compounds of in table 6h and table 4a. In one embodiment the amylin polypeptide according to the present invention is selected from the compounds which are in common between the presented compounds of in table 6h and table 4c. In one embodiment the amylin polypeptide according to the present invention is selected from the compounds which are in common between the presented compounds of in table 6h and table 5. In one embodiment the amylin polypeptide according to the present invention is selected from the compounds which are in common between the presented compounds of in table 6h and table 5a. In one embodiment the amylin polypeptide according to the present invention is selected from the compounds which are in common between the presented compounds of in table 6h and table 5b. In one embodiment the amylin polypeptide according to the present invention is selected from the compounds which are in common between the presented compounds of in table 6h and table 5c. In one embodiment the amylin polypeptide according to the present invention is selected from the compounds which are in common between the presented compounds of in table 6h and table 8. In one embodiment the amylin polypeptide according to the present invention is selected from the compounds which are in common between the presented compounds of in table 6h and table 8a. In one embodiment the amylin polypeptide according to the present invention is selected from the compounds which are in common between the presented compounds of in table 6h and table 9. In one embodiment the amylin polypeptide according to the present invention is selected from the compounds which are in common between the presented compounds of in table 6h and table 9a.

In one embodiment the amylin polypeptide according to the present invention is selected from the compounds which are in common between the presented compounds of in table 6i and table 4. In one embodiment the amylin polypeptide according to the present invention is selected from the compounds which are in common between the presented compounds of in table 6i and table 4a. In one embodiment the amylin polypeptide according to the present invention is selected from the compounds which are in common between the presented compounds of in table 6i and table 4b. In one embodiment the amylin polypeptide according to the present invention is selected from the compounds which are in common between the presented compounds of in table 6i and table 4a. In one embodiment the amylin polypeptide according to the present invention is selected from the compounds which are in common between the presented compounds of in table 6i and table 4c. In one embodiment the amylin polypeptide according to the present invention is selected from the compounds which are in common between the presented compounds of in table 6i and table 5. In one embodiment the amylin polypeptide according to the present invention is selected from the compounds which are in common between the presented compounds of in table 6i and table 5a. In one embodiment the amylin polypeptide according to the present invention is selected from the compounds which are in common between the presented compounds of in table 6i and table 5b. In one embodiment the amylin polypeptide according to the present invention is selected from the compounds which are in common between the presented compounds of in table 6i and table 5c. In one embodiment the amylin polypeptide according to the present invention is selected from the compounds which are in common between the presented compounds of in table 6i and table 8. In one embodiment the amylin polypeptide according to the present invention is selected from the compounds which are in common between the presented compounds of in table 6i and table 8a. In one embodiment the amylin polypeptide according to the present invention is selected from the compounds which are in common between the presented compounds of in table 6i and table 9. In one embodiment the amylin polypeptide according to the present invention is selected from the compounds which are in common between the presented compounds of in table 6i and table 9a.

In one embodiment the amylin polypeptide according to the present invention is selected from the compounds which are in common between the presented compounds of in table 6j and table 4. In one embodiment the amylin polypeptide according to the present invention is selected from the compounds which are in common between the presented compounds of in table 6j and table 4a. In one embodiment the amylin polypeptide according to the present invention is selected from the compounds which are in common between the presented compounds of in table 6j and table 4b. In one embodiment the amylin polypeptide according to the present invention is selected from the compounds which are in common between the presented compounds of in table 6j and table 4a. In one embodiment the amylin polypeptide according to the present invention is selected from the compounds which are in common between the presented compounds of in table 6j and table 4c. In one embodiment the amylin polypeptide according to the present invention is selected from the compounds which are in common between the presented compounds of in table 6j and table 5. In one embodiment the amylin polypeptide according to the present invention is selected from the compounds which are in common between the presented compounds of in table 6j and table 5a. In one embodiment the amylin polypeptide according to the present invention is selected from the compounds which are in common between the presented compounds of in table 6j and table 5b. In one embodiment the amylin polypeptide according to the present invention is selected from the compounds which are in common between the presented compounds of in table 6j and table 5c. In one embodiment the amylin polypeptide according to the present invention is selected from the compounds which are in common between the presented compounds of in table 6j and table 8. In one embodiment the amylin polypeptide according to the present invention is selected from the compounds which are in common between the presented compounds of in table 6j and table 8a. In one embodiment the amylin polypeptide according to the present invention is selected from the compounds which are in common between the presented compounds of in table 6j and table 9. In one embodiment the amylin polypeptide according to the present invention is selected from the compounds which are in common between the presented compounds of in table 6j and table 9a.

In one embodiment the amylin polypeptide according to the present invention is selected from the compounds which are in common between the presented compounds of in table 6k and table 4. In one embodiment the amylin polypeptide according to the present invention is selected from the compounds which are in common between the presented compounds of in table 6k and table 4a. In one embodiment the amylin polypeptide according to the present invention is selected from the compounds which are in common between the presented compounds of in table 6k and table 4b. In one embodiment the amylin polypeptide according to the present invention is selected from the compounds which are in common between the presented compounds of in table 6k and table 4a. In one embodiment the amylin polypeptide according to the present invention is selected from the compounds which are in common between the presented compounds of in table 6k and table 4c. In one embodiment the amylin polypeptide according to the present invention is selected from the compounds which are in common between the presented compounds of in table 6k and table 5. In one embodiment the amylin polypeptide according to the present invention is selected from the compounds which are in common between the presented compounds of in table 6k and table 5a. In one embodiment the amylin polypeptide according to the present invention is selected from the compounds which are in common between the presented compounds of in table 6k and table 5b. In one embodiment the amylin polypeptide according to the present invention is selected from the compounds which are in common between the presented compounds of in table 6k and table 5c. In one embodiment the amylin polypeptide according to the present invention is selected from the compounds which are in common between the presented compounds of in table 6k and table 8. In one embodiment the amylin polypeptide according to the present invention is selected from the compounds which are in common between the presented compounds of in table 6k and table 8a. In one embodiment the amylin polypeptide according to the present invention is selected from the compounds which are in common between the presented compounds of in table 6k and table 9. In one embodiment the amylin polypeptide according to the present invention is selected from the compounds which are in common between the presented compounds of in table 6k and table 9a.

In one embodiment the amylin polypeptide according to the present invention is selected from the compounds which are in common between the presented compounds of in table 6l and table 4. In one embodiment the amylin polypeptide according to the present invention is selected from the compounds which are in common between the presented compounds of in table 6l and table 4a. In one embodiment the amylin polypeptide according to the present invention is selected from the compounds which are in common between the presented compounds of in table 6l and table 4b. In one embodiment the amylin polypeptide according to the present invention is selected from the compounds which are in common between the presented compounds of in table 6l and table 4a. In one embodiment the amylin polypeptide according to the present invention is selected from the compounds which are in common between the presented compounds of in table 6l and table 4c. In one embodiment the amylin polypeptide according to the present invention is selected from the compounds which are in common between the presented compounds of in table 6l and table 5. In one embodiment the amylin polypeptide according to the present invention is selected from the compounds which are in common between the presented compounds of in table 6l and table 5a. In one embodiment the amylin polypeptide according to the present invention is selected from the compounds which are in common between the presented compounds of in table 6l and table 5b. In one embodiment the amylin polypeptide according to the present invention is selected from the compounds which are in common between the presented compounds of in table 6l and table 5c. In one embodiment the amylin polypeptide according to the present invention is selected from the compounds which are in common between the presented compounds of in table 6l and table 8. In one embodiment the amylin polypeptide according to the present invention is selected from the compounds which are in common between the presented compounds of in table 6l and table 8a. In one embodiment the amylin polypeptide according to the present invention is selected from the compounds which are in common between the presented compounds of in table 6l and table 9. In one embodiment the amylin polypeptide according to the present invention is selected from the compounds which are in common between the presented compounds of in table 6l and table 9a.

In one embodiment the amylin polypeptide according to the present invention is selected from the compounds which are in common between the presented compounds of in table 6m and table 4. In one embodiment the amylin polypeptide according to the present invention is selected from the compounds which are in common between the presented compounds of in table 6m and table 4a. In one embodiment the amylin polypeptide according to the present invention is selected from the compounds which are in common between the presented compounds of in table 6m and table 4b. In one embodiment the amylin polypeptide according to the present invention is selected from the compounds which are in common between the presented compounds of in table 6m and table 4a. In one embodiment the amylin polypeptide according to the present invention is selected from the compounds which are in common between the presented compounds of in table 6m and table 4c. In one embodiment the amylin polypeptide according to the present invention is selected from the compounds which are in common between the presented compounds of in table 6m and table 5. In one embodiment the amylin polypeptide according to the present invention is selected from the compounds which are in common between the presented compounds of in table 6m and table 5a. In one embodiment the amylin polypeptide according to the present invention is selected from the compounds which are in common between the presented compounds of in table 6m and table 5b. In one embodiment the amylin polypeptide according to the present invention is selected from the compounds which are in common between the presented compounds of in table 6m and table 5c. In one embodiment the amylin polypeptide according to the present invention is selected from the compounds which are in common between the presented compounds of in table 6m and table 8. In one embodiment the amylin polypeptide according to the present invention is selected from the compounds which are in common between the presented compounds of in table 6m and table 8a. In one embodiment the amylin polypeptide according to the present invention is selected from the compounds which are in common between the presented compounds of in table 6m and table 9. In one embodiment the amylin polypeptide according to the present invention is selected from the compounds which are in common between the presented compounds of in table 6m and table 9a.

In one embodiment the amylin polypeptide according to the present invention is selected from the compounds which are in common between the presented compounds of in table 6n and table 4. In one embodiment the amylin polypeptide according to the present invention is selected from the compounds which are in common between the presented compounds of in table 6n and table 4a. In one embodiment the amylin polypeptide according to the present invention is selected from the compounds which are in common between the presented compounds of in table 6n and table 4b. In one embodiment the amylin polypeptide according to the present invention is selected from the compounds which are in common between the presented compounds of in table 6n and table 4a. In one embodiment the amylin polypeptide according to the present invention is selected from the compounds which are in common between the presented compounds of in table 6n and table 4c. In one embodiment the amylin polypeptide according to the present invention is selected from the compounds which are in common between the presented compounds of in table 6n and table 5. In one embodiment the amylin polypeptide according to the present invention is selected from the compounds which are in common between the presented compounds of in table 6n and table 5a. In one embodiment the amylin polypeptide according to the present invention is selected from the compounds which are in common between the presented compounds of in table 6n and table 5b. In one embodiment the amylin polypeptide according to the present invention is selected from the compounds which are in common between the presented compounds of in table 6n and table 5c. In one embodiment the amylin polypeptide according to the present invention is selected from the compounds which are in common between the presented compounds of in table 6n and table 8. In one embodiment the amylin polypeptide according to the present invention is selected from the compounds which are in common between the presented compounds of in table 6n and table 8a. In one embodiment the amylin polypeptide according to the present invention is selected from the compounds which are in common between the presented compounds of in table 6n and table 9. In one embodiment the amylin polypeptide according to the present invention is selected from the compounds which are in common between the presented compounds of in table 6n and table 9a.

In one embodiment the amylin polypeptide according to the present invention is selected from the compounds which are in common between the presented compounds of in table 6o and table 4. In one embodiment the amylin polypeptide according to the present invention is selected from the compounds which are in common between the presented compounds of in table 6o and table 4a. In one embodiment the amylin polypeptide according to the present invention is selected from the compounds which are in common between the presented compounds of in table 6o and table 4b. In one embodiment the amylin polypeptide according to the present invention is selected from the compounds which are in common between the presented compounds of in table 6o and table 4a. In one embodiment the amylin polypeptide according to the present invention is selected from the compounds which are in common between the presented compounds of in table 6o and table 4c. In one embodiment the amylin polypeptide according to the present invention is selected from the compounds which are in common between the presented compounds of in table 6o and table 5. In one embodiment the amylin polypeptide according to the present invention is selected from the compounds which are in common between the presented compounds of in table 6o and table 5a. In one embodiment the amylin polypeptide according to the present invention is selected from the compounds which are in common between the presented compounds of in table 6o and table 5b. In one embodiment the amylin polypeptide according to the present invention is selected from the compounds which are in common between the presented compounds of in table 6o and table 5c. In one embodiment the amylin polypeptide according to the present invention is selected from the compounds which are in common between the presented compounds of in table 6o and table 8. In one embodiment the amylin polypeptide according to the present invention is selected from the compounds which are in common between the presented compounds of in table 6o and table 8a. In one embodiment the amylin polypeptide according to the present invention is selected from the compounds which are in common between the presented compounds of in table 6o and table 9. In one embodiment the amylin polypeptide according to the present invention is selected from the compounds which are in common between the presented compounds of in table 6o and table 9a.

In one embodiment the amylin polypeptide according to the present invention is selected from the compounds presented in table 6, except the compounds presented in table 6d. In one embodiment the amylin polypeptide according to the present invention is selected from the compounds presented in table 6, except the compounds presented in table 6e. In one embodiment the amylin polypeptide according to the present invention is selected from the compounds presented in table 6, except the compounds presented in table 6f. In one embodiment the amylin polypeptide according to the present invention is selected from the compounds presented in table 6, except the compounds presented in table 6h. In one embodiment the amylin polypeptide according to the present invention is selected from the compounds presented in table 6, except the compounds presented in table 6l. In one embodiment the amylin polypeptide according to the present invention is selected from the compounds presented in table 6, except the compounds presented in table 6o.

In one embodiment the amylin polypeptide according to the present invention is selected from the compounds presented in table 6a, except the compounds presented in table 6d. In one embodiment the amylin polypeptide according to the present invention is selected from the compounds presented in table 6a, except the compounds presented in table 6e. In one embodiment the amylin polypeptide according to the present invention is selected from the compounds presented in table 6a, except the compounds presented in table 6f. In one embodiment the amylin polypeptide according to the present invention is selected from the compounds presented in table 6a, except the compounds presented in table 6h. In one embodiment the amylin polypeptide according to the present invention is selected from the compounds presented in table 6a, except the compounds presented in table 6l. In one embodiment the amylin polypeptide according to the present invention is selected from the compounds presented in table 6a, except the compounds presented in table 6o.

In one embodiment the amylin compound according to this invention I selected form the group consisting of compound (example) no: 52, 86, 89, 118, 109 or 106.

In one embodiment the amylin compound according to this invention I selected form the group consisting of compound (example) no: 52. In one embodiment the amylin compound according to this invention I selected form the group consisting of compound (example) no: 86. In one embodiment the amylin compound according to this invention I selected form the group consisting of compound (example) no: 89. In one embodiment the amylin compound according to this invention I selected form the group consisting of compound (example) no: 118. In one embodiment the amylin compound according to this invention I selected form the group consisting of compound (example) no: 109. In one embodiment the amylin compound according to this invention I selected form the group consisting of compound (example) no: 106.

Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 6

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 1 | 14D, 17R, 21P, 26P, 35D | 1177 | 224 | 2697 | 12.0 |
| 2 | 14D, 17R, 21P, 27P, 35D | 411 | 182 | 2998 | 16.4 |
| 3 | 14D, 17R, 22P, 26P, 35D | 1131 | 205 | 1380 | 6.7 |
| 4 | 14E, 17R, 21P, 25P, 28P, 29P, 37P | 321 | 60 | 70 | 1.2 |
| 5 | 14E, 17R, 21P, 26P, 37P | 374 | 162 | 160 | 1.0 |

TABLE 6-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 6 | 14E, 17R, 21P, 25P, 28P, 29P | 996 | 128 | 729 | 5.7 |
| 7 | 14E, 17R, 21P, 26P | 674 | 255 | 1156 | 4.5 |
| 8 | 14E, 17R, 21P, 27P, 37P | 72 | 82 | 87 | 1.1 |
| 9 | 14E, 17R, 21P, 27P | 143 | 175 | 1288 | 7.4 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 15 | 14E, 17R, 21P, 27P | 597 | 386 | 3432 | 8.9 |
| 16 | 14E, 17R, 21P, 27P, 35R | 894 | 363 | 2215 | 6.1 |
| 17 | 14E, 17R, 21P, 27P, 34H | 878 | 268 | 2351 | 8.8 |
| 18 | 14E, 17R, 21P, 27P, 35H | 554 | 154 | 742 | 4.8 |
| 19 | 14E, 17R, 21P, 27P | 556 | 307 | 5321 | 17.4 |
| 20 | 14E, 17R, 21P, 27P, 37P | 217 | 80 | 285 | 3.6 |
| 21 | 17R, 21P, 27P | 585 | 148 | 611 | 4.1 |
| 22 | 14E, 17R, 21P, 27P, 35E | 794 | 270 | 1026 | 3.8 |
| 23 | 17R, 21P, 27P, 35E | 871 | 340 | 3025 | 8.9 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 28 | 17R, 21P, 27P, 31P, 35E | 610 | 220 | 2033 | 9.2 |
| 29 | 17R, 21P, 27P, 34P, 35E | 577 | 99 | 857 | 8.7 |
| 30 | 14H, 17R, 21P, 27P, 35E | 919 | 134 | 1677 | 12.6 |
| 31 | 14E, 17R, 21P, 27P, 31P | 204 | 112 | 717 | 6.4 |
| 32 | 14E, 17R, 21P, 27P, 34P | 100 | 50 | 327 | 6.6 |
| 33 | 14E, 17R, 21P, 28P, 35E | 915 | 243 | 528 | 2.2 |
| 34 | 17R, 21P, 27P, 35K | 1139 | 313 | 2615 | 8.4 |
| 35 | 17R, 21P, 27P, 35K | 970 | 364 | 5459 | 15.0 |
| 36 | 14E, 17R, 21P, 27P, 34K | 403 | 189 | 1280 | 6.8 |
| 37 | 14E, 17R, 21P, 27P, 29P | 970 | 92 | 372 | 4.0 |
| 38 | 17R, 21P, 27P, 35R | 249 | 352 | 18260 | 51.9 |
| 39 | 17R, 21P, 27P, 34R | 665 | 217 | 2522 | 11.6 |
| 40 | 17R, 21P, 27P, 34H | 549 | 164 | 2680 | 16.4 |
| 41 | 17R, 21P, 27P | 427 | 260 | 4346 | 16.7 |
| 42 | 17R, 21P, 27P | 264 | 146 | 1975 | 13.5 |
| 43 | 17R, 21P, 27P | 76 | 141 | 920 | 6.5 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 46 | −1G, 1R, 17R, 21P, 27P | 195 | 88 | 899 | 10.2 |
| 47 | −1G, 1R, 17R, 21P, 27P, 35H | 344 | 222 | 1322 | 6.0 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 51 | 14E, 17R, 21P, 27P, 35R | 828 | 372 | 5216 | 14.0 |
| 52 | 14D, 17R, 21P, 27P, 35R | 697 | 340 | 14074 | 41.4 |
| 53 | 17R, 21P, 27P, 28P, 31P | 52 | 64 | 625 | 9.8 |
| 54 | 17R, 21P, 27P, 29P, 31P | 30 | 103 | 987 | 9.6 |
| 55 | 17R, 21P, 27P, 28P, 34P | 42 | 68 | 731 | 10.8 |
| 56 | 17R, 21P, 27P, 29P, 34P | 49 | 102 | 506 | 5.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 59 | 14D, 17R, 21K, 27P, 35D | 1193 | 389 | 1953 | 5.0 |
| 60 | 17R, 21P, 27P, 35H | 695 | 351 | 5355 | 15.3 |
| 61 | 14H, 17R, 21P, 27P, 31P | 122 | 51 | 554 | 10.9 |
| 62 | 14H, 17R, 21P, 27P, 31P | 98 | 44 | 539 | 12.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 67 | 14H, 17R, 21P, 27P, 34P | 90 | 69 | 354 | 5.2 |
| 68 | 14H, 17R, 21P, 27P, 34P | 88 | 54 | 932 | 17.4 |
| 69 | 14H, 17R, 21P, 27P | 133 | 94 | 1248 | 13.3 |
| 70 | 14H, 17R, 21P, 27P | 169 | 40 | 715 | 17.9 |
| 71 | 14G, 17R, 21P, 27P, 31P | 48 | 56 | 527 | 9.4 |
| 72 | 14A, 17R, 21P, 27P, 31P | 172 | 106 | 4758 | 44.9 |
| 73 | 14S, 17R, 21P, 27P, 31P | 104 | 85 | 961 | 11.3 |
| 74 | 14K, 17R, 21P, 27P, 31P | 791 | 666 | 37520 | 56.3 |
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 80 | 14H, 17R, 21P, 27P, 34H | 290 | 139 | 2141 | 15.4 |

TABLE 6-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 81 | 14H, 17R, 21P, 27P, 34H | 271 | 130 | 1727 | 13.3 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 87 | 14E, 17R, 21P, 27P, 34H | 633 | 285 | 1095 | 3.8 |
| 88 | 14E, 17R, 21P, 27P, 34R | 750 | 773 | 6555 | 8.5 |
| 89 | 14E, 17R, 21P, 27P, 35R | 1160 | 404 | 11221 | 27.8 |
| 90 | 14H, 17R, 21P, 27P | 61 | 33 | 236 | 7.2 |
| 91 | 17R, 21P, 27P, 34H | 119 | 40 | 1477 | 36.9 |
| 92 | 14H, 17R, 21P, 27P | 179 | 85 | 2378 | 28.0 |
| 93 | 14A, 17R, 21P, 27P, 34H | 176 | 118 | 1145 | 9.7 |
| 94 | 14A, 17R, 21P, 27P, 34P | 148 | 70 | 316 | 4.5 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 99 | −1G, 1R, 14H, 17R, 21P, 27P | 348 | 82 | 818 | 10.0 |
| 100 | −1G, 1R, 14H, 17R, 21P, 27P, 34H | 1015 | 253 | 1726 | 6.8 |
| 101 | −1G, 1R, 14A, 17R, 21P, 27P, 34H | 426 | 109 | 537 | 4.9 |
| 102 | −1G, 1R, 14H, 17R, 21P, 27P, 34P | 217 | 62 | 179 | 2.9 |
| 103 | −1G, 1R, 14A, 17R, 21P, 27P, 34P | 114 | 70 | 148 | 2.1 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 107 | 14E, 17R, 21P, 27P, 34H, 35E | 387 | 405 | 2541 | 6.3 |
| 108 | 14E, 17R, 21P, 27P, 34R, 35E | 232 | 421 | 2745 | 6.5 |
| 109 | 14E, 17R, 21P, 27P, 34P, 35E | 140 | 161 | 841 | 5.2 |
| 110 | 14E, 17R, 21P, 27P, 34P, 35R | 326 | 278 | 8158 | 29.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |
| 114 | 14E, 17R, 21P, 27P, 34P, 37P | 214 | 105 | 90 | 0.9 |
| 115 | 14H, 17R, 21P, 27P, 34P, 37P | 131 | 52 | 40 | 0.8 |
| 116 | 14H, 17R, 21P, 27P, 31P, 34P | 82 | 71 | 345 | 4.9 |
| 117 | 14E, 17R, 21P, 27P, 34P, 35R | 163 | 376 | 6380 | 17.0 |
| 118 | 14E, 17R, 21P, 27P, 34P, 35H | 179 | 101 | 1451 | 14.4 |
| 119 | 17R, 21P, 27P, 31P, 34P, 35R | 880 | 333 | 8660 | 26.0 |
| 120 | 14S, 17R, 21P, 27P, 34P, 35E | 76 | 109 | 887 | 8.1 |
| 121 | 14E, 17R, 21P, 31P, 34P, 35E | 69 | 222 | 1280 | 5.8 |
| 122 | 14D, 17R, 21P, 27P, 34P, 35E | 172 | 159 | 843 | 5.3 |
| 123 | 14D, 17R, 21P, 27P, 34P, 35E | 196 | 288 | 1115 | 3.9 |
| 124 | 14E, 17R, 21P, 27P, 34P, 35H | 377 | 172 | 2833 | 16.4 |
| 125 | 14E, 17R, 21P, 27P, 34P, 35E, 37P | 533 | 132 | 102 | 0.8 |
| 126 | 14E, 17R, 23P, 34P, 35E | 1187 | 5168 | 89580 | 17.3 |
| 127 | 14E, 17R, 21P, 27P, 34P, 37F | 152 | 216 | 2140 | 9.9 |
| 128 | 14E, 17R, 21P, 27P, 35H | 992 | 425 | 5575 | 13.1 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6a

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 1 | 14D, 17R, 21P, 26P, 35D | 1177 | 224 | 2697 | 12.0 |
| 2 | 14D, 17R, 21P, 27P, 35D | 411 | 182 | 2998 | 16.4 |
| 3 | 14D, 17R, 22P, 26P, 35D | 1131 | 205 | 1380 | 6.7 |
| 6 | 14E, 17R, 21P, 25P, 28P, 29P | 996 | 128 | 729 | 5.7 |
| 9 | 14E, 17R, 21P, 27P | 143 | 175 | 1288 | 7.4 |
| 15 | 14E, 17R, 21P, 27P | 597 | 386 | 3432 | 8.9 |
| 16 | 14E, 17R, 21P, 27P, 35R | 894 | 363 | 2215 | 6.1 |

TABLE 6a-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 17 | 14E, 17R, 21P, 27P, 34H | 878 | 268 | 2351 | 8.8 |
| 19 | 14E, 17R, 21P, 27P | 556 | 307 | 5321 | 17.4 |
| 23 | 17R, 21P, 27P, 35E | 871 | 340 | 3025 | 8.9 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 28 | 17R, 21P, 27P, 31P, 35E | 610 | 220 | 2033 | 9.2 |
| 29 | 17R, 21P, 27P, 34P, 35E | 577 | 99 | 857 | 8.7 |
| 30 | 14H, 17R, 21P, 27P, 35E | 919 | 134 | 1677 | 12.6 |
| 31 | 14E, 17R, 21P, 27P, 31P | 204 | 112 | 717 | 6.4 |
| 32 | 14E, 17R, 21P, 27P, 34P | 100 | 50 | 327 | 6.6 |
| 34 | 17R, 21P, 27P, 35K | 1139 | 313 | 2615 | 8.4 |
| 35 | 17R, 21P, 27P, 35K | 970 | 364 | 5459 | 15.0 |
| 36 | 14E, 17R, 21P, 27P, 34K | 403 | 189 | 1280 | 6.8 |
| 38 | 17R, 21P, 27P, 35R | 249 | 352 | 18260 | 51.9 |
| 39 | 17R, 21P, 27P, 34R | 665 | 217 | 2522 | 11.6 |
| 40 | 17R, 21P, 27P, 34H | 549 | 164 | 2680 | 16.4 |
| 41 | 17R, 21P, 27P | 427 | 260 | 4346 | 16.7 |
| 42 | 17R, 21P, 27P | 264 | 146 | 1975 | 13.5 |
| 43 | 17R, 21P, 27P | 76 | 141 | 920 | 6.5 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 46 | −1G, 1R, 17R, 21P, 27P | 195 | 88 | 899 | 10.2 |
| 47 | −1G, 1R, 17R, 21P, 27P, 35H | 344 | 222 | 1322 | 6.0 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 51 | 14E, 17R, 21P, 27P, 35R | 828 | 372 | 5216 | 14.0 |
| 52 | 14D, 17R, 21P, 27P, 35R | 697 | 340 | 14074 | 41.4 |
| 53 | 17R, 21P, 27P, 28P, 31P | 52 | 64 | 625 | 9.8 |
| 54 | 17R, 21P, 27P, 29P, 31P | 30 | 103 | 987 | 9.6 |
| 55 | 17R, 21P, 27P, 28P, 34P | 42 | 68 | 731 | 10.8 |
| 56 | 17R, 21P, 27P, 29P, 34P | 49 | 102 | 506 | 5.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 59 | 14D, 17R, 21K, 27P, 35D | 1193 | 389 | 1953 | 5.0 |
| 60 | 17R, 21P, 27P, 35H | 695 | 351 | 5355 | 15.3 |
| 61 | 14H, 17R, 21P, 27P, 31P | 122 | 51 | 554 | 10.9 |
| 62 | 14H, 17R, 21P, 27P, 31P | 98 | 44 | 539 | 12.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 67 | 14H, 17R, 21P, 27P, 34P | 90 | 69 | 354 | 5.2 |
| 68 | 14H, 17R, 21P, 27P, 34P | 88 | 54 | 932 | 17.4 |
| 69 | 14H, 17R, 21P, 27P | 133 | 94 | 1248 | 13.3 |
| 70 | 14H, 17R, 21P, 27P | 169 | 40 | 715 | 17.9 |
| 71 | 14G, 17R, 21P, 27P, 31P | 48 | 56 | 527 | 9.4 |
| 72 | 14A, 17R, 21P, 27P, 31P | 172 | 106 | 4758 | 44.9 |
| 73 | 14S, 17R, 21P, 27P, 31P | 104 | 85 | 961 | 11.3 |
| 74 | 14K, 17R, 21P, 27P, 31P | 791 | 666 | 37520 | 56.3 |
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 80 | 14H, 17R, 21P, 27P, 34H | 290 | 139 | 2141 | 15.4 |
| 81 | 14H, 17R, 21P, 27P, 34H | 271 | 130 | 1727 | 13.3 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 88 | 14E, 17R, 21P, 27P, 34R | 750 | 773 | 6555 | 8.5 |
| 89 | 14E, 17R, 21P, 27P, 35R | 1160 | 404 | 11221 | 27.8 |
| 90 | 14H, 17R, 21P, 27P | 61 | 33 | 236 | 7.2 |
| 91 | 17R, 21P, 27P, 34H | 119 | 40 | 1477 | 36.9 |
| 92 | 14H, 17R, 21P, 27P | 179 | 85 | 2378 | 28.0 |
| 93 | 14A, 17R, 21P, 27P, 34H | 176 | 118 | 1145 | 9.7 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 99 | −1G, 1R, 14H, 17R, 21P, 27P | 348 | 82 | 818 | 10.0 |

TABLE 6a-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 100 | −1G, 1R, 14H, 17R, 21P, 27P, 34H | 1015 | 253 | 1726 | 6.8 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 107 | 14E, 17R, 21P, 27P, 34H, 35E | 387 | 405 | 2541 | 6.3 |
| 108 | 14E, 17R, 21P, 27P, 34R, 35E | 232 | 421 | 2745 | 6.5 |
| 109 | 14E, 17R, 21P, 27P, 34P, 35E | 140 | 161 | 841 | 5.2 |
| 110 | 14E, 17R, 21P, 27P, 34P, 35R | 326 | 278 | 8158 | 29.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |
| 117 | 14E, 17R, 21P, 27P, 34P, 35R | 163 | 376 | 6380 | 17.0 |
| 118 | 14E, 17R, 21P, 27P, 34P, 35H | 179 | 101 | 1451 | 14.4 |
| 119 | 17R, 21P, 27P, 31P, 34P, 35R | 880 | 333 | 8660 | 26.0 |
| 120 | 14S, 17R, 21P, 27P, 34P, 35E | 76 | 109 | 887 | 8.1 |
| 121 | 14E, 17R, 21P, 31P, 34P, 35E | 69 | 222 | 1280 | 5.8 |
| 122 | 14D, 17R, 21P, 27P, 34P, 35E | 172 | 159 | 843 | 5.3 |
| 124 | 14E, 17R, 21P, 27P, 34P, 35H | 377 | 172 | 2833 | 16.4 |
| 126 | 14E, 17R, 23P, 34P, 35E | 1187 | 5168 | 89580 | 17.3 |
| 127 | 14E, 17R, 21P, 27P, 34P, 37F | 152 | 216 | 2140 | 9.9 |
| 128 | 14E, 17R, 21P, 27P, 35H | 992 | 425 | 5575 | 13.1 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6b

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 1 | 14D, 17R, 21P, 26P, 35D | 1177 | 224 | 2697 | 12.0 |
| 2 | 14D, 17R, 21P, 27P, 35D | 411 | 182 | 2998 | 16.4 |
| 19 | 14E, 17R, 21P, 27P | 556 | 307 | 5321 | 17.4 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 30 | 14H, 17R, 21P, 27P, 35E | 919 | 134 | 1677 | 12.6 |
| 35 | 17R, 21P, 27P, 35K | 970 | 364 | 5459 | 15.0 |
| 38 | 17R, 21P, 27P, 35R | 249 | 352 | 18260 | 51.9 |
| 39 | 17R, 21P, 27P, 34R | 665 | 217 | 2522 | 11.6 |
| 40 | 17R, 21P, 27P, 34H | 549 | 164 | 2680 | 16.4 |
| 41 | 17R, 21P, 27P | 427 | 260 | 4346 | 16.7 |
| 42 | 17R, 21P, 27P | 264 | 146 | 1975 | 13.5 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 46 | −1G, 1R, 17R, 21P, 27P | 195 | 88 | 899 | 10.2 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 51 | 14E, 17R, 21P, 27P, 35R | 828 | 372 | 5216 | 14.0 |
| 52 | 14D, 17R, 21P, 27P, 35R | 697 | 340 | 14074 | 41.4 |
| 55 | 17R, 21P, 27P, 28P, 34P | 42 | 68 | 731 | 10.8 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 61 | 14H, 17R, 21P, 27P, 31P | 122 | 51 | 554 | 10.9 |
| 62 | 14H, 17R, 21P, 27P, 31P | 98 | 44 | 539 | 12.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 68 | 14H, 17R, 21P, 27P, 34P | 88 | 54 | 932 | 17.4 |
| 69 | 14H, 17R, 21P, 27P | 133 | 94 | 1248 | 13.3 |
| 70 | 14H, 17R, 21P, 27P | 169 | 40 | 715 | 17.9 |
| 72 | 14A, 17R, 21P, 27P, 31P | 172 | 106 | 4758 | 44.9 |
| 73 | 14S, 17R, 21P, 27P, 31P | 104 | 85 | 961 | 11.3 |
| 74 | 14K, 17R, 21P, 27P, 31P | 791 | 666 | 37520 | 56.3 |

TABLE 6b-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 80 | 14H, 17R, 21P, 27P, 34H | 290 | 139 | 2141 | 15.4 |
| 81 | 14H, 17R, 21P, 27P, 34H | 271 | 130 | 1727 | 13.3 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 89 | 14E, 17R, 21P, 27P, 35R | 1160 | 404 | 11221 | 27.8 |
| 91 | 17R, 21P, 27P, 34H | 119 | 40 | 1477 | 36.9 |
| 92 | 14H, 17R, 21P, 27P | 179 | 85 | 2378 | 28.0 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 99 | −1G, 1R, 14H, 17R, 21P, 27P | 348 | 82 | 818 | 10.0 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 110 | 14E, 17R, 21P, 27P, 34P, 35R | 326 | 278 | 8158 | 29.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |
| 117 | 14E, 17R, 21P, 27P, 34P, 35R | 163 | 376 | 6380 | 17.0 |
| 118 | 14E, 17R, 21P, 27P, 34P, 35H | 179 | 101 | 1451 | 14.4 |
| 119 | 17R, 21P, 27P, 31P, 34P, 35R | 880 | 333 | 8660 | 26.0 |
| 124 | 14E, 17R, 21P, 27P, 34P, 35H | 377 | 172 | 2833 | 16.4 |
| 126 | 14E, 17R, 23P, 34P, 35E | 1187 | 5168 | 89580 | 17.3 |
| 128 | 14E, 17R, 21P, 27P, 35H | 992 | 425 | 5575 | 13.1 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6c

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 2 | 14D, 17R, 21P, 27P, 35D | 411 | 182 | 2998 | 16.4 |
| 19 | 14E, 17R, 21P, 27P | 556 | 307 | 5321 | 17.4 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 35 | 17R, 21P, 27P, 35K | 970 | 364 | 5459 | 15.0 |
| 38 | 17R, 21P, 27P, 35R | 249 | 352 | 18260 | 51.9 |
| 40 | 17R, 21P, 27P, 34H | 549 | 164 | 2680 | 16.4 |
| 41 | 17R, 21P, 27P | 427 | 260 | 4346 | 16.7 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 52 | 14D, 17R, 21P, 27P, 35R | 697 | 340 | 14074 | 41.4 |
| 55 | 17R, 21P, 27P, 28P, 34P | 42 | 68 | 731 | 10.8 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 68 | 14H, 17R, 21P, 27P, 34P | 88 | 54 | 932 | 17.4 |
| 70 | 14H, 17R, 21P, 27P | 169 | 40 | 715 | 17.9 |
| 72 | 14A, 17R, 21P, 27P, 31P | 172 | 106 | 4758 | 44.9 |

TABLE 6c-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 74 | 14K, 17R, 21P, 27P, 31P | 791 | 666 | 37520 | 56.3 |
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 89 | 14E, 17R, 21P, 27P, 35R | 1160 | 404 | 11221 | 27.8 |
| 91 | 17R, 21P, 27P, 34H | 119 | 40 | 1477 | 36.9 |
| 92 | 14H, 17R, 21P, 27P | 179 | 85 | 2378 | 28.0 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 104 | 14E, 17R, 21P, 27P, 34H, 35E | 525 | 445 | 7053 | 15.8 |
| 110 | 14E, 17R, 21P, 27P, 34P, 35R | 326 | 278 | 8158 | 29.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |
| 117 | 14E, 17R, 21P, 27P, 34P, 35R | 163 | 376 | 6380 | 17.0 |
| 119 | 17R, 21P, 27P, 31P, 34P, 35R | 880 | 333 | 8660 | 26.0 |
| 124 | 14E, 17R, 21P, 27P, 34P, 35H | 377 | 172 | 2833 | 16.4 |
| 126 | 14E, 17R, 23P, 34P, 35E | 1187 | 5168 | 89580 | 17.3 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6d

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 4 | 14E, 17R, 21P, 25P, 28P, 29P, 37P | 321 | 60 | 70 | 1.2 |
| 5 | 14E, 17R, 21P, 26P, 37P | 374 | 162 | 160 | 1.0 |
| 8 | 14E, 17R, 21P, 27P, 37P | 72 | 82 | 87 | 1.1 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 18 | 14E, 17R, 21P, 27P, 35H | 554 | 154 | 742 | 4.8 |
| 20 | 14E, 17R, 21P, 27P, 37P | 217 | 80 | 285 | 3.6 |
| 21 | 17R, 21P, 27P | 585 | 148 | 611 | 4.1 |
| 22 | 14E, 17R, 21P, 27P, 35E | 794 | 270 | 1026 | 3.8 |
| 33 | 14E, 17R, 21P, 28P, 35E | 915 | 243 | 528 | 2.2 |
| 37 | 14E, 17R, 21P, 27P, 29P | 970 | 92 | 372 | 4.0 |
| 94 | 14A, 17R, 21P, 27P, 34P | 148 | 70 | 316 | 4.5 |
| 101 | −1G, 1R, 14A, 17R, 21P, 27P, 34H | 426 | 109 | 537 | 4.9 |
| 102 | −1G, 1R, 14H, 17R, 21P, 27P, 34P | 217 | 62 | 179 | 2.9 |
| 103 | −1G, 1R, 14A, 17R, 21P, 27P, 34P | 114 | 70 | 148 | 2.1 |
| 114 | 14E, 17R, 21P, 27P, 34P, 37P | 214 | 105 | 90 | 0.9 |
| 115 | 14H, 17R, 21P, 27P, 34P, 37P | 131 | 52 | 40 | 0.8 |
| 116 | 14H, 17R, 21P, 27P, 31P, 34P | 82 | 71 | 345 | 4.9 |
| 123 | 14D, 17R, 21P, 27P, 34P, 35E | 196 | 288 | 1115 | 3.9 |
| 125 | 14E, 17R, 21P, 27P, 34P, 35E, 37P | 533 | 132 | 102 | 0.8 |

TABLE 6e

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 4 | 14E, 17R, 21P, 25P, 28P, 29P, 37P | 321 | 60 | 70 | 1.2 |
| 5 | 14E, 17R, 21P, 26P, 37P | 374 | 162 | 160 | 1.0 |
| 8 | 14E, 17R, 21P, 27P, 37P | 72 | 82 | 87 | 1.1 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 20 | 14E, 17R, 21P, 27P, 37P | 217 | 80 | 285 | 3.6 |
| 22 | 14E, 17R, 21P, 27P, 35E | 794 | 270 | 1026 | 3.8 |
| 33 | 14E, 17R, 21P, 28P, 35E | 915 | 243 | 528 | 2.2 |
| 102 | −1G, 1R, 14H, 17R, 21P, 27P, 34P | 217 | 62 | 179 | 2.9 |
| 103 | −1G, 1R, 14A, 17R, 21P, 27P, 34P | 114 | 70 | 148 | 2.1 |
| 114 | 14E, 17R, 21P, 27P, 34P, 37P | 214 | 105 | 90 | 0.9 |
| 115 | 14H, 17R, 21P, 27P, 34P, 37P | 131 | 52 | 40 | 0.8 |
| 123 | 14D, 17R, 21P, 27P, 34P, 35E | 196 | 288 | 1115 | 3.9 |
| 125 | 14E, 17R, 21P, 27P, 34P, 35E, 37P | 533 | 132 | 102 | 0.8 |

TABLE 6f

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 18 | 14E, 17R, 21P, 27P, 35H | 554 | 154 | 742 | 4.8 |
| 22 | 14E, 17R, 21P, 27P, 35E | 794 | 270 | 1026 | 3.8 |
| 23 | 17R, 21P, 27P, 35E | 871 | 340 | 3025 | 8.9 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 28 | 17R, 21P, 27P, 31P, 35E | 610 | 220 | 2033 | 9.2 |
| 29 | 17R, 21P, 27P, 34P, 35E | 577 | 99 | 857 | 8.7 |
| 30 | 14H, 17R, 21P, 27P, 35E | 919 | 134 | 1677 | 12.6 |
| 33 | 14E, 17R, 21P, 28P, 35E | 915 | 243 | 528 | 2.2 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 46 | −1G, 1R, 17R, 21P, 27P | 195 | 88 | 899 | 10.2 |
| 47 | −1G, 1R, 17R, 21P, 27P, 35H | 344 | 222 | 1322 | 6.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 66 | 14H, 17R, 21P, 27P, 35H | 396 | 27 | 542 | 20.1 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 107 | 14E, 17R, 21P, 27P, 34H, 35E | 387 | 405 | 2541 | 6.3 |
| 108 | 14E, 17R, 21P, 27P, 34R, 35E | 232 | 421 | 2745 | 6.5 |
| 109 | 14E, 17R, 21P, 27P, 34P, 35E | 140 | 161 | 841 | 5.2 |
| 118 | 14E, 17R, 21P, 27P, 34P, 35H | 179 | 101 | 1451 | 14.4 |
| 120 | 14S, 17R, 21P, 27P, 34P, 35E | 76 | 109 | 887 | 8.1 |
| 121 | 14E, 17R, 21P, 31P, 34P, 35E | 69 | 222 | 1280 | 5.8 |
| 122 | 14D, 17R, 21P, 27P, 34P, 35E | 172 | 159 | 843 | 5.3 |
| 123 | 14D, 17R, 21P, 27P, 34P, 35E | 196 | 288 | 1115 | 3.9 |
| 124 | 14E, 17R, 21P, 27P, 34P, 35H | 377 | 172 | 2833 | 16.4 |
| 125 | 14E, 17R, 21P, 27P, 34P, 35E, 37P | 533 | 132 | 102 | 0.8 |
| 126 | 14E, 17R, 23P, 34P, 35E | 1187 | 5168 | 89580 | 17.3 |
| 128 | 14E, 17R, 21P, 27P, 35H | 992 | 425 | 5575 | 13.1 |

TABLE 6g

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 4 | 14E, 17R, 21P, 25P, 28P, 29P, 37P | 321 | 60 | 70 | 1.2 |
| 5 | 14E, 17R, 21P, 26P, 37P | 374 | 162 | 160 | 1.0 |
| 8 | 14E, 17R, 21P, 27P, 37P | 72 | 82 | 87 | 1.1 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 20 | 14E, 17R, 21P, 27P, 37P | 217 | 80 | 285 | 3.6 |
| 114 | 14E, 17R, 21P, 27P, 34P, 37P | 214 | 105 | 90 | 0.9 |
| 115 | 14H, 17R, 21P, 27P, 34P, 37P | 131 | 52 | 40 | 0.8 |
| 125 | 14E, 17R, 21P, 27P, 34P, 35E, 37P | 533 | 132 | 102 | 0.8 |

TABLE 6h

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 17 | 14E, 17R, 21P, 27P, 34H | 878 | 268 | 2351 | 8.8 |
| 40 | 17R, 21P, 27P, 34H | 549 | 164 | 2680 | 16.4 |
| 86 | 17R, 21P, 27P, 34H | 833 | 298 | 19157 | 64.4 |
| 87 | 14E, 17R, 21P, 27P, 34H | 633 | 285 | 1095 | 3.8 |
| 91 | 17R, 21P, 27P, 34H | 119 | 40 | 1477 | 36.9 |
| 92 | 14H, 17R, 21P, 27P | 179 | 85 | 2378 | 28.0 |
| 93 | 14A, 17R, 21P, 27P, 34H | 176 | 118 | 1145 | 9.7 |
| 97 | 17R, 21P, 27P, 34H | 568 | 356 | 11750 | 33.0 |
| 100 | −1G, 1R, 14H, 17R, 21P, 27P, 34H | 1015 | 253 | 1726 | 6.8 |
| 101 | −1G, 1R, 14A, 17R, 21P, 27P, 34H | 426 | 109 | 537 | 4.9 |
| 104 | 14E, 17R, 21P, 27P, 34H, 35E | 525 | 445 | 7053 | 15.8 |
| 107 | 14E, 17R, 21P, 27P, 34H, 35E | 387 | 405 | 2541 | 6.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |

TABLE 6i

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 4 | 14E, 17R, 21P, 25P, 28P, 29P, 37P | 321 | 60 | 70 | 1.2 |
| 5 | 14E, 17R, 21P, 26P, 37P | 374 | 162 | 160 | 1.0 |
| 6 | 14E, 17R, 21P, 25P, 28P, 29P | 996 | 128 | 729 | 5.7 |
| 7 | 14E, 17R, 21P, 26P | 674 | 255 | 1156 | 4.5 |
| 8 | 14E, 17R, 21P, 27P, 37P | 72 | 82 | 87 | 1.1 |
| 9 | 14E, 17R, 21P, 27P | 143 | 175 | 1288 | 7.4 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 15 | 14E, 17R, 21P, 27P | 597 | 386 | 3432 | 8.9 |
| 16 | 14E, 17R, 21P, 27P, 35R | 894 | 363 | 2215 | 6.1 |
| 17 | 14E, 17R, 21P, 27P, 34H | 878 | 268 | 2351 | 8.8 |
| 18 | 14E, 17R, 21P, 27P, 35H | 554 | 154 | 742 | 4.8 |
| 19 | 14E, 17R, 21P, 27P | 556 | 307 | 5321 | 17.4 |
| 20 | 14E, 17R, 21P, 27P, 37P | 217 | 80 | 285 | 3.6 |
| 22 | 14E, 17R, 21P, 27P, 35E | 794 | 270 | 1026 | 3.8 |
| 31 | 14E, 17R, 21P, 27P, 31P | 204 | 112 | 717 | 6.4 |

TABLE 6i-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 32 | 14E, 17R, 21P, 27P, 34P | 100 | 50 | 327 | 6.6 |
| 33 | 14E, 17R, 21P, 28P, 35E | 915 | 243 | 528 | 2.2 |
| 36 | 14E, 17R, 21P, 27P, 34K | 403 | 189 | 1280 | 6.8 |
| 37 | 14E, 17R, 21P, 27P, 29P | 970 | 92 | 372 | 4.0 |
| 51 | 14E, 17R, 21P, 27P, 35R | 828 | 372 | 5216 | 14.0 |
| 87 | 14E, 17R, 21P, 27P, 34H | 633 | 285 | 1095 | 3.8 |
| 88 | 14E, 17R, 21P, 27P, 34R | 750 | 773 | 6555 | 8.5 |
| 89 | 14E, 17R, 21P, 27P, 35R | 1160 | 404 | 11221 | 27.8 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 107 | 14E, 17R, 21P, 27P, 34H, 35E | 387 | 405 | 2541 | 6.3 |
| 108 | 14E, 17R, 21P, 27P, 34R, 35E | 232 | 421 | 2745 | 6.5 |
| 109 | 14E, 17R, 21P, 27P, 34P, 35E | 140 | 161 | 841 | 5.2 |
| 110 | 14E, 17R, 21P, 27P, 34P, 35R | 326 | 278 | 8158 | 29.3 |
| 114 | 14E, 17R, 21P, 27P, 34P, 37P | 214 | 105 | 90 | 0.9 |
| 117 | 14E, 17R, 21P, 27P, 34H, 35R | 163 | 376 | 6380 | 17.0 |
| 118 | 14E, 17R, 21P, 27P, 34P, 35H | 179 | 101 | 1451 | 14.4 |
| 121 | 14E, 17R, 21P, 31P, 34P, 35E | 69 | 222 | 1280 | 5.8 |
| 124 | 14E, 17R, 21P, 27P, 34P, 35H | 377 | 172 | 2833 | 16.4 |
| 125 | 14E, 17R, 21P, 27P, 34P, 35E, 37P | 533 | 132 | 102 | 0.8 |
| 126 | 14E, 17R, 23P, 34P, 35E | 1187 | 5168 | 89580 | 17.3 |
| 127 | 14E, 17R, 21P, 27P, 34P, 37F | 152 | 216 | 2140 | 9.9 |
| 128 | 14E, 17R, 21P, 27P, 35H | 992 | 425 | 5575 | 13.1 |

TABLE 6j

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 2 | 14D, 17R, 21P, 27P, 35D | 411 | 182 | 2998 | 16.4 |
| 8 | 14E, 17R, 21P, 27P, 37P | 72 | 82 | 87 | 1.1 |
| 9 | 14E, 17R, 21P, 27P | 143 | 175 | 1288 | 7.4 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 15 | 14E, 17R, 21P, 27P | 597 | 386 | 3432 | 8.9 |
| 16 | 14E, 17R, 21P, 27P, 35R | 894 | 363 | 2215 | 6.1 |
| 17 | 14E, 17R, 21P, 27P, 34H | 878 | 268 | 2351 | 8.8 |
| 18 | 14E, 17R, 21P, 27P, 35H | 554 | 154 | 742 | 4.8 |
| 19 | 14E, 17R, 21P, 27P | 556 | 307 | 5321 | 17.4 |
| 20 | 14E, 17R, 21P, 27P, 37P | 217 | 80 | 285 | 3.6 |
| 21 | 17R, 21P, 27P | 585 | 148 | 611 | 4.1 |
| 22 | 14E, 17R, 21P, 27P, 35E | 794 | 270 | 1026 | 3.8 |
| 23 | 17R, 21P, 27P, 35E | 871 | 340 | 3025 | 8.9 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 28 | 17R, 21P, 27P, 31P, 35E | 610 | 220 | 2033 | 9.2 |
| 29 | 17R, 21P, 27P, 34P, 35E | 577 | 99 | 857 | 8.7 |
| 30 | 14H, 17R, 21P, 27P, 35E | 919 | 134 | 1677 | 12.6 |
| 31 | 14E, 17R, 21P, 27P, 31P | 204 | 112 | 717 | 6.4 |
| 32 | 14E, 17R, 21P, 27P, 34P | 100 | 50 | 327 | 6.6 |
| 34 | 17R, 21P, 27P, 35K | 1139 | 313 | 2615 | 8.4 |
| 35 | 17R, 21P, 27P, 35K | 970 | 364 | 5459 | 15.0 |
| 36 | 14E, 17R, 21P, 27P, 34K | 403 | 189 | 1280 | 6.8 |
| 37 | 14E, 17R, 21P, 27P, 29P | 970 | 92 | 372 | 4.0 |
| 38 | 17R, 21P, 27P, 35R | 249 | 352 | 18260 | 51.9 |
| 39 | 17R, 21P, 27P, 34R | 665 | 217 | 2522 | 11.6 |
| 40 | 17R, 21P, 27P, 34H | 549 | 164 | 2680 | 16.4 |
| 41 | 17R, 21P, 27P | 427 | 260 | 4346 | 16.7 |
| 42 | 17R, 21P, 27P | 264 | 146 | 1975 | 13.5 |
| 43 | 17R, 21P, 27P | 76 | 141 | 920 | 6.5 |
| 44 | -1K, 1R, 17R, 21P, 27P, 35H | 275 | 198 | 4751 | 24.0 |
| 45 | -1K, 1R, 17R, 21P, 27P, 35H | 552 | 594 | 10100 | 17.0 |
| 46 | -1G, 1R, 17R, 21P, 27P | 195 | 88 | 899 | 10.2 |

TABLE 6j-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 47 | −1G, 1R, 17R, 21P, 27P, 35H | 344 | 222 | 1322 | 6.0 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 51 | 14E, 17R, 21P, 27P, 35R | 828 | 372 | 5216 | 14.0 |
| 52 | 14D, 17R, 21P, 27P, 35R | 697 | 340 | 14074 | 41.4 |
| 53 | 17R, 21P, 27P, 28P, 31P | 52 | 64 | 625 | 9.8 |
| 54 | 17R, 21P, 27P, 29P, 31P | 30 | 103 | 987 | 9.6 |
| 55 | 17R, 21P, 27P, 28P, 34P | 42 | 68 | 731 | 10.8 |
| 56 | 17R, 21P, 27P, 29P, 34P | 49 | 102 | 506 | 5.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 61 | 14H, 17R, 21P, 27P, 31P | 122 | 51 | 554 | 10.9 |
| 62 | 14H, 17R, 21P, 27P, 31P | 98 | 44 | 539 | 12.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 67 | 14H, 17R, 21P, 27P, 34P | 90 | 69 | 354 | 5.2 |
| 68 | 14H, 17R, 21P, 27P, 34P | 88 | 54 | 932 | 17.4 |
| 69 | 14H, 17R, 21P, 27P | 133 | 94 | 1248 | 13.3 |
| 70 | 14H, 17R, 21P, 27P | 169 | 40 | 715 | 17.9 |
| 71 | 14G, 17R, 21P, 27P, 31P | 48 | 56 | 527 | 9.4 |
| 72 | 14A, 17R, 21P, 27P, 31P | 172 | 106 | 4758 | 44.9 |
| 73 | 14S, 17R, 21P, 27P, 31P | 104 | 85 | 961 | 11.3 |
| 74 | 14K, 17R, 21P, 27P, 31P | 791 | 666 | 37520 | 56.3 |
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 80 | 14H, 17R, 21P, 27P, 34H | 290 | 139 | 2141 | 15.4 |
| 81 | 14H, 17R, 21P, 27P, 34H | 271 | 130 | 1727 | 13.3 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 87 | 14E, 17R, 21P, 27P, 34H | 633 | 285 | 1095 | 3.8 |
| 88 | 14E, 17R, 21P, 27P, 34R | 750 | 773 | 6555 | 8.5 |
| 89 | 14E, 17R, 21P, 27P, 35R | 1160 | 404 | 11221 | 27.8 |
| 90 | 14H, 17R, 21P, 27P | 61 | 33 | 236 | 7.2 |
| 91 | 17R, 21P, 27P, 34H | 119 | 40 | 1477 | 36.9 |
| 92 | 14H, 17R, 21P, 27P | 179 | 85 | 2378 | 28.0 |
| 93 | 14A, 17R, 21P, 27P, 34H | 176 | 118 | 1145 | 9.7 |
| 94 | 14A, 17R, 21P, 27P, 34P | 148 | 70 | 316 | 4.5 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 99 | −1G, 1R, 14H, 17R, 21P, 27P | 348 | 82 | 818 | 10.0 |
| 100 | −1G, 1R, 14H, 17R, 21P, 27P, 34H | 1015 | 253 | 1726 | 6.8 |
| 101 | −1G, 1R, 14A, 17R, 21P, 27P, 34H | 426 | 109 | 537 | 4.9 |
| 102 | −1G, 1R, 14H, 17R, 21P, 27P, 34P | 217 | 62 | 179 | 2.9 |

TABLE 6j-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 119 | 17R, 21P, 27P, 31P, 34P, 35R | 880 | 333 | 8660 | 26.0 |
| 120 | 14S, 17R, 21P, 27P, 34P, 35E | 76 | 109 | 887 | 8.1 |
| 122 | 14D, 17R, 21P, 27P, 34P, 35E | 172 | 159 | 843 | 5.3 |
| 123 | 14D, 17R, 21P, 27P, 34P, 35E | 196 | 288 | 1115 | 3.9 |
| 124 | 14E, 17R, 21P, 27P, 34P, 35H | 377 | 172 | 2833 | 16.4 |
| 125 | 14E, 17R, 21P, 27P, 34P, 35E, 37P | 533 | 132 | 102 | 0.8 |
| 127 | 14E, 17R, 21P, 27P, 34P, 37F | 152 | 216 | 2140 | 9.9 |
| 128 | 14E, 17R, 21P, 27P, 35H | 992 | 425 | 5575 | 13.1 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6k

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 2 | 14D, 17R, 21P, 27P, 35D | 411 | 182 | 2998 | 16.4 |
| 15 | 14E, 17R, 21P, 27P | 597 | 386 | 3432 | 8.9 |
| 16 | 14E, 17R, 21P, 27P, 35R | 894 | 363 | 2215 | 6.1 |
| 17 | 14E, 17R, 21P, 27P, 34H | 878 | 268 | 2351 | 8.8 |
| 19 | 14E, 17R, 21P, 27P | 556 | 307 | 5321 | 17.4 |
| 23 | 17R, 21P, 27P, 35E | 871 | 340 | 3025 | 8.9 |
| 24 | 17R, 21P, 27P | 1138 | 433 | 10000 | 23.1 |
| 25 | 17R, 21P, 27P, 35E | 768 | 217 | 10000 | 46.2 |
| 26 | 17R, 21P, 27P, 35E | 532 | 212 | 6338 | 29.9 |
| 27 | 17R, 21P, 27P, 35E | 837 | 133 | 3001 | 22.6 |
| 28 | 17R, 21P, 27P, 31P, 35E | 610 | 220 | 2033 | 9.2 |
| 29 | 17R, 21P, 27P, 34P, 35E | 577 | 99 | 857 | 8.7 |
| 30 | 14H, 17R, 21P, 27P, 35E | 919 | 134 | 1677 | 12.6 |
| 31 | 14E, 17R, 21P, 27P, 31P | 204 | 112 | 717 | 6.4 |
| 32 | 14E, 17R, 21P, 27P, 34P | 100 | 50 | 327 | 6.6 |
| 34 | 17R, 21P, 27P, 35K | 1139 | 313 | 2615 | 8.4 |
| 35 | 17R, 21P, 27P, 35K | 970 | 364 | 5459 | 15.0 |
| 36 | 14E, 17R, 21P, 27P, 34K | 403 | 189 | 1280 | 6.8 |
| 38 | 17R, 21P, 27P, 35R | 249 | 352 | 18260 | 51.9 |
| 39 | 17R, 21P, 27P, 34R | 665 | 217 | 2522 | 11.6 |
| 40 | 17R, 21P, 27P, 34H | 549 | 164 | 2680 | 16.4 |
| 41 | 17R, 21P, 27P | 427 | 260 | 4346 | 16.7 |
| 42 | 17R, 21P, 27P | 264 | 146 | 1975 | 13.5 |
| 43 | 17R, 21P, 27P | 76 | 141 | 920 | 6.5 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 46 | −1G, 1R, 17R, 21P, 27P | 195 | 88 | 899 | 10.2 |
| 47 | −1G, 1R, 17R, 21P, 27P, 35H | 344 | 222 | 1322 | 6.0 |
| 48 | 17R, 21P, 27P | 443 | 116 | 1968 | 17.0 |
| 49 | 17R, 21P, 27P, 31P | 1191 | 106 | 2390 | 22.5 |
| 50 | 17R, 21P, 27P, 34P | 38 | 38 | 662 | 17.4 |
| 51 | 14E, 17R, 21P, 27P, 35R | 828 | 372 | 5216 | 14.0 |
| 52 | 14D, 17R, 21P, 27P, 35R | 697 | 340 | 14074 | 41.4 |
| 53 | 17R, 21P, 27P, 28P, 31P | 52 | 64 | 625 | 9.8 |
| 54 | 17R, 21P, 27P, 29P, 31P | 30 | 103 | 987 | 9.6 |
| 55 | 17R, 21P, 27P, 28P, 34P | 42 | 68 | 731 | 10.8 |
| 56 | 17R, 21P, 27P, 29P, 34P | 49 | 102 | 506 | 5.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 61 | 14H, 17R, 21P, 27P, 31P | 122 | 51 | 554 | 10.9 |
| 62 | 14H, 17R, 21P, 27P, 31P | 98 | 44 | 539 | 12.3 |
| 63 | 14R, 17R, 21P, 27P, 31P | 825 | 37 | 5131 | 138.7 |
| 64 | 14R, 17R, 21P, 27P, 31P | 444 | 378 | 22940 | 60.7 |
| 65 | 14R, 17R, 21P, 27P, 34P | 649 | 242 | 9331 | 38.6 |
| 66 | 14H, 17R, 21P, 27P, 35H | 396 | 27 | 542 | 20.1 |
| 67 | 14H, 17R, 21P, 27P, 34P | 90 | 69 | 354 | 5.2 |
| 68 | 14H, 17R, 21P, 27P, 34P | 88 | 54 | 932 | 17.4 |
| 69 | 14H, 17R, 21P, 27P | 133 | 94 | 1248 | 13.3 |
| 70 | 14H, 17R, 21P, 27P | 169 | 40 | 715 | 17.9 |
| 71 | 14G, 17R, 21P, 27P, 31P | 48 | 56 | 527 | 9.4 |

TABLE 6k-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 72 | 14A, 17R, 21P, 27P, 31P | 172 | 106 | 4758 | 44.9 |
| 73 | 14S, 17R, 21P, 27P, 31P | 104 | 85 | 961 | 11.3 |
| 74 | 14K, 17R, 21P, 27P, 31P | 791 | 666 | 37520 | 56.3 |
| 75 | 14T, 17R, 21P, 27P, 31P | 666 | 296 | 9069 | 30.6 |
| 76 | 17R, 21P, 27P, 34H | 215 | 297 | 7370 | 24.8 |
| 77 | 17R, 21P, 27P, 34H | 428 | 145 | 5398 | 37.3 |
| 78 | 17R, 21P, 27P, 34R | 602 | 316 | 8165 | 25.8 |
| 79 | 17R, 21P, 27P, 34R | 790 | 161 | 3938 | 24.5 |
| 80 | 14H, 17R, 21P, 27P, 34H | 290 | 139 | 2141 | 15.4 |
| 81 | 14H, 17R, 21P, 27P, 34H | 271 | 130 | 1727 | 13.3 |
| 82 | 14R, 17R, 21P, 27P | 636 | 215 | 12730 | 59.2 |
| 83 | 14R, 17R, 21P, 27P | 939 | 405 | 16840 | 41.6 |
| 84 | 14H, 17R, 21P, 27P, 34R | 743 | 169 | 5486 | 32.5 |
| 85 | 14H, 17R, 21P, 27P, 34R | 876 | 146 | 3882 | 26.6 |
| 86 | 17R, 21P, 27P, 34H | 833 | 298 | 19157 | 64.4 |
| 88 | 14E, 17R, 21P, 27P, 34R | 750 | 773 | 6555 | 8.5 |
| 89 | 14E, 17R, 21P, 27P, 35R | 1160 | 404 | 11221 | 27.8 |
| 90 | 14H, 17R, 21P, 27P | 61 | 33 | 236 | 7.2 |
| 91 | 17R, 21P, 27P, 34H | 119 | 40 | 1477 | 36.9 |
| 92 | 14H, 17R, 21P, 27P | 179 | 85 | 2378 | 28.0 |
| 93 | 14A, 17R, 21P, 27P, 34H | 176 | 118 | 1145 | 9.7 |
| 95 | 17R, 21P, 27P, 34R | 967 | 651 | 21500 | 33.0 |
| 96 | 17R, 21P, 27P, 31P | 166 | 181 | 3801 | 21.0 |
| 97 | 17R, 21P, 27P, 34H | 568 | 356 | 11750 | 33.0 |
| 98 | 17R, 21P, 27P, 34P | 91 | 84 | 1634 | 19.5 |
| 99 | −1G, 1R, 14H, 17R, 21P, 27P | 348 | 82 | 818 | 10.0 |
| 100 | −1G, 1R, 14H, 17R, 21P, 27P, 34H | 1015 | 253 | 1726 | 6.8 |
| 104 | 14E, 17R, 21P, 27P, 34H, 35E | 525 | 445 | 7053 | 15.8 |
| 105 | 14E, 17R, 21P, 27P, 34R, 35E | 957 | 703 | 7426 | 10.6 |
| 106 | 14E, 17R, 21P, 27P, 34P, 35E | 121 | 225 | 2362 | 10.5 |
| 107 | 14E, 17R, 21P, 27P, 34H, 35E | 387 | 405 | 2541 | 6.3 |
| 108 | 14E, 17R, 21P, 27P, 34R, 35E | 232 | 421 | 2745 | 6.5 |
| 109 | 14E, 17R, 21P, 27P, 34P, 35E | 140 | 161 | 841 | 5.2 |
| 110 | 14E, 17R, 21P, 27P, 34P, 35R | 326 | 278 | 8158 | 29.3 |
| 111 | 17R, 21P, 27P, 34H | 580 | 34 | 2214 | 65.1 |
| 112 | 17R, 21P, 27P, 34H | 1037 | 28 | 1087 | 38.8 |
| 113 | 17R, 21P, 27P, 34H | 382 | 96 | 5846 | 60.9 |
| 117 | 14E, 17R, 21P, 27P, 34P, 35R | 163 | 376 | 6380 | 17.0 |
| 118 | 14E, 17R, 21P, 27P, 34P, 35H | 179 | 101 | 1451 | 14.4 |
| 119 | 17R, 21P, 27P, 31P, 34P, 35R | 880 | 333 | 8660 | 26.0 |
| 120 | 14S, 17R, 21P, 27P, 34P, 35E | 76 | 109 | 887 | 8.1 |
| 122 | 14D, 17R, 21P, 27P, 34P, 35E | 172 | 159 | 843 | 5.3 |
| 124 | 14E, 17R, 21P, 27P, 34P, 35H | 377 | 172 | 2833 | 16.4 |
| 127 | 14E, 17R, 21P, 27P, 34P, 37F | 152 | 216 | 2140 | 9.9 |
| 128 | 14E, 17R, 21P, 27P, 35H | 992 | 425 | 5575 | 13.1 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6l

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 8 | 14E, 17R, 21P, 27P, 37P | 72 | 82 | 87 | 1.1 |
| 10 | 14D, 17R, 21P, 27P, 37P | 82 | 72 | 70 | 1.0 |
| 11 | 14E, 17R, 21P, 27P, 35D, 37P | 105 | 120 | 112 | 0.9 |
| 12 | 14E, 17R, 21P, 27P, 37P | 142 | 101 | 185 | 1.8 |
| 13 | 14E, 17R, 21P, 27P, 37P | 264 | 213 | 470 | 2.2 |
| 14 | 14E, 17R, 21P, 27P, 37P | 196 | 146 | 238 | 1.6 |
| 18 | 14E, 17R, 21P, 27P, 35H | 554 | 154 | 742 | 4.8 |
| 20 | 14E, 17R, 21P, 27P, 37P | 217 | 80 | 285 | 3.6 |
| 21 | 17R, 21P, 27P | 585 | 148 | 611 | 4.1 |
| 22 | 14E, 17R, 21P, 27P, 35E | 794 | 270 | 1026 | 3.8 |
| 37 | 14E, 17R, 21P, 27P, 29P | 970 | 92 | 372 | 4.0 |
| 87 | 14E, 17R, 21P, 27P, 34H | 633 | 285 | 1095 | 3.8 |
| 88 | 14E, 17R, 21P, 27P, 34R | 750 | 773 | 6555 | 8.5 |

TABLE 6l-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 94 | 14A, 17R, 21P, 27P, 34P | 148 | 70 | 316 | 4.5 |
| 101 | −1G, 1R, 14A, 17R, 21P, 27P, 34H | 426 | 109 | 537 | 4.9 |
| 102 | −1G, 1R, 14H, 17R, 21P, 27P, 34P | 217 | 62 | 179 | 2.9 |
| 103 | −1G, 1R, 14A, 17R, 21P, 27P, 34P | 114 | 70 | 148 | 2.1 |
| 114 | 14E, 17R, 21P, 27P, 34P, 37P | 214 | 105 | 90 | 0.9 |
| 115 | 14H, 17R, 21P, 27P, 34P, 37P | 131 | 52 | 40 | 0.8 |
| 116 | 14H, 17R, 21P, 27P, 31P, 34P | 82 | 71 | 345 | 4.9 |
| 123 | 14D, 17R, 21P, 27P, 34P, 35E | 196 | 288 | 1115 | 3.9 |
| 125 | 14E, 17R, 21P, 27P, 34P, 35E, 37P | 533 | 132 | 102 | 0.8 |
| 127 | 14E, 17R, 21P, 27P, 34P, 37F | 152 | 216 | 2140 | 9.9 |

TABLE 6m

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 16 | 14E, 17R, 21P, 27P, 35R | 894 | 363 | 2215 | 6.1 |
| 38 | 17R, 21P, 27P, 35R | 249 | 352 | 18260 | 51.9 |
| 89 | 14E, 17R, 21P, 27P, 35R | 1160 | 404 | 11221 | 27.8 |
| 110 | 14E, 17R, 21P, 27P, 34P, 35R | 326 | 278 | 8158 | 29.3 |
| 117 | 14E, 17R, 21P, 27P, 34P, 35R | 163 | 376 | 6380 | 17.0 |
| 119 | 17R, 21P, 27P, 31P, 34P, 35R | 880 | 333 | 8660 | 26.0 |
| 129 | 14D, 17R, 21P, 27P, 34P, 35R | 281 | 146 | 3640 | 24.9 |
| 130 | 14D, 17R, 21P, 27P, 34P, 35R | 453 | 162 | 7280 | 44.9 |
| 131 | 14d, 17R, 21P, 27P, 35R | 365 | 383 | 100000 | 261.1 |
| 132 | 14D, 17R, 21P, 27P, 35R | 266 | 11 | 318 | 28.9 |

TABLE 6n

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 18 | 14E, 17R, 21P, 27P, 35H | 554 | 154 | 742 | 4.8 |
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 47 | −1G, 1R, 17R, 21P, 27P, 35H | 344 | 222 | 1322 | 6.0 |
| 57 | 17R, 21P, 27P, 31P, 35H | 115 | 89 | 3119 | 35.0 |
| 58 | 17R, 21P, 27P, 34P, 35H | 88 | 47 | 1028 | 21.9 |
| 60 | 17R, 21P, 27P, 35H | 695 | 351 | 5355 | 15.3 |
| 66 | 14H, 17R, 21P, 27P, 35H | 396 | 27 | 542 | 20.1 |
| 118 | 14E, 17R, 21P, 27P, 34P, 35H | 179 | 101 | 1451 | 14.4 |
| 124 | 14E, 17R, 21P, 27P, 34P, 35H | 377 | 172 | 2833 | 16.4 |
| 128 | 14E, 17R, 21P, 27P, 35H | 992 | 425 | 5575 | 13.1 |

TABLE 6o

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 44 | −1K, 1R, 17R, 21P, 27P, 35H | 275 | 198 | 4751 | 24.0 |
| 45 | −1K, 1R, 17R, 21P, 27P, 35H | 552 | 594 | 10100 | 17.0 |
| 57 | 17R, 21P, 27P, 31P, 35H | 115 | 89 | 3119 | 35.0 |

TABLE 60-continued

| Example no. | Sequence modifications | hAmylin-R bind IC50 (pM) | hAmylin-R funct. EC50 (pM) | hCTR funct. EC50 (pM) | Ratio hCT/hAmylin funct. |
|---|---|---|---|---|---|
| 58 | 17R, 21P, 27P, 34P, 35H | 88 | 47 | 1028 | 21.9 |
| 60 | 17R, 21P, 27P, 35H | 695 | 351 | 5355 | 15.3 |
| 66 | 14H, 17R, 21P, 27P, 35H | 396 | 27 | 542 | 20.1 |
| 118 | 14E, 17R, 21P, 27P, 34P, 35H | 179 | 101 | 1451 | 14.4 |
| 124 | 14E, 17R, 21P, 27P, 34P, 35H | 377 | 172 | 2833 | 16.4 |
| 128 | 14E, 17R, 21P, 27P, 35H | 992 | 425 | 5575 | 13.1 |

Binding to Rat Amylin Receptors and Rat Calcitonin Receptors

The in vitro data regarding binding to rat amylin receptors and rat calcitonin receptors and the corresponding selectivity values are shown in Table 7 (below). For ease of reference, the human binding data are also included.

Table 7 discloses compounds that have a hAmylinR IC50 value of less than 1200 pM and indicates values for rat binding selectivity of at least 10 or less than 10. Preferred compounds have a rat binding selectivity of at least 10. These preferred compounds are shown in Table 7a. In Tables 7 and 7a we have also included the human ratios for comparison purposes. As before a ratio of hCT/hAmylin binding of at least 10 is preferred. Table 7b presents those preferred compounds. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

In one embodiment the amylin polypeptide according to the present invention is selected from the compounds which are in common between the presented compounds of in table 7 and table 4. In one embodiment the amylin polypeptide according to the present invention is selected from the compounds which are in common between the presented compounds of in table 7 and table 4a. In one embodiment the amylin polypeptide according to the present invention is selected from the compounds which are in common between the presented compounds of in table 7 and table 4b. In one embodiment the amylin polypeptide according to the present invention is selected from the compounds which are in common between the presented compounds of in table 7 and table 4a. In one embodiment the amylin polypeptide according to the present invention is selected from the compounds which are in common between the presented compounds of in table 7 and table 4c. In one embodiment the amylin polypeptide according to the present invention is selected from the compounds which are in common between the presented compounds of in table 7 and table 5. In one embodiment the amylin polypeptide according to the present invention is selected from the compounds which are in common between the presented compounds of in table 7 and table 5a. In one embodiment the amylin polypeptide according to the present invention is selected from the compounds which are in common between the presented compounds of in table 7 and table 5b. In one embodiment the amylin polypeptide according to the present invention is selected from the compounds which are in common between the presented compounds of in table 7 and table 5c. In one embodiment the amylin polypeptide according to the present invention is selected from the compounds which are in common between the presented compounds of in table 7 and table 8. In one embodiment the amylin polypeptide according to the present invention is selected from the compounds which are in common between the presented compounds of in table 7 and table 8a. In one embodiment the amylin polypeptide according to the present invention is selected from the compounds which are in common between the presented compounds of in table 7 and table 9. In one embodiment the amylin polypeptide according to the present invention is selected from the compounds which are in common between the presented compounds of in table 7 and table 9a.

In one embodiment the amylin polypeptide according to the present invention is selected from the compounds which are in common between the presented compounds of in table 7a and table 4. In one embodiment the amylin polypeptide according to the present invention is selected from the compounds which are in common between the presented compounds of in table 7a and table 4a. In one embodiment the amylin polypeptide according to the present invention is selected from the compounds which are in common between the presented compounds of in table 7a and table 4b. In one embodiment the amylin polypeptide according to the present invention is selected from the compounds which are in common between the presented compounds of in table 7a and table 4a. In one embodiment the amylin polypeptide according to the present invention is selected from the compounds which are in common between the presented compounds of in table 7a and table 4c. In one embodiment the amylin polypeptide according to the present invention is selected from the compounds which are in common between the presented compounds of in table 7a and table 5. In one embodiment the amylin polypeptide according to the present invention is selected from the compounds which are in common between the presented compounds of in table 7a and table 5a. In one embodiment the amylin polypeptide according to the present invention is selected from the compounds which are in common between the presented compounds of in table 7a and table 5b. In one embodiment the amylin polypeptide according to the present invention is selected from the compounds which are in common between the presented compounds of in table 7a and table 5c. In one embodiment the amylin polypeptide according to the present invention is selected from the compounds which are in common between the presented compounds of in table 7a and table 8. In one embodiment the amylin polypeptide according to the present invention is selected from the compounds which are in common between the presented compounds of in table 7a and table 8a. In one embodiment the amylin polypeptide according to the present invention is selected from the compounds which are in common between the presented compounds of in table 7a and table 9. In one embodiment the amylin polypeptide according to the present invention is selected from the compounds which are in common between the presented compounds of in table 7a and table 9a.

In one embodiment the amylin polypeptide according to the present invention is selected from the compounds which are in common between the presented compounds of in table 7b and table 4. In one embodiment the amylin polypeptide according to the present invention is selected from the compounds which are in common between the presented compounds of in table 7b and table 4a. In one embodiment the amylin polypeptide according to the present invention is selected from the compounds which are in common between the presented compounds of in table 7b and table 4b. In one embodiment the amylin polypeptide according to the present invention is selected from the compounds which are in common between the presented compounds of in table 7b and table 4a. In one embodiment the amylin polypeptide according to the present invention is selected from the compounds which are in common between the presented compounds of in table 7b and table 4c. In one embodiment the amylin polypeptide according to the present invention is selected from the compounds which are in common between the presented compounds of in table 7b and table 5. In one embodiment the amylin polypeptide according to the present invention is selected from the compounds which are in common between the presented compounds of in table 7b and table 5a. In one embodiment the amylin polypeptide according to the present invention is selected from the compounds which are in common between the presented compounds of in table 7b and table 5b. In one embodiment the amylin polypeptide according to the present invention is selected from the compounds which are in common between the presented compounds of in table 7b and table 5c. In one embodiment the amylin polypeptide according to the present invention is selected from the compounds which are in common between the presented compounds of in table 7b and table 8. In one embodiment the amylin polypeptide according to the present invention is selected from the compounds which are in common between the presented compounds of in table 7b and table 8a. In one embodiment the amylin polypeptide according to the present invention is selected from the compounds which are in common between the presented compounds of in table 7b and table 9. In one embodiment the amylin polypeptide according to the present invention is selected from the compounds which are in common between the presented compounds of in table 7b and table 9a In one embodiment the amylin polypeptide according to the present invention is selected from the compounds which are in common between the presented compounds of in table 7c and table 4. In one embodiment the amylin polypeptide according to the present invention is selected from the compounds which are in common between the presented compounds of in table 7c and table 4a. In one embodiment the amylin polypeptide according to the present invention is selected from the compounds which are in common between the presented compounds of in table 7c and table 4b. In one embodiment the amylin polypeptide according to the present invention is selected from the compounds which are in common between the presented compounds of in table 7c and table 4a. In one embodiment the amylin polypeptide according to the present invention is selected from the compounds which are in common between the presented compounds of in table 7c and table 4c. In one embodiment the amylin polypeptide according to the present invention is selected from the compounds which are in common between the presented compounds of in table 7c and table 5. In one embodiment the amylin polypeptide according to the present invention is selected from the compounds which are in common between the presented compounds of in table 7c and table 5a. In one embodiment the amylin polypeptide according to the present invention is selected from the compounds which are in common between the presented compounds of in table 7c and table 5b. In one embodiment the amylin polypeptide according to the present invention is selected from the compounds which are in common between the presented compounds of in table 7c and table 5c. In one embodiment the amylin polypeptide according to the present invention is selected from the compounds which are in common between the presented compounds of in table 7c and table 8. In one embodiment the amylin polypeptide according to the present invention is selected from the compounds which are in common between the presented compounds of in table 7c and table 8a. In one embodiment the amylin polypeptide according to the present invention is selected from the compounds which are in common between the presented compounds of in table 7c and table 9. In one embodiment the amylin polypeptide according to the present invention is selected from the compounds which are in common between the presented compounds of in table 7c and table 9a In one embodiment the amylin polypeptide according to the present invention is selected from the compounds presented in table 7, except the compounds presented in table 6d. In one embodiment the amylin polypeptide according to the present invention is selected from the compounds presented in table 7, except the compounds presented in table 6e. In one embodiment the amylin polypeptide according to the present invention is selected from the compounds presented in table 7, except the compounds presented in table 6f. In one embodiment the amylin polypeptide according to the present invention is selected from the compounds presented in table 7, except the compounds presented in table 6h. In one embodiment the amylin polypeptide according to the present invention is selected from the compounds presented in table 7, except the compounds presented in table 6l. In one embodiment the amylin polypeptide according to the present invention is selected from the compounds presented in table 7, except the compounds presented in table 6o.

In one embodiment the amylin polypeptide according to the present invention is selected from the compounds presented in table 7a, except the compounds presented in table 6d. In one embodiment the amylin polypeptide according to the present invention is selected from the compounds presented in table 7a, except the compounds presented in table 6e. In one embodiment the amylin polypeptide according to the present invention is selected from the compounds presented in table 7a, except the compounds presented in table 6f. In one embodiment the amylin polypeptide according to the present invention is selected from the compounds presented in table 7a, except the compounds presented in table 6h. In one embodiment the amylin polypeptide according to the present invention is selected from the compounds presented in table 7a, except the compounds presented in table 6l. In one embodiment the amylin polypeptide according to the present invention is selected from the compounds presented in table 7a, except the compounds presented in table 6o.

In one embodiment the amylin polypeptide according to the present invention is selected from the compounds presented in table 7b, except the compounds presented in table 6d. In one embodiment the amylin polypeptide according to the present invention is selected from the compounds presented in table 7b, except the compounds presented in table 6e. In one embodiment the amylin polypeptide according to the present invention is selected from the compounds presented in table 7b, except the compounds presented in table 6f. In one embodiment the amylin polypeptide according to the present invention is selected from the compounds presented in table 7b, except the compounds presented in table 6h. In one embodiment the amylin polypeptide according to the sented in table 7b, except the compounds presented in table 6l. In one embodiment the amylin polypeptide according to the present invention is selected from the compounds presented in table 7b, except the compounds presented in table 6o.

In one embodiment the amylin polypeptide according to the present invention is selected from the compounds presented in table 7c, except the compounds presented in table 6d. In one embodiment the amylin polypeptide according to the present invention is selected from the compounds presented in table 7c, except the compounds presented in table 6e. In one embodiment the amylin polypeptide according to the present invention is selected from the compounds presented in table 7c, except the compounds presented in table 6f. In one embodiment the amylin polypeptide according to the present invention is selected from the compounds presented in table 7c, except the compounds presented in table 6h. In one embodiment the amylin polypeptide according to the present invention is selected from the compounds presented in table 7c, except the compounds presented in table 6l. In one embodiment the amylin polypeptide according to the present invention is selected from the compounds presented in table 7c, except the compounds presented in table 6o.

TABLE 7

| Example no. | Sequence modifications | rAmylin-R bind IC50 (pM) | rCTR bind IC50 (pM) | Ratio rCT/rAmylin binding | Ratio hCT/hAmylin binding |
| --- | --- | --- | --- | --- | --- |
| 1 | 14D, 17R, 21P, 26P, 35D | 1300 | 135100 | 103.9 | 27.6 |
| 2 | 14D, 17R, 21P, 27P, 35D | 295 | 107798 | 365.7 | 47.5 |
| 3 | 14D, 17R, 22P, 26P, 35D | 1002 | 16748 | 16.7 | 17.3 |
| 4 | 14E, 17R, 21P, 25P, 28P, 29P, 37P | 1305 | 4051 | 3.1 | 2.1 |
| 5 | 14E, 17R, 21P, 26P, 37P | 1296 | 4652 | 3.6 | 1.4 |
| 6 | 14E, 17R, 21P, 25P, 28P, 29P | 2373 | 51550 | 21.7 | 20.0 |
| 7 | 14E, 17R, 21P, 26P | 1125 | 47250 | 42.0 | 16.5 |
| 8 | 14E, 17R, 21P, 27P, 37P | | | | 0.5 |
| 9 | 14E, 17R, 21P, 27P | | | | 8.0 |
| 10 | 14D, 17R, 21P, 27P, 37P | | | | 1.2 |
| 11 | 14E, 17R, 21P, 27P, 35D, 37P | | | | 1.0 |
| 12 | 14E, 17R, 21P, 27P, 37P | 544 | 2709 | 5.0 | 2.5 |
| 13 | 14E, 17R, 21P, 27P, 37P | | | | 1.2 |
| 14 | 14E, 17R, 21P, 27P, 37P | | | | 2.2 |
| 15 | 14E, 17R, 21P, 27P | | | | 26.0 |
| 16 | 14E, 17R, 21P, 27P, 35R | 1210 | 55220 | 45.6 | 19.1 |
| 17 | 14E, 17R, 21P, 27P, 34H | 2710 | 97230 | 35.9 | 12.5 |
| 18 | 14E, 17R, 21P, 27P, 35H | 476 | 13000 | 27.3 | 9.2 |
| 19 | 14E, 17R, 21P, 27P | 1022 | 95610 | 93.6 | 36.7 |
| 20 | 14E, 17R, 21P, 27P, 37P | 696 | 4430 | 6.4 | 3.6 |
| 21 | 17R, 21P, 27P | 1484 | 27935 | 18.8 | 24.4 |
| 22 | 14E, 17R, 21P, 27P, 35E | 2189 | 62460 | 28.5 | 12.3 |
| 23 | 17R, 21P, 27P, 35E | 1120 | 79870 | 71.3 | 25.0 |
| 24 | 17R, 21P, 27P | 3006 | 349700 | 116.3 | 90.0 |
| 25 | 17R, 21P, 27P, 35E | 3485 | 131300 | 37.7 | 56.5 |
| 26 | 17R, 21P, 27P, 35E | 491 | 151700 | 309.2 | 47.5 |
| 27 | 17R, 21P, 27P, 35E | 614 | 90190 | 146.8 | 41.3 |
| 28 | 17R, 21P, 27P, 31P, 35E | 1224 | 54897 | 44.9 | 20.5 |
| 29 | 17R, 21P, 27P, 34P, 35E | 322 | 21560 | 67.0 | 13.9 |
| 30 | 14H, 17R, 21P, 27P, 35E | 3143 | 113600 | 36.1 | 23.6 |
| 31 | 14E, 17R, 21P, 27P, 31P | 619 | 26510 | 42.8 | 16.0 |
| 32 | 14E, 17R, 21P, 27P, 34P | 176 | 5976 | 34.0 | 10.9 |
| 33 | 14E, 17R, 21P, 28P, 35E | 2295 | 28885 | 12.6 | 3.9 |
| 34 | 17R, 21P, 27P, 35K | 1715 | 89170 | 52.0 | 64.4 |
| 35 | 17R, 21P, 27P, 35K | 948 | 61740 | 65.1 | 50.3 |
| 36 | 14E, 17R, 21P, 27P, 34K | 1856 | 60060 | 32.4 | 15.7 |
| 37 | 14E, 17R, 21P, 27P, 29P | 514 | 7354 | 14.3 | 2.3 |
| 38 | 17R, 21P, 27P, 35R | 383 | 38020 | 99.2 | 84.9 |
| 39 | 17R, 21P, 27P, 34R | 1770 | 96440 | 54.5 | 29.0 |
| 40 | 17R, 21P, 27P, 34H | 1498 | 69248 | 46.2 | 31.1 |
| 41 | 17R, 21P, 27P | 1371 | 74090 | 54.0 | 49.9 |
| 42 | 17R, 21P, 27P | 603 | 15340 | 25.4 | 30.7 |
| 43 | 17R, 21P, 27P | 110 | 7601 | 69.1 | 34.7 |
| 44 | −1K, 1R, 17R, 21P, 27P, 35H | 369 | 19650 | 53.3 | 17.7 |
| 45 | −1K, 1R, 17R, 21P, 27P, 35H | 623 | 41790 | 67.1 | 26.8 |
| 46 | −1G, 1R, 17R, 21P, 27P | 330 | 46780 | 141.8 | 48.9 |
| 47 | −1G, 1R, 17R, 21P, 27P, 35H | 203 | 17110 | 84.3 | 44.9 |
| 48 | 17R, 21P, 27P | 558 | 112300 | 201.3 | 69.7 |
| 49 | 17R, 21P, 27P, 31P | 1078 | 51410 | 47.7 | 10.8 |
| 50 | 17R, 21P, 27P, 34P | 69 | 5634 | 81.7 | 36.0 |
| 51 | 14E, 17R, 21P, 27P, 35R | 523 | 61963 | 118.6 | 37.5 |
| 52 | 14D, 17R, 21P, 27P, 35R | 335 | 159464 | 476.7 | 81.6 |
| 53 | 17R, 21P, 27P, 28P, 31P | 84 | 10930 | 130.1 | 103.5 |
| 54 | 17R, 21P, 27P, 29P, 31P | 49 | 8789 | 179.4 | 146.1 |
| 55 | 17R, 21P, 27P, 28P, 34P | 81 | 6254 | 77.2 | 51.8 |
| 56 | 17R, 21P, 27P, 29P, 34P | 40 | 5256 | 131.4 | 42.6 |
| 57 | 17R, 21P, 27P, 31P, 35H | 181 | 24400 | 134.8 | 133.0 |
| 58 | 17R, 21P, 27P, 34P, 35H | 135 | 10340 | 76.6 | 109.4 |

TABLE 7-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 59 | 14D, 17R, 21K, 27P, 35D | 659 | 18755 | 28.5 | 4.3 |
| 60 | 17R, 21P, 27P, 35H | 215 | 26310 | 122.4 | 45.2 |
| 61 | 14H, 17R, 21P, 27P, 31P | 842 | 33403 | 39.7 | 66.7 |
| 62 | 14H, 17R, 21P, 27P, 31P | 420 | 17956 | 42.8 | 63.0 |
| 63 | 14R, 17R, 21P, 27P, 31P | 3485 | 123900 | 35.6 | 157.1 |
| 64 | 14R, 17R, 21P, 27P, 31P | 1974 | 127800 | 64.7 | 126.1 |
| 65 | 14R, 17R, 21P, 27P, 34P | 1158 | 107934 | 93.2 | 82.4 |
| 66 | 14H, 17R, 21P, 27P, 35H | 581 | 20780 | 35.8 | 45.5 |
| 67 | 14H, 17R, 21P, 27P, 34P | 172 | 14670 | 85.4 | 51.6 |
| 68 | 14H, 17R, 21P, 27P, 34P | 234 | 28486 | 121.9 | 64.4 |
| 69 | 14H, 17R, 21P, 27P | 450 | 46820 | 104.0 | 65.3 |
| 70 | 14H, 17R, 21P, 27P | 355 | 34240 | 96.5 | 60.8 |
| 71 | 14G, 17R, 21P, 27P, 31P | 276 | 44820 | 162.4 | 32.0 |
| 72 | 14A, 17R, 21P, 27P, 31P | 851 | 220700 | 259.3 | 246.6 |
| 73 | 14S, 17R, 21P, 27P, 31P | 283 | 50290 | 177.7 | 51.7 |
| 74 | 14K, 17R, 21P, 27P, 31P | 4894 | 109050 | 22.3 | 101.0 |
| 75 | 14T, 17R, 21P, 27P, 31P | 4025 | 442000 | 109.8 | 91.4 |
| 76 | 17R, 21P, 27P, 34H | 686 | 38935 | 56.8 | 80.0 |
| 77 | 17R, 21P, 27P, 34H | 1496 | 204700 | 136.8 | 118.4 |
| 78 | 17R, 21P, 27P, 34R | 1296 | 90560 | 69.9 | 60.7 |
| 79 | 17R, 21P, 27P, 34R | 1652 | 35510 | 21.5 | 46.1 |
| 80 | 14H, 17R, 21P, 27P, 34H | 1670 | 60400 | 36.2 | 68.1 |
| 81 | 14H, 17R, 21P, 27P, 34H | 1424 | 61150 | 42.9 | 87.2 |
| 82 | 14R, 17R, 21P, 27P | 1643 | 142900 | 87.0 | 139.6 |
| 83 | 14R, 17R, 21P, 27P | 2828 | 140500 | 49.7 | 145.6 |
| 84 | 14H, 17R, 21P, 27P, 34R | 5054 | 476533 | 94.3 | 119.6 |
| 85 | 14H, 17R, 21P, 27P, 34R | 3140 | 146100 | 46.5 | 91.8 |
| 86 | 17R, 21P, 27P, 34H | 2802 | 352205 | 125.7 | 159.3 |
| 87 | 14E, 17R, 21P, 27P, 34H | 2073 | 94463 | 45.6 | 35.6 |
| 88 | 14E, 17R, 21P, 27P, 34R | 2311 | 196100 | 84.9 | 46.5 |
| 89 | 14E, 17R, 21P, 27P, 35R | 2368 | 115459 | 48.8 | 28.0 |
| 90 | 14H, 17R, 21P, 27P | 246 | 18220 | 74.1 | 42.2 |
| 91 | 17R, 21P, 27P, 34H | 386 | 29450 | 76.3 | 100.8 |
| 92 | 14H, 17R, 21P, 27P | 668 | 104500 | 156.4 | 145.0 |
| 93 | 14A, 17R, 21P, 27P, 34H | 1577 | 131200 | 83.2 | 101.0 |
| 94 | 14A, 17R, 21P, 27P, 34P | 397 | 111065 | 280.1 | 46.3 |
| 95 | 17R, 21P, 27P, 34R | 5446 | 388500 | 71.3 | 63.4 |
| 96 | 17R, 21P, 27P, 31P | 529 | 62180 | 117.5 | 79.6 |
| 97 | 17R, 21P, 27P, 34H | 2239 | 159100 | 71.1 | 103.7 |
| 98 | 17R, 21P, 27P, 34P | 137 | 24050 | 175.5 | 74.1 |
| 99 | −1G, 1R, 14H, 17R, 21P, 27P | 2700 | 215515 | 79.8 | 100.4 |
| 100 | −1G, 1R, 14H, 17R, 21P, 27P, 34H | 11235 | 311380 | 27.7 | 65.3 |
| 101 | −1G, 1R, 14A, 17R, 21P, 27P, 34H | 8068 | 491585 | 60.9 | 68.6 |
| 102 | −1G, 1R, 14H, 17R, 21P, 27P, 34P | 674 | 65880 | 97.7 | 36.2 |
| 103 | −1G, 1R, 14A, 17R, 21P, 27P, 34P | 436 | 56295 | 129.1 | 26.5 |
| 104 | 14E, 17R, 21P, 27P, 34H, 35E | 3136 | 498050 | 158.8 | 29.1 |
| 105 | 14E, 17R, 21P, 27P, 34R, 35E | 2859 | 452250 | 158.2 | 14.7 |
| 106 | 14E, 17R, 21P, 27P, 34P, 35E | 182 | 16106 | 88.5 | 17.6 |
| 107 | 14E, 17R, 21P, 27P, 34H, 35E | 958 | 33100 | 34.6 | 11.1 |
| 108 | 14E, 17R, 21P, 27P, 34R, 35E | 1062 | 86080 | 81.1 | 28.5 |
| 109 | 14E, 17R, 21P, 27P, 34P, 35E | 164 | 10388 | 63.2 | 13.3 |
| 110 | 14E, 17R, 21P, 27P, 34P, 35R | 339 | 38260 | 112.9 | 53.6 |
| 111 | 17R, 21P, 27P, 34H | 1237 | 404300 | 326.8 | 18.5 |
| 112 | 17R, 21P, 27P, 34H | 2523 | 706600 | 280.1 | 23.5 |
| 113 | 17R, 21P, 27P, 34H | 1168 | 47040 | 40.3 | 59.4 |
| 114 | 14E, 17R, 21P, 27P, 34P, 37P | 188 | 206 | 1.1 | 0.5 |
| 115 | 14H, 17R, 21P, 27P, 34P, 37P | 125 | 371 | 3.0 | 1.2 |
| 116 | 14H, 17R, 21P, 27P, 31P, 34P | 125 | 9054 | 72.4 | 24.8 |
| 117 | 14E, 17R, 21P, 27P, 34P, 35R | 339 | 15410 | 45.5 | 38.6 |
| 118 | 14E, 17R, 21P, 27P, 34P, 35H | 104 | 5432 | 52.2 | 21.2 |
| 119 | 17R, 21P, 27P, 31P, 34P, 35R | 381 | 52360 | 137.4 | 48.6 |
| 120 | 14S, 17R, 21P, 27P, 34P, 35E | 161 | 139700 | 867.7 | 45.3 |
| 121 | 14E, 17R, 21P, 31P, 34P, 35E | 449 | 33540 | 74.7 | 22.6 |
| 122 | 14D, 17R, 21P, 27P, 34P, 35E | 324 | 31920 | 98.5 | 49.8 |
| 123 | 14D, 17R, 21P, 27P, 34P, 35E | 300 | 18590 | 62.0 | 16.7 |
| 124 | 14E, 17R, 21P, 27P, 34P, 35H | 288 | 21045 | 73.0 | 27.3 |
| 125 | 14E, 17R, 21P, 27P, 34P, 35E, 37P | 152 | 1608 | 10.6 | 0.4 |
| 126 | 14E, 17R, 23P, 34P, 35E | 659 | 86760 | 131.7 | 7.8 |
| 127 | 14E, 17R, 21P, 27P, 34P, 37F | 205 | 23360 | 114.0 | 18.0 |
| 128 | 14E, 17R, 21P, 27P, 35H | 1157 | 26310 | 22.7 | 26.4 |

TABLE 7-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 129 | 14D, 17R, 21P, 27P, 34P, 35R | 504 | 58470 | 116.0 | 151.1 |
| 130 | 14D, 17R, 21P, 27P, 34P, 35R | 930 | 222700 | 239.5 | 280.0 |
| 131 | 14d, 17R, 21P, 27P, 35R | 1692 | 535900 | 316.7 | 306.6 |
| 132 | 14D, 17R, 21P, 27P, 35R | | 30880 | | 28.2 |

TABLE 7a

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 1 | 14D, 17R, 21P, 26P, 35D | 1300 | 135100 | 103.9 | 27.6 |
| 2 | 14D, 17R, 21P, 27P, 35D | 295 | 107798 | 365.7 | 47.5 |
| 3 | 14D, 17R, 22P, 26P, 35D | 1002 | 16748 | 16.7 | 17.3 |
| 6 | 14E, 17R, 21P, 25P, 28P, 29P | 2373 | 51550 | 21.7 | 20.0 |
| 7 | 14E, 17R, 21P, 26P | 1125 | 47250 | 42.0 | 16.5 |
| 15 | 14E, 17R, 21P, 27P | | | | 26.0 |
| 16 | 14E, 17R, 21P, 27P, 35R | 1210 | 55220 | 45.6 | 19.1 |
| 17 | 14E, 17R, 21P, 27P, 34H | 2710 | 97230 | 35.9 | 12.5 |
| 18 | 14E, 17R, 21P, 27P, 35H | 476 | 13000 | 27.3 | 9.2 |
| 19 | 14E, 17R, 21P, 27P | 1022 | 95610 | 93.6 | 36.7 |
| 21 | 17R, 21P, 27P | 1484 | 27935 | 18.8 | 24.4 |
| 22 | 14E, 17R, 21P, 27P, 35E | 2189 | 62460 | 28.5 | 12.3 |
| 23 | 17R, 21P, 27P, 35E | 1120 | 79870 | 71.3 | 25.0 |
| 24 | 17R, 21P, 27P | 3006 | 349700 | 116.3 | 90.0 |
| 25 | 17R, 21P, 27P, 35E | 3485 | 131300 | 37.7 | 56.5 |
| 26 | 17R, 21P, 27P, 35E | 491 | 151700 | 309.2 | 47.5 |
| 27 | 17R, 21P, 27P, 35E | 614 | 90190 | 146.8 | 41.3 |
| 28 | 17R, 21P, 27P, 31P, 35E | 1224 | 54897 | 44.9 | 20.5 |
| 29 | 17R, 21P, 27P, 34P, 35E | 322 | 21560 | 67.0 | 13.9 |
| 30 | 14H, 17R, 21P, 27P, 35E | 3143 | 113600 | 36.1 | 23.6 |
| 31 | 14E, 17R, 21P, 27P, 31P | 619 | 26510 | 42.8 | 16.0 |
| 32 | 14E, 17R, 21P, 27P, 34P | 176 | 5976 | 34.0 | 10.9 |
| 33 | 14E, 17R, 21P, 28P, 35E | 2295 | 28885 | 12.6 | 3.9 |
| 34 | 17R, 21P, 27P, 35K | 1715 | 89170 | 52.0 | 64.4 |
| 35 | 17R, 21P, 27P, 35K | 948 | 61740 | 65.1 | 50.3 |
| 36 | 14E, 17R, 21P, 27P, 34K | 1856 | 60060 | 32.4 | 15.7 |
| 37 | 14E, 17R, 21P, 27P, 29P | 514 | 7354 | 14.3 | 2.3 |
| 38 | 17R, 21P, 27P, 35R | 383 | 38020 | 99.2 | 84.9 |
| 39 | 17R, 21P, 27P, 34R | 1770 | 96440 | 54.5 | 29.0 |
| 40 | 17R, 21P, 27P, 34H | 1498 | 69248 | 46.2 | 31.1 |
| 41 | 17R, 21P, 27P | 1371 | 74090 | 54.0 | 49.9 |
| 42 | 17R, 21P, 27P | 603 | 15340 | 25.4 | 30.7 |
| 43 | 17R, 21P, 27P | 110 | 7601 | 69.1 | 34.7 |
| 44 | −1K, 1R, 17R, 21P, 27P, 35H | 369 | 19650 | 53.3 | 17.7 |
| 45 | −1K, 1R, 17R, 21P, 27P, 35H | 623 | 41790 | 67.1 | 26.8 |
| 46 | −1G, 1R, 17R, 21P, 27P | 330 | 46780 | 141.8 | 48.9 |
| 47 | −1G, 1R, 17R, 21P, 27P, 35H | 203 | 17110 | 84.3 | 44.9 |
| 48 | 17R, 21P, 27P | 558 | 112300 | 201.3 | 69.7 |
| 49 | 17R, 21P, 27P, 31P | 1078 | 51410 | 47.7 | 10.8 |
| 50 | 17R, 21P, 27P, 34P | 69 | 5634 | 81.7 | 36.0 |
| 51 | 14E, 17R, 21P, 27P, 35R | 523 | 61963 | 118.6 | 37.5 |
| 52 | 14D, 17R, 21P, 27P, 35R | 335 | 159464 | 476.7 | 81.6 |
| 53 | 17R, 21P, 27P, 28P, 31P | 84 | 10930 | 130.1 | 103.5 |
| 54 | 17R, 21P, 27P, 29P, 31P | 49 | 8789 | 179.4 | 146.1 |
| 55 | 17R, 21P, 27P, 28P, 34P | 81 | 6254 | 77.2 | 51.8 |
| 56 | 17R, 21P, 27P, 29P, 34P | 40 | 5256 | 131.4 | 42.6 |
| 57 | 17R, 21P, 27P, 31P, 35H | 181 | 24400 | 134.8 | 133.0 |
| 58 | 17R, 21P, 27P, 34P, 35H | 135 | 10340 | 76.6 | 109.4 |
| 59 | 14D, 17R, 21K, 27P, 35D | 659 | 18755 | 28.5 | 4.3 |
| 60 | 17R, 21P, 27P, 35H | 215 | 26310 | 122.4 | 45.2 |
| 61 | 14H, 17R, 21P, 27P, 31P | 842 | 33403 | 39.7 | 66.7 |
| 62 | 14H, 17R, 21P, 27P, 31P | 420 | 17956 | 42.8 | 63.0 |
| 63 | 14R, 17R, 21P, 27P, 31P | 3485 | 123900 | 35.6 | 157.1 |
| 64 | 14R, 17R, 21P, 27P, 31P | 1974 | 127800 | 64.7 | 126.1 |
| 65 | 14R, 17R, 21P, 27P, 34P | 1158 | 107934 | 93.2 | 82.4 |
| 66 | 14H, 17R, 21P, 27P, 35H | 581 | 20780 | 35.8 | 45.5 |
| 67 | 14H, 17R, 21P, 27P, 34P | 172 | 14670 | 85.4 | 51.6 |
| 68 | 14H, 17R, 21P, 27P, 34P | 234 | 28486 | 121.9 | 64.4 |
| 69 | 14H, 17R, 21P, 27P | 450 | 46820 | 104.0 | 65.3 |
| 70 | 14H, 17R, 21P, 27P | 355 | 34240 | 96.5 | 60.8 |

TABLE 7a-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 71 | 14G, 17R, 21P, 27P, 31P | 276 | 44820 | 162.4 | 32.0 |
| 72 | 14A, 17R, 21P, 27P, 31P | 851 | 220700 | 259.3 | 246.6 |
| 73 | 14S, 17R, 21P, 27P, 31P | 283 | 50290 | 177.7 | 51.7 |
| 74 | 14K, 17R, 21P, 27P, 31P | 4894 | 109050 | 22.3 | 101.0 |
| 75 | 14T, 17R, 21P, 27P, 31P | 4025 | 442000 | 109.8 | 91.4 |
| 76 | 17R, 21P, 27P, 34H | 686 | 38935 | 56.8 | 80.0 |
| 77 | 17R, 21P, 27P, 34H | 1496 | 204700 | 136.8 | 118.4 |
| 78 | 17R, 21P, 27P, 34R | 1296 | 90560 | 69.9 | 60.7 |
| 79 | 17R, 21P, 27P, 34R | 1652 | 35510 | 21.5 | 46.1 |
| 80 | 14H, 17R, 21P, 27P, 34H | 1670 | 60400 | 36.2 | 68.1 |
| 81 | 14H, 17R, 21P, 27P, 34H | 1424 | 61150 | 42.9 | 87.2 |
| 82 | 14R, 17R, 21P, 27P | 1643 | 142900 | 87.0 | 139.6 |
| 83 | 14R, 17R, 21P, 27P | 2828 | 140500 | 49.7 | 145.6 |
| 84 | 14H, 17R, 21P, 27P, 34R | 5054 | 476533 | 94.3 | 119.6 |
| 85 | 14H, 17R, 21P, 27P, 34R | 3140 | 146100 | 46.5 | 91.8 |
| 86 | 17R, 21P, 27P, 34H | 2802 | 352205 | 125.7 | 159.3 |
| 87 | 14E, 17R, 21P, 27P, 34H | 2073 | 94463 | 45.6 | 35.6 |
| 88 | 14E, 17R, 21P, 27P, 34R | 2311 | 196100 | 84.9 | 46.5 |
| 89 | 14E, 17R, 21P, 27P, 35R | 2368 | 115459 | 48.8 | 28.0 |
| 90 | 14H, 17R, 21P, 27P | 246 | 18220 | 74.1 | 42.2 |
| 91 | 17R, 21P, 27P, 34H | 386 | 29450 | 76.3 | 100.8 |
| 92 | 14H, 17R, 21P, 27P | 668 | 104500 | 156.4 | 145.0 |
| 93 | 14A, 17R, 21P, 27P, 34H | 1577 | 131200 | 83.2 | 101.0 |
| 94 | 14A, 17R, 21P, 27P, 34P | 397 | 111065 | 280.1 | 46.3 |
| 95 | 17R, 21P, 27P, 34R | 5446 | 388500 | 71.3 | 63.4 |
| 96 | 17R, 21P, 27P, 31P | 529 | 62180 | 117.5 | 79.6 |
| 97 | 17R, 21P, 27P, 34H | 2239 | 159100 | 71.1 | 103.7 |
| 98 | 17R, 21P, 27P, 34P | 137 | 24050 | 175.5 | 74.1 |
| 99 | −1G, 1R, 14H, 17R, 21P, 27P | 2700 | 215515 | 79.8 | 100.4 |
| 100 | −1G, 1R, 14H, 17R, 21P, 27P, 34H | 11235 | 311380 | 27.7 | 65.3 |
| 101 | −1G, 1R, 14A, 17R, 21P, 27P, 34H | 8068 | 491585 | 60.9 | 68.6 |
| 102 | −1G, 1R, 14H, 17R, 21P, 27P, 34P | 674 | 65880 | 97.7 | 36.2 |
| 103 | −1G, 1R, 14A, 17R, 21P, 27P, 34P | 436 | 56295 | 129.1 | 26.5 |
| 104 | 14E, 17R, 21P, 27P, 34H, 35E | 3136 | 498050 | 158.8 | 29.1 |
| 105 | 14E, 17R, 21P, 27P, 34R, 35E | 2859 | 452250 | 158.2 | 14.7 |
| 106 | 14E, 17R, 21P, 27P, 34P, 35E | 182 | 16106 | 88.5 | 17.6 |
| 107 | 14E, 17R, 21P, 27P, 34H, 35E | 958 | 33100 | 34.6 | 11.1 |
| 108 | 14E, 17R, 21P, 27P, 34R, 35E | 1062 | 86080 | 81.1 | 28.5 |
| 109 | 14E, 17R, 21P, 27P, 34P, 35E | 164 | 10388 | 63.2 | 13.3 |
| 110 | 14E, 17R, 21P, 27P, 34P, 35R | 339 | 38260 | 112.9 | 53.6 |
| 111 | 17R, 21P, 27P, 34H | 1237 | 404300 | 326.8 | 18.5 |
| 112 | 17R, 21P, 27P, 34H | 2523 | 706600 | 280.1 | 23.5 |
| 113 | 17R, 21P, 27P, 34H | 1168 | 47040 | 40.3 | 59.4 |
| 116 | 14H, 17R, 21P, 27P, 31P, 34P | 125 | 9054 | 72.4 | 24.8 |
| 117 | 14E, 17R, 21P, 27P, 34P, 35R | 339 | 15410 | 45.5 | 38.6 |
| 118 | 14E, 17R, 21P, 27P, 34P, 35H | 104 | 5432 | 52.2 | 21.2 |
| 119 | 17R, 21P, 27P, 31P, 34P, 35R | 381 | 52360 | 137.4 | 48.6 |
| 120 | 14S, 17R, 21P, 27P, 34P, 35E | 161 | 139700 | 867.7 | 45.3 |
| 121 | 14E, 17R, 21P, 31P, 34P, 35E | 449 | 33540 | 74.7 | 22.6 |
| 122 | 14D, 17R, 21P, 27P, 34P, 35E | 324 | 31920 | 98.5 | 49.8 |
| 123 | 14D, 17R, 21P, 27P, 34P, 35E | 300 | 18590 | 62.0 | 16.7 |
| 124 | 14E, 17R, 21P, 27P, 34P, 35H | 288 | 21045 | 73.0 | 27.3 |
| 125 | 14E, 17R, 21P, 27P, 34P, 35E, 37P | 152 | 1608 | 10.6 | 0.4 |
| 126 | 14E, 17R, 23P, 34P, 35E | 659 | 86760 | 131.7 | 7.8 |
| 127 | 14E, 17R, 21P, 27P, 34P, 37F | 205 | 23360 | 114.0 | 18.0 |
| 128 | 14E, 17R, 21P, 27P, 35H | 1157 | 26310 | 22.7 | 26.4 |
| 129 | 14D, 17R, 21P, 27P, 34P, 35R | 504 | 58470 | 116.0 | 151.1 |
| 130 | 14D, 17R, 21P, 27P, 34P, 35R | 930 | 222700 | 239.5 | 280.0 |
| 131 | 14d, 17R, 21P, 27P, 35R | 1692 | 535900 | 316.7 | 306.6 |
| 132 | 14D, 17R, 21P, 27P, 35R | | 30880 | | 28.2 |

TABLE 7b

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 1 | 14D, 17R, 21P, 26P, 35D | 1300 | 135100 | 103.9 | 27.6 |
| 2 | 14D, 17R, 21P, 27P, 35D | 295 | 107798 | 365.7 | 47.5 |
| 3 | 14D, 17R, 22P, 26P, 35D | 1002 | 16748 | 16.7 | 17.3 |
| 6 | 14E, 17R, 21P, 25P, 28P, 29P | 2373 | 51550 | 21.7 | 20.0 |
| 7 | 14E, 17R, 21P, 26P | 1125 | 47250 | 42.0 | 16.5 |
| 15 | 14E, 17R, 21P, 27P | | | | 26.0 |
| 16 | 14E, 17R, 21P, 27P, 35R | 1210 | 55220 | 45.6 | 19.1 |
| 17 | 14E, 17R, 21P, 27P, 34H | 2710 | 97230 | 35.9 | 12.5 |
| 19 | 14E, 17R, 21P, 27P | 1022 | 95610 | 93.6 | 36.7 |
| 21 | 17R, 21P, 27P | 1484 | 27935 | 18.8 | 24.4 |
| 22 | 14E, 17R, 21P, 27P, 35E | 2189 | 62460 | 28.5 | 12.3 |
| 23 | 17R, 21P, 27P, 35E | 1120 | 79870 | 71.3 | 25.0 |
| 24 | 17R, 21P, 27P | 3006 | 349700 | 116.3 | 90.0 |
| 25 | 17R, 21P, 27P, 35E | 3485 | 131300 | 37.7 | 56.5 |
| 26 | 17R, 21P, 27P, 35E | 491 | 151700 | 309.2 | 47.5 |
| 27 | 17R, 21P, 27P, 35E | 614 | 90190 | 146.8 | 41.3 |
| 28 | 17R, 21P, 27P, 31P, 35E | 1224 | 54897 | 44.9 | 20.5 |
| 29 | 17R, 21P, 27P, 34P, 35E | 322 | 21560 | 67.0 | 13.9 |
| 30 | 14H, 17R, 21P, 27P, 35E | 3143 | 113600 | 36.1 | 23.6 |
| 31 | 14E, 17R, 21P, 27P, 31P | 619 | 26510 | 42.8 | 16.0 |
| 32 | 14E, 17R, 21P, 27P, 34P | 176 | 5976 | 34.0 | 10.9 |
| 34 | 17R, 21P, 27P, 35K | 1715 | 89170 | 52.0 | 64.4 |
| 35 | 17R, 21P, 27P, 35K | 948 | 61740 | 65.1 | 50.3 |
| 36 | 14E, 17R, 21P, 27P, 34K | 1856 | 60060 | 32.4 | 15.7 |
| 38 | 17R, 21P, 27P, 35R | 383 | 38020 | 99.2 | 84.9 |
| 39 | 17R, 21P, 27P, 34R | 1770 | 96440 | 54.5 | 29.0 |
| 40 | 17R, 21P, 27P, 34H | 1498 | 69248 | 46.2 | 31.1 |
| 41 | 17R, 21P, 27P | 1371 | 74090 | 54.0 | 49.9 |
| 42 | 17R, 21P, 27P | 603 | 15340 | 25.4 | 30.7 |
| 43 | 17R, 21P, 27P | 110 | 7601 | 69.1 | 34.7 |
| 44 | −1K, 1R, 17R, 21P, 27P, 35H | 369 | 19650 | 53.3 | 17.7 |
| 45 | −1K, 1R, 17R, 21P, 27P, 35H | 623 | 41790 | 67.1 | 26.8 |
| 46 | −1G, 1R, 17R, 21P, 27P | 330 | 46780 | 141.8 | 48.9 |
| 47 | −1G, 1R, 17R, 21P, 27P, 35H | 203 | 17110 | 84.3 | 44.9 |
| 48 | 17R, 21P, 27P | 558 | 112300 | 201.3 | 69.7 |
| 49 | 17R, 21P, 27P, 31P | 1078 | 51410 | 47.7 | 10.8 |
| 50 | 17R, 21P, 27P, 34P | 69 | 5634 | 81.7 | 36.0 |
| 51 | 14E, 17R, 21P, 27P, 35R | 523 | 61963 | 118.6 | 37.5 |
| 52 | 14D, 17R, 21P, 27P, 35R | 335 | 159464 | 476.7 | 81.6 |
| 53 | 17R, 21P, 27P, 28P, 31P | 84 | 10930 | 130.1 | 103.5 |
| 54 | 17R, 21P, 27P, 29P, 31P | 49 | 8789 | 179.4 | 146.1 |
| 55 | 17R, 21P, 27P, 28P, 34P | 81 | 6254 | 77.2 | 51.8 |
| 56 | 17R, 21P, 27P, 29P, 34P | 40 | 5256 | 131.4 | 42.6 |
| 57 | 17R, 21P, 27P, 31P, 35H | 181 | 24400 | 134.8 | 133.0 |
| 58 | 17R, 21P, 27P, 34P, 35H | 135 | 10340 | 76.6 | 109.4 |
| 60 | 17R, 21P, 27P, 35H | 215 | 26310 | 122.4 | 45.2 |
| 61 | 14H, 17R, 21P, 27P, 31P | 842 | 33403 | 39.7 | 66.7 |
| 62 | 14H, 17R, 21P, 27P, 31P | 420 | 17956 | 42.8 | 63.0 |
| 63 | 14R, 17R, 21P, 27P, 31P | 3485 | 123900 | 35.6 | 157.1 |
| 64 | 14R, 17R, 21P, 27P, 31P | 1974 | 127800 | 64.7 | 126.1 |
| 65 | 14R, 17R, 21P, 27P, 34P | 1158 | 107934 | 93.2 | 82.4 |
| 66 | 14H, 17R, 21P, 27P, 35H | 581 | 20780 | 35.8 | 45.5 |
| 67 | 14H, 17R, 21P, 27P, 34P | 172 | 14670 | 85.4 | 51.6 |
| 68 | 14H, 17R, 21P, 27P, 34P | 234 | 28486 | 121.9 | 64.4 |
| 69 | 14H, 17R, 21P, 27P | 450 | 46820 | 104.0 | 65.3 |
| 70 | 14H, 17R, 21P, 27P | 355 | 34240 | 96.5 | 60.8 |
| 71 | 14G, 17R, 21P, 27P, 31P | 276 | 44820 | 162.4 | 32.0 |
| 72 | 14A, 17R, 21P, 27P, 31P | 851 | 220700 | 259.3 | 246.6 |
| 73 | 14S, 17R, 21P, 27P, 31P | 283 | 50290 | 177.7 | 51.7 |
| 74 | 14K, 17R, 21P, 27P, 31P | 4894 | 109050 | 22.3 | 101.0 |
| 75 | 14T, 17R, 21P, 27P, 31P | 4025 | 442000 | 109.8 | 91.4 |
| 76 | 17R, 21P, 27P, 34H | 686 | 38935 | 56.8 | 80.0 |
| 77 | 17R, 21P, 27P, 34H | 1496 | 204700 | 136.8 | 118.4 |
| 78 | 17R, 21P, 27P, 34R | 1296 | 90560 | 69.9 | 60.7 |
| 79 | 17R, 21P, 27P, 34R | 1652 | 35510 | 21.5 | 46.1 |
| 80 | 14H, 17R, 21P, 27P, 34H | 1670 | 60400 | 36.2 | 68.1 |
| 81 | 14H, 17R, 21P, 27P, 34H | 1424 | 61150 | 42.9 | 87.2 |
| 82 | 14R, 17R, 21P, 27P | 1643 | 142900 | 87.0 | 139.6 |
| 83 | 14R, 17R, 21P, 27P | 2828 | 140500 | 49.7 | 145.6 |
| 84 | 14H, 17R, 21P, 27P, 34R | 5054 | 476533 | 94.3 | 119.6 |
| 85 | 14H, 17R, 21P, 27P, 34R | 3140 | 146100 | 46.5 | 91.8 |
| 86 | 17R, 21P, 27P, 34H | 2802 | 352205 | 125.7 | 159.3 |
| 87 | 14E, 17R, 21P, 27P, 34H | 2073 | 94463 | 45.6 | 35.6 |
| 88 | 14E, 17R, 21P, 27P, 34R | 2311 | 196100 | 84.9 | 46.5 |
| 89 | 14E, 17R, 21P, 27P, 35R | 2368 | 115459 | 48.8 | 28.0 |

TABLE 7b-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 90 | 14H, 17R, 21P, 27P | 246 | 18220 | 74.1 | 42.2 |
| 91 | 17R, 21P, 27P, 34H | 386 | 29450 | 76.3 | 100.8 |
| 92 | 14H, 17R, 21P, 27P | 668 | 104500 | 156.4 | 145.0 |
| 93 | 14A, 17R, 21P, 27P, 34H | 1577 | 131200 | 83.2 | 101.0 |
| 94 | 14A, 17R, 21P, 27P, 34P | 397 | 111065 | 280.1 | 46.3 |
| 95 | 17R, 21P, 27P, 34R | 5446 | 388500 | 71.3 | 63.4 |
| 96 | 17R, 21P, 27P, 31P | 529 | 62180 | 117.5 | 79.6 |
| 97 | 17R, 21P, 27P, 34H | 2239 | 159100 | 71.1 | 103.7 |
| 98 | 17R, 21P, 27P, 34P | 137 | 24050 | 175.5 | 74.1 |
| 99 | -1G, 1R, 14H, 17R, 21P, 27P | 2700 | 215515 | 79.8 | 100.4 |
| 100 | -1G, 1R, 14H, 17R, 21P, 27P, 34H | 11235 | 311380 | 27.7 | 65.3 |
| 101 | -1G, 1R, 14A, 17R, 21P, 27P, 34H | 8068 | 491585 | 60.9 | 68.6 |
| 102 | -1G, 1R, 14H, 17R, 21P, 27P, 34P | 674 | 65880 | 97.7 | 36.2 |
| 103 | -1G, 1R, 14A, 17R, 21P, 27P, 34P | 436 | 56295 | 129.1 | 26.5 |
| 104 | 14E, 17R, 21P, 27P, 34H, 35E | 3136 | 498050 | 158.8 | 29.1 |
| 105 | 14E, 17R, 21P, 27P, 34R, 35E | 2859 | 452250 | 158.2 | 14.7 |
| 106 | 14E, 17R, 21P, 27P, 34P, 35E | 182 | 16106 | 88.5 | 17.6 |
| 107 | 14E, 17R, 21P, 27P, 34H, 35E | 958 | 33100 | 34.6 | 11.1 |
| 108 | 14E, 17R, 21P, 27P, 34R, 35E | 1062 | 86080 | 81.1 | 28.5 |
| 109 | 14E, 17R, 21P, 27P, 34P, 35E | 164 | 10388 | 63.2 | 13.3 |
| 110 | 14E, 17R, 21P, 27P, 34P, 35R | 339 | 38260 | 112.9 | 53.6 |
| 111 | 17R, 21P, 27P, 34H | 1237 | 404300 | 326.8 | 18.5 |
| 112 | 17R, 21P, 27P, 34H | 2523 | 706600 | 280.1 | 23.5 |
| 113 | 17R, 21P, 27P, 34H | 1168 | 47040 | 40.3 | 59.4 |
| 116 | 14H, 17R, 21P, 27P, 31P, 34P | 125 | 9054 | 72.4 | 24.8 |
| 117 | 14E, 17R, 21P, 27P, 34P, 35R | 339 | 15410 | 45.5 | 38.6 |
| 118 | 14E, 17R, 21P, 27P, 34P, 35H | 104 | 5432 | 52.2 | 21.2 |
| 119 | 17R, 21P, 27P, 31P, 34P, 35R | 381 | 52360 | 137.4 | 48.6 |
| 120 | 14S, 17R, 21P, 27P, 34P, 35E | 161 | 139700 | 867.7 | 45.3 |
| 121 | 14E, 17R, 21P, 31P, 34P, 35E | 449 | 33540 | 74.7 | 22.6 |
| 122 | 14D, 17R, 21P, 27P, 34P, 35E | 324 | 31920 | 98.5 | 49.8 |
| 123 | 14D, 17R, 21P, 27P, 34P, 35E | 300 | 18590 | 62.0 | 16.7 |
| 124 | 14E, 17R, 21P, 27P, 34P, 35H | 288 | 21045 | 73.0 | 27.3 |
| 127 | 14E, 17R, 21P, 27P, 34P, 37F | 205 | 23360 | 114.0 | 18.0 |
| 128 | 14E, 17R, 21P, 27P, 35H | 1157 | 26310 | 22.7 | 26.4 |
| 129 | 14D, 17R, 21P, 27P, 34P, 35R | 504 | 58470 | 116.0 | 151.1 |
| 130 | 14D, 17R, 21P, 27P, 34P, 35R | 930 | 222700 | 239.5 | 280.0 |
| 131 | 14d, 17R, 21P, 27P, 35R | 1692 | 535900 | 316.7 | 306.6 |
| 132 | 14D, 17R, 21P, 27P, 35R |  | 30880 |  | 28.2 |

TABLE 7c

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 1 | 14D, 17R, 21P, 26P, 35D | 1300 | 135100 | 103.9 | 27.6 |
| 2 | 14D, 17R, 21P, 27P, 35D | 295 | 107798 | 365.7 | 47.5 |
| 6 | 14E, 17R, 21P, 25P, 28P, 29P | 2373 | 51550 | 21.7 | 20.0 |
| 15 | 14E, 17R, 21P, 27P |  |  |  | 26.0 |
| 19 | 14E, 17R, 21P, 27P | 1022 | 95610 | 93.6 | 36.7 |
| 21 | 17R, 21P, 27P | 1484 | 27935 | 18.8 | 24.4 |
| 22 | 14E, 17R, 21P, 27P, 35E | 2189 | 62460 | 28.5 | 12.3 |
| 23 | 17R, 21P, 27P, 35E | 1120 | 79870 | 71.3 | 25.0 |
| 24 | 17R, 21P, 27P | 3006 | 349700 | 116.3 | 90.0 |
| 25 | 17R, 21P, 27P, 35E | 3485 | 131300 | 37.7 | 56.5 |
| 26 | 17R, 21P, 27P, 35E | 491 | 151700 | 309.2 | 47.5 |
| 27 | 17R, 21P, 27P, 35E | 614 | 90190 | 146.8 | 41.3 |
| 28 | 17R, 21P, 27P, 31P, 35E | 1224 | 54897 | 44.9 | 20.5 |
| 30 | 14H, 17R, 21P, 27P, 35E | 3143 | 113600 | 36.1 | 23.6 |
| 34 | 17R, 21P, 27P, 35K | 1715 | 89170 | 52.0 | 64.4 |
| 35 | 17R, 21P, 27P, 35K | 948 | 61740 | 65.1 | 50.3 |
| 36 | 14E, 17R, 21P, 27P, 34K | 1856 | 60060 | 32.4 | 15.7 |
| 38 | 17R, 21P, 27P, 35R | 383 | 38020 | 99.2 | 84.9 |
| 39 | 17R, 21P, 27P, 34R | 1770 | 96440 | 54.5 | 29.0 |
| 40 | 17R, 21P, 27P, 34H | 1498 | 69248 | 46.2 | 31.1 |
| 41 | 17R, 21P, 27P | 1371 | 74090 | 54.0 | 49.9 |

TABLE 7c-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 42 | 17R, 21P, 27P | 603 | 15340 | 25.4 | 30.7 |
| 43 | 17R, 21P, 27P | 110 | 7601 | 69.1 | 34.7 |
| 45 | −1K, 1R, 17R, 21P, 27P, 35H | 623 | 41790 | 67.1 | 26.8 |
| 46 | −1G, 1R, 17R, 21P, 27P | 330 | 46780 | 141.8 | 48.9 |
| 47 | −1G, 1R, 17R, 21P, 27P, 35H | 203 | 17110 | 84.3 | 44.9 |
| 48 | 17R, 21P, 27P | 558 | 112300 | 201.3 | 69.7 |
| 50 | 17R, 21P, 27P, 34P | 69 | 5634 | 81.7 | 36.0 |
| 51 | 14E, 17R, 21P, 27P, 35R | 523 | 61963 | 118.6 | 37.5 |
| 52 | 14D, 17R, 21P, 27P, 35R | 335 | 159464 | 476.7 | 81.6 |
| 53 | 17R, 21P, 27P, 28P, 31P | 84 | 10930 | 130.1 | 103.5 |
| 54 | 17R, 21P, 27P, 29P, 31P | 49 | 8789 | 179.4 | 146.1 |
| 55 | 17R, 21P, 27P, 28P, 34P | 81 | 6254 | 77.2 | 51.8 |
| 56 | 17R, 21P, 27P, 29P, 34P | 40 | 5256 | 131.4 | 42.6 |
| 57 | 17R, 21P, 27P, 31P, 35H | 181 | 24400 | 134.8 | 133.0 |
| 58 | 17R, 21P, 27P, 34P, 35H | 135 | 10340 | 76.6 | 109.4 |
| 60 | 17R, 21P, 27P, 35H | 215 | 26310 | 122.4 | 45.2 |
| 61 | 14H, 17R, 21P, 27P, 31P | 842 | 33403 | 39.7 | 66.7 |
| 62 | 14H, 17R, 21P, 27P, 31P | 420 | 17956 | 42.8 | 63.0 |
| 63 | 14R, 17R, 21P, 27P, 31P | 3485 | 123900 | 35.6 | 157.1 |
| 64 | 14R, 17R, 21P, 27P, 31P | 1974 | 127800 | 64.7 | 126.1 |
| 65 | 14R, 17R, 21P, 27P, 34P | 1158 | 107934 | 93.2 | 82.4 |
| 66 | 14H, 17R, 21P, 27P, 35H | 581 | 20780 | 35.8 | 45.5 |
| 67 | 14H, 17R, 21P, 27P, 34P | 172 | 14670 | 85.4 | 51.6 |
| 68 | 14H, 17R, 21P, 27P, 34P | 234 | 28486 | 121.9 | 64.4 |
| 69 | 14H, 17R, 21P, 27P | 450 | 46820 | 104.0 | 65.3 |
| 70 | 14H, 17R, 21P, 27P | 355 | 34240 | 96.5 | 60.8 |
| 71 | 14G, 17R, 21P, 27P, 31P | 276 | 44820 | 162.4 | 32.0 |
| 72 | 14A, 17R, 21P, 27P, 31P | 851 | 220700 | 259.3 | 246.6 |
| 73 | 14S, 17R, 21P, 27P, 31P | 283 | 50290 | 177.7 | 51.7 |
| 74 | 14K, 17R, 21P, 27P, 31P | 4894 | 109050 | 22.3 | 101.0 |
| 75 | 14T, 17R, 21P, 27P, 31P | 4025 | 442000 | 109.8 | 91.4 |
| 76 | 17R, 21P, 27P, 34H | 686 | 38935 | 56.8 | 80.0 |
| 77 | 17R, 21P, 27P, 34H | 1496 | 204700 | 136.8 | 118.4 |
| 78 | 17R, 21P, 27P, 34R | 1296 | 90560 | 69.9 | 60.7 |
| 79 | 17R, 21P, 27P, 34R | 1652 | 35510 | 21.5 | 46.1 |
| 80 | 14H, 17R, 21P, 27P, 34H | 1670 | 60400 | 36.2 | 68.1 |
| 81 | 14H, 17R, 21P, 27P, 34H | 1424 | 61150 | 42.9 | 87.2 |
| 82 | 14R, 17R, 21P, 27P | 1643 | 142900 | 87.0 | 139.6 |
| 83 | 14R, 17R, 21P, 27P | 2828 | 140500 | 49.7 | 145.6 |
| 84 | 14H, 17R, 21P, 27P, 34R | 5054 | 476533 | 94.3 | 119.6 |
| 85 | 14H, 17R, 21P, 27P, 34R | 3140 | 146100 | 46.5 | 91.8 |
| 86 | 17R, 21P, 27P, 34H | 2802 | 352205 | 125.7 | 159.3 |
| 87 | 14E, 17R, 21P, 27P, 34H | 2073 | 94463 | 45.6 | 35.6 |
| 88 | 14E, 17R, 21P, 27P, 34R | 2311 | 196100 | 84.9 | 46.5 |
| 89 | 14E, 17R, 21P, 27P, 35R | 2368 | 115459 | 48.8 | 28.0 |
| 90 | 14H, 17R, 21P, 27P | 246 | 18220 | 74.1 | 42.2 |
| 91 | 17R, 21P, 27P, 34H | 386 | 29450 | 76.3 | 100.8 |
| 92 | 14H, 17R, 21P, 27P | 668 | 104500 | 156.4 | 145.0 |
| 93 | 14A, 17R, 21P, 27P, 34H | 1577 | 131200 | 83.2 | 101.0 |
| 94 | 14A, 17R, 21P, 27P, 34P | 397 | 111065 | 280.1 | 46.3 |
| 95 | 17R, 21P, 27P, 34R | 5446 | 388500 | 71.3 | 63.4 |
| 96 | 17R, 21P, 27P, 31P | 529 | 62180 | 117.5 | 79.6 |
| 97 | 17R, 21P, 27P, 34H | 2239 | 159100 | 71.1 | 103.7 |
| 98 | 17R, 21P, 27P, 34P | 137 | 24050 | 175.5 | 74.1 |
| 99 | −1G, 1R, 14H, 17R, 21P, 27P | 2700 | 215515 | 79.8 | 100.4 |
| 100 | −1G, 1R, 14H, 17R, 21P, 27P, 34H | 11235 | 311380 | 27.7 | 65.3 |
| 101 | −1G, 1R, 14A, 17R, 21P, 27P, 34H | 8068 | 491585 | 60.9 | 68.6 |
| 102 | −1G, 1R, 14H, 17R, 21P, 27P, 34P | 674 | 65880 | 97.7 | 36.2 |
| 103 | −1G, 1R, 14A, 17R, 21P, 27P, 34P | 436 | 56295 | 129.1 | 26.5 |
| 104 | 14E, 17R, 21P, 27P, 34H, 35E | 3136 | 498050 | 158.8 | 29.1 |
| 108 | 14E, 17R, 21P, 27P, 34R, 35E | 1062 | 86080 | 81.1 | 28.5 |
| 110 | 14E, 17R, 21P, 27P, 34P, 35R | 339 | 38260 | 112.9 | 53.6 |
| 112 | 17R, 21P, 27P, 34H | 2523 | 706600 | 280.1 | 23.5 |
| 113 | 17R, 21P, 27P, 34H | 1168 | 47040 | 40.3 | 59.4 |
| 116 | 14H, 17R, 21P, 27P, 31P, 34P | 125 | 9054 | 72.4 | 24.8 |
| 117 | 14E, 17R, 21P, 27P, 34P, 35R | 339 | 15410 | 45.5 | 38.6 |
| 118 | 14E, 17R, 21P, 27P, 34P, 35H | 104 | 5432 | 52.2 | 21.2 |
| 119 | 17R, 21P, 27P, 31P, 34P, 35R | 381 | 52360 | 137.4 | 48.6 |
| 120 | 14S, 17R, 21P, 27P, 34P, 35E | 161 | 139700 | 867.7 | 45.3 |
| 121 | 14E, 17R, 21P, 31P, 34P, 35E | 449 | 33540 | 74.7 | 22.6 |
| 122 | 14D, 17R, 21P, 27P, 34P, 35E | 324 | 31920 | 98.5 | 49.8 |

TABLE 7c-continued

| Example no. | Sequence modifications | rAmylin-R bind IC50 (pM) | rCTR bind IC50 (pM) | Ratio rCT/rAmylin binding | Ratio hCT/hAmylin binding |
|---|---|---|---|---|---|
| 124 | 14E, 17R, 21P, 27P, 34P, 35H | 288 | 21045 | 73.0 | 27.3 |
| 128 | 14E, 17R, 21P, 27P, 35H | 1157 | 26310 | 22.7 | 26.4 |
| 129 | 14D, 17R, 21P, 27P, 34P, 35R | 504 | 58470 | 116.0 | 151.1 |
| 130 | 14D, 17R, 21P, 27P, 34P, 35R | 930 | 222700 | 239.5 | 280.0 |
| 131 | 14d, 17R, 21P, 27P, 35R | 1692 | 535900 | 316.7 | 306.6 |
| 132 | 14D, 17R, 21P, 27P, 35R | | 30880 | | 28.2 |

Solubility

The solubility of the polypeptides was tested as described in assay (IV) and results shown in Table 8 and in Table 9.

The compounds disclosed in Table 8 and Table 9 have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 8

| Example no. | Solubility pH 3.0 Concentration (μM) | Solubility pH 4.0 Concentration (μM) | Solubility pH 5.0 Concentration (μM) | Solubility pH 6.0 Concentration (μM) |
|---|---|---|---|---|
| 1 | ≥200 | ≥200 | 172 | ≥200 |
| 2 | ≥200 | ≥200 | ≥200 | ≥200 |
| 3 | | ≥200 | 96 | 141 | 189 |
| 4 | | | | |
| 5 | | | | |
| 6 | | | | |
| 7 | | | | |
| 8 | ≥200 | ≥200 | ≥200 | ≥200 |
| 9 | ≥200 | ≥200 | ≥200 | ≥200 |
| 10 | ≥200 | ≥200 | ≥200 | ≥200 |
| 11 | ≥200 | ≥200 | ≥200 | ≥200 |
| 12 | ≥200 | ≥200 | ≥200 | ≥200 |
| 13 | | | | |
| 14 | ≥200 | ≥200 | ≥200 | ≥200 |
| 15 | ≥200 | ≥200 | ≥200 | ≥200 |
| 16 | ≥200 | ≥200 | ≥200 | ≥200 |
| 17 | ≥200 | ≥200 | ≥200 | ≥200 |
| 18 | ≥200 | ≥200 | ≥200 | ≥200 |
| 19 | ≥200 | ≥200 | ≥200 | ≥200 |
| 20 | ≥200 | ≥200 | ≥200 | ≥200 |
| 21 | ≥200 | ≥200 | ≥200 | ≥200 |
| 22 | ≥200 | ≥200 | ≥200 | 195 |
| 23 | ≥200 | ≥200 | ≥200 | ≥200 |
| 24 | ≥200 | ≥200 | ≥200 | ≥200 |
| 25 | ≥200 | ≥200 | ≥200 | ≥200 |
| 26 | ≥200 | ≥200 | ≥200 | ≥200 |
| 27 | ≥200 | ≥200 | ≥200 | ≥200 |
| 28 | ≥200 | ≥200 | ≥200 | ≥200 |
| 29 | ≥200 | ≥200 | ≥200 | ≥200 |
| 30 | ≥200 | ≥200 | ≥200 | ≥200 |
| 31 | ≥200 | ≥200 | ≥200 | ≥200 |
| 32 | ≥200 | ≥200 | ≥200 | ≥200 |
| 33 | ≥200 | ≥200 | ≥200 | ≥200 |
| 34 | ≥200 | ≥200 | ≥200 | ≥200 |
| 35 | ≥200 | ≥200 | ≥200 | ≥200 |
| 36 | ≥200 | ≥200 | ≥200 | ≥200 |
| 37 | ≥200 | ≥200 | ≥200 | ≥200 |
| 38 | ≥200 | ≥200 | ≥200 | ≥200 |
| 39 | ≥200 | ≥200 | ≥200 | ≥200 |
| 40 | ≥200 | ≥200 | ≥200 | ≥200 |
| 41 | | | | |
| 42 | ≥200 | ≥200 | ≥200 | ≥200 |
| 43 | ≥200 | ≥200 | ≥200 | ≥200 |
| 44 | ≥200 | ≥200 | ≥200 | ≥200 |
| 45 | ≥200 | ≥200 | ≥200 | ≥200 |
| 46 | ≥200 | ≥200 | ≥200 | ≥200 |
| 47 | ≥200 | ≥200 | ≥200 | ≥200 |
| 48 | ≥200 | ≥200 | ≥200 | ≥200 |
| 49 | ≥200 | ≥200 | ≥200 | ≥200 |
| 50 | ≥200 | ≥200 | ≥200 | ≥200 |
| 51 | ≥200 | ≥200 | ≥200 | ≥200 |
| 52 | ≥200 | ≥200 | ≥200 | ≥200 |
| 53 | ≥200 | ≥200 | ≥200 | ≥200 |
| 54 | ≥200 | ≥200 | ≥200 | ≥200 |
| 55 | ≥200 | ≥200 | ≥200 | ≥200 |
| 56 | ≥200 | ≥200 | ≥200 | ≥200 |
| 57 | ≥200 | ≥200 | ≥200 | ≥200 |
| 58 | ≥200 | ≥200 | ≥200 | ≥200 |
| 59 | ≥200 | ≥200 | ≥200 | ≥200 |
| 60 | ≥200 | ≥200 | ≥200 | ≥200 |
| 61 | ≥200 | ≥200 | ≥200 | ≥200 |
| 62 | ≥200 | ≥200 | ≥200 | ≥200 |
| 63 | ≥200 | ≥200 | ≥200 | ≥200 |
| 64 | ≥200 | ≥200 | ≥200 | ≥200 |
| 65 | ≥200 | ≥200 | ≥200 | ≥200 |
| 66 | ≥200 | ≥200 | ≥200 | ≥200 |
| 67 | ≥200 | ≥200 | ≥200 | ≥200 |
| 68 | ≥200 | ≥200 | ≥200 | ≥200 |
| 69 | ≥200 | ≥200 | ≥200 | ≥200 |
| 70 | ≥200 | ≥200 | ≥200 | ≥200 |
| 71 | ≥200 | ≥200 | ≥200 | ≥200 |
| 72 | ≥200 | ≥200 | ≥200 | ≥200 |
| 73 | ≥200 | ≥200 | ≥200 | ≥200 |
| 74 | ≥200 | ≥200 | ≥200 | ≥200 |
| 75 | ≥200 | ≥200 | ≥200 | ≥200 |
| 76 | ≥200 | ≥200 | ≥200 | ≥200 |
| 77 | ≥200 | ≥200 | ≥200 | ≥200 |
| 78 | ≥200 | ≥200 | ≥200 | ≥200 |
| 79 | ≥200 | ≥200 | ≥200 | ≥200 |
| 80 | ≥200 | ≥200 | ≥200 | ≥200 |
| 81 | ≥200 | ≥200 | ≥200 | ≥200 |
| 82 | ≥200 | ≥200 | ≥200 | ≥200 |
| 83 | ≥200 | ≥200 | ≥200 | ≥200 |
| 84 | ≥200 | ≥200 | ≥200 | ≥200 |
| 85 | ≥200 | ≥200 | ≥200 | ≥200 |
| 86 | ≥200 | ≥200 | ≥200 | ≥200 |
| 87 | ≥200 | ≥200 | ≥200 | 156 |
| 88 | ≥200 | ≥200 | ≥200 | ≥200 |
| 89 | ≥200 | ≥200 | ≥200 | ≥200 |
| 90 | ≥200 | ≥200 | ≥200 | ≥200 |
| 91 | ≥200 | ≥200 | ≥200 | ≥200 |
| 92 | ≥200 | ≥200 | ≥200 | ≥200 |
| 93 | ≥200 | ≥200 | ≥200 | ≥200 |
| 94 | ≥200 | ≥200 | ≥200 | ≥200 |
| 95 | ≥200 | ≥200 | ≥200 | ≥200 |
| 96 | ≥200 | ≥200 | ≥200 | ≥200 |
| 97 | ≥200 | ≥200 | ≥200 | ≥200 |
| 98 | ≥200 | ≥200 | | |
| 99 | ≥200 | ≥200 | ≥200 | ≥200 |
| 100 | ≥200 | ≥200 | | ≥200 |
| 101 | ≥200 | ≥200 | ≥200 | ≥200 |

TABLE 8-continued

| Example no. | Solubility pH 3.0 Concentration (μM) | Solubility pH 4.0 Concentration (μM) | Solubility pH 5.0 Concentration (μM) | Solubility pH 6.0 Concentration (μM) |
|---|---|---|---|---|
| 102 | ≥200 | 197 | 195 | ≥200 |
| 103 | ≥200 | ≥200 | ≥200 | ≥200 |
| 104 | ≥200 | ≥200 | ≥200 | ≥200 |
| 105 | ≥200 | ≥200 | ≥200 | ≥200 |
| 106 | ≥200 | ≥200 | ≥200 | ≥200 |
| 107 | ≥200 | ≥200 | ≥200 | ≥200 |
| 108 | ≥200 | ≥200 | ≥200 | ≥200 |
| 109 | ≥200 | ≥200 | ≥200 | ≥200 |
| 110 | ≥200 | ≥200 | ≥200 | ≥200 |
| 111 | ≥200 | ≥200 | ≥200 | ≥200 |
| 112 | ≥200 | ≥200 | ≥200 | ≥200 |
| 113 | ≥200 | ≥200 | ≥200 | ≥200 |
| 114 | ≥200 | ≥200 | ≥200 | ≥200 |
| 115 | ≥200 | ≥200 | ≥200 | ≥200 |
| 116 | ≥200 | ≥200 | ≥200 | ≥200 |
| 117 | ≥200 | ≥200 | ≥200 | ≥200 |
| 118 | ≥200 | ≥200 | ≥200 | ≥200 |
| 119 | 174 | ≥200 | ≥200 | ≥200 |
| 120 | ≥200 | ≥200 | ≥200 | ≥200 |
| 121 | | ≥200 | ≥200 | ≥200 |
| 122 | ≥200 | ≥200 | ≥200 | ≥200 |
| 123 | ≥200 | ≥200 | ≥200 | ≥200 |
| 124 | ≥200 | ≥200 | ≥200 | ≥200 |
| 125 | ≥200 | ≥200 | ≥200 | ≥200 |
| 126 | | 7 | 0 | 64 |
| 127 | | | | |
| 128 | ≥200 | ≥200 | ≥200 | ≥200 |
| 129 | ≥200 | ≥200 | ≥200 | ≥200 |
| 130 | ≥200 | ≥200 | ≥200 | ≥200 |
| 131 | | | | |
| 132 | ≥200 | ≥200 | ≥200 | ≥200 |

TABLE 8a

| Example no. | Solubility pH 3.0 Concentration (μM) | Solubility pH 4.0 Concentration (μM) | Solubility pH 5.0 Concentration (μM) | Solubility pH 6.0 Concentration (μM) |
|---|---|---|---|---|
| 126 | | 7 | 0 | 64 |

TABLE 9

| Example no. | Solubility pH 6.5 Concentration (μM) | Solubility pH 7.0 Concentration (μM) | Solubility pH 7.5 Concentration (μM) | Solubility pH 8.0 Concentration (μM) |
|---|---|---|---|---|
| 1 | ≥200 | ≥200 | ≥200 | ≥200 |
| 2 | 190 | ≥200 | ≥200 | ≥200 |
| 3 | ≥200 | 195 | ≥200 | ≥200 |
| 4 | | | | |
| 5 | | | | |
| 6 | | | | |
| 7 | | | | |
| 8 | ≥200 | ≥200 | ≥200 | ≥200 |
| 9 | ≥200 | ≥200 | ≥200 | ≥200 |
| 10 | ≥200 | ≥200 | ≥200 | ≥200 |
| 11 | ≥200 | ≥200 | ≥200 | ≥200 |
| 12 | ≥200 | ≥200 | ≥200 | ≥200 |
| 13 | | | | |
| 14 | ≥200 | ≥200 | ≥200 | ≥200 |
| 15 | ≥200 | ≥200 | ≥200 | ≥200 |
| 16 | ≥200 | ≥200 | ≥200 | ≥200 |
| 17 | ≥200 | ≥200 | 159 | 154 |
| 18 | ≥200 | 177 | 122 | 111 |
| 19 | ≥200 | ≥200 | ≥200 | ≥200 |

TABLE 9-continued

| Example no. | Solubility pH 6.5 Concentration (μM) | Solubility pH 7.0 Concentration (μM) | Solubility pH 7.5 Concentration (μM) | Solubility pH 8.0 Concentration (μM) |
|---|---|---|---|---|
| 20 | ≥200 | ≥200 | ≥200 | ≥200 |
| 21 | ≥200 | ≥200 | ≥200 | 195 |
| 22 | ≥200 | ≥200 | ≥200 | ≥200 |
| 23 | ≥200 | ≥200 | ≥200 | ≥200 |
| 24 | ≥200 | ≥200 | ≥200 | ≥200 |
| 25 | ≥200 | ≥200 | ≥200 | ≥200 |
| 26 | ≥200 | ≥200 | ≥200 | ≥200 |
| 27 | ≥200 | ≥200 | ≥200 | ≥200 |
| 28 | ≥200 | ≥200 | ≥200 | ≥200 |
| 29 | ≥200 | ≥200 | ≥200 | ≥200 |
| 30 | ≥200 | ≥200 | ≥200 | ≥200 |
| 31 | ≥200 | ≥200 | ≥200 | ≥200 |
| 32 | ≥200 | ≥200 | ≥200 | ≥200 |
| 33 | ≥200 | ≥200 | ≥200 | ≥200 |
| 34 | ≥200 | ≥200 | ≥200 | ≥200 |
| 35 | ≥200 | ≥200 | ≥200 | ≥200 |
| 36 | ≥200 | ≥200 | ≥200 | ≥200 |
| 37 | ≥200 | ≥200 | ≥200 | ≥200 |
| 38 | ≥200 | ≥200 | ≥200 | ≥200 |
| 39 | ≥200 | ≥200 | ≥200 | ≥200 |
| 40 | ≥200 | ≥200 | ≥200 | ≥200 |
| 41 | | | | |
| 42 | ≥200 | 163 | 84 | 65 |
| 43 | ≥200 | ≥200 | ≥200 | ≥200 |
| 44 | ≥200 | ≥200 | 87 | 39 |
| 45 | ≥200 | ≥200 | ≥200 | 110 |
| 46 | ≥200 | 186 | 106 | 145 |
| 47 | ≥200 | ≥200 | 50 | 68 |
| 48 | ≥200 | ≥200 | ≥200 | ≥200 |
| 49 | ≥200 | ≥200 | ≥200 | ≥200 |
| 50 | ≥200 | ≥200 | ≥200 | ≥200 |
| 51 | ≥200 | ≥200 | 183 | 109 |
| 52 | ≥200 | 155 | 106 | 110 |
| 53 | ≥200 | ≥200 | ≥200 | ≥200 |
| 54 | ≥200 | ≥200 | ≥200 | ≥200 |
| 55 | ≥200 | ≥200 | ≥200 | 119 |
| 56 | ≥200 | ≥200 | ≥200 | 147 |
| 57 | ≥200 | ≥200 | 142 | 101 |
| 58 | ≥200 | ≥200 | 96 | 48 |
| 59 | ≥200 | ≥200 | ≥200 | ≥200 |
| 60 | ≥200 | ≥200 | 186 | 98 |
| 61 | ≥200 | ≥200 | ≥200 | 153 |
| 62 | ≥200 | ≥200 | ≥200 | 189 |
| 63 | ≥200 | ≥200 | ≥200 | ≥200 |
| 64 | ≥200 | ≥200 | ≥200 | ≥200 |
| 65 | ≥200 | ≥200 | ≥200 | ≥200 |
| 66 | ≥200 | ≥200 | 131 | 52 |
| 67 | ≥200 | ≥200 | ≥200 | 178 |
| 68 | ≥200 | ≥200 | 193 | 138.5 |
| 69 | ≥200 | ≥200 | ≥200 | ≥200 |
| 70 | ≥200 | ≥200 | ≥200 | ≥200 |
| 71 | ≥200 | ≥200 | ≥200 | ≥200 |
| 72 | ≥200 | ≥200 | ≥200 | 194 |
| 73 | ≥200 | ≥200 | ≥200 | 172 |
| 74 | ≥200 | ≥200 | ≥200 | ≥200 |
| 75 | ≥200 | ≥200 | 193 | 150 |
| 76 | ≥200 | ≥200 | ≥200 | 139.5 |
| 77 | ≥200 | ≥200 | 147 | 59 |
| 78 | ≥200 | ≥200 | ≥200 | ≥200 |
| 79 | ≥200 | ≥200 | ≥200 | ≥200 |
| 80 | ≥200 | ≥200 | ≥200 | ≥200 |
| 81 | ≥200 | ≥200 | ≥200 | ≥200 |
| 82 | ≥200 | ≥200 | ≥200 | ≥200 |
| 83 | ≥200 | ≥200 | ≥200 | ≥200 |
| 84 | ≥200 | ≥200 | ≥200 | ≥200 |
| 85 | ≥200 | ≥200 | ≥200 | ≥200 |
| 86 | ≥200 | ≥200 | 157 | ≥200 |
| 87 | 144 | 146 | ≥200 | ≥200 |
| 88 | ≥200 | 162 | 113 | 108 |
| 89 | ≥200 | 172 | 161.5 | 149 |
| 90 | ≥200 | ≥200 | ≥200 | ≥200 |
| 91 | ≥200 | ≥200 | ≥200 | ≥200 |
| 92 | ≥200 | ≥200 | ≥200 | ≥200 |
| 93 | ≥200 | ≥200 | ≥200 | ≥200 |

TABLE 9-continued

| Example no. | Solubility pH 6.5 Concentration (μM) | Solubility pH 7.0 Concentration (μM) | Solubility pH 7.5 Concentration (μM) | Solubility pH 8.0 Concentration (μM) |
|---|---|---|---|---|
| 94 | ≥200 | ≥200 | ≥200 | ≥200 |
| 95 | ≥200 | ≥200 | ≥200 | ≥200 |
| 96 | ≥200 | ≥200 | ≥200 | ≥200 |
| 97 | ≥200 | ≥200 | 88 | 43 |
| 98 | ≥200 | ≥200 | ≥200 | 176 |
| 99 | ≥200 | 154 | 94 | 120 |
| 100 | ≥200 | 109 | 26 | 31 |
| 101 | ≥200 | 182 | 69 | 83 |
| 102 | ≥200 | 154 | 88 | 113 |
| 103 | ≥200 | ≥200 | 141 | 194 |
| 104 | ≥200 | ≥200 | ≥200 | ≥200 |
| 105 | ≥200 | ≥200 | ≥200 | ≥200 |
| 106 | ≥200 | ≥200 | ≥200 | ≥200 |
| 107 | ≥200 | ≥200 | ≥200 | ≥200 |
| 108 | ≥200 | ≥200 | ≥200 | ≥200 |
| 109 | ≥200 | ≥200 | ≥200 | ≥200 |
| 110 | ≥200 | ≥200 | 184 | 166 |
| 111 | ≥200 | ≥200 | ≥200 | 165 |
| 112 | ≥200 | ≥200 | ≥200 | ≥200 |
| 113 | ≥200 | | 154 | 96 |
| 114 | ≥200 | ≥200 | ≥200 | ≥200 |
| 115 | ≥200 | ≥200 | ≥200 | ≥200 |
| 116 | ≥200 | ≥200 | ≥200 | 180 |
| 117 | ≥200 | ≥200 | ≥200 | 147 |
| 118 | ≥200 | ≥200 | ≥200 | ≥200 |
| 119 | 174 | 182 | 112 | 32 |
| 120 | ≥200 | ≥200 | ≥200 | ≥200 |
| 121 | ≥200 | ≥200 | ≥200 | ≥200 |
| 122 | ≥200 | ≥200 | ≥200 | ≥200 |
| 123 | ≥200 | ≥200 | ≥200 | ≥200 |
| 124 | ≥200 | ≥200 | ≥200 | 165 |
| 125 | ≥200 | ≥200 | ≥200 | ≥200 |
| 126 | 131 | 198 | ≥200 | |
| 127 | | | | |
| 128 | ≥200 | ≥200 | ≥200 | ≥200 |
| 129 | ≥200 | ≥200 | 187 | 102 |
| 130 | ≥200 | ≥200 | ≥200 | ≥200 |
| 131 | | | | |
| 132 | ≥200 | ≥200 | ≥200 | ≥200 |

TABLE 9a

| Example no. | Solubility pH 6.5 Concentration (μM) | Solubility pH 7.0 Concentration (μM) | Solubility pH 7.5 Concentration (μM) | Solubility pH 8.0 Concentration (μM) |
|---|---|---|---|---|
| 58 | ≥200 | ≥200 | 96 | 48 |
| 66 | ≥200 | ≥200 | 131 | 52 |
| 77 | ≥200 | ≥200 | 147 | 59 |
| 97 | ≥200 | ≥200 | 88 | 43 |
| 100 | ≥200 | 109 | 26 | 31 |
| 119 | 174 | 182 | 112 | 32 |

Physical Stability

The polypeptides were tested for physical stability in the ThT assay (Assay (III)) and the data is presented in Table 10.

The compounds disclosed in Table 10 have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 10

| Example no. | Sequence modifications | pI | ThT pH 4.0 lag time (h) | ThT pH 4.0 recovery (%) |
|---|---|---|---|---|
| 1 | 14D, 17R, 21P, 26P, 35D | 4.8 | 0 | 0 |
| 2 | 14D, 17R, 21P, 27P, 35D | 4.8 | 10 | 1 |
| 3 | 14D, 17R, 22P, 26P, 35D | 4.8 | | |
| 4 | 14E, 17R, 21P, 25P, 28P, 29P, 37P | 8.6 | | |
| 5 | 14E, 17R, 21P, 26P, 37P | 8.6 | | |
| 6 | 14E, 17R, 21P, 25P, 28P, 29P | 8.2 | | |
| 7 | 14E, 17R, 21P, 26P | 8.2 | | |
| 8 | 14E, 17R, 21P, 27P, 37P | 8.6 | 45 | 94 |
| 9 | 14E, 17R, 21P, 27P | 8.2 | 19 | 51 |
| 10 | 14D, 17R, 21P, 27P, 37P | 8.6 | 45 | 91 |
| 11 | 14E, 17R, 21P, 27P, 35D, 37P | 5.9 | 45 | 89 |
| 12 | 14E, 17R, 21P, 27P, 37P | 7.2 | 45 | 83 |
| 13 | 14E, 17R, 21P, 27P, 37P | 5.8 | 45 | 75 |
| 14 | 14E, 17R, 21P, 27P, 37P | 5.9 | 45 | 88 |
| 15 | 14E, 17R, 21P, 27P | 5.9 | 45 | 20 |
| 16 | 14E, 17R, 21P, 27P, 35R | 10.1 | 45 | 89 |
| 17 | 14E, 17R, 21P, 27P, 34H | 8.4 | 45 | 92 |
| 18 | 14E, 17R, 21P, 27P, 35H | 8.4 | 45 | 100 |
| 19 | 14E, 17R, 21P, 27P | 8.2 | 9 | 0 |
| 20 | 14E, 17R, 21P, 27P, 37P | 8.6 | 45 | 88 |
| 21 | 17R, 21P, 27P | 10.1 | 24 | 75 |
| 22 | 14E, 17R, 21P, 27P, 35E | 5.9 | 45 | 89 |
| 23 | 17R, 21P, 27P, 35E | 8.2 | 3 | 0 |
| 24 | 17R, 21P, 27P | 10.1 | 34 | 0 |
| 25 | 17R, 21P, 27P, 35E | 7.2 | 2 | 0 |
| 26 | 17R, 21P, 27P, 35E | 7.2 | 12 | 0 |
| 27 | 17R, 21P, 27P, 35E | 7.2 | 28 | 3 |
| 28 | 17R, 21P, 27P, 31P, 35E | 8.2 | 40 | 74 |
| 29 | 17R, 21P, 27P, 34P, 35E | 8.2 | 16 | 19 |
| 30 | 14H, 17R, 21P, 27P, 35E | 8.4 | 16 | 59 |

TABLE 10-continued

| Example no. | Sequence modifications | pI | ThT pH 4.0 lag time (h) | ThT pH 4.0 recovery (%) |
|---|---|---|---|---|
| 31 | 14E, 17R, 21P, 27P, 31P | 8.2 | 45 | 85 |
| 32 | 14E, 17R, 21P, 27P, 34P | 8.2 | 45 | 78 |
| 33 | 14E, 17R, 21P, 28P, 35E | 5.9 | 9 | 0 |
| 34 | 17R, 21P, 27P, 35K | 10.6 | 35 | 99 |
| 35 | 17R, 21P, 27P, 35K | 10.2 | 45 | 100 |
| 36 | 14E, 17R, 21P, 27P, 34K | 9.9 | 45 | 100 |
| 37 | 14E, 17R, 21P, 27P, 29P | 8.2 | 15 | 98 |
| 38 | 17R, 21P, 27P, 35R | 11.4 | 27 | 67 |
| 39 | 17R, 21P, 27P, 34R | 11.7 | 45 | 100 |
| 40 | 17R, 21P, 27P, 34H | 10.1 | 26 | 92 |
| 41 | 17R, 21P, 27P | 8.8 | 7 | 4 |
| 42 | 17R, 21P, 27P | 11.5 | 2 | 9 |
| 43 | 17R, 21P, 27P | 11.5 | 4 | 9 |
| 44 | −1K, 1R, 17R, 21P, 27P, 35H | 11.4 | 45 | 81 |
| 45 | −1K, 1R, 17R, 21P, 27P, 35H | 11.4 | 45 | 87 |
| 46 | −1G, 1R, 17R, 21P, 27P | 11.4 | 24 | 0 |
| 47 | −1G, 1R, 17R, 21P, 27P, 35H | 11.4 | 45 | 84 |
| 48 | 17R, 21P, 27P | 8.8 | 25 | 1 |
| 49 | 17R, 21P, 27P, 31P | 8.8 | 8 | 5 |
| 50 | 17R, 21P, 27P, 34P | 8.8 | 2 | 8 |
| 51 | 14E, 17R, 21P, 27P, 35R | 8.8 | 7 | 91 |
| 52 | 14D, 17R, 21P, 27P, 35R | 7.2 | 41 | 98 |
| 53 | 17R, 21P, 27P, 28P, 31P | 8.8 | 18 | 0 |
| 54 | 17R, 21P, 27P, 29P, 31P | 8.8 | 15 | 0 |
| 55 | 17R, 21P, 27P, 28P, 34P | 8.8 | 24 | 0 |
| 56 | 17R, 21P, 27P, 29P, 34P | 8.8 | 22 | 0 |
| 57 | 17R, 21P, 27P, 31P, 35H | 8.8 | 45 | 86 |
| 58 | 17R, 21P, 27P, 34P, 35H | 8.8 | 38 | 86 |
| 59 | 14D, 17R, 21K, 27P, 35D | 5.8 | 23 | 5 |
| 60 | 17R, 21P, 27P, 35H | 8.8 | 45 | 92 |
| 61 | 14H, 17R, 21P, 27P, 31P | 8.8 | 45 | 92 |
| 62 | 14H, 17R, 21P, 27P, 31P | 8.8 | 45 | 92 |
| 63 | 14R, 17R, 21P, 27P, 31P | 11.4 | 45 | 92 |
| 64 | 14R, 17R, 21P, 27P, 31P | 11.4 | 45 | 85 |
| 65 | 14R, 17R, 21P, 27P, 34P | 11.4 | 45 | 86 |
| 66 | 14H, 17R, 21P, 27P, 35H | 8.8 | 45 | 88 |
| 67 | 14H, 17R, 21P, 27P, 34P | 8.8 | 26 | 58 |
| 68 | 14H, 17R, 21P, 27P, 34P | 8.8 | 24 | 73 |
| 69 | 14H, 17R, 21P, 27P | 8.8 | 22 | 13 |
| 70 | 14H, 17R, 21P, 27P | 8.8 | 7 | 0 |
| 71 | 14G, 17R, 21P, 27P, 31P | 8.8 | 11 | 0 |
| 72 | 14A, 17R, 21P, 27P, 31P | 8.8 | 13 | 0 |
| 73 | 14S, 17R, 21P, 27P, 31P | 8.8 | 12 | 1 |
| 74 | 14K, 17R, 21P, 27P, 31P | 10.2 | 45 | 87 |
| 75 | 14T, 17R, 21P, 27P, 31P | 8.8 | 25 | 12 |
| 76 | 17R, 21P, 27P, 34H | 8.8 | 22 | 31 |
| 77 | 17R, 21P, 27P, 34H | 8.8 | 21 | 64 |
| 78 | 17R, 21P, 27P, 34R | 11.4 | 13 | 15 |
| 79 | 17R, 21P, 27P, 34R | 11.4 | 21 | 81 |
| 80 | 14H, 17R, 21P, 27P, 34H | 8.8 | 28 | 90 |
| 81 | 14H, 17R, 21P, 27P, 34H | 8.8 | 45 | 93 |
| 82 | 14R, 17R, 21P, 27P | 11.4 | 12 | 63 |
| 83 | 14R, 17R, 21P, 27P | 11.4 | 12 | 79 |
| 84 | 14H, 17R, 21P, 27P, 34R | 11.4 | 45 | 100 |
| 85 | 14H, 17R, 21P, 27P, 34R | 11.4 | 45 | 100 |
| 86 | 17R, 21P, 27P, 34H | 7.4 | 32 | 60 |
| 87 | 14E, 17R, 21P, 27P, 34H | 6.6 | 45 | 74 |
| 88 | 14E, 17R, 21P, 27P, 34R | 7.2 | 45 | 100 |
| 89 | 14E, 17R, 21P, 27P, 35R | 7.2 | 43 | 86 |
| 90 | 14H, 17R, 21P, 27P | 11.5 | 10 | 42 |
| 91 | 17R, 21P, 27P, 34H | 11.5 | 4 | 88 |
| 92 | 14H, 17R, 21P, 27P | 7.4 | 8 | 0 |
| 93 | 14A, 17R, 21P, 27P, 34H | 8.8 | 16 | 89 |
| 94 | 14A, 17R, 21P, 27P, 34P | 8.8 | 10 | 0 |
| 95 | 17R, 21P, 27P, 34R | 11.4 | 37 | 76 |
| 96 | 17R, 21P, 27P, 31P | 8.8 | 12 | 32 |
| 97 | 17R, 21P, 27P, 34H | 8.8 | 30 | 77 |
| 98 | 17R, 21P, 27P, 34P | 8.8 | 4 | 0 |
| 99 | −1G, 1R, 14H, 17R, 21P, 27P | 11.4 | 17 | 29 |
| 100 | −1G, 1R, 14H, 17R, 21P, 27P, 34H | 11.4 | 33 | 77 |
| 101 | −1G, 1R, 14A, 17R, 21P, 27P, 34H | 11.4 | 45 | 85 |
| 102 | −1G, 1R, 14H, 17R, 21P, 27P, 34P | 11.4 | 26 | 77 |
| 103 | −1G, 1R, 14A, 17R, 21P, 27P, 34P | 11.4 | 45 | 82 |
| 104 | 14E, 17R, 21P, 27P, 34H, 35E | 5.7 | 45 | 97 |
| 105 | 14E, 17R, 21P, 27P, 34R, 35E | 5.9 | 45 | 90 |
| 106 | 14E, 17R, 21P, 27P, 34P, 35E | 4.9 | 33 | 56 |

TABLE 10-continued

| Example no. | Sequence modifications | pI | ThT pH 4.0 lag time (h) | ThT pH 4.0 recovery (%) |
|---|---|---|---|---|
| 107 | 14E, 17R, 21P, 27P, 34H, 35E | 6.6 | 45 | 88 |
| 108 | 14E, 17R, 21P, 27P, 34R, 35E | 7.2 | 45 | 87 |
| 109 | 14E, 17R, 21P, 27P, 34P, 35E | 5.9 | 35 | 43 |
| 110 | 14E, 17R, 21P, 27P, 34P, 35R | 7.2 | 17 | 3 |
| 111 | 17R, 21P, 27P, 34H | 8.8 | 10 | 79 |
| 112 | 17R, 21P, 27P, 34H | 8.8 | 30 | 86 |
| 113 | 17R, 21P, 27P, 34H | 8.8 | 45 | 89 |
| 114 | 14E, 17R, 21P, 27P, 34P, 37P | 7.2 | 45 | 100 |
| 115 | 14H, 17R, 21P, 27P, 34P, 37P | 10.4 | 45 | 100 |
| 116 | 14H, 17R, 21P, 27P, 31P, 34P | 8.8 | 45 | 88 |
| 117 | 14E, 17R, 21P, 27P, 34P, 35R | 8.8 | 45 | 78 |
| 118 | 14E, 17R, 21P, 27P, 34P, 35H | 7.4 | 45 | 100 |
| 119 | 17R, 21P, 27P, 31P, 34P, 35R | 8.2 | 10 | 93 |
| 120 | 14S, 17R, 21P, 27P, 34P, 35E | 5.8 | 14 | 1 |
| 121 | 14E, 17R, 21P, 31P, 34P, 35E | 4.9 | 3 | 0 |
| 122 | 14D, 17R, 21P, 27P, 34P, 35E | 4.8 | 45 | 100 |
| 123 | 14D, 17R, 21P, 27P, 34P, 35E | 5.9 | 30 | 11 |
| 124 | 14E, 17R, 21P, 27P, 34P, 35H | 6.6 | 45 | 90 |
| 125 | 14E, 17R, 21P, 27P, 34P, 35E, 37P | 4.9 | 23 | 24 |
| 126 | 14E, 17R, 23P, 34P, 35E | 4.9 | 0 | 0 |
| 127 | 14E, 17R, 21P, 27P, 34P, 37F | 5.8 | 25 | 0 |
| 128 | 14E, 17R, 21P, 27P, 35H | 7.4 | 41 | 100 |
| 129 | 14D, 17R, 21P, 27P, 34P, 35R | 8.8 | 45 | 100 |
| 130 | 14D, 17R, 21P, 27P, 34P, 35R | 7.2 | 45 | 98 |
| 131 | 14d, 17R, 21P, 27P, 35R | 7.2 | | |
| 132 | 14D, 17R, 21P, 27P, 35R | 13.0 | | |

Food Intake

The polypeptides were tested with respect to their effect in the Food Intake assay (Assay (I)) and the results shown in Table 11.

The compounds disclosed in Table 11 have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 11

| Example # | Food intake reduction 0-24 h 30 nmol/kg (%) | Food intake reduction 24-48 h 30 nmol/kg (%) | Food intake reduction 0-24 h 3 nmol/kg (%) | Food intake reduction 24-48 h 3 nmol/kg (%) |
|---|---|---|---|---|
| 2 | 72 | 62 | 39 | 10 |
| 24 | 22 | 1 | | |
| 28 | 49 | 38 | | |
| 30 | 41 | 17 | | |
| 32 | 62 | 7 | | |
| 34 | 37 | 25 | | |
| 35 | 51 | 15 | | |
| 38 | 47 | 0 | | |
| 39 | 36 | 8 | | |
| 40 | 51 | 26 | | |
| 45 | 27 | 3 | | |
| 47 | 51 | 0 | | |
| 51 | 52 | 30 | | |
| 52 | 63 | 50 | 25 | 15 |
| 57 | 62 | 16 | | |
| 60 | 69 | 21 | | |
| 61 | 53 | 18 | | |
| 62 | 62 | 18 | | |
| 64 | 4 | 3 | | |
| 65 | 10 | 0 | | |
| 67 | 47 | 0 | | |
| 68 | 33 | 0 | | |
| 76 | 31 | 2 | | |
| 77 | 40 | 16 | | |
| 80 | 46 | 9 | | |
| 81 | 40 | 3 | | |
| 84 | 10 | 0 | | |
| 85 | 30 | 6 | | |
| 86 | 48 | 26 | | |
| 87 | 29 | 20 | | |
| 88 | 31 | 15 | | |
| 89 | 46 | 37 | | |
| 95 | 22 | 0 | | |
| 104 | 31 | 28 | | |
| 106 | 63 | 69 | | |
| 108 | 29 | 0 | | |
| 109 | 89 | 91 | 57 | 50 |
| 110 | 68 | 31 | | |
| 111 | 17 | 0 | | |
| 113 | 48 | 2 | | |
| 117 | 61 | 4 | | |
| 118 | 77 | 30 | 43 | 1 |
| 120 | 66 | 61 | | |
| 122 | | | 50 | 50 |
| 124 | 73 | 38 | | |
| 130 | 80 | 27 | | |
| 131 | 17 | 14 | | |

Pharmacokinetic Profile (PK)

PK miniping i.v. T½ (hours)

The half life of the polypeptides of the present invention were tested in mini pigs as described in Assay (IX) and the data are given in Table 12.

The compounds disclosed in Table 13 have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as UPAC nomenclature may be found in Table 14.

TABLE 12

| Example # | PK minipig i.v. T½ (hours) |
|---|---|
| 52 | 99.5 |
| 76 | 76 |
| 77 | 81 |
| 85 | 85 |
| 86 | 103.9 |
| 106 | 49 |
| 109 | 95 |

PK rat i.v. T½ (hours)

The half life of the polypeptides of the present invention were tested in rats as described in Assay (X) and the data are given in Table 13.

The compounds disclosed in Table 13 have a hAmylinR IC50 value of less than 1200 pM. Details of the albumin binding moiety, linker and acylation sites have been removed from these Tables. For full structural information please consult the entry with a corresponding compound number in Table 2. Further details regarding the compounds, such as IUPAC nomenclature may be found in Table 14.

TABLE 13

| Example # | PK rat i.v. T½ (hours) |
|---|---|
| 65 | 3 |
| 67 | 7 |
| 110 | 14 |
| 109 | 17 |
| 77 | 18 |
| 86 | 20 |
| 52 | 21 |
| 89 | 23 |
| 2 | 28 |
| 106 | 37 |

Compounds

Some of the preferred compounds of the present invention are presented in Table 14.

TABLE 14

| Compound (Example) No. | IUPAC Nomenclature |
|---|---|
| 1 | $N^{\epsilon 1}$-[(4S)-4-carboxy-4-[[(4S)-4-carboxy-4-(19-carboxynonadecanoylamino)butanoyl]amino]butanoyl]-[Asp14,Arg17,Pro21,Pro26,Asp35]-h-amylin |
| 2 | $N^{\epsilon 1}$-[(4S)-4-carboxy-4-[[(4S)-4-carboxy-4-(19-carboxynonadecanoylamino)butanoyl]amino]butanoyl]-[Asp14,Arg17,Pro21,Pro27,Asp35]-h-amylin |
| 3 | $N^{\epsilon 1}$-[(4S)-4-carboxy-4-[[(4S)-4-carboxy-4-(19-carboxynonadecanoylamino)butanoyl]amino]butanoyl]-[Asp14,Arg17,Pro22,Pro26,Asp35]-h-amylin |
| 4 | $N^{\alpha 1}$-[(4S)-4-carboxy-4-(19-carboxynonadecanoylamino)butanoyl]-[Glu14,Arg17,Pro21,Pro25,Pro28,Pro29,Pro37]-h-amylin |
| 5 | $N^{\alpha 1}$-[(4S)-4-carboxy-4-(19-carboxynonadecanoylamino)butanoyl]-[Glu14,Arg17,Pro21,Pro26,Pro37]-h-amylin |
| 6 | $N^{\alpha 1}$-[(4S)-4-carboxy-4-(19-carboxynonadecanoylamino)butanoyl]-[Glu14,Arg17,Pro21,Pro25,Pro28,Pro29]-h-amylin |
| 7 | $N^{\alpha 1}$-[(4S)-4-carboxy-4-(19-carboxynonadecanoylamino)butanoyl]-[Glu14,Arg17,Pro21,Pro26]-h-amylin |
| 8 | $N^{\alpha 1}$-[(4S)-4-carboxy-4-(19-carboxynonadecanoylamino)butanoyl]-[Glu14,Arg17,Pro21,Pro27,Pro37]-h-amylin |
| 9 | $N^{\alpha 1}$-[(4S)-4-carboxy-4-(19-carboxynonadecanoylamino)butanoyl]-[Glu14,Arg17,Pro21,Pro27]-h-amylin |
| 10 | $N^{\alpha 1}$-[(4S)-4-carboxy-4-(19-carboxynonadecanoylamino)butanoyl]-[Asp14,Arg17,Pro21,Pro27,Pro37]-h-amylin |
| 11 | $N^{\alpha 1}$-[(4S)-4-carboxy-4-(19-carboxynonadecanoylamino)butanoyl]-[Glu14,Arg17,Pro21,Pro27,Asp35,Pro37]-h-amylin |
| 12 | $N^{\epsilon 1}$-[(4S)--4-carboxy-4-(19-carboxynonadecanoylamino)butanoyl]-[Glu14,Arg17,Pro21,Pro27,Pro37]-h-amylin |
| 13 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro37]-h-amylin |
| 14 | $N^{\alpha 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro37]-h-amylin |
| 15 | $N^{\alpha 1} N^{\alpha 1}$-[(4S)-4-carboxy-4-[[(4S)-4-carboxy-4-(19-carboxynonadecanoylamino)butanoyl]amino]butanoyl]-[Glu14,Arg17,Pro21,Pro27]-h-amylin |
| 16 | $N^{\alpha 1}$-[(4S)-4-carboxy-4-(19-carboxynonadecanoylamino)butanoyl]-[Glu14,Arg17,Pro21,Pro27,Arg35]-h-amylin |
| 17 | $N^{\alpha 1}$-[(4S)-4-carboxy-4-(19-carboxynonadecanoylamino)butanoyl]-[Glu14,Arg17,Pro21,Pro27,His34]-h-amylin |
| 18 | $N^{\alpha 1}$-[(4S)-4-carboxy-4-(19-carboxynonadecanoylamino)butanoyl]-[Glu14,Arg17,Pro21,Pro27,His35]-h-amylin |
| 19 | $N^{\alpha 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Glu14,Arg17,Pro21,Pro27]-h-amylin |
| 20 | $N^{\alpha 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Glu14,Arg17,Pro21,Pro27,Pro37]-h-amylin |
| 21 | $N^{\alpha 1}$-[(4S)-4-carboxy-4-(19-carboxynonadecanoylamino)butanoyl]-[Arg17,Pro21,Pro27]-h-amylin |

TABLE 14-continued

| Compound (Example) No. | IUPAC Nomenclature |
|---|---|
| 22 | $N^{\alpha 1}N^{\alpha 1}$-[(4S)-4-carboxy-4-(19-carboxynonadecanoylamino)butanoyl]-[Glu14,Arg17,Pro21,Pro27,Glu35]-h-amylin |
| 23 | $N^{\alpha 1}$-[(4S)-4-carboxy-4-(19-carboxynonadecanoylamino)butanoyl]-[Arg17,Pro21,Pro27,Glu35]-h-amylin |
| 24 | $N^{\alpha 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27]-h-amylin |
| 25 | $N^{\epsilon 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27,Glu35]-h-amylin |
| 26 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Glu35]-h-amylin |
| 27 | $N^{\epsilon 1}$-[(4S)-4-carboxy-4-(19-carboxynonadecanoylamino)butanoyl]-[Arg17,Pro21,Pro27,Glu35]-h-amylin |
| 28 | $N^{\alpha 1}$-[(4S)-4-carboxy-4-(19-carboxynonadecanoylamino)butanoyl]-[Arg17,Pro21,Pro27,Pro31,Glu35]-h-amylin |
| 29 | $N^{\alpha 1}$-[(4S)-4-carboxy-4-(19-carboxynonadecanoylamino)butanoyl]-[Arg17,Pro21,Pro27,Pro34,Glu35]-h-amylin |
| 30 | $N^{\alpha 1}$-[(4S)-4-carboxy-4-(19-carboxynonadecanoylamino)butanoyl]-[His14,Arg17,Pro21,Pro27,Glu35]-h-amylin |
| 31 | $N^{\alpha 1}$-[(4S)-4-carboxy-4-(19-carboxynonadecanoylamino)butanoyl]-[Glu14,Arg17,Pro21,Pro27,Pro31]-h-amylin |
| 32 | $N^{\alpha 1}$-[(4S)-4-carboxy-4-(19-carboxynonadecanoylamino)butanoyl]-[Glu14,Arg17,Pro21,Pro27,Pro34]-h-amylin |
| 33 | $N^{\alpha 1}$-[(4S)-4-carboxy-4-(19-carboxynonadecanoylamino)butanoyl]-[Glu14,Arg17,Pro21,Pro28,Glu35]-h-amylin |
| 34 | $N^{\alpha 1}$-[(4S)-4-carboxy-4-(19-carboxynonadecanoylamino)butanoyl]-[Arg17,Pro21,Pro27,Lys35]-h-amylin |
| 35 | $N^{\epsilon 1}$-[(4S)-4-carboxy-4-(19-carboxynonadecanoylamino)butanoyl]-[Arg17,Pro21,Pro27,Lys35]-h-amylin |
| 36 | N{Alpha-1}-[(4S)-4-carboxy-4-(19-carboxynonadecanoylamino)butanoyl]-[Glu14,Arg17,Pro21,Pro27,Lys34]-h-amylin |
| 37 | $N^{\alpha 1}$-[(4S)-4-carboxy-4-(19-carboxynonadecanoylamino)butanoyl]-[Glu14,Arg17,Pro21,Pro27,Pro29]-h-amylin |
| 38 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Arg35]-h-amylin |
| 39 | $N^{\alpha 1}$-[(4S)-4-carboxy-4-(19-carboxynonadecanoylamino)butanoyl]-[Arg17,Pro21,Pro27,Arg34]-h-amylin |
| 40 | $N^{\alpha 1}$-[(4S)-4-carboxy-4-(19-carboxynonadecanoylamino)butanoyl]-[Arg17,Pro21,Pro27,His34]-h-amylin |
| 41 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27]-h-amylin |
| 42 | $N^{\epsilon 1}$-19-carboxynonadecanoyl-[Arg17,Pro21,Pro27]-h-amylin |
| 43 | $N^{\epsilon 1}$-[2-[2-[2-(19-carboxynonadecanoylamino)ethoxy]ethoxy]acetyl]-[Arg17,Pro21,Pro27]-h-amylin |
| 44 | $N^{\epsilon}$-[(4S)-4-carboxy-4-(19-carboxynonadecanoylamino)butanoyl]Lys[Arg1,Arg17,Pro21,Pro27,His35]-h-amylin |
| 45 | $N^{\epsilon}$-[2-[2-[2-[[(4S)-4-carboxy-4-(19-carboxynonadecanoylamino)butanoyl]amino]ethoxy]ethoxy]acetyl]Lys[Arg1,Arg17,Pro21,Pro27,His35]-h-amylin |
| 46 | $N^{-1}$-[(4S)-4-carboxy-4-(19-carboxynonadecanoylamino)butanoyl]-Gly[Arg1,Arg17,Pro21,Pro27]-h-amylin |
| 47 | $N^{-1}$-[(4S)-4-carboxy-4-(19-carboxynonadecanoylamino)butanoyl]-Gly[Arg1,Arg17,Pro21,Pro27,His35]-h-amylin |
| 48 | $N^{\epsilon 1}$-[(4S)-4-carboxy-4-(19-carboxynonadecanoylamino)butanoyl]-[Arg17,Pro21,Pro27]-h-amylin |
| 49 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro31]-h-amylin |
| 50 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro34]-h-amylin |
| 51 | $N^{\epsilon 1}$-[(4S)-4-carboxy-4-(19-carboxynonadecanoylamino)butanoyl]-[Glu14,Arg17,Pro21,Pro27,Arg35]-h-amylin |
| 52 | $N^{\epsilon 1}$-[(4S)-4-carboxy-4-[[(4S)-4-carboxy-4-(19-carboxynonadecanoylamino)butanoyl]amino]butanoyl]-[Asp14,Arg17,Pro21,Pro27,Arg35]-h-amylin |
| 53 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro28,Pro31]-h-amylin |

TABLE 14-continued

| Compound (Example) No. | IUPAC Nomenclature |
|---|---|
| 54 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro29,Pro31]-h-amylin |
| 55 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro28,Pro34]-h-amylin |
| 56 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro29,Pro34]-h-amylin |
| 57 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro31,His35]-h-amylin |
| 58 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Pro34,His35]-h-amylin |
| 59 | $N^{\epsilon 21}$-[(4S)-4-carboxy-4-[[(4S)-4-carboxy-4-(19-carboxynonadecanoylamino)butanoyl]amino]butanoyl]-[Asp14,Arg17,Lys21,Pro27,Asp35]-h-amylin |
| 60 | $N^{\epsilon 1}$-[(4S)-4-carboxy-4-(19-carboxynonadecanoylamino)butanoyl]-[Arg17,Pro21,Pro27,His35]-h-amylin |
| 61 | $N^{\epsilon 1}$-[2-[2-[2-[[(4S)-4-carboxy-4-(19-carboxynonadecanoylamino)butanoyl]amino]ethoxy]ethoxy]acetyl]-[His14,Arg17,Pro21,Pro27,Pro31]-h-amylin |
| 62 | $N^{\epsilon 1}$-[(4S)-4-carboxy-4-(19-carboxynonadecanoylamino)butanoyl]-[His14,Arg17,Pro21,Pro27,Pro31]-h-amylin |
| 63 | $N^{\epsilon 1}$-[(4S)-4-carboxy-4-(19-carboxynonadecanoylamino)butanoyl]-[Arg14,Arg17,Pro21,Pro27,Pro31]-h-amylin |
| 64 | $N^{\epsilon 1}$-[2-[2-[2-[[(4S)-4-carboxy-4-(19-carboxynonadecanoylamino)butanoyl]amino]ethoxy]ethoxy]acetyl]-[Arg14,Arg17,Pro21,Pro27,Pro31]-h-amylin |
| 65 | $N^{\epsilon 1}$-[(4S)-4-carboxy-4-(19-carboxynonadecanoylamino)butanoyl]-[Arg14,Arg17,Pro21,Pro27,Pro34]-h-amylin |
| 66 | $N^{\epsilon 1}$-[(4S)-4-carboxy-4-(19-carboxynonadecanoylamino)butanoyl]-[His14,Arg17,Pro21,Pro27,His35]-h-amylin |
| 67 | $N^{\epsilon 1}N^{\epsilon 1}$-[(4S)-4-carboxy-4-(19-carboxynonadecanoylamino)butanoyl]-[His14,Arg17,Pro21,Pro27,Pro34]-h-amylin |
| 68 | $N^{\epsilon 1}$-[2-[2-[2-[[(4S)-4-carboxy-4-(19-carboxynonadecanoylamino)butanoyl]amino]ethoxy]ethoxy]acetyl]-[His14,Arg17,Pro21,Pro27,Pro34]-h-amylin |
| 69 | $N^{\epsilon 1}$-[2-[2-[2-[[(4S)-4-carboxy-4-(19-carboxynonadecanoylamino)butanoyl]amino]ethoxy]ethoxy]acetyl]-[His14,Arg17,Pro21,Pro27]-h-amylin |
| 70 | $N^{\epsilon 1}$-[(4S)-4-carboxy-4-(19-carboxynonadecanoylamino)butanoyl]-[His14,Arg17,Pro21,Pro27]-h-amylin |
| 71 | $N^{\epsilon 1}$-[2-[2-[2-[[(4S)-4-carboxy-4-(19-carboxynonadecanoylamino)butanoyl]amino]ethoxy]ethoxy]acetyl]-[Gly14,Arg17,Pro21,Pro27,Pro31]-h-amylin |
| 72 | $N^{\epsilon 1}$-[2-[2-[2-[[(4S)-4-carboxy-4-(19-carboxynonadecanoylamino)butanoyl]amino]ethoxy]ethoxy]acetyl]-[Ala14,Arg17,Pro21,Pro27,Pro31]-h-amylin |
| 73 | $N^{\epsilon 1}$-[2-[2-[2-[[(4S)-4-carboxy-4-(19-carboxynonadecanoylamino)butanoyl]amino]ethoxy]ethoxy]acetyl]-[Ser14,Arg17,Pro21,Pro27,Pro31]-h-amylin |
| 74 | $N^{\epsilon 1}$-[2-[2-[2-[[(4S)-4-carboxy-4-(19-carboxynonadecanoylamino)butanoyl]amino]ethoxy]ethoxy]acetyl]-[Lys14,Arg17,Pro21,Pro27,Pro31]-h-amylin |
| 75 | $N^{\epsilon 1}$-[2-[2-[2-[[(4S)-4-carboxy-4-(19-carboxynonadecanoylamino)butanoyl]amino]ethoxy]ethoxy]acetyl]-[Thr14,Arg17,Pro21,Pro27,Pro31]-h-amylin |
| 76 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,His34]-h-amylin |
| 77 | $N^{\epsilon 1}$-[(4S)-4-carboxy-4-(19-carboxynonadecanoylamino)butanoyl]-[Arg17,Pro21,Pro27,His34]-h-amylin |
| 78 | $N^{\epsilon 1}$-[2-[2-[2-[[(4S)-4-carboxy-4-(19-carboxynonadecanoylamino)butanoyl]amino]ethoxy]ethoxy]acetyl]-[Arg17,Pro21,Pro27,Arg34]-h-amylin |
| 79 | $N^{\epsilon 1}$-[(4S)-4-carboxy-4-(19-carboxynonadecanoylamino)butanoyl]-[Arg17,Pro21,Pro27,Arg34]-h-amylin |
| 80 | $N^{\epsilon 1}$-[2-[2-[2-[[(4S)-4-carboxy-4-(19-carboxynonadecanoylamino)butanoyl]amino]ethoxy]ethoxy]acetyl]-[His14,Arg17,Pro21,Pro27,His34]-h-amylin |
| 81 | $N^{\epsilon 1}$-[(4S)-4-carboxy-4-(19-carboxynonadecanoylamino)butanoyl]-[His14,Arg17,Pro21,Pro27,His34]-h-amylin |

TABLE 14-continued

| Compound (Example) No. | IUPAC Nomenclature |
|---|---|
| 82 | $N^{\epsilon 1}$-[2-[2-[2-[[(4S)-4-carboxy-4-(19-carboxynonadecanoylamino)butanoyl]amino]ethoxy]ethoxy]acetyl]-[Arg14,Arg17,Pro21,Pro27]-h-amylin |
| 83 | $N^{\epsilon 1}$-[(4S)-4-carboxy-4-(19-carboxynonadecanoylamino)butanoyl]-[Arg14,Arg17,Pro21,Pro27]-h-amylin |
| 84 | $N^{\epsilon 1}$-[2-[2-[2-[[(4S)-4-carboxy-4-(19-carboxynonadecanoylamino)butanoyl]amino]ethoxy]ethoxy]acetyl]-[His14,Arg17,Pro21,Pro27,Arg34]-h-amylin |
| 85 | $N^{\epsilon 1}$-[(4S)-4-carboxy-4-(19-carboxynonadecanoylamino)butanoyl]-[His14,Arg17,Pro21,Pro27,Arg34]-h-amylin |
| 86 | $N^{\epsilon 1}$-[(4S)-4-carboxy-4-[[(4S)-4-carboxy-4-(19-carboxynonadecanoylamino)butanoyl]amino]butanoyl]-[Arg17,Pro21,Pro27,His34]-h-amylin |
| 87 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,His34]-h-amylin |
| 88 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Arg34]-h-amylin |
| 89 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Arg35]-h-amylin |
| 90 | $N^{\epsilon 1}$-[2-[2-[2-(19-carboxynonadecanoylamino)ethoxy]ethoxy]acetyl]-[His14,Arg17,Pro21,Pro27]-h-amylin |
| 91 | $N^{\epsilon 1}$-[2-[2-[2-(19-carboxynonadecanoylamino)ethoxy]ethoxy]acetyl]-[Arg17,Pro21,Pro27,His34]-h-amylin |
| 92 | $N^{\epsilon 1}$-[(4S)-4-carboxy-4-[[(4S)-4-carboxy-4-(19-carboxynonadecanoylamino)butanoyl]amino]butanoyl]-[His14,Arg17,Pro21,Pro27]-h-amylin |
| 93 | $N^{\epsilon 1}$-[(4S)-4-carboxy-4-(19-carboxynonadecanoylamino)butanoyl]-[Ala14,Arg17,Pro21,Pro27,His34]-h-amylin |
| 94 | $N^{\epsilon 1}$-[(4S)-4-carboxy-4-(19-carboxynonadecanoylamino)butanoyl]-[Ala14,Arg17,Pro21,Pro27,Pro34]-h-amylin |
| 95 | $N^{\epsilon 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27,Arg34]-h-amylin |
| 96 | $N^{\epsilon 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27,Pro31]-h-amylin |
| 97 | $N^{\epsilon 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27,His34]-h-amylin |
| 98 | $N^{\epsilon 1}$-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]-[Arg17,Pro21,Pro27,Pro34]-h-amylin |
| 99 | N{-1}-[(4S)-4-carboxy-4-(19-carboxynonadecanoylamino)butanoyl]-Gly[Arg1,His14,Arg17,Pro21,Pro27]-h-amylin |
| 100 | $N^{-1}$-[(4S)-4-carboxy-4-(19-carboxynonadecanoylamino)butanoyl]-Gly[Arg1,His14,Arg17,Pro21,Pro27,His34]-h-amylin |
| 101 | $N^{-1}$-[(4S)-4-carboxy-4-(19-carboxynonadecanoylamino)butanoyl]-Gly[Arg1,Ala14,Arg17,Pro21,Pro27,His34]-h-amylin |
| 102 | $N^{-1}$-[(4S)-4-carboxy-4-(19-carboxynonadecanoylamino)butanoyl]-Gly[Arg1,His14,Arg17,Pro21,Pro27,Pro34]-h-amylin |
| 103 | $N^{-1}$-[(4S)-4-carboxy-4-(19-carboxynonadecanoylamino)butanoyl]-Gly[Arg1,Ala14,Arg17,Pro21,Pro27,Pro34]-h-amylin |
| 104 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,His34,Glu35]-h-amylin |
| 105 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Arg34,Glu35]-h-amylin |
| 106 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro34,Glu35]-h-amylin |
| 107 | $N^{\epsilon 1}$-[(4S)-4-carboxy-4-(19-carboxynonadecanoylamino)butanoyl]-[Glu14,Arg17,Pro21,Pro27,His34,Glu35]-h-amylin |
| 108 | $N^{\epsilon 1}$-[(4S)-4-carboxy-4-(19-carboxynonadecanoylamino)butanoyl]-[Glu14,Arg17,Pro21,Pro27,Arg34,Glu35]-h-amylin |
| 109 | $N^{\epsilon 1}$-[(4S)-4-carboxy-4-(19-carboxynonadecanoylamino)butanoyl]-[Glu14,Arg17,Pro21,Pro27,Pro34,Glu35]-h-amylin |
| 110 | $N^{\epsilon 1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro34,Arg35]-h-amylin |
| 111 | $N^{\epsilon 1}$-[(4S)-4-carboxy-4-(15-carboxypentadecanoylamino)butanoyl]-[Arg17,Pro21,Pro27,His34]-h-amylin |

TABLE 14-continued

| Compound (Example) No. | IUPAC Nomenclature |
|---|---|
| 112 | N$^{e1}$-[(4S)-4-carboxy-4-(13-carboxytridecanoylamino)butanoyl]-[Arg17,Pro21,Pro27,His34]-h-amylin |
| 113 | N$^{e1}$-[(4S)-4-carboxy-4-(17-carboxyheptadecanoylamino)butanoyl]-[Arg17,Pro21,Pro27,His34]-h-amylin |
| 114 | N$^{e1}$-[(4S)-4-carboxy-4-(19-carboxynonadecanoylamino)butanoyl]-[Glu14,Arg17,Pro21,Pro27,Pro34,Pro37]-h-amylin |
| 115 | N$^{e1}$-[(4S)-4-carboxy-4-(19-carboxynonadecanoylamino)butanoyl]-[His14,Arg17,Pro21,Pro27,Pro34,Pro37]-h-amylin |
| 116 | N$^{e1}$-[(4S)-4-carboxy-4-(19-carboxynonadecanoylamino)butanoyl]-[His14,Arg17,Pro21,Pro27,Pro31,Pro34]-h-amylin |
| 117 | N$^{e1}$-[(4S)-4-carboxy-4-(19-carboxynonadecanoylamino)butanoyl]-[Glu14,Arg17,Pro21,Pro27,Pro34,Arg35]-h-amylin |
| 118 | N$^{e1}$-[(4S)-4-carboxy-4-(19-carboxynonadecanoylamino)butanoyl]-[Glu14,Arg17,Pro21,Pro27,Pro34,His35]-h-amylin |
| 119 | N$^{e1}$-[(4S)-4-carboxy-4-[[(4S)-4-carboxy-4-(19-carboxynonadecanoylamino)butanoyl]amino]butanoyl]-[Arg17,Pro21,Pro27,Pro31,Pro34,Arg35]-h-amylin |
| 120 | N$^{e1}$-[(4S)-4-carboxy-4-[[(4S)-4-carboxy-4-(19-carboxynonadecanoylamino)butanoyl]amino]butanoyl]-[Ser14,Arg17,Pro21,Pro27,Pro34,Glu35]-h-amylin |
| 121 | N$^{e1}$-[(4S)-4-carboxy-4-[[(4S)-4-carboxy-4-(19-carboxynonadecanoylamino)butanoyl]amino]butanoyl]-[Glu14,Arg17,Pro21,Pro31,Pro34,Glu35]-h-amylin |
| 122 | N$^{e1}$-[(4S)-4-carboxy-4-[[(4S)-4-carboxy-4-(19-carboxynonadecanoylamino)butanoyl]amino]butanoyl]-[Asp14,Arg17,Pro21,Pro27,Pro34,Glu35]-h-amylin |
| 123 | N$^{e1}$-[(4S)-4-carboxy-4-(19-carboxynonadecanoylamino)butanoyl]-[Asp14,Arg17,Pro21,Pro27,Pro34,Glu35]-h-amylin |
| 124 | N$^{e1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro34,His35]-h-amylin |
| 125 | N$^{e1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro34,Glu35,Pro37]-h-amylin |
| 126 | N$^{e1}$-[(4S)-4-carboxy-4-[[(4S)-4-carboxy-4-(19-carboxynonadecanoylamino)butanoyl]amino]butanoyl]-[Glu14,Arg17,Pro23,Pro34,Glu35]-h-amylin |
| 127 | N$^{e1}$-[(4S)-4-carboxy-4-[[(4S)-4-carboxy-4-(19-carboxynonadecanoylamino)butanoyl]amino]butanoyl]-[Glu14,Arg17,Pro21,Pro27,Pro34,Phe37]-h-amylin |
| 128 | N$^{e1}$-[(4S)-4-carboxy-4-(19-carboxynonadecanoylamino)butanoyl]-[Glu14,Arg17,Pro21,Pro27,His35]-h-amylin |
| 129 | N$^{e1}$-[(4S)-4-carboxy-4-(19-carboxynonadecanoylamino)butanoyl]-[Asp14,Arg17,Pro21,Pro27,Pro34,Arg35]-h-amylin |
| 130 | N$^{e1}$-[(4S)-4-carboxy-4-[[(4S)-4-carboxy-4-(19-carboxynonadecanoylamino)butanoyl]amino]butanoyl]-[Asp14,Arg17,Pro21,Pro27,Pro34,Arg35]-h-amylin |
| 131 | N$^{e1}$-[(4S)-4-carboxy-4-[[(4S)-4-carboxy-4-(19-carboxynonadecanoylamino)butanoyl]amino]butanoyl]-[D-Asp14,Arg17,Pro21,Pro27,Arg35]-h-amylin |
| 132 | [Asp14,Arg17,Pro21,Pro27,Arg35]-h-amylin |

TABLE 15

| Compound (Example) No | Dose (nmol/kg) | Food intake red (%)* 0-24 h | Food intake red (%)* 24-48 h | Plasma calcium red (%)** 0-12 h |
|---|---|---|---|---|
| Pramlintide | 1000 | 25 | 0 | 28 |
| Salmon calcitonin | 3 | nt | nt | 35 |
| Salmon calcitonin | 30 | 87 | 19 | 39 |
| 2 | 3 | 39 | 10 | nt |
| 2 | 30 | 72 | 62 | nt |
| 2 | 100 | nt | nt | 9 |
| 51 | 30 | 52 | 30 | 10 |
| 52 | 3 | 25 | 15 | nt |
| 52 | 30 | 63 | 50 | 12 |
| 86 | 30 | 48 | 26 | 0 |
| 89 | 30 | 46 | 37 | 7 |
| 106 | 30 | 63 | 69 | 6 |
| 109 | 3 | 57 | 50 | 7 |
| 109 | 30 | 89 | 91 | 27 |
| 110 | 30 | 68 | 31 | 8 |
| 117 | 30 | 61 | 4 | 9 |
| 118 | 3 | 43 | 1 | nt |
| 118 | 30 | 77 | 30 | 26 |
| 124 | 10 | nt | nt | 3 |
| 124 | 30 | 73 | 38 | 11 |

*Reduction of food intake in rats after single s.c. administration compared to vehicle treated rats
**Maximal plasma calcium reduction in rats after single s.c. administration compared to vehicle treated rats
nt: not tested

Observations

Without wishing to be bound by theory, for some of the preferred embodiments of the present invention, a substitution at amino acid residue 17 and preferably also a substitution at amino acid residue 27 and/or a substitution at amino acid residue 35 can provide an increased potency for the polypeptides of the present invention. Other substitutions can provide further improvements in potency for the polypeptides of the present invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

SEQUENCE LISTING

SEQ ID NO: 1
Lys-Cys-Asn-Thr-Ala-Thr-Cys-Ala-Thr-Gln-Arg-Leu-

Ala-Asn-Phe-Leu-Val-His-Ser-Ser-Asn-Asn-Phe-Gly-

Ala-Ile-Leu-Ser-Ser-Thr-Asn-Val-Gly-Ser-Asn-Thr-

Tyr

SEQ ID NO: 2
Ala-Cys-Asn-Thr-Ala-Thr-Cys-Ala-Thr-Gln-Arg-Leu-

Ala-Asp-Phe-Leu-Arg-His-Ser-Ser-Pro-Asn-Phe-Gly-

-continued

SEQUENCE LISTING

Pro-Pro-Pro-Pro-Pro-Thr-Pro-Val-Gly-Pro-Asp-Thr-

Pro

SEQ ID NO: 3
Lys-Cys-Asn-Thr-Ala-Thr-Cys-Ala-Thr-Gln-Arg-Leu-

Ala-Asp-Phe-Leu-Arg-His-Ser-Ser-Pro-Asn-Phe-Gly-

Ala-Ile-Pro-Ser-Ser-Thr-Asn-Val-Gly-Ser-Asn-Thr-

Tyr

SEQ ID NO: 4
Lys-Cys-Asn-Thr-Ala-Thr-Cys-Ala-Thr-Gln-Arg-Leu-

Ala-Asp-Phe-Leu-Arg-His-Ser-Ser-Pro-Asn-Phe-Gly-

Ala-Ile-Pro-Ser-Ser-Thr-Asn-Val-Gly-Ser-Arg-Thr-

Tyr

SEQ ID NO: 5
$Xaa_1$-Cys-Asn-Thr-Ala-Thr-Cys-Ala-Thr-Gln-Arg-

Leu-Ala-$Xaa_{14}$-Phe-Leu-$Xaa_{17}$-His-Ser-Ser-$Xaa_{21}$-

Asn-Phe-Gly-$Xaa_{25}$-$Xaa_{26}$-$Xaa_{27}$-$Xaa_{28}$-$Xaa_{29}$-

Thr-$Xaa_{31}$-Val-Gly-$Xaa_{34}$-$Xaa_{35}$-Thr-$Xaa_{37}$ wherein $Xaa_1$ is independently selected from Ala, Cys, Glu, Gly, His, Arg, Ser and Lys;

$Xaa_{14}$ is independently selected from Asp, Glu, His, Asn, Arg, Gly, Ala, Ser, Lys, Thr and Cys;

$Xaa_{17}$ is independently selected from Arg and Val;

$Xaa_{21}$ is Pro;

$Xaa_{25}$ is independently selected from Pro and Ala;

$Xaa_{26}$ is independently selected from Pro and Ile;

$Xaa_{27}$ is independently selected from Pro and Leu;

$Xaa_{28}$ is independently selected from Pro and Ser;

$Xaa_{29}$ is independently selected from Pro and Ser;

$Xaa_{31}$ is independently selected from Pro and Asn;

$Xaa_{34}$ is independently selected from Pro, His, Lys, Arg and Ser $Xaa_{35}$ is independently selected from Asp, Arg, Glu, Lys, His and Asn;

$Xaa_{37}$ is independently selected from Pro and Tyr;

and where the C-terminal may optionally be derivatized.

The invention claimed is:

1. A polypeptide comprising the analogue of SEQ ID No: 1 having about a 10-fold or greater selectivity for binding to the human amylin receptor over binding to the human calcitonin receptor and wherein:

(a) said analogue of SEQ ID No: 1 comprises a proline residue at position 21;

wherein the amino acid sequence numbering of the analogue corresponds to the amino acid numbering sequence of SEQ ID No: 1; and (b) wherein the polypeptide has at least one substituent attached to at least one of its amino acid residues.

2. The polypeptide according to claim 1 wherein the polypeptide has an $IC_{50}$ in a human amylin receptor binding assay of about 1200 pM or less.

3. The polypeptide according to claim 1 wherein the analogue comprises a proline or leucine residue at position 27.

4. The polypeptide according to claim 1 wherein the analogue comprises a proline residue at position 27.

5. The polypeptide according to claim 1 wherein the analogue comprises an amino acid residue at position 14 which is aspartic acid, an amino acid residue at position 17 which is arginine, an amino acid residue at position 21 which is proline, an amino acid residue at position 27 which is proline and an amino acid residue at position 35 which is arginine.

6. The polypeptide according to claim 1 comprising an analogue of SEQ ID No: 1 according to formula (I):

(I)

$Xaa_1$-Cys-Asn-Thr-Ala-Thr-Cys-Ala-Thr-Gln-Arg-Leu-Ala-$Xaa_{14}$-Phe-Leu-$Xaa_{17}$-His-Ser-Ser-$Xaa_{21}$-Asn-Phe-Gly-$Xaa_{25}$-$Xaa_{26}$-$Xaa_{27}$-$Xaa_{28}$-$Xaa_{29}$-Thr-$Xaa_{31}$-Val-Gly-$Xaa_{34}$-$Xaa_{35}$-Thr-$Xaa_{37}$;

wherein $Xaa_1$ is independently selected from Ala, Cys, Glu, Gly, His, Arg, Ser and Lys;

$Xaa_{14}$ is independently selected from Asp, Glu, His, Asn, Arg, Gly, Ala, Ser, Lys, Thr and Cys;

$Xaa_{17}$ is independently selected from Arg and Val;

$Xaa_{21}$ is Pro;

$Xaa_{25}$ is independently selected from Pro and Ala;

Xaa$_{26}$ is independently selected from Pro and Ile;
Xaa$_{27}$ is independently selected from Pro and Leu;
Xaa$_{28}$ is independently selected from Pro and Ser;
Xaa$_{29}$ is independently selected from Pro and Ser;
Xaa$_{31}$ is independently selected from Pro and Asn;
Xaa$_{34}$ is independently selected from Pro, His, Lys, Arg and Ser
Xaa$_{35}$ is independently selected from Asp, Arg, Glu, Lys, His and Asn;
Xaa$_{37}$ is independently selected from Pro and Tyr;
and where the C-terminal may optionally be derivatized.

7. The polypeptide according to claim 6 wherein Xaa$_1$ is Lys, Xaa$_{14}$ is Asp, Xaa$_{17}$ is Arg, Xaa$_{21}$ is Pro, Xaa$_{25}$ is Ala, Xaa$_{26}$ is Ile, Xaa$_{27}$ is Pro, Xaa$_{28}$ is Ser, Xaa$_{29}$ is Ser, Xaa$_{31}$ is Asn, Xaa$_{34}$ is Ser, Xaa$_{35}$ is Asn, Xaa$_{37}$ is Tyr.

8. The polypeptide according to claim 1 wherein the substituent group is selected from the group consisting of C20diacid, C20diacid-γGlu, C20diacid-γGlu-γGlu, C20diacid-γGlu-γGlu-γGlu, C20diacid-OEG, C20diacid-γGlu-OEG, C20diacid-γGlu-OEG-OEG, C18diacid-γGlu, C16diacid-γGlu, and C14diacid-γGlu.

9. The polypeptide according to claim 1 wherein a substituent is attached to the α-amino group of the N-terminal amino acid residue or to a Lys residue or cysteine residue only.

10. The polypeptide according to claim 1, selected from the group consisting of any of the polypeptides presented in Table 2.

11. The polypeptide according to claim 1, selected from the group consisting of any of the polypeptides presented in Table 3.

12. A method of treating hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers and/or for use in decreasing food intake, decreasing β-cell apoptosis, increasing β-cell function and β-cell mass, and/or for restoring glucose sensitivity to β-cells, comprising administering the polypeptide of claim 1 to a patient in need thereof.

13. A pharmaceutical composition comprising the polypeptide of claim 1 and a pharmaceutically acceptable excipient.

14. A process for preparing a pharmaceutical composition comprising mixing the polypeptide of claim 1 with a pharmaceutically acceptable excipient.

* * * * *